US012655183B2

(12) United States Patent
Liu et al.

(10) Patent No.: US 12,655,183 B2
(45) Date of Patent: Jun. 16, 2026

(54) METHODS AND COMPOSITIONS FOR TREATING AND/OR PREVENTING A DISEASE OR DISORDER ASSOCIATED WITH ABNORMAL LEVEL AND/OR ACTIVITY OF THE IFP35 FAMILY OF PROTEINS

(71) Applicant: GUANGZHOU INNO-ENMAI BIOMEDICAL TECHNOLOGY CO., LTD, Guangzhou (CN)

(72) Inventors: Yingfang Liu, Beijing (CN); Huanhuan Liang, Beijing (CN); Juan Shen, Beijing (CN); Zhikai Xiahou, Beijing (CN)

(73) Assignee: GUANGZHOU INNO-ENMAI BIOMEDICAL TECHNOLOGY CO., LTD, Guangzhou (CN)

( * ) Notice: Subject to any disclaimer, the term of this patent is extended or adjusted under 35 U.S.C. 154(b) by 338 days.

(21) Appl. No.: 17/930,635

(22) Filed: Sep. 8, 2022

(65) Prior Publication Data

US 2023/0265135 A1    Aug. 24, 2023

Related U.S. Application Data

(62) Division of application No. 15/505,600, filed as application No. PCT/CN2015/000602 on Aug. 21, 2015, now Pat. No. 11,466,061.

(30) Foreign Application Priority Data

Aug. 22, 2014    (CN) ......................... 201410418773.1

(51) Int. Cl.
| | |
|---|---|
| *G01N 33/68* | (2006.01) |
| *A61K 39/00* | (2006.01) |
| *C07K 14/47* | (2006.01) |
| *C07K 16/18* | (2006.01) |
| *C07K 16/24* | (2006.01) |
| *C12N 15/113* | (2010.01) |

(52) U.S. Cl.
CPC .......... *C07K 14/47* (2013.01); *A61K 39/0011* (2013.01); *C07K 16/18* (2013.01); *C07K 16/24* (2013.01); *C12N 15/113* (2013.01); *G01N 33/68* (2013.01); *A61K 2039/505* (2013.01); *C07K 2317/565* (2013.01); *C07K 2317/567* (2013.01); *C07K 2317/76* (2013.01); *C12N 2310/11* (2013.01); *G01N 2500/04* (2013.01); *G01N 2500/20* (2013.01)

(58) Field of Classification Search
CPC ................................................... G01N 33/68
See application file for complete search history.

(56) References Cited

U.S. PATENT DOCUMENTS

2003/0157685 A1    8/2003    Zervos

FOREIGN PATENT DOCUMENTS

| | | | |
|---|---|---|---|
| CN | 1703523 | A | 11/2005 |
| CN | 101218355 | A | 7/2008 |
| CN | 101365802 | A | 2/2009 |
| CN | 101473045 | A | 7/2009 |
| CN | 101479389 | A | 7/2009 |
| CN | 114796497 | A | 7/2022 |
| CN | 115054687 | A | 9/2022 |
| KR | 101326367 | B1 | 11/2013 |

OTHER PUBLICATIONS

De Masi et al, (2020), Life Sciences 259, 118233.*
Jing et al, PNAS, (2021), vol. 118, No. 32, e2102642118, https://doi.org/10.1073/pnas.2102642118.*
Bin W.; Human anatomy and physiology [M]. China Light Industry Press, 2012. p. 273.
Jie Wang, Bo Yang, Yu Hu, Yuhan Zheng, Haiyan Zhou, Yanming Wang, Yonglei Ma, Kairui Mao, Leilei Yang, Guomei Lin, Yongyong Ji, Xiaodong Wu, Bing Sun; Negative Regulation of Nmi on Virus-Triggered Type I IFN Production by Targeting IRF7. J Immunol Sep. 15, 2013; 191 (6): 3393ao, Leilei Yang, Guomei Lin, Yongyong Ji, Xiaod.
First notice of examination opinions for CN2022105375855 dated Mar. 20, 2023.
Second notice of examination opinions for CN2022105375855 dated Sep. 29, 2023.
Rejection decision for CN2022105375855 dated Jan. 16, 2024.
Notification of Reexamination for CN2015800452105 dated Aug. 17, 2022.
Reexamination Decision for CN2015800452105 dated Oct. 19, 2022.
Notification to Grant Patent Right for Invention for CN2015800452105 dated Nov. 16, 2022.
4th Office Action for EP20150834006 dated Feb. 3, 2023.
Delves, Peter J.; Roitt's Essential Immunology 12E, 12th Edition; Wiley-Blackwell Publishers; May 17, 2011.
Abbas, Abul K. et al; "Cellular and Molecular Immunology: with Student Consult Online;" Elseiver Health Science Division; Jun. 28, 2011.
Michael T. Lotze; Albert Deisseroth; Anna Rubartelli. (2007). Damage associated molecular pattern molecules. , 124 (1), 1ong Ji, Xiao016/j.clim.2007.02.006.

(Continued)

*Primary Examiner* — Prema M Mertz
(74) *Attorney, Agent, or Firm* — D'Ambrosio & Menon, PLLC; Usha Menon

(57) ABSTRACT

The present invention relates to methods and compositions for treating and/or preventing a disease or disorder associated with abnormally high level of the IFP35 family of proteins, including IFP35 and NMI, methods and compositions for diagnosis, prognosis or treatment monitoring of a disease or disorder associated with abnormally high level of the IFP35 family of proteins, including IFP35 and NMI, and methods and compositions for identifying a modulator of the IFP35 family of proteins, including IFP35 and NMI.

2 Claims, 58 Drawing Sheets

Specification includes a Sequence Listing.

(56)          References Cited

OTHER PUBLICATIONS

Kox M, van Eijk LT, Zwaag J, van den Wildenberg J, Sweep FC, van der Hoeven JG, Pickkers P. Voluntary activation of the sympathetic nervous system and attenuation of the innate immune response in humans. Proc Natl Acad Sci U S A. May 20, 2014; 111(20):7379-84. doi: 10.1073/pnas.1322174111. Epub May 5, 2014. PMID: 24799686; PMCID: PMC4034215.

Jounai N, Kobiyama K, Takeshita F,et al. Recognition of damage-associated molecular patterns related to nucleic acids during inflammation and vaccination[J]. Frontiers Media SA, 2013.DOI:10.3389/fcimb.2012.00168.

Tincani A, Andreoli L, Bazzani C, et al. Inflammatory molecules: a target for treatment of systemic autoimmune diseases. [J]. Autoimmunity reviews, 2007(1):7.

Hearing Notice from Indian Patent Office in Reference of Application IN201717008979A dated Mar. 3, 2023.

Intimation of grant from Indian Patent Office for IN201717008979A dated Dec. 13, 2023.

* cited by examiner

Fig.1A
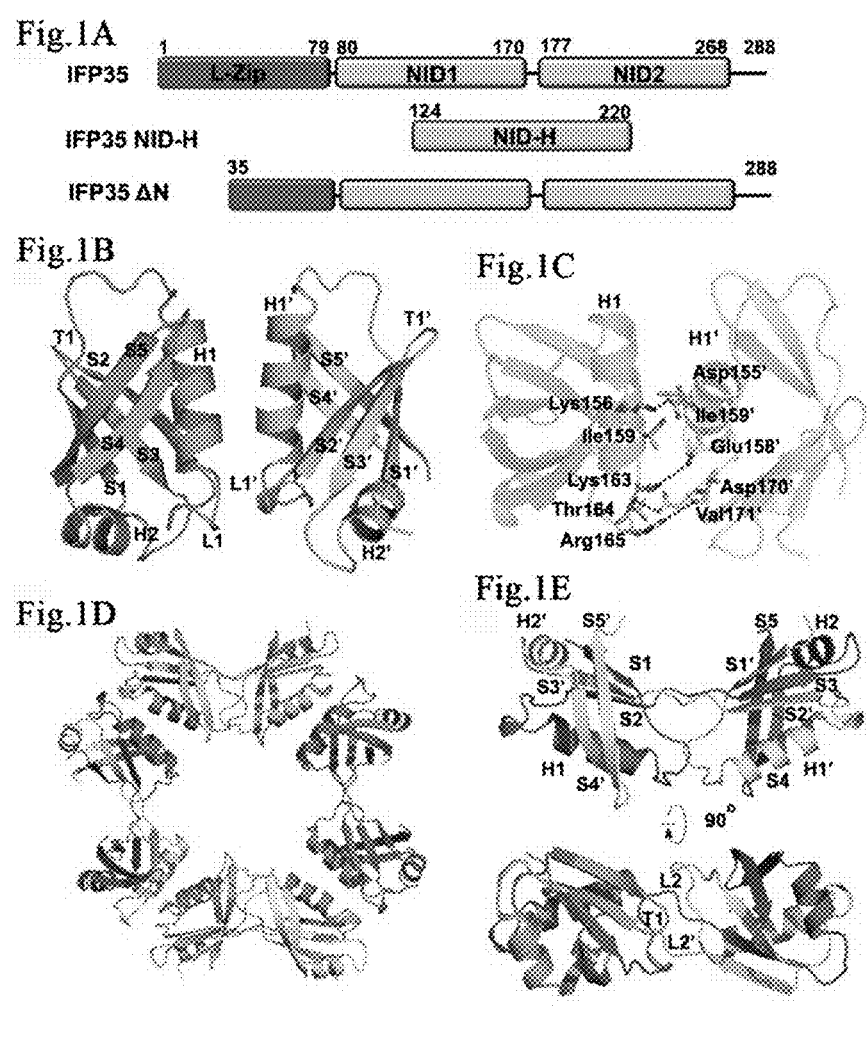
Fig.1B
Fig.1C
Fig.1D
Fig.1E
Fig.2A
Fig.2B
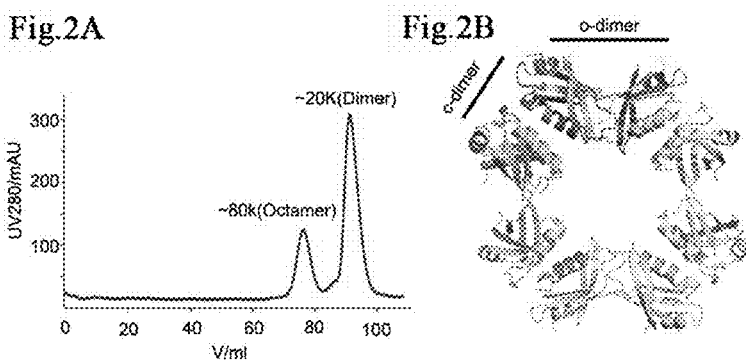
Fig.2C
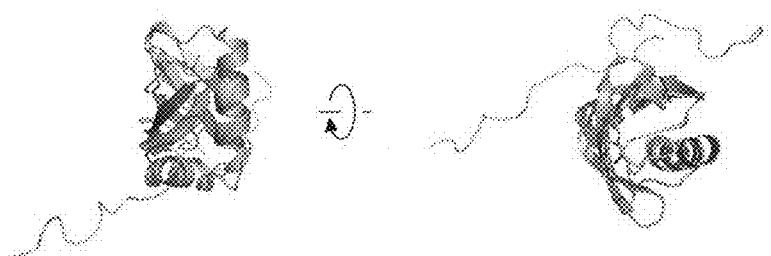

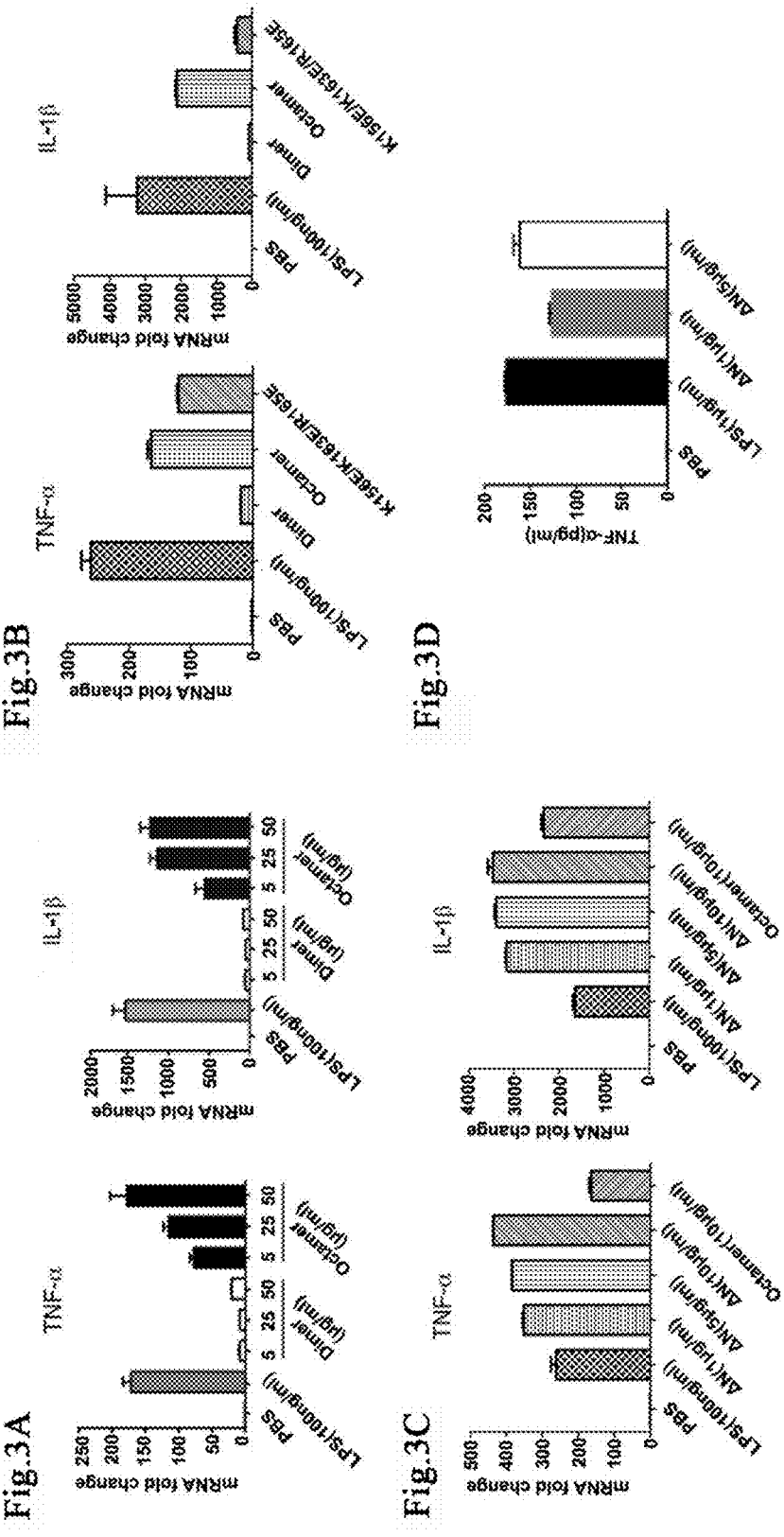

Fig. 4

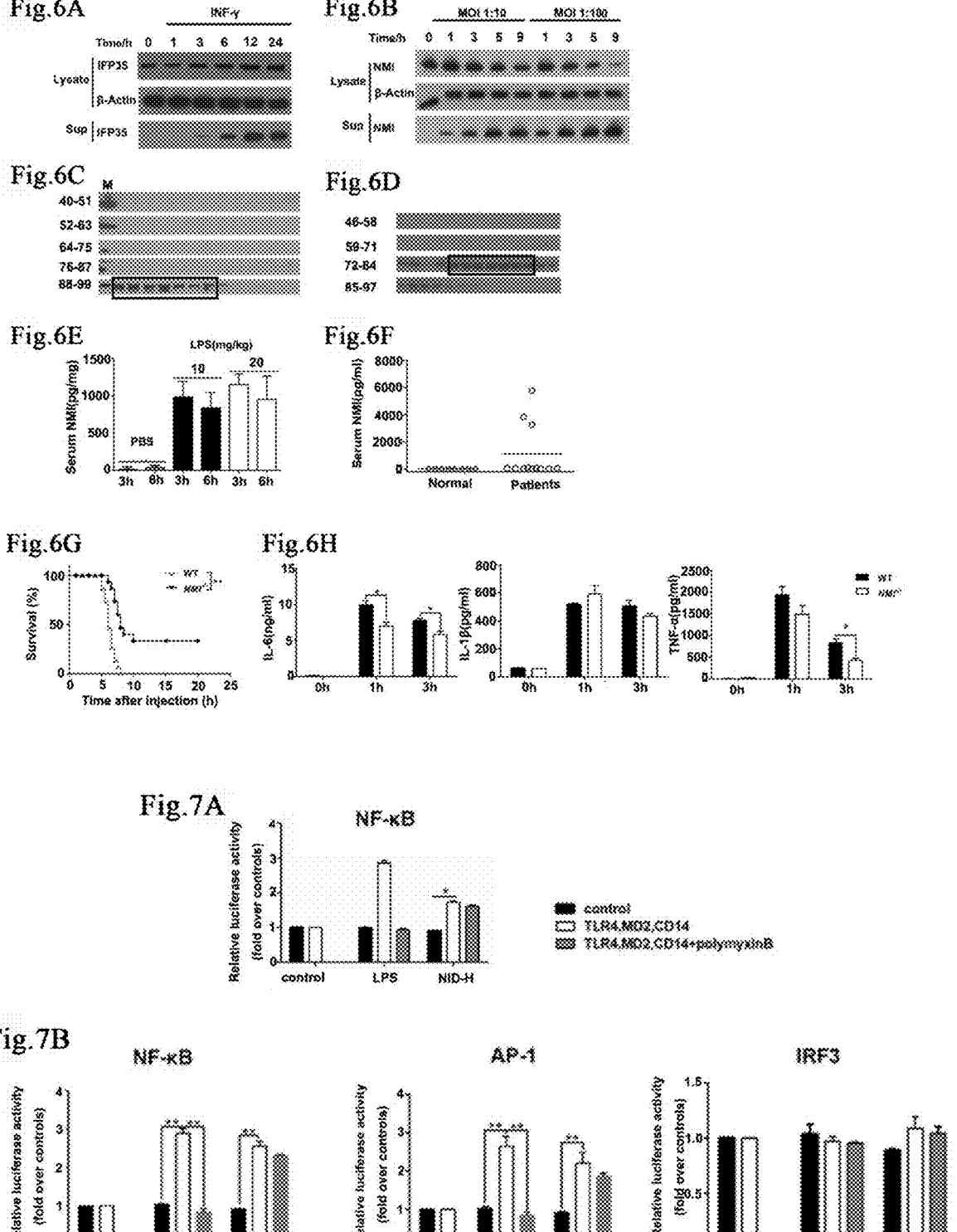

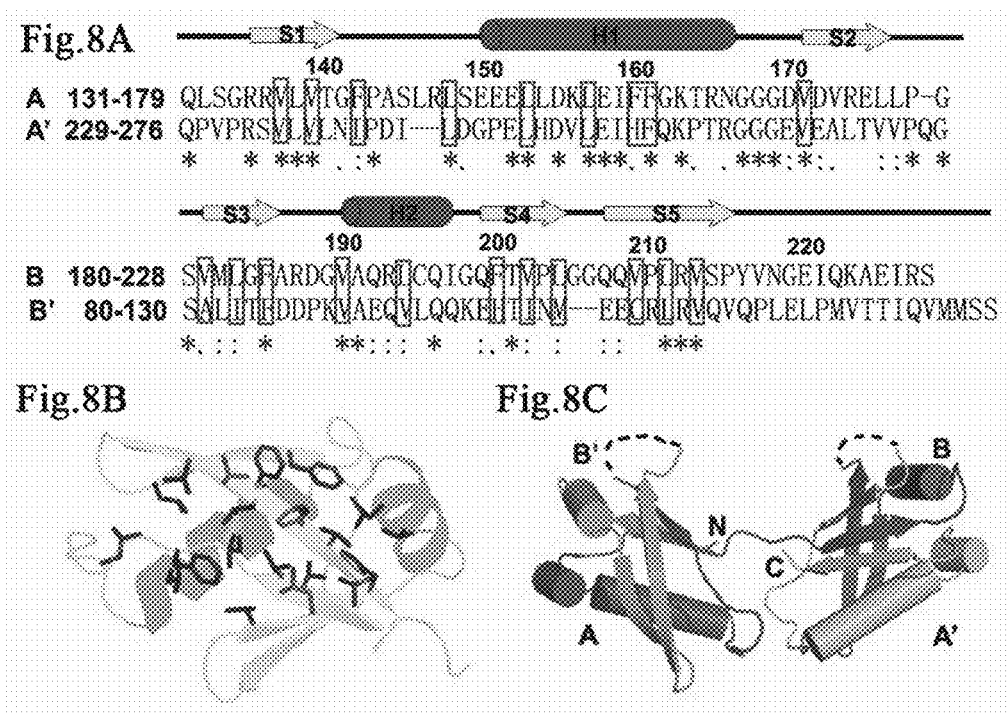
Fig.8A
Fig.8B
Fig.8C
Fig. 9
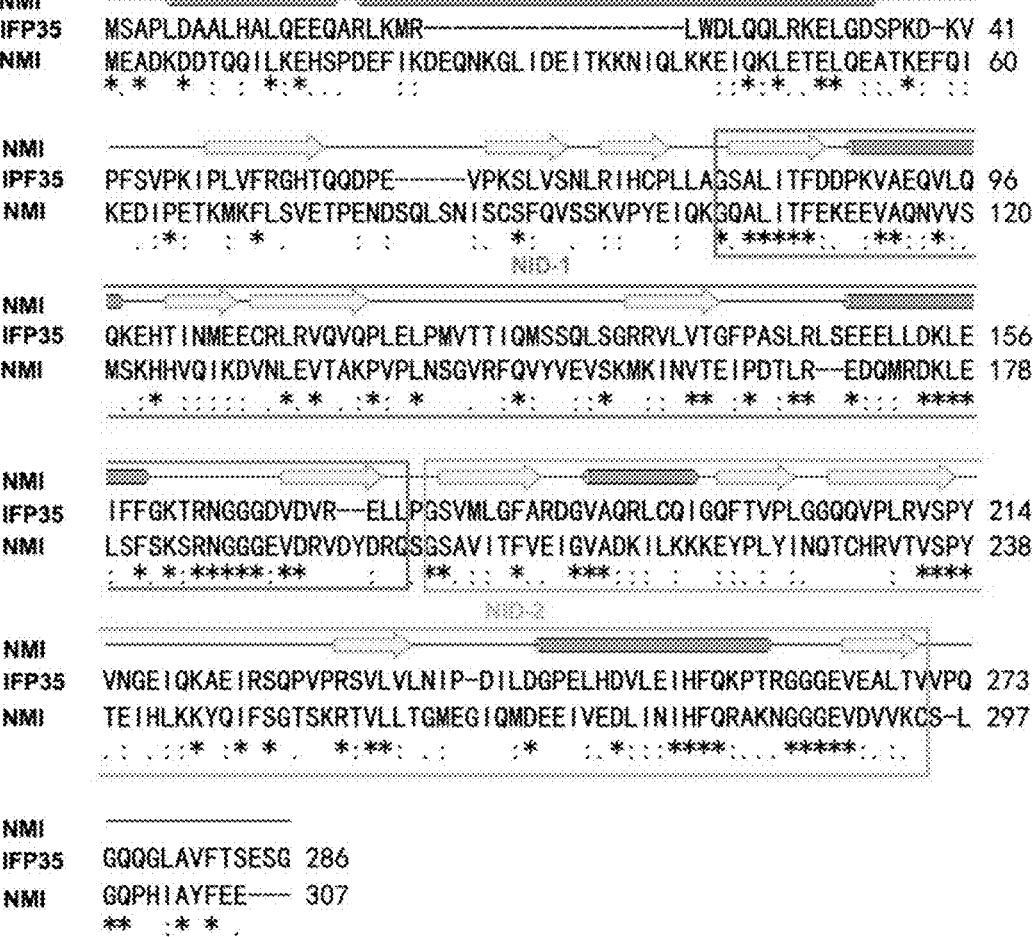

Fig.10A
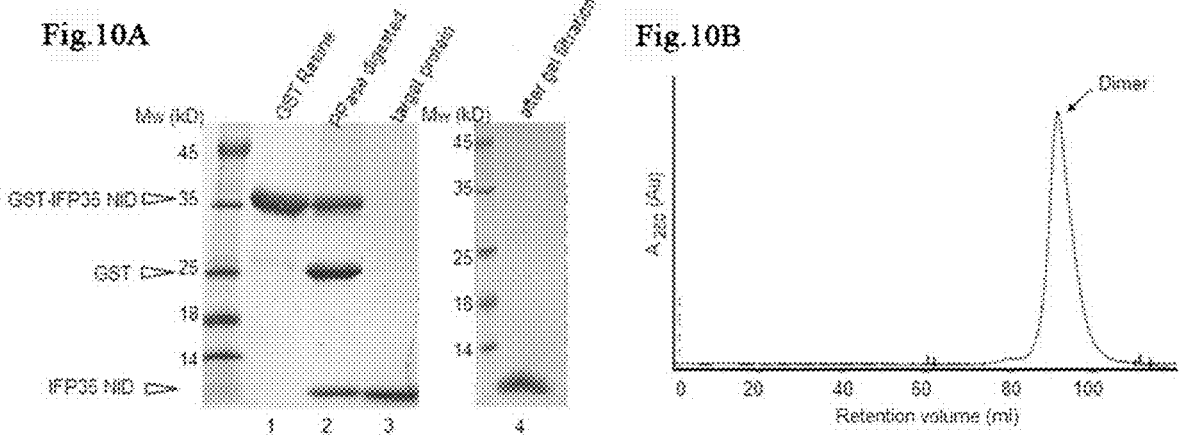
Fig.10B
Fig.11A
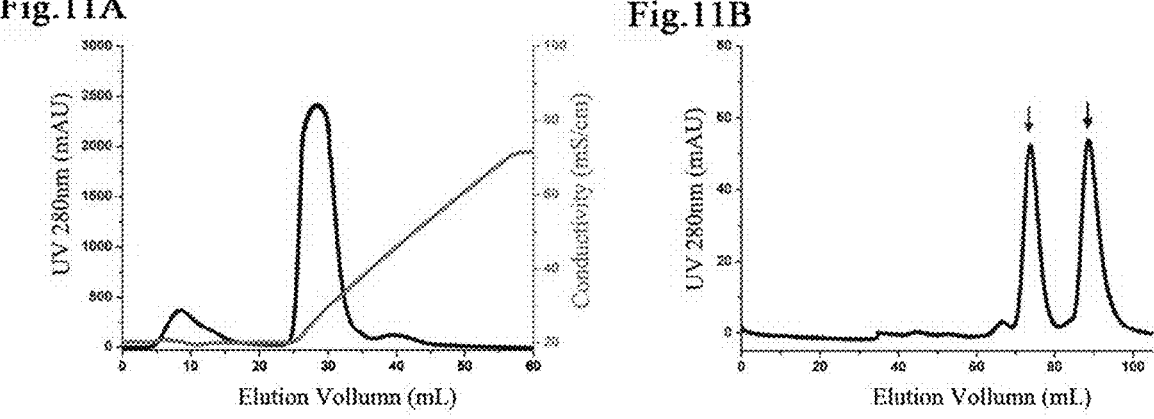
Fig.11B
Fig.11C
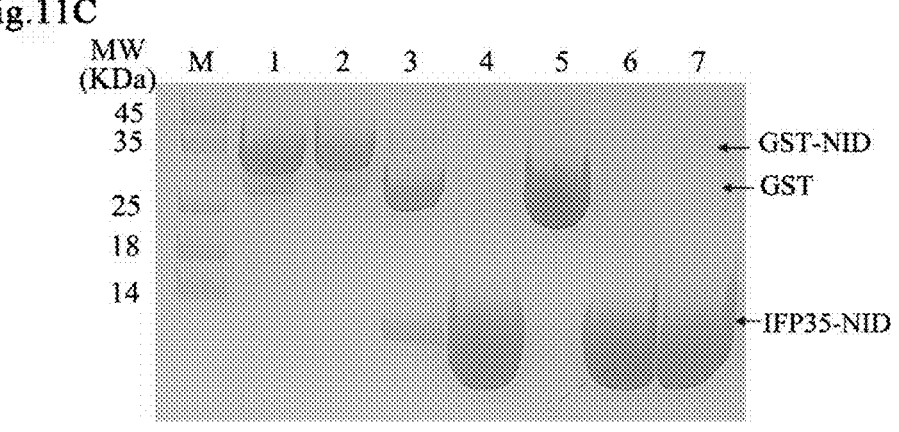

Fig.14A
Fig.14B
Fig.14C
Fig.14D
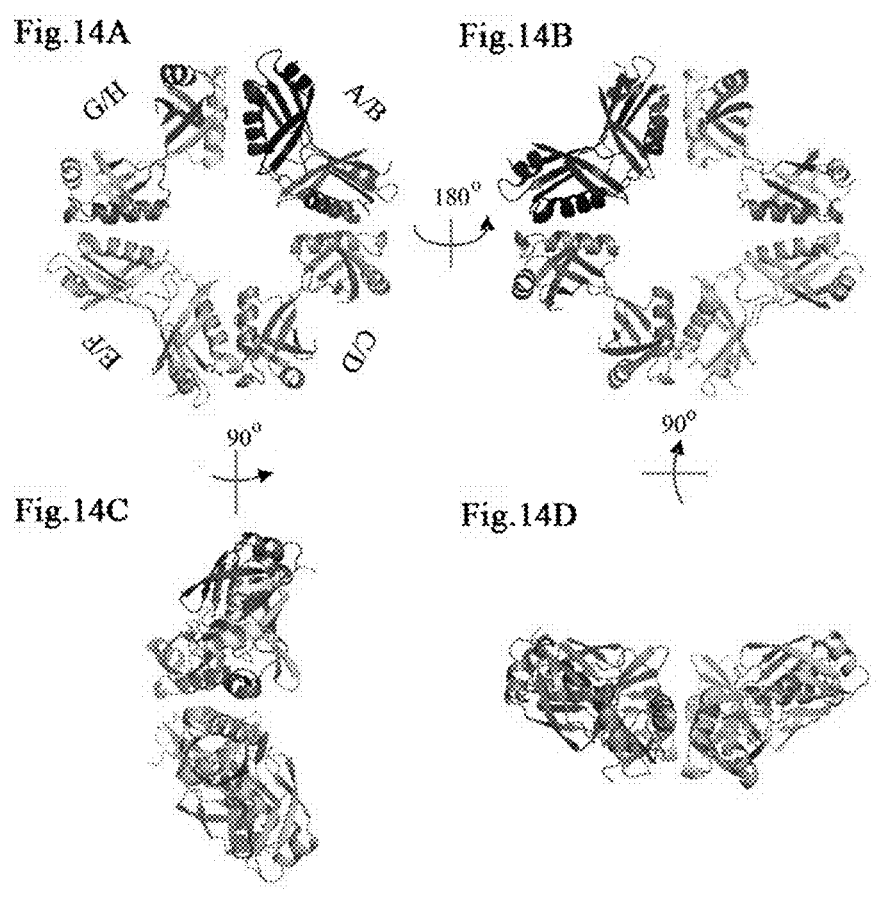
Fig.15A
Fig.15B
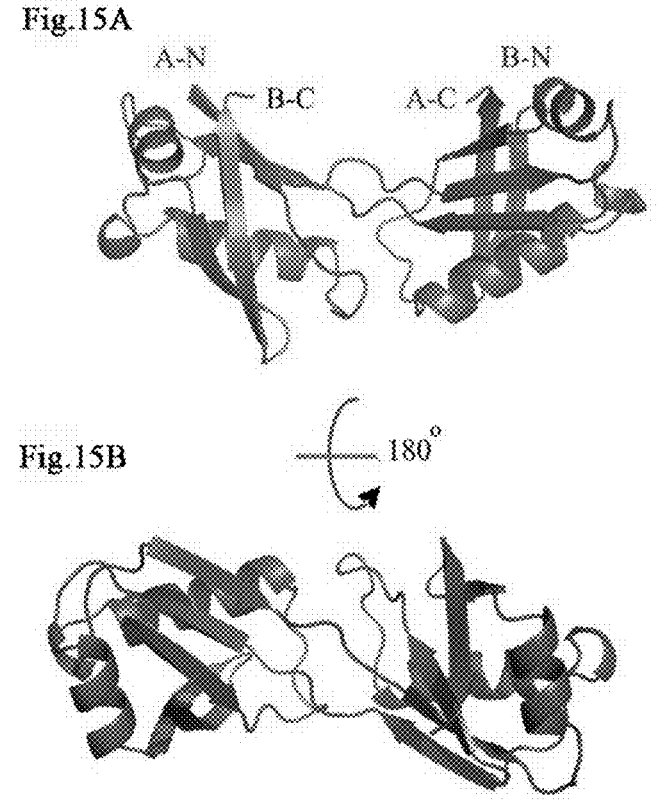

Mw(kD)
45
35
25
18
14

GST-Resine
PPase digested
Target protein

←— GST-NMI(NID)
←— GST
←—NMI(NID)

20KD

6*His-NMI

Mw(kD)
45
35
25
18
14

150KD

Fig.21A
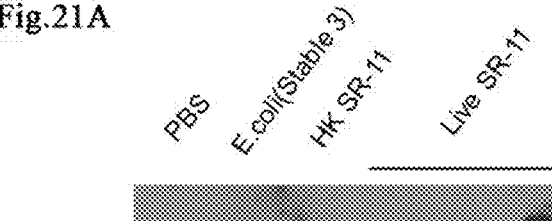
Fig.21B
Fig.22A
TNF-α
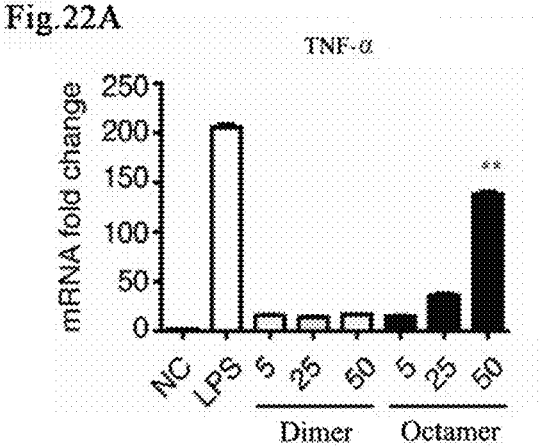
Fig.22B
IL-1β
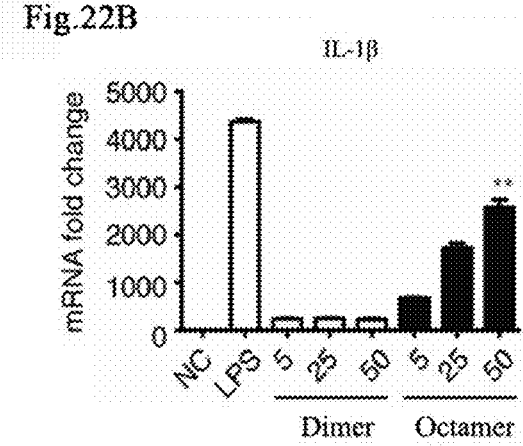
Fig.22C
iNOS
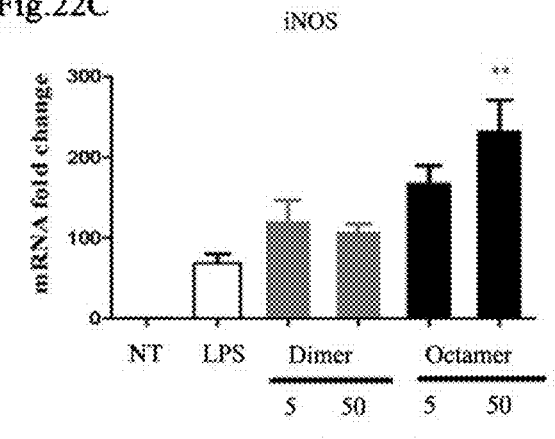
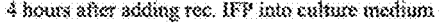
4 hours after adding rec. IFP into culture medium
Fig.22D
CD86
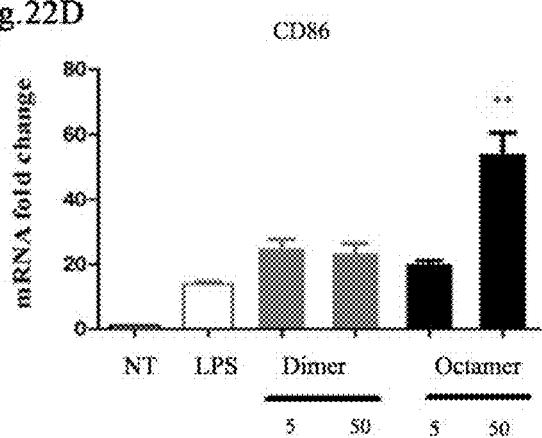
4 hours after adding rec. IFP into culture medium i.p. injection of LPS Fig. 28
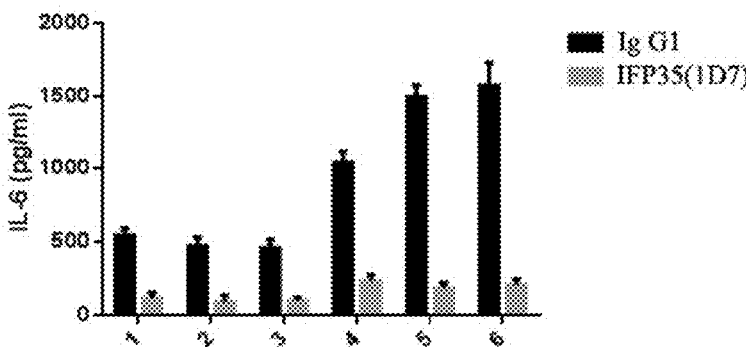
Fig. 29
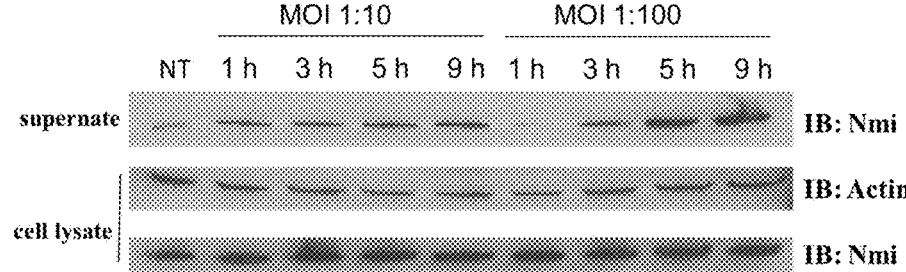
Fig.30A
Fig.30B
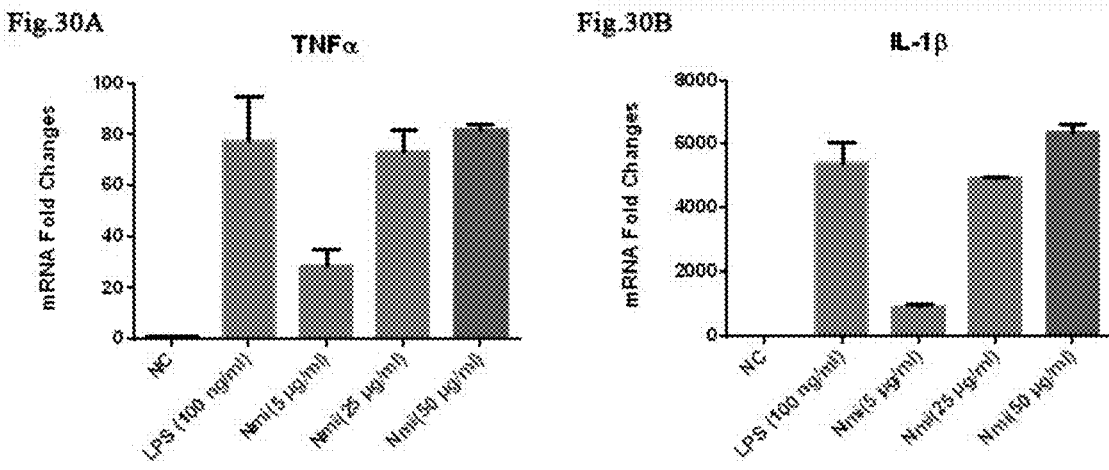
Fig. 31
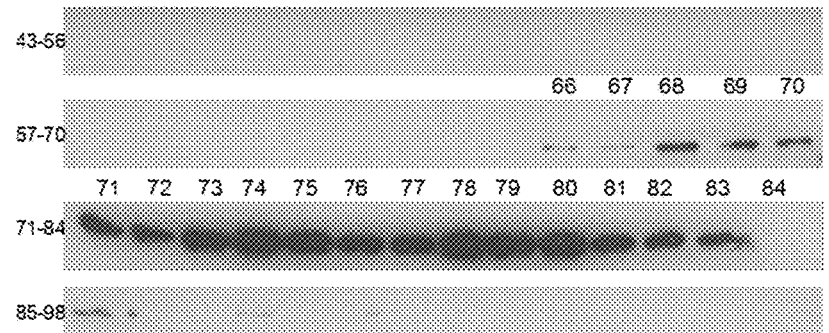

SEQUENCE LISTING

Sequence total quantity: 51
```
SEQ ID NO: 1          moltype = DNA  length = 867
FEATURE               Location/Qualifiers
source                1..867
                      mol_type = other DNA
                      organism = Homo sapiens
```

```
SEQUENCE: 1
atgtcagccc cactggatgc cgccctccac gcccttcagg aggagcaggc cagactcaag    60
atggaggctgt gggacctgca gcagctgaga aaggagctcg gggactcccc caaagacaag   120
gtcccatttt cagtgcccaa gatcccctg gtattccgag gacacaccca gcaggacccg     180
gaagtgccta agtctttagt ttccaatttg cggatccact gccctctgct tgcgggctct    240
gctctgatca cctttgatga cccaaagtg gctgagcagg tgctgcaaca aaaggagcac    300
acgatcaaca tggaggagtg ccggctgcgg gtgcaggtcc agcccttgga gctgcccatg   360
gtcaccacca tccaggtgat gatgtccagc cagttgagtg gccggagggt gttggtcact   420
ggatttcctg ccagcctcag gctgagtgag gaggagctgc tggacaagct agagatcttc    480
tttggcaaga ctaggaacgg aggtggcgat gtggacgttc gagtgctact gccagggagt   540
gtcatgctgg ggtttgctag ggatggagtg gctcagcgtc tgtgccaaat cggccagttc   600
acagtgccac tgggtgggca gcaagtccct ctgagagtct ctccgtatgt gaacggggag    660
atccagaagg ctgagatcag gtcgcagcca gttccccgct cggtactggt gctcaacatt   720
cctgatatct tggatggccc ggagctgcat gacgtcctgg agatccactt ccagaagccc   780
acccgcgggg gcggggaggt agaggccctg acagtcgtac cccaaggaca gcagggccta   840
gcagtcttca cctctgagtc aggctag                                        867

SEQ ID NO: 2            moltype = AA   length = 288
FEATURE                 Location/Qualifiers
source                  1..288
                        mol_type = protein
                        organism = Homo sapiens
SEQUENCE: 2
MSAPLDAALH ALQEEQARLK MRLWDLQQLR KELGDSPKDK VPFSVPKIPL VFRGHTQQDP    60
EVPKSLVSNL RIHCPLLAGS ALITFDDPKV AEQVLQQKEH TINMEECRLR VQVQPLELPM   120
VTTIQVMMSS QLSGRRVLVT GFPASLRLSE EELLDKLEIF FGKTRNGGGD VDVRELLPGS   180
VMLGFARDGV AQRLCQIGQF TVPLGGQQVP LRVSPYVNGE IQKAEIRSQP VPRSVLVLNI   240
PDILDGPELH DVLEIHFQKP TRGGGEVEAL TVVPQGQQGL AVFTSESG                 288

SEQ ID NO: 3            moltype = DNA   length = 861
FEATURE                 Location/Qualifiers
source                  1..861
                        mol_type = other DNA
                        organism = Homo sapiens
SEQUENCE: 3
atgtctgtga ccctgcaaac tgtcctctac agtcttcagg aggagcaagc caggctcaag    60
atggaggctgc aggagctgca gcagctcaaa agggagcgca caggctctcc cggagccaag   120
atcccattct cagtacctga agttcctctg gtattccaag gccaaactaa gcagggcagg    180
caagtgccca agtttgtagt ttctaacttg aaggtcgact gccctctgcc tgaaggttct    240
gctctggtca cctttgagga ccccaaagtg gttgatcggt tgctacaaca aaaggaacac   300
agagttaact tagaggactg ccggctgcgg gtgcaggtcc agcccttgga gctgcctgtg   360
gtgaccaaca ttcaggtgtc cagccagcca gataaccaca gggtgctcgt tagtggtttt   420
cctgctggac ttaggctgag tgaagaggaa ctgttggaca agctggagat cttctttggc   480
aaggccaaga atggaggtgg ggatgtagag acccggggac tgctgcaagg gaccgtcatg   540
ctagggtttg ctgatgaaga agtggcccag cacttatgcc agattggcca gttcagagtc    600
ccactggacc ggcagcaggt cctcctgagg gtctctccct atgtgagtgg tgagatccag    660
aaagccgaga tcaaattcca gcaagcccct cattcagtgc tggtgacaaa tattcctgat   720
gtcatggatg cccaggaact gcatgacatc cttgagatcc acttccagaa gcccactcgt    780
gggggcgggg aggtggaggc cctgacagtt gtgccttcag gcagcagggg cctggctatc    840
ttcacttccg agtcaagcta g                                              861

SEQ ID NO: 4            moltype = AA   length = 286
FEATURE                 Location/Qualifiers
source                  1..286
                        mol_type = protein
                        organism = Homo sapiens
SEQUENCE: 4
MSVTLQTVLY SLQEEQARLK MRLQELQQLK RERTGSPGAK IPFSVPEVPL VFQGQTKQGR    60
QVPKFVVSNL KVCCPLPEGS ALVTFEDPKV VDRLLQQKEH TINIQVSSQP DNHRVLVSGF   120
PAGLRLSEEE LLDKLEIFFG KAKNGGGDVE TREMLQGTVM LGFADEEVAQ HLCQIGQFRV   180
PLDRQQVLLR VSPYVSGEIQ KAEIKFQQAP HSVLVTNIPD VMDAQELHDI LEIHFQKPTR   240
GGGEVEALTV VPSGQQGLAI FTSESS                                         286

SEQ ID NO: 5            moltype = DNA   length = 945
FEATURE                 Location/Qualifiers
source                  1..945
                        mol_type = other DNA
                        organism = Homo sapiens
SEQUENCE: 5
atggatgctg ataaagacaa cataaagcaa gcttgtgatg agcgctcagc agagatggac    60
gatatgagag cgaacagag catgggattg gttcatgaaa ttatgagtga aaacaaagaa    120
ctagacgagg agatcaaaaa acttgaagct gaattgcagt cggatgccag agaattccaa    180
attaaagaga atgtaccaga aaaaaagctt aaattgacct cagtggagag tcctaaggat    240
ggctgccatt tctcaaatag ctcctgttcc tttcaagtga gctcacaaat tctctatgag   300
ctgcaggaag gccaagcgct catcacctt gagaaggaag aagtcgcaca aaatgtgata    360
tcgatgggga tcatgtcgt gcagatgaa ggcaccccag tgaaggtctc tgcacaccca    420
gtcccactaa acacaggcgt cagattccag gttcatgtgg acatttctaa aatgaagatc   480
aatgttacgg gaattcccga tgagctgtct gaggagcaga caaggacaa actggagctg    540
agcttctgta agtccaggaa tggcggcggc gaagtggaaa gcgtggatta tgacaggaag   600
```

-continued

```
tccagaagcg ctgtcatcac ttttgtggaa actggcgttg ttgacaagat tttgaaaaag  660
aaaacctatc ctctctacat gaatcagaag tgccatagcg ttgctgtttc tccatgtata  720
gaacgatgct tagaaaagta ccaggtgttt tcagctgtgt ccaaaaagac agtgcttctg  780
accgattag aaggcattcc tgtagatgag gagactgggg aggacttact caacatccac  840
ttccaacgga agaataacgg aggggagaa gtggaggtgg tcaagtgttc tctagaccag  900
tccttcgcag cgtattttaa agaagaggcc agagaaacca tatga              945

SEQ ID NO: 6              moltype = AA  length = 314
FEATURE                   Location/Qualifiers
source                    1..314
                          mol_type = protein
                          organism = Homo sapiens
SEQUENCE: 6
MDADKDNIKQ ACDERSAEMD DMRGEQSMGL VHEIMSENKE LDEEIKKLEA ELQSDAREFQ  60
IKENVPEKKL KLTSVESPKD GCHFSNSSCS FQVSSQILYE LQEGQALITF EKEEVAQNVI  120
SMGNHVVQME GTPVKVSAHP VPLNTGVRFQ VHVDISKMKI NVTGIPDELS EEQTRDKLEL  180
SFCKSRNGGG EVESVDYDRK SRSAVITFVE TGVVDKILKK KTYPLYMNQK CHSVAVSPCI  240
ERCLEKYQVF SAVSKKTVLL TGLEGIPVDE ETGEDLLNIH FQRKNNGGGE VEVVKCSLDQ  300
SFAAYFKEEA RETI                                                   314

SEQ ID NO: 7              moltype = DNA  length = 924
FEATURE                   Location/Qualifiers
source                    1..924
                          mol_type = other DNA
                          organism = Homo sapiens
SEQUENCE: 7
atggaagctg ataaagatga cacacaacaa attcttaagg agcattcgcc agatgaattt  60
ataaaagatg aacaaaataa gggactaatt gatgaaatta caaagaaaaa tattcagcta  120
aagaaggaga tccaaaagct tgaaacggag ttacaagagg ctaccaaaga attccagatt  180
aaagaggata ttcctgaaac aaagatgaaa ttcttatcag ttgaaactcc tgagaatgac  240
agccagttgt caaatatctc ctgttcgttt caagtgagct cgaaagttcc ttatgagata  300
caaaaaggac aagcacttat caccttttgaa aaagaagaag ttgctcaaaa tgtggtaagc  360
atgagtaaac atcatgtaca gataaaagat gtaaatctgg aggttacggc caagccagtt  420
ccattaaatt caggagtcag attccaggtt tatgtagaag tttctaaaat gaaaatcaat  480
gttactgaaa ttcctgacac actgcgtgaa gatcaaatga gagacaaact agagctgagc  540
ttttcaaagt tccgaaatgg aggcggagag gtggaccgcg tggactatga cagacagtcc  600
gggagtgcag tcatcacgtt tgtggagatt ggagtggctg acaagatttt gaaaaagaaa  660
gaatacccctc tttatataaa tcaaacctgc catagagtta ctgtttctcc atacacagaa  720
atacacttga aaaagtatca gatattttca ggaacatcca agaggacagt gcttctgaca  780
ggaatggaag gcattcaaat ggatgaagaa attgtggagg atttaattaa cattcacttt  840
caacgggcaa agaatggagg tggagaagta gatgtggtca agtgttctct aggtcaacct  900
cacatagcat actttgaaga atag                                        924

SEQ ID NO: 8              moltype = AA  length = 307
FEATURE                   Location/Qualifiers
source                    1..307
                          mol_type = protein
                          organism = Homo sapiens
SEQUENCE: 8
MEADKDDTQQ ILKEHSPDEF IKDEQNKGLI DEITKKNIQL KKEIQKLETE LQEATKEFQI  60
KEDIPETKMK FLSVETPEND SQLSNISCSF QVSSKVPYEI QKGQALITFE KEEVAQNVVS  120
MSKHHVQIKD VNLEVTAKPV PLNSGVRFQV YVEVSKMKIN VTEIPDTLRE DQMRDKLELS  180
FSKFRNGGGE VDRVDYDRQS GSAVITFVEI GVADKILKKK EYPLYINQTC HRVTVSPYTE  240
IHLKKYQIFS GTSKRTVLLT GMEGIQMDEE IVEDLINIHF QRAKNGGGEV DVVKCSLGQP  300
HIAYFEE                                                           307

SEQ ID NO: 9              moltype = AA  length = 120
FEATURE                   Location/Qualifiers
source                    1..120
                          mol_type = protein
                          organism = Homo sapiens
SEQUENCE: 9
VQLVESGPEL KKPGETVKIS CKASGYTFTN YGMNWVKQAP GKGLKWMGWI NTYTGEPTFA  60
DDFKGRFAFS LETSASTAYL QINNLKNEDT ATYFCARYGY SWAMDYWGQG TSVTVSSAST  120

SEQ ID NO: 10             moltype = AA  length = 107
FEATURE                   Location/Qualifiers
source                    1..107
                          mol_type = protein
                          organism = Homo sapiens
SEQUENCE: 10
DIVMTQSPAI MSASPGEKVT MTCSASSSVS YMHWYQQKSG TSPKRWIYDT SKLASGVPAR  60
FSGSGSGTSY SLTISSMEAE DAATYYCQQW SSNPPITFGA GTKLEIK              107

SEQ ID NO: 11             moltype = DNA  length = 342
FEATURE                   Location/Qualifiers
source                    1..342
                          mol_type = other DNA
                          organism = Homo sapiens
```

```
SEQUENCE: 11
tggtcgacgc tgaggagacg gtgactgagg ttccttgacc ccagtagtcc atagcccaag   60
agtacccgta tcttgcacag aaatatgtag ccgtgtcctc attcttgagg ttgttgatct  120
gcaaataggc agtgctggca gaggtttcca aagagaaggc aaaccgtccc ttgaagtcat  180
cagcaaatgt tggctctcca gtgtaggtgt ttatccagcc catccacttt aaaccctttc  240
ctggagcctg cttcacccag ttcattccat agtttgtgaa ggtatacccca gaagccttgc  300
aggagatctt gactgtctct cctgactcct taagctgcac ct                      342

SEQ ID NO: 12          moltype = DNA  length = 321
FEATURE                Location/Qualifiers
source                 1..321
                       mol_type = other DNA
                       organism = Homo sapiens
SEQUENCE: 12
gacattgtga tgacccagtc tccagcaatc atgtctgcat ctccagggga gaaggtcacc   60
atgacctgca gtgccagctc aagtgtaagt tacatgcact ggtaccagca gaagtcaggc  120
acctccccca aaagatggat ttatgacaca tccaaactgg cttctggagt ccctgctcgc  180
ttcagtggca gtgggtctgg gacctcttac tctctcacaa tcagcagcat ggaggctgaa  240
gatgctgcca cttattactg ccagcagtgg agtagtaacc cacccatcac gttcggtgct  300
ggcaccaagc tggaaatcaa a                                             321

SEQ ID NO: 13          moltype = DNA  length = 20
FEATURE                Location/Qualifiers
misc_feature           1..20
                       note = Primer
source                 1..20
                       mol_type = other DNA
                       organism = synthetic construct
SEQUENCE: 13
cagaacatca tccctgcatc                                                20

SEQ ID NO: 14          moltype = DNA  length = 20
FEATURE                Location/Qualifiers
misc_feature           1..20
                       note = Primer
source                 1..20
                       mol_type = other DNA
                       organism = synthetic construct
SEQUENCE: 14
tacttggcag gtttctccag                                                20

SEQ ID NO: 15          moltype = DNA  length = 20
FEATURE                Location/Qualifiers
misc_feature           1..20
                       note = Primer
source                 1..20
                       mol_type = other DNA
                       organism = synthetic construct
SEQUENCE: 15
ccagtgtggg aagctgtctt                                                20

SEQ ID NO: 16          moltype = DNA  length = 20
FEATURE                Location/Qualifiers
misc_feature           1..20
                       note = Primer
source                 1..20
                       mol_type = other DNA
                       organism = synthetic construct
SEQUENCE: 16
aagcaaaaga ggaggcaaca                                                20

SEQ ID NO: 17          moltype = DNA  length = 24
FEATURE                Location/Qualifiers
misc_feature           1..24
                       note = Primer
source                 1..24
                       mol_type = other DNA
                       organism = synthetic construct
SEQUENCE: 17
aaggagaacc aagcaacgac aaaa                                           24

SEQ ID NO: 18          moltype = DNA  length = 24
FEATURE                Location/Qualifiers
misc_feature           1..24
                       note = Primer
source                 1..24
                       mol_type = other DNA
                       organism = synthetic construct
SEQUENCE: 18
```

```
tggggaactc tgcagactca aact                                            24

SEQ ID NO: 19            moltype = DNA  length = 28
FEATURE                  Location/Qualifiers
misc_feature             1..28
                         note = Primer
source                   1..28
                         mol_type = other DNA
                         organism = synthetic construct
SEQUENCE: 19
ggtagatcta tgtcagcccc actggatg                                        28

SEQ ID NO: 20            moltype = DNA  length = 34
FEATURE                  Location/Qualifiers
misc_feature             1..34
                         note = Primer
source                   1..34
                         mol_type = other DNA
                         organism = synthetic construct
SEQUENCE: 20
ggtgaattcc tagcctgact cagaggtgaa gact                                 34

SEQ ID NO: 21            moltype = DNA  length = 30
FEATURE                  Location/Qualifiers
misc_feature             1..30
                         note = Primer
source                   1..30
                         mol_type = other DNA
                         organism = synthetic construct
SEQUENCE: 21
ggtggatccc caggtgatga tgtccagcca                                      30

SEQ ID NO: 22            moltype = DNA  length = 36
FEATURE                  Location/Qualifiers
misc_feature             1..36
                         note = Primer
source                   1..36
                         mol_type = other DNA
                         organism = synthetic construct
SEQUENCE: 22
ggtgaattct tactccccgt tcacatacgg agagac                               36

SEQ ID NO: 23            moltype = DNA  length = 33
FEATURE                  Location/Qualifiers
misc_feature             1..33
                         note = Primer
source                   1..33
                         mol_type = other DNA
                         organism = synthetic construct
SEQUENCE: 23
ggtgaattca gggtgttggt cactggattt cct                                  33

SEQ ID NO: 24            moltype = DNA  length = 36
FEATURE                  Location/Qualifiers
misc_feature             1..36
                         note = Primer
source                   1..36
                         mol_type = other DNA
                         organism = synthetic construct
SEQUENCE: 24
ggtgaattct tactccccgt tcacatacgg agagac                               36

SEQ ID NO: 25            moltype = DNA  length = 30
FEATURE                  Location/Qualifiers
misc_feature             1..30
                         note = Primer
source                   1..30
                         mol_type = other DNA
                         organism = synthetic construct
SEQUENCE: 25
ggtggatcca tggaagctga taaagatgac                                      30

SEQ ID NO: 26            moltype = DNA  length = 33
FEATURE                  Location/Qualifiers
misc_feature             1..33
                         note = Primer
source                   1..33
                         mol_type = other DNA
                         organism = synthetic construct
```

-continued

```
SEQUENCE: 26
ggtctcgagc tattcttcaa agtatgctat gtg                                     33

SEQ ID NO: 27          moltype = DNA  length = 32
FEATURE                Location/Qualifiers
misc_feature           1..32
                       note = Primer
source                 1..32
                       mol_type = other DNA
                       organism = synthetic construct
SEQUENCE: 27
ggtggatcct ctaaaatgaa aatcaatgtt ac                                      32

SEQ ID NO: 28          moltype = DNA  length = 32
FEATURE                Location/Qualifiers
misc_feature           1..32
                       note = Primer
source                 1..32
                       mol_type = other DNA
                       organism = synthetic construct
SEQUENCE: 28
ggtctcgagt tattctgtgt atggagaaac ag                                      32

SEQ ID NO: 29          moltype = DNA  length = 30
FEATURE                Location/Qualifiers
misc_feature           1..30
                       note = Primer
source                 1..30
                       mol_type = other DNA
                       organism = synthetic construct
SEQUENCE: 29
cgcggatcca tggatgctga taaagacaac                                         30

SEQ ID NO: 30          moltype = DNA  length = 30
FEATURE                Location/Qualifiers
misc_feature           1..30
                       note = Primer
source                 1..30
                       mol_type = other DNA
                       organism = synthetic construct
SEQUENCE: 30
ccgctcgagt catatggttt ctctggcctc                                         30

SEQ ID NO: 31          moltype = DNA  length = 33
FEATURE                Location/Qualifiers
misc_feature           1..33
                       note = Primer
source                 1..33
                       mol_type = other DNA
                       organism = synthetic construct
SEQUENCE: 31
cgcggatccg ttcatgtgga catttctaaa atg                                     33

SEQ ID NO: 32          moltype = DNA  length = 34
FEATURE                Location/Qualifiers
misc_feature           1..34
                       note = Primer
source                 1..34
                       mol_type = other DNA
                       organism = synthetic construct
SEQUENCE: 32
ccgctcgagt caaaacacct ggtacttttc taag                                    34

SEQ ID NO: 33          moltype = DNA  length = 24
FEATURE                Location/Qualifiers
misc_feature           1..24
                       note = Primer
source                 1..24
                       mol_type = other DNA
                       organism = synthetic construct
SEQUENCE: 33
aaggagaacc aagcaacgac aaaa                                               24

SEQ ID NO: 34          moltype = DNA  length = 24
FEATURE                Location/Qualifiers
misc_feature           1..24
                       note = Primer
source                 1..24
                       mol_type = other DNA
```

-continued

```
                                    organism = synthetic construct
SEQUENCE: 34
tggggaactc tgcagactca aact                                        24

SEQ ID NO: 35          moltype = DNA  length = 20
FEATURE                Location/Qualifiers
misc_feature           1..20
                       note = Primer
source                 1..20
                       mol_type = other DNA
                       organism = synthetic construct
SEQUENCE: 35
ccagtgtggg aagctgtctt                                             20

SEQ ID NO: 36          moltype = DNA  length = 20
FEATURE                Location/Qualifiers
misc_feature           1..20
                       note = Primer
source                 1..20
                       mol_type = other DNA
                       organism = synthetic construct
SEQUENCE: 36
aagcaaaaga ggaggcaaca                                             20

SEQ ID NO: 37          moltype = DNA  length = 21
FEATURE                Location/Qualifiers
misc_feature           1..21
                       note = Primer
source                 1..21
                       mol_type = other DNA
                       organism = synthetic construct
SEQUENCE: 37
aggtcggtgt gaacggattt g                                           21

SEQ ID NO: 38          moltype = DNA  length = 23
FEATURE                Location/Qualifiers
misc_feature           1..23
                       note = Primer
source                 1..23
                       mol_type = other DNA
                       organism = synthetic construct
SEQUENCE: 38
tgtagaccat gtagttgagg tca                                         23

SEQ ID NO: 39          moltype = DNA  length = 23
FEATURE                Location/Qualifiers
misc_feature           1..23
                       note = Primer
source                 1..23
                       mol_type = other DNA
                       organism = synthetic construct
SEQUENCE: 39
gacattgtga tgwcacagtc tcc                                         23

SEQ ID NO: 40          moltype = DNA  length = 23
FEATURE                Location/Qualifiers
misc_feature           1..23
                       note = Primer
source                 1..23
                       mol_type = other DNA
                       organism = synthetic construct
SEQUENCE: 40
gatrttktga tgacycarrc tcc                                         23

SEQ ID NO: 41          moltype = DNA  length = 23
FEATURE                Location/Qualifiers
misc_feature           1..23
                       note = Primer
source                 1..23
                       mol_type = other DNA
                       organism = synthetic construct
SEQUENCE: 41
gacattgtgc tgacccaatc tcc                                         23

SEQ ID NO: 42          moltype = DNA  length = 23
FEATURE                Location/Qualifiers
misc_feature           1..23
                       note = Primer
source                 1..23
```

```
                          mol_type = other DNA
                          organism = synthetic construct
SEQUENCE: 42
gacattgtgc tgacacagtc tcc                                              23

SEQ ID NO: 43            moltype = DNA   length = 23
FEATURE                  Location/Qualifiers
misc_feature             1..23
                          note = Primer
source                   1..23
                          mol_type = other DNA
                          organism = synthetic construct
SEQUENCE: 43
saaawtgtkc tcacccagtc tcc                                              23

SEQ ID NO: 44            moltype = DNA   length = 20
FEATURE                  Location/Qualifiers
misc_feature             1..20
                          note = Primer
source                   1..20
                          mol_type = other DNA
                          organism = synthetic construct
SEQUENCE: 44
gayatymaga tgacmcagwc                                                  20

SEQ ID NO: 45            moltype = DNA   length = 21
FEATURE                  Location/Qualifiers
misc_feature             1..21
                          note = Primer
source                   1..21
                          mol_type = other DNA
                          organism = synthetic construct
SEQUENCE: 45
gayattgtga tgacmcagwc t                                                21

SEQ ID NO: 46            moltype = DNA   length = 21
FEATURE                  Location/Qualifiers
misc_feature             1..21
                          note = Primer
source                   1..21
                          mol_type = other DNA
                          organism = synthetic construct
SEQUENCE: 46
tttbakytcc agcttggtsc c                                                21

SEQ ID NO: 47            moltype = DNA   length = 22
FEATURE                  Location/Qualifiers
misc_feature             1..22
                          note = Primer
source                   1..22
                          mol_type = other DNA
                          organism = synthetic construct
SEQUENCE: 47
aggtgcagct kmaggagtca gg                                               22

SEQ ID NO: 48            moltype = DNA   length = 20
FEATURE                  Location/Qualifiers
misc_feature             1..20
                          note = Primer
source                   1..20
                          mol_type = other DNA
                          organism = synthetic construct
SEQUENCE: 48
aggtycagct kcarsartct                                                  20

SEQ ID NO: 49            moltype = DNA   length = 20
FEATURE                  Location/Qualifiers
misc_feature             1..20
                          note = Primer
source                   1..20
                          mol_type = other DNA
                          organism = synthetic construct
SEQUENCE: 49
aggtccarct gcagcagyct                                                  20

SEQ ID NO: 50            moltype = DNA   length = 22
FEATURE                  Location/Qualifiers
misc_feature             1..22
                          note = Primer
```

-continued

```
source                  1..22
                        mol_type = other DNA
                        organism = synthetic construct
SEQUENCE: 50
aggtgmagct kgwggartct gg                                        22

SEQ ID NO: 51           moltype = DNA   length = 22
FEATURE                 Location/Qualifiers
misc_feature            1..22
                        note = Primer
source                  1..22
                        mol_type = other DNA
                        organism = synthetic construct
SEQUENCE: 51
tggtcgacgc tgaggagacg gt                                        22
```

METHODS AND COMPOSITIONS FOR TREATING AND/OR PREVENTING A DISEASE OR DISORDER ASSOCIATED WITH ABNORMAL LEVEL AND/OR ACTIVITY OF THE IFP35 FAMILY OF PROTEINS

CROSS-REFERENCE TO RELATED APPLICATIONS

The present application is a divisional application of U.S. patent application Ser. No. 15/505,600, filed on Feb. 21, 2017, entitled "METHODS AND COMPOSITIONS FOR TREATING AND/OR PREVENTING A DISEASE OR DISORDER ASSOCIATED WITH ABNORMAL LEVEL AND/OR ACTIVITY OF THE IFP35 FAMILY OF PRO-TEINS," now allowed, which application is a national stage application of PCT/CN2015/000602, filed on Aug. 21, 2015, which PCT application claims priority to Chinese patent application No. 201410418773.1, filed Aug. 22, 2014. The disclosures and contents of the above-referenced applications are incorporated herein by reference in their entireties for all purposes.

SEQUENCE LISTING

The content of the following submission in XML file is incorporated herein by reference in its entirety: a computer readable form (CRF) of the Sequence Listing (file name: 17930635 Sequence Listing.XML, created on 5 May. 2023, size: 66,122 bytes).

TECHNICAL FIELD

In some aspects, the present disclosure relates to methods and compositions for treating and/or preventing a disease or disorder associated with abnormally level and/or activity of the IFP35 family of proteins, including IFP35 and NMI; methods and compositions for diagnosis, prognosis or treatment monitoring of a disease or disorder associated with abnormally level and/or activity of the IFP35 family of proteins; and methods and compositions for identifying a modulator of the IFP35 family of proteins.

BACKGROUND ART

Endogenous danger signals are "damage-associated molecular patterns" (DAMPs) that are released from necrotic or stressed cells which trigger the inflammatory response. For instance, cells produce endogenous DAMPs for immune regulation after infection or injury. See Gallucci et al., Current Opinion in Immunology 13, 114-119 (2001); Matzinger, Science 296, 301-305 (2002); and Hirsiger et al., Mediators of Inflammation, 315941 (2012). The known DAMPs include not only small molecules such as uric acid, cholesterol and ATP (see Gombault et al., Frontiers in Immunology 3, 414 (2012); Heil et al., Frontiers in Plant Science 5, 578 (2014); and Shi, Journal of Clinical Investigation 120, 1809-1811 (2010)), but also proteins such as high-mobility group box protein I (HMGB1) (see Tsung et al., Journal of Internal Medicine 276, 425-443 (2014); and Wang et al., Science 285, 248-251 (1999)), heat shock proteins (HSPs) (see Tamura et al., Immunotherapy 4, 841-852 (2012)), interleukin-1α (IL-1α) (see Dinarello, Annual Review of Immunology 27, 519-550 (2009)), inter-leukin-33 (IL-33) (see Liew et al., Nature Reviews Immunology 10, 103-110 (2010)), myeloid-related protein-8

(Mrp8) and myeloid-related protein-14 (Mrp14) (see Vogl et al., Nature Medicine 13, 1042-1049 (2007); and Austermann et al., Cell Reports 9, 2112-2123 (2014)). DAMPs may play important roles in pathogen elimination and damage repair. However, uncontrolled activation of inflammation by DAMPs will lead to persistent over-expression of toxic cytokines, which are major risk factors for sepsis shock and systemic inflammatory response syndrome. See Srikrishna et al., Neoplasia 11, 615-628 (2009); and Piccinini et al., Mediators of Inflammation, doi:10. 1155/2010/672395 (2010).

Thousands of cytokines are involved in the immune response. Being selectively activated or restrained, they constitute a complicate but precisely under-controlled network to perform antiviral or immune regulation functions. See Dinarello, Chest 118, 503-508 (2000). In addition, they are considered to be broadly involved in other cellular activities, for instance, suppressing tumor growth, promoting catabiosis, and inducing apoptosis. See Crusz et al., Nature Reviews Clinical Oncology, doi:10.1038/nrclinonc.2015.105 (2015); Chen et al., Drug Design, Development and Therapy 9, 2941-2946 (2015); Villeda et al., Nature 477, 90-94 (2011); and Eckhardt et al., Cell Death Disease 5, e1562 (2014). However, the functional mechanisms of these proteins are largely unclear.

SUMMARY

In one aspect, disclosed herein is a method for treating and/or preventing a disease or disorder associated with abnormally high level and/or activity of IFP35 (Interferon-induced Protein 35kD) and/or NMI (N-Myc-interacting protein) in a subject. In some embodiments, the method comprises administering, to a subject in need of such treatment and/or prevention, an effective amount of an agent that prevents or reduces production and/or an activity of IFP35 and/or NMI in the subject.

In any of the preceding embodiments, the disease or disorder associated with abnormally high level and/or activity of IFP35 and/or NMI can be associated with excessive immune response. In any of the preceding embodiments, the disease or disorder can be associated with cytokine storm. In any of the preceding embodiments, the disease or disorder can be selected from the group consisting of inflammation, infection, organ damage, sepsis, and autoimmune disease. In any of the preceding embodiments, the method can be for treating a disease or disorder associated with abnormally high level and/or activity of IFP35 and/or NMI. In any of the preceding embodiments, the method can be for preventing a disease or disorder associated with abnormally high level and/or activity of IFP35 and/or NMI.

In any of the preceding embodiments, the agent can comprise a molecule, such as a small molecule or a poly-peptide, that inhibits or reduces the expression and/or activity of IFP35 and/or NMI. In any of the preceding embodiments, the agent can comprise an antibody or antigen binding fragment thereof that inhibits or reduces the expression and/or activity of IFP35 and/or NMI. In any of the preceding embodiments, the agent can comprise a poly-nucleotide, such as an siRNA, shRNA, or miRNA, that targets the gene encoding IFP35 and/or NMI. In any of the preceding embodiments, the agent can comprise an anti-sense polynucleotide, such as an antisense RNA, that targets the gene encoding IFP35 and/or NMI. In any of the preceding embodiments, the agent can comprise a molecule that inhibits or reduces the oligomerization of IFP35 and/or NMI. In any of the preceding embodiments, the agent can comprise a molecule that inhibits or reduces the expression and/or activity of an interferon, thereby inhibiting or reducing the expression and/or activity of IFP35 and/or NMI. In any of the preceding embodiments, the agent can comprise a molecule that inhibits or reduces the secretion of IFP35 and/or NMI. In any of the preceding embodiments, the agent can comprise a molecule that inhibits or reduces the interaction between IFP35 and/or NMI and a cellular receptor of IFP35 and/or NMI. In any of the preceding embodiments, the agent can comprise a molecule that inhibits or reduces the interaction between IFP35 and/or NMI and a IFP35 and/or NMI cell surface receptor.

In any of the preceding embodiments, the prevention or reduction of the production and/or the activity of IFP35 and/or NMI can result in the inhibition or reduction of the expression and/or activity of an inflammatory factor, and/or inhibiting or reduction of NF-κB signaling. In one aspect, the inflammatory factor comprises IL-1β, TNF-α, iNOS, and/or CD86, and the NF-κB signaling is mediate by a TLR such as TLR4.

In any of the preceding embodiments, the agent can comprise an antibody or antigen binding fragment that specifically binds to IFP35 and/or an antibody or antigen binding fragment that specifically binds to NMI. In one aspect, the antibody or antigen binding fragment specifically binds one or more NIDs (NMI/IFP35 domains).

In any of the preceding embodiments, the method can further comprise administering a pharmaceutically acceptable carrier or excipient. In any of the preceding embodiments, the agent can be administered via an oral, nasal, inhalational, parental, intravenous, intraperitoneal, subcutaneous, intramuscular, intradermal, topical, or rectal route. In any of the preceding embodiments, the agent can be administered at an amount that reduces production and/or an activity of IFP35 and/or NMI in the subject to a level that is substantially identical to a production and/or an activity level of IFP35 and/or NMI in a comparable subject that does not have a disease or disorder associated with abnormally high level and/or activity of IFP35 and/or NMI.

In any of the preceding embodiments, the subject can be a mammal. In some embodiments, the mammal is a human or a non-human mammal.

In another aspect, disclosed herein is a pharmaceutical composition for treating and/or preventing a disease or disorder associated with abnormally high level and/or activity of IFP35 and/or NMI in a subject. In some aspects, the pharmaceutical composition comprises an effective amount of an agent that prevents or reduces production and/or an activity of IFP35 and/or NMI in a subject and a pharmaceutically acceptable carrier or excipient. In any of the preceding embodiments, the pharmaceutical composition can further comprise an effective amount of a drug for the treatment and/or prevention of a disease or disorder associated with abnormally high level and/or activity of IFP35 and/or NMI in the subject.

In yet another aspect, disclosed herein is use of an effective amount of an agent that prevents or reduces production and/or an activity of IFP35 and/or NMI in a subject for the manufacture of a medicament for treating and/or preventing a disease or disorder associated with abnormally high level and/or activity of IFP35 and/or NMI in the subject. In some aspects, the disease or disorder associated with abnormally high level and/or activity of IFP35 and/or NMI is inflammation, infection, sepsis, organ damage, and autoimmune disease.

In still another aspect, disclosed herein is an antibody or antigen binding fragment thereof that specifically binds to IFP35 and/or NMI. In some aspects, the antibody or antigen binding fragment specifically binds to an epitope within SEQ ID NO: 2, SEQ ID NO: 4, SEQ ID NO: 6, or SEQ ID NO: 8. In some embodiments, the antibody or antigen binding fragment specifically binds to an epitope within amino acids 81-170, 177-268, or 136-216 of SEQ ID NO: 2. In other embodiments, the antibody or antigen binding fragment specifically binds to an epitope within amino acids 81-168, 175-266, or 134-214 of SEQ ID NO: 4. In still other embodiments, the antibody or antigen binding fragment specifically binds to an epitope within amino acids 104-193, 202-293, or 151-250 of SEQ ID NO: 6. In other embodiments, the antibody or antigen binding fragment specifically binds to an epitope within amino acids 103-192, 201-292, or 151-240 of SEQ ID NO: 8.

In another aspect, disclosed herein is an antibody or antigen binding fragment thereof that specifically binds to IFP35 and/or NMI, and the antibody or antigen binding fragment thereof comprises a heavy chain variable region comprising a complementarity determining region (CDR) consisting of the amino acid sequences of a CDR in the heavy chain variable region sequence set forth in SEQ ID NO: 9 and/or a light chain variable region comprising a CDR consisting of the amino acid sequence of a CDR in the light chain variable region sequence set forth in SEQ ID NO: 10. In one embodiment, the antibody or antigen binding fragment thereof comprises a heavy chain variable region set forth in SEQ ID NO: 9 and a light chain variable region set forth in SEQ ID NO:10.

In any of the preceding embodiments, the antibody can be a monoclonal antibody, a polyclonal antibody, or a bi-specific antibody. In any of the preceding embodiments, the antigen binding fragment can be an Fab, F(ab')2, Fv or scFv fragment. In any of the preceding embodiments, the antibody or antigen binding fragment can further comprise a human heavy chain constant region and a human light chain constant region.

In any of the preceding embodiments, the antibody or antigen binding fragment can be a fully human antibody or antigen binding fragment or a humanized antibody or antigen binding fragment. In any of the preceding embodiments, the antibody or antigen binding fragment can be recombinantly produced.

In one aspect, disclosed herein is a method for treating and/or preventing a disease or disorder associated with abnormally high level and/or activity and/or activity of IFP35 and/or NMI in a subject. The method can comprise administering, to a subject in need of such treatment and/or prevention, an effective amount of the antibody or antigen binding fragment according to any of the preceding embodiments. In any of the preceding embodiments, the disease or disorder can be associated with excessive immune response. In any of the preceding embodiments, the disease or disorder can be associated with cytokine storm. In any of the preceding embodiments, the disease or disorder associated with abnormally high level and/or activity of IFP35 and/or NMI can be selected from the group consisting of inflammation, infection, organ damage, sepsis, and autoimmune disease. In any of the preceding embodiments, the prevention or reduction of the production and/or the activity of IFP35 and/or NMI can result in the inhibition or reduction of the expression and/or activity of an inflammatory factor, and/or inhibiting or reduction of NF-κB signaling. In one aspect, the inflammatory factor comprises IL-1β, TNF-α, iNOS, and/or CD86, and the NF-κB signaling is mediate by a TLR such as TLR4.

In one aspect, disclosed herein is an isolated polynucleotide encoding an antibody or antigen binding fragment thereof that specifically binds to IFP35 and/or NMI. In some embodiments, the antibody or antigen binding fragment thereof comprises a heavy chain variable region comprising a complementarity determining region (CDR) consisting of the amino acid sequence of a CDR in the heavy chain variable region sequence set forth in SEQ ID NO: 9 and/or a light chain variable region comprising a CDR consisting of the amino acid sequences of a CDR in the light chain variable region sequence set forth in SEQ ID NO: 10. In some aspects, the antibody or antigen binding fragment thereof comprises a heavy chain variable region set forth in SEQ ID NO: 9 and a light chain variable region set forth in SEQ ID NO:10.

In one aspect, also disclosed herein is an isolated vector comprising the polynucleotide according to any of the preceding embodiments. In another aspect, also disclosed herein is an isolated host cell comprising the vector according to any of the preceding embodiments.

In another aspect, disclosed herein is a host cell which is selected from the group consisting of the following: (a) a host cell transformed with an expression vector comprising a polynucleotide comprising a sequence encoding a heavy chain variable region of an antibody or antigen binding fragment thereof and a polynucleotide comprising a sequence encoding a light chain variable region of an antibody or antigen binding fragment thereof, and (b) a host cell transformed with an expression vector comprising a polynucleotide comprising a sequence encoding a heavy chain variable region of an antibody or antigen binding fragment thereof and an expression vector comprising a polynucleotide comprising a sequence encoding a light chain variable region of an antibody or antigen binding fragment thereof. In some embodiments, the antibody or fragment comprises a heavy chain variable region comprising a complementarity determining region (CDR) consisting of the amino acid sequences of a CDR in the heavy chain variable region sequence set forth in SEQ ID NO: 9 and/or a light chain variable region comprising a CDR consisting of the amino acid sequences of a CDR in the light chain variable region sequence set forth in SEQ ID NO: 10. In any of the preceding embodiments, the host cell can be a eukaryotic cell such as a CHO cell.

In another aspect, disclosed herein is a method of making an anti-IFP35 antibody or antigen binding fragment thereof and/or an anti-NMI antibody or antigen binding fragment thereof. In some aspects, the method comprises: a) culturing the host cell of any one of preceding embodiments under conditions suitable for expression of the polynucleotide encoding the antibody or antigen binding fragment; and b) isolating the antibody or antigen binding fragment. In one aspect, also disclosed herein is an antibody or antigen binding fragment produced by the method according to any of the preceding embodiments.

In some embodiments, disclosed herein is an isolated polypeptide comprising, consisting essentially of, or consisting of: (1) the sequence set forth in amino acids 81-170, 177-268, or 136-216 of SEQ ID NO: 2; or (2) the sequence set forth in amino acids 81-168, 175-266, or 134-214 of SEQ ID NO: 4; or (3) the sequence set forth in amino acids 104-193, 202-293 or 151-250 of SEQ ID NO: 6; or (4) the sequence set forth in amino acids 103-192, 201-292, or 151-240 of SEQ ID NO: 8.

In some embodiments, disclosed herein is an isolated polypeptide comprising, consisting essentially of, or consisting of the sequence set forth in amino acids 81-170, 177-268, or 136-216 of SEQ ID NO: 2, wherein one or more of the amino acid residues at positions 145, 147, 150, 151, 172, 173, 175, 177, 182, 188, 192, 212, 199, 201, 207, 208, 210, 214, and 216 of SEQ ID NO: 2 (Ser145, Arg147, Glu150, Glu151, Asp172, Val173, Glu175, Leu177, Met182, Asp188, Gln192, Arg212, Gln199, Thr201, Gln207, Gln208, Pro210, Ser214, and Tyr216) are mutated and/or modified. In some aspects, according to structure-based sequence alignment, the left NID domain outside of the determined IFP35 NID-H domain structure has similar structure to NID-H. Ser234, Leu236, Arg1 10, Arg 108, Arg233, Leu 82, Glu268, Thr271, Val273, Glu92, Asp87, Asp245, and Gly246 of SEQ ID NO: 2 are the amino acid residues in the left NID domain that correspond to the surface residues in the determined NID domain structure of IFP35. In any of the preceding embodiments, the mutation(s) can substantially reduce or eliminate binding of the polypeptide to a IFP35 receptor or an inhibitory antibody specific for IFP35.

In some embodiments, disclosed herein is an isolated polypeptide comprising, consisting essentially of, or consisting of the sequence set forth in amino acids 81-168, 175-266, or 134-214 of SEQ ID NO: 4, wherein one or more of the amino acid residues at positions 143, 145, 148, 149, 170, 172, 173, 175, 180, 186, 190, 210, 197, 199, 204, 205, 206, 208, 212, and 214 of SEQ ID NO: 4 (Ser143, Arg145, Glu148, Glu149, Glu170, Arg172, Glu173, Leu175, Met180, Glu186, Gln190, Arg210, Gln197, Arg199, Arg204, Gln205, Gln206, Leu208, Ser212, and Tyr214) are mutated and/or modified. In any of the preceding embodiments, the mutation(s) can substantially reduce or eliminate binding of the polypeptide to a IFP35 receptor or an inhibitory antibody specific for IFP35.

In some embodiments, disclosed herein is an isolated polypeptide comprising, consisting essentially of, or consisting of the sequence set forth in amino acids104-193, 202-293, or 151-250 of SEQ ID NO: 6, wherein one or more of the amino acid residues at positions 107, 112, 117, 159, 172, 173, 192, 197, 215, 256, 267, and 292 of SEQ ID NO: 6 (Leu107, Lys112, Gln117, Lys159, Glu172, Glu173, Glu192, Asp197, Asp215, Lys256, Asp267, and Glu292) are mutated and/or modified. In any of the preceding embodiments, the mutation(s) can substantially reduce or eliminate binding of the polypeptide to a NMI receptor or an inhibitory antibody specific for NMI.

In some embodiments, disclosed herein is an isolated polypeptide comprising, consisting essentially of, or consisting of the sequence set forth in amino acids 103-192, 201-292, or 151-240 of SEQ ID NO: 8, wherein one or more of the amino acid residues at positions 106, 111, 116, 158, 171, 172, 191, 196, 214, 255, 266, and 291 of SEQ ID NO: 8 (Leu106, Lys111, Gln116, Lys158, Glu171, Asp172, Asp191, Asp196, Asp214, Arg255, Asp266, and Asp291) are mutated and/or modified. In any of the preceding embodiments, the mutation(s) can substantially reduce or eliminate binding of the polypeptide to a NMI receptor or an inhibitory antibody specific for NMI.

In one aspect, disclosed herein is a pharmaceutical composition comprising the polypeptide of any one of the preceding embodiments. In some embodiments, the pharmaceutical composition comprises a pharmaceutically acceptable carrier or excipient.

In one aspect, disclosed herein is a method for stimulating an immune response in a subject, and the method comprises administering, to a subject in need of such stimulation, an effective amount of the polypeptide or the pharmaceutical composition of any one of the preceding embodiments. In one aspect, the subject has a proliferation disorder, a neoplasm, a tumor or a cancer. In another aspect, the prolifera-
tion disorder is selected from the group consisting of sar-
coma, epidermoid cancer, fibrosarcoma, cervical cancer,
gastric carcinoma, skin cancer, leukemia, lymphoma, lung
cancer, non-small cell lung cancer, colon cancer, CNS
cancer, melanoma, ovarian cancer, renal cancer, prostate
cancer, breast cancer, liver cancer, head and neck cancers,
pancreatic cancer, bladder cancer and esophageal cancer. In
any of the preceding embodiments, the stimulation of the
immune response can comprise stimulation of the expres-
sion and/or activity of an inflammatory factor, the recruit-
ment of immune cells such as neutrophils, and/or NF-κB
signaling. In some aspects, the inflammatory factor com-
prises IL-1β, TNF-α, iNOS, and/or CD86, and the NF-κB
signaling is mediate by a TLR such as TLR4. In any one of
the preceding embodiments, the stimulation of NF-κB sig-
naling can comprise an increase in phosphorylated IκBα
and/or a reduction in total IκBα.

In some aspects, provided herein are compositions and
methods for activating, boosting, augmenting, and/or poten-
tiating immune response in a subject. The present compo-
sitions and methods can be used to treat and/or prevent any
suitable disease or disorder associated with abnormally low
level of a IFP35 family protein such as IFP35 and/or NMI
in a subject. For example, the disease or disorder associated
with abnormally low level of IFP35 and/or NMI in a subject
can be a proliferation disorder, a neoplasm, a tumor or a
cancer. Exemplary proliferation disorders include sarcoma,
epidermoid cancer, fibrosarcoma, cervical cancer, gastric
carcinoma, skin cancer, leukemia, lymphoma, lung cancer,
e.g., non-small cell lung cancer (NSCLC), colon cancer,
CNS cancer, melanoma, ovarian cancer, renal cancer, pros-
tate cancer, breast cancer, liver cancer, head and neck
cancers, pancreatic cancer, bladder cancer and esophageal
cancer.

In another aspect, disclosed herein is an isolated poly-
nucleotide encoding a polypeptide comprising the polypep-
tide of any one of the preceding embodiments. In yet another
aspect, disclosed herein is an isolated vector comprising the
polynucleotide of any one of the preceding embodiments. In
still another aspect, disclosed herein is an isolated host cell
comprising the vector of any one of the preceding embodi-
ments. In some aspects, the host cell is a eukaryotic cell such
as a CHO cell. In some aspects, disclosed herein is a method
of making an isolated polynucleotide, and the method com-
prises: a) culturing the host cell under conditions suitable for
expression of the polynucleotide encoding a polypeptide
comprising the polypeptide of any of the preceding embodi-
ments; and b) isolating the polypeptide.

In some aspects, disclosed herein is a method of diagno-
sis, prognosis or treatment monitoring of a disease or
disorder associated with abnormally high level and/or activ-
ity of IFP35 and/or NMI in a subject. In some aspects, the
method comprises assessing the level and/or an activity of
IFP35 and/or NMI in a subject suspected of or being treated
for a disease or disorder associated with abnormally high
level and/or activity of IFP35 and/or NMI. In one embodi-
ment, the disease or disorder associated with abnormally
high level and/or activity of IFP35 and/or NMI is associated
with excessive immune response. In another embodiment,
the disease or disorder associated with abnormally high level
and/or activity of IFP35 and/or NMI is associated with
cytokine storm. In any of the preceding embodiments, the
disease or disorder associated with abnormally high level
and/or activity of IFP35 and/or NMI can be selected from
the group consisting of inflammation, infection, organ dam-
age, sepsis, and autoimmune disease.

In any of the preceding embodiments, the method can be
used for diagnosis of a disease or disorder associated with
abnormally high level and/or activity of IFP35 and/or NMI
in a subject, and wherein a level and/or an activity of IFP35
and/or NMI in a subject that is at least 10%, 20%, 30%, 40%,
50%, 60%, 70%, 80%, 90%, 100%, 150%, 200%, 300%,
400%, or 500% higher than a level and/or an activity of
IFP35 and/or NMI in a comparable subject that does not
have a disease or disorder associated with abnormally high
level and/or activity of IFP35 and/or NMI, e.g., inflamma-
tion, infection, organ damage, sepsis, and autoimmune dis-
ease, indicates that the subject has the disease or disorder
associated with abnormally high level and/or activity of
IFP35 and/or NMI.

In any of the preceding embodiments, the method can
further comprise assessing the level of IFP35 and/or NMI in
a subject suspected of or being treated for a disease or
disorder associated with abnormally high level and/or activ-
ity of IFP35 and/or NMI. In any of the preceding embodi-
ments, the method can comprise assessing an activity of
IFP35 and/or NMI in a subject suspected of or being treated
for a disease or disorder associated with abnormally high
level and/or activity of IFP35 and/or NMI. In any of the
preceding embodiments, the level and/or an activity of
IFP35 and/or NMI can be assessed at the DNA, RNA and/or
protein level. In one aspect, the level of IFP35 and/or NMI
is assessed at the DNA and/or RNA level using a polynucle-
otide that is complementary to at least 10 consecutive
nucleotides in the IFP35 and/or NMI DNA or RNA. In
another aspect, the level of IFP35 and/or NMI is assessed at
the protein level using an antibody that specifically binds to
IFP35 and/or NMI.

Also disclosed herein, in one aspect, is a kit of diagnosis,
prognosis or treatment monitoring of a disease or disorder
associated with abnormally high level and/or activity of
IFP35 and/or NMI in a subject. In some aspects, the kit
comprises a means for assessing the level and/or an activity
of IFP35 and/or NMI in a subject suspected of or being
treated for a disease or disorder associated with abnormally
high level and/or activity of IFP35 and/or NMI.

Also disclosed herein, in one aspect, is a method of
companion diagnostics of a disease or disorder associated
with abnormally high level and/or activity of IFP35 and/or
NMI in a subject. In some aspects, the method comprises
determining the genetic status of IFP35 and/or NMI gene in
a subject being treated for the disease or disorder associated
with abnormally high level and/or activity of IFP35 and/or
NMI. In one aspect, the genetic status of IFP35 and/or NMI
gene in a subject is determined using a polynucleotide that
is complementary to at least 10 consecutive nucleotides in
the IFP35 and/or NMI DNA or RNA.

Also disclosed herein, in one aspect, is a kit of companion
diagnostics of a disease or disorder associated with abnor-
mally high level and/or activity of IFP35 and/or NMI in a
subject. In one aspect, the kit comprises a means for deter-
mining the genetic status of IFP35 and/or NMI gene in a
subject being treated for the disease or disorder associated
with abnormally high level and/or activity of IFP35 and/or
NMI.

In one aspect, disclosed herein is a method for identifying
a modulator of IFP35 and/or NMI. In some aspects, the
method comprises: a) contacting IFP35 and/or NMI with a
test substance and assessing an activity of IFP35 and/or NMI
that has been contacted by the test substance; b) assessing an
activity of the IFP35 and/or NMI that has not been contacted
by the test substance; and c) comparing the activities of
IFP35 and/or NMI assessed in steps a) and b), and identifying the test substance as a modulator of IFP35 and/or NMI when the activities of IFP35 and/or NMI assessed in steps a) and b) are different. In one aspect, the test substances are small molecules, a polypeptide library comprising mutants and/or fragments of IFP35 and/or NMI, antibodies that specifically bind IFP35 and/or NMI, a polynucleotide, such as an siRNA, shRNA, miRNA, or antisense RNAs. In any of the preceding embodiments, the method can be used to identify an inhibitor of an activity of IFP35 and/or NMI. In any of the preceding embodiments, the method can be used to identify a drug for treating and/or preventing a disease or disorder associated with abnormal level and/or activity of IFP35 and/or NMI in a subject. In some aspects, the disease or disorder associated with abnormal level and/or activity of IFP35 and/or NMI is a proliferation disorder, a neoplasm, a tumor or a cancer. In some embodiments, the disease or disorder, such as a proliferation disorder, a neoplasm, a tumor or a cancer, is associated with abnormally low level and/or activity of a IFP35 family protein such as IFP35 or NMI.

In some aspects, also disclosed herein is a drug candidate identified by a method of any one of the preceding embodiments.

BRIEF DESCRIPTION OF THE DRAWINGS

FIGS. 1A-E show a crystal structure of NID-H (heterozygous NID). FIG. 1A: Truncations and putative domains of IFP35 are shown and the boundaries between domains are noted in the sequence. FIG. 1B: The structure of the IFP35 dimer (closed conformational dimer, c-dimer) with secondary structure elements noted. FIG. 1C: Residues involved in the intra-molecule interactions are labeled and shown in sticks. For clarity, only half of the interactions are shown. FIG. 1D: The ring structure of the octamer, in which monomers are shown. FIG. 1E: Dimer with domain-swapping conformation (open conformational dimer, o-dimer) is highlighted with secondary structure elements noted on the upper figure. A NID-H molecule from c-dimer is superimposed on the o-dimer as shown in the lower figure.

FIGS. 2A-C show the two stable aggregation states, dimer and octamer, of NID-H. FIG. 2A: Size-exclusion chromatography analysis of NID-H using Superdex-200 (16/60 or 10/30) column (GE). The UV absorptions at 280 nm are shown in blue. The elution volumes of two peaks are 75 ml and 90 ml, suggesting dimer and octamer formation. FIG. 2B: O-dimer and c-dimer superimposed on the octamer. Four o-dimers interact with one another through al-al interactions, and form a ring like octamer structure. FIG. 2C: Structure comparison between NID-H and RNA recognition motif (RRM). The R.M.S.D. between them is about 1.3 A.

FIGS. 3A-D show that the open conformational dimer (o-dimer) of NID-H is responsible for immune response stimulation. FIG. 3A: Octameric NID-H up-regulates the transcription of TNF-α and IL-1β in RAW 264.7 cells. The cellular mRNA of TNF-α and IL-1β were detected by RT-PCR using GAPDH as internal control. FIG. 3B: Dimeric stated mutation on al, K156E/K163E/R165E, partially up-regulates the transcription of TNF-α and IL-1β. FIG. 3C: IFP35 without the L-zip domain (Δ N) stimulated immune response more effectively than NID-H octamer. FIG. 3D: Similar with LPS, Δ N could effectively stimulate the TNF-α release of RAW264.7 cells. TNF-α levels in cell culture were determined by ELISA after 4 h of incubation.

FIG. 4 shows that human source NMI protein up-regulates the transcription of TNF-α and IL-1β in THP1 cells. PBS buffer was used as negative control (NC). Results came from an average of three independently replicates. Error bars indicate the standard deviation among them.

FIGS. 5A-G show IFP35 possesses characteristics of endogenous DAMPs. FIG. 5A: IFP35 released by RAW264.7 cells stimulated by LPS. RAW 264.7 macrophages were pretreated with 100 ng/mL LPS. Cell lysate and supernatants at 0, 1, 2, 3, 5, 9 hours were analyzed by western blot of IFP35, HMGB1 and β-Actin. FIG. 5B: IFP35 is accumulated in the serum of LPS induced septic mice. Serum concentrations of IFP35 in mice were determined by ELISA 3 h and 6 h after injection of LPS. FIG. 5C: IFP35 is accumulated in the serum of septic patients. This data was obtained from the serum of 12 patients and 8 normal individuals. FIG. 5D: Survival rate of the septic mice administrated with IgG and IFP35 monoclonal antibodies (Anti-NID-H) was presented. Mice received LPS injection (i.p.) followed by treatment with anti-IFP35 antibody or IgG. Animal survival rate was assessed in n=15 mice/group. FIG. 5E: Anti-NID-H neutralization attenuated the release of early inflammatory cytokines such as IL-6, TNF-α and IL-1β, detected using ELISA. FIG. 5F: Survival of wild-type (n=12) and IFP35$^{-/-}$ mice (n=12) treated with LPS and D-gal. FIG. 5G: The release of early inflammatory cytokines in the serum of IFP35 knock-out mice is reduced. Serum concentrations of IL-6, TNF-α and IL-1β in IFP35$^{-/-}$ and wild-type mice as determined by ELISA 1h and 3h after injection of LPS and D-gal.

FIGS. 6A-H show IFP35 family members are released as endogenous DAMPs. FIG. 6A: IFP35 released by RAW cells stimulated by 10 ng/ml INF-γ. FIG. 6B: NMI released by RAW cells stimulated by Salmonella (SR). FIGS. 6C-D: The aggregation state of IFP35 (FIG. 6C) and NMI (FIG. 6D) were detected. After stimulating the RAW cells with SR. the cell culture were collected and the released IFP35 family members were detected the by gel filtration (Superdex-200 (16/60 or 10/30) column, GE) and western blot. The elution volume of IFP 35 is about 90 ml, as shown in FIG. 6C, suggesting a 35kD monomer. NMI showed multiple aggregation states detected by gel filtration. The elution volume of its major conformation is about 76-82 ml, indicating that released NMI existed as dimer in solution. FIG. 6E: NMI is accumulated in the serum of LPS induced septic mice, as determined by ELISA 3 h and 6 h after injection of LPS. FIG. 6F: NMI is accumulated in the serum of septic patients. Serum was obtained from 8 healthy people and 12 septic patients. Serum concentrations of NMI were determined by ELISA. FIG. 6G: NMI knock-out mice is resistant to LPS challenge. The survival rate of wide type (WT) (n=14) and Nmi$^{-/-}$ mice (KO) (n=14) administrated with LPS was presented. FIG. 6H: The release of inflammatory cytokines such as IL-6, TNF-α and IL-1β in the serum of Nmi$^{-/-}$ mice is reduced. The results got from WT and KO mice are shown in gray and black, respectively. All the results were confirmed by multiple independently analyzed biological replicates.

FIGS. 7A-B show IFP35 stimulates the cytokines storm based on TLR4/MD2/CD14 complex. FIG. 7A: Octameric NID-H induced NF-κB promoter activity in a HEK293 cell line transfected with TLR4, CD14, MD2 and NF-κB promoter luciferase plasmid. 24 hours after transfection, cells were stimulated with 10 μg/ml Octameric NID-H or 100 ng/ml LPS for 4 h (in the presence or absence of 25 mg/ml polymyxin B) and assayed for luciferase activity. The luciferase activity trigged by LPS can be blocked by polymyxin B, an effective antibiotic for Gram-negative infections. FIG. 7B: Purified IFP35 (ΔN), a N-terminal truncation of IFP35 and LPS induce NF-κB and AP-1 but not IRF3 promoter activity. The genes of TLR4, MD2 and CD14 and NF-κB promoter (or AP-1, IRF3) with luciferase activity were transiently transfected into HEK293 cells. IFP35 was used at 1 [μg/ml, while 100 ng/ml LPS were administrated as positive control.

FIGS. 8A-C show the structure model of tandem NID domains in IFP35. FIGS. 8A-B: Secondary structure elements and sequence alignment of A and A' as well as B and B' are shown in FIG. 8A. The identical residues are labeled with "*", while residues with similar features are labeled with ":" or ".". Residues in the hydrophobic core of NID-H structure are shown in FIG. 8B which is highlighted in squares in FIG. 8A. FIG. 8C: The double-barrel structure of tandem NIDs. In FIG. 8C, Part B' is shown in green and Part A' is shown in cyan. The NID-H structure is shown in purple.

FIG. 9 shows sequence alignment of IFP35 and NMI generated by ClustalW. The identical residues are labeled with "*", while residues with similar features are labeled with ":" or ".". The secondary structure elements of NMI are predicted by PsiPred. The α-helixes and β-strands are shown in red and yellow, respectively. The two NID domains parallel to those in IFP35 are labeled and highlighted in squares.

FIGS. 10A-B illustrate the process of IFP35 protein purification.

FIGS. 11A-C show the different oligomer states of IFP35.

FIGS. 12A-D show the IFP35-NID crystal.

FIGS. 13A-D show the structure of the dimeric IFP35-NID.

FIGS. 14A-D show the structure of the octameric IFP35-NID.

FIGS. 15A-B show the structure of dimer with domain-swapping conformation.

Figures 16A, 16B, 16C, 17A, 17B, 17C, 17D:
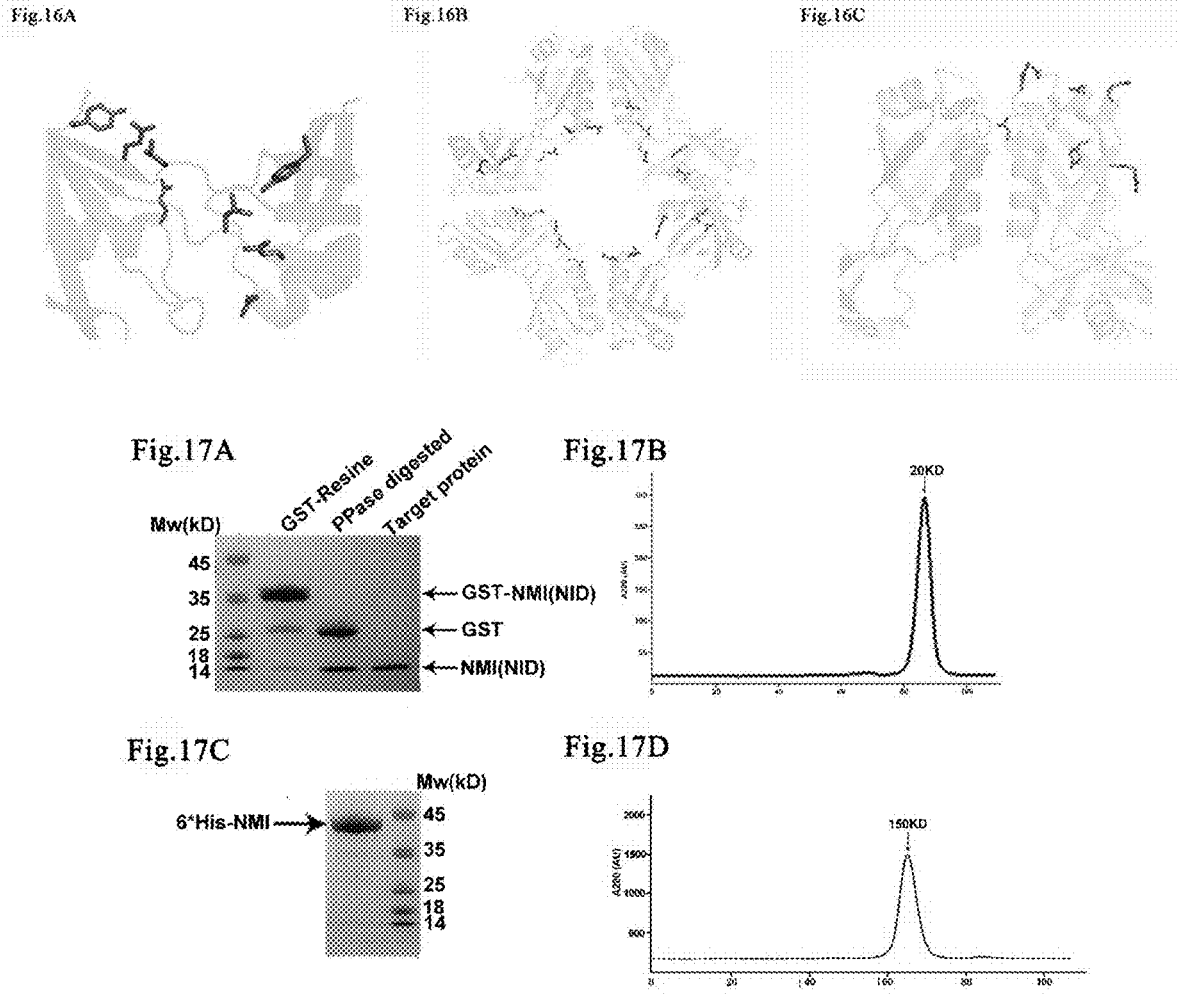

FIGS. 16A-C show the residues of some areas.

FIGS. 17A-D show the purification of the recombinant NMI.

Figure 18A:
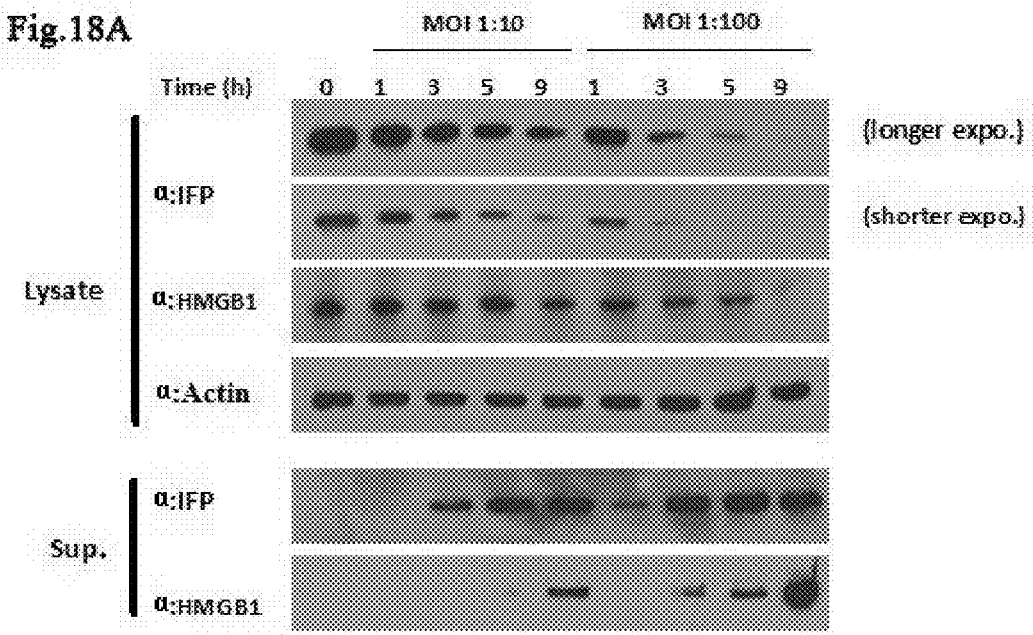
Figure 18B:
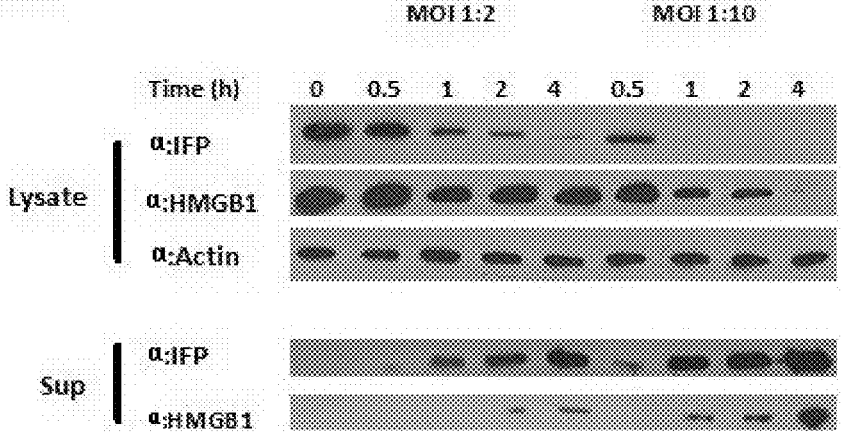
Figure 18C:
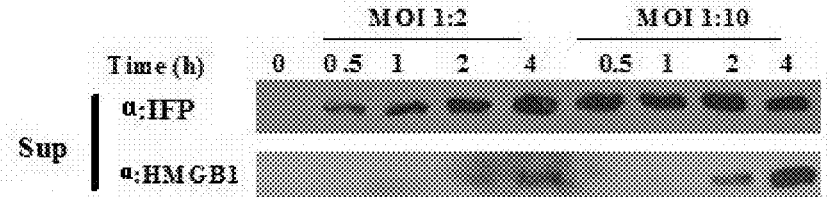

FIGS. 18A-C reveal the expression level of IFP35 when stimulated by salmonella.

Figure 19:
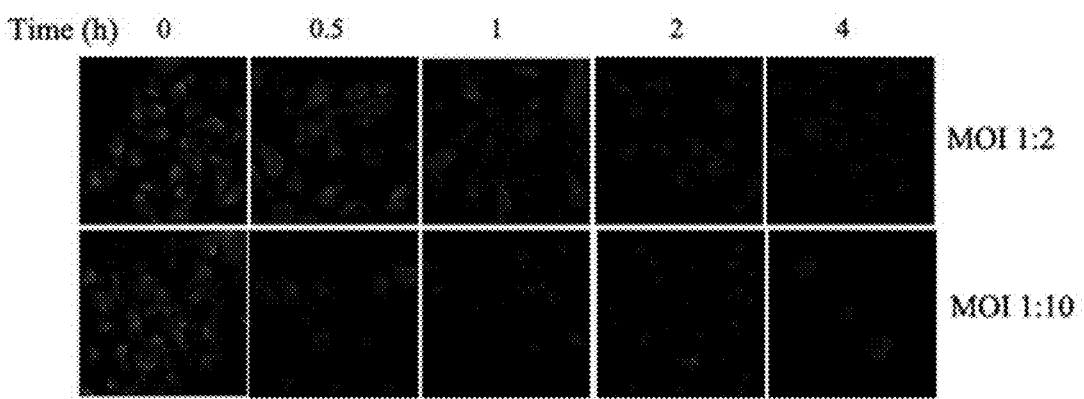

FIG. 19 shows that the abundance of IFP35 changed with time as measured by immunofluorescence.

Figure 20A:
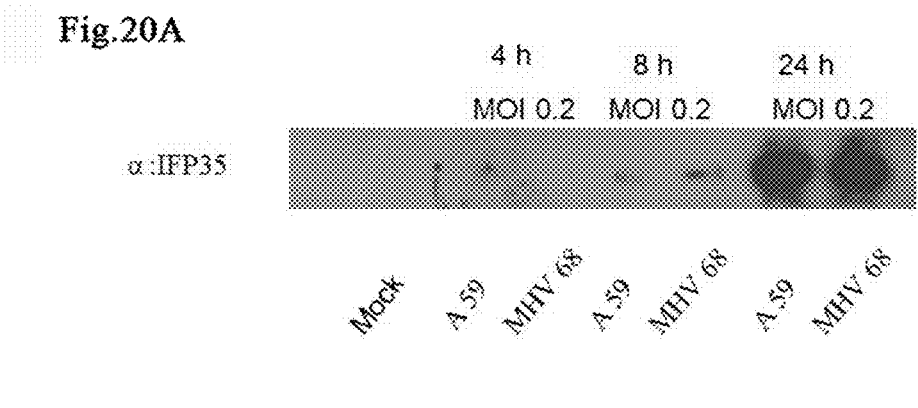
Figure 20B:
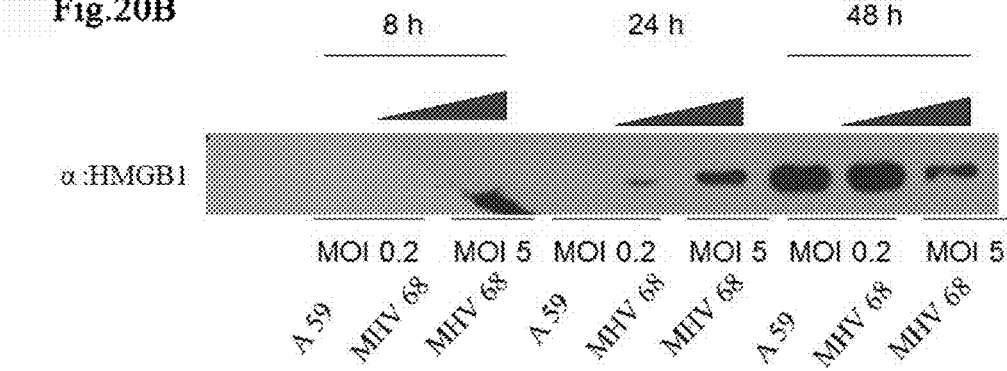

FIGS. 20A-B show the abundance of IFP35 secreted to the medium at different periods when cells are infected by the virus.

FIGS. 21A-B show a model of mouse peritonitis.

FIGS. 22A-D show the contribution of the IFP35 with different oligomer states during the process of stimulating inflammation.

Figure 23:
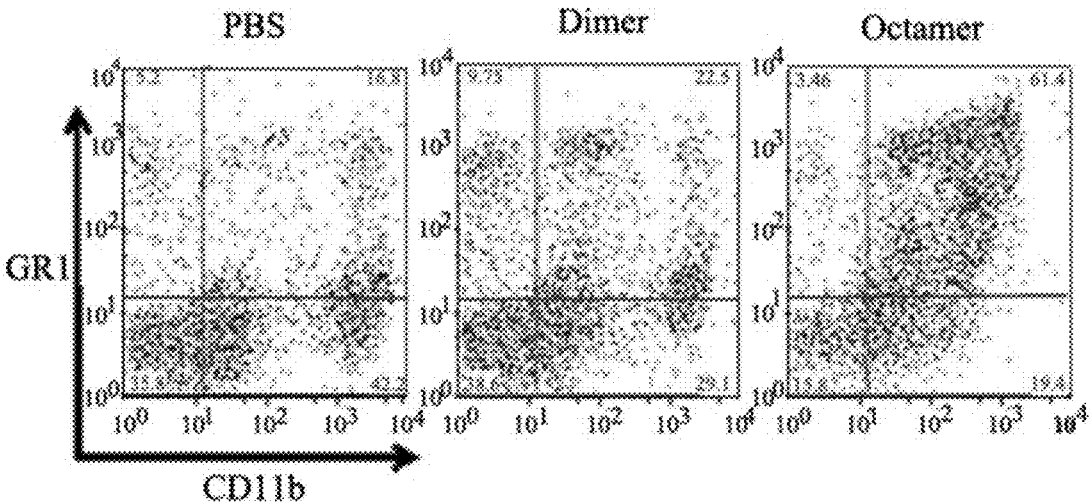

FIG. 23 shows the result of Flow cytometry analysis, which illustrates octameric IFP35-nid can recruit large amount of neutrophil granulocytes.

Figure 24:
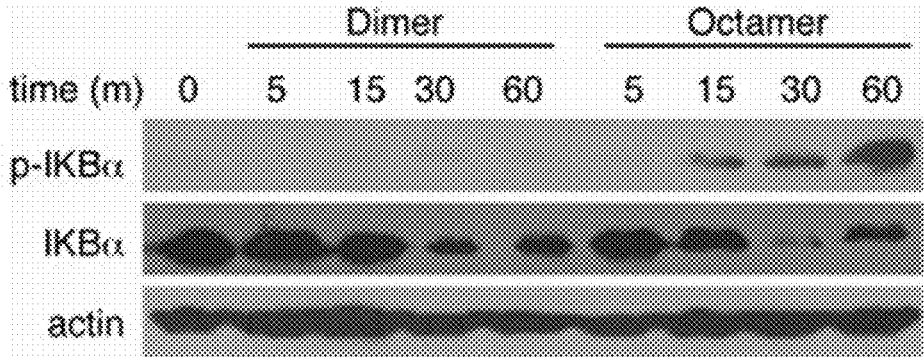

FIG. 24 shows exogenous octameric IFP35-NID can stimulate NF-κB pathway in macrophages.

Figure 25A:
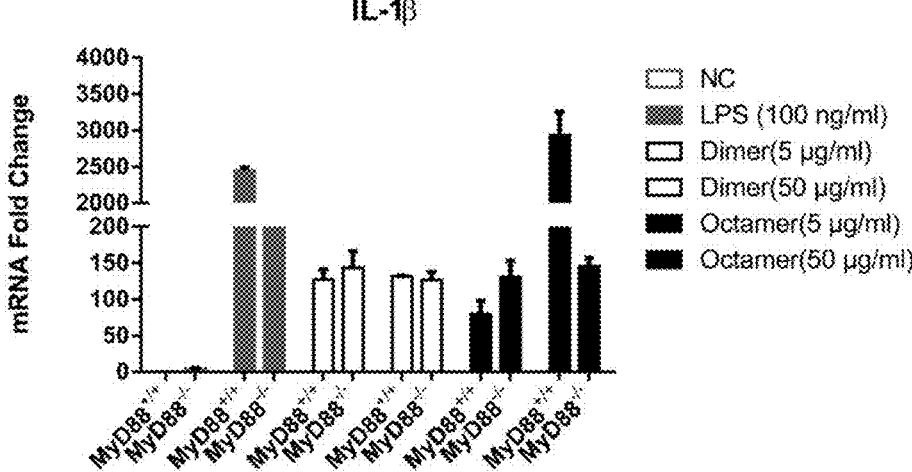
Figure 25B:
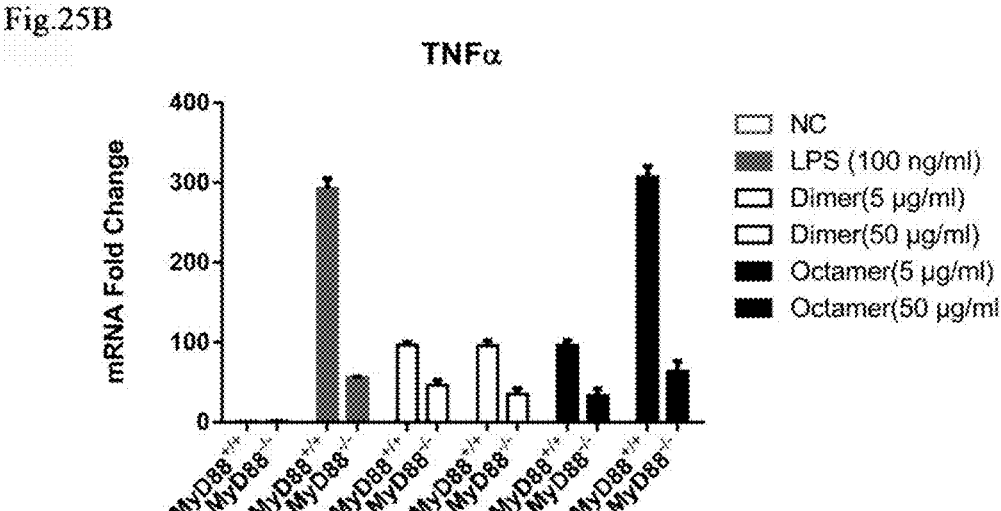

FIGS. 25A-B illustrate that IFP35 can stimulate inflammation through myd88 signal pathway.

Figure 26A:
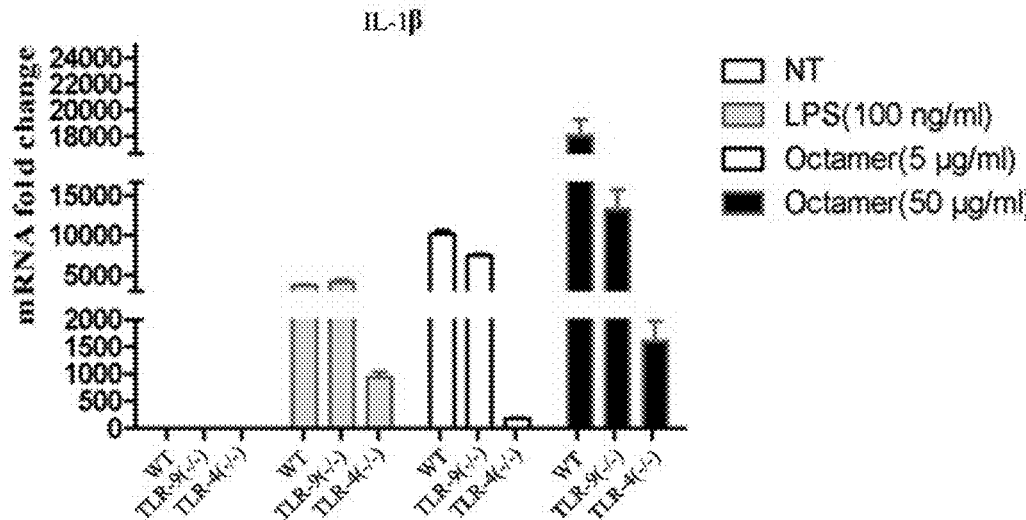
Figure 26B:
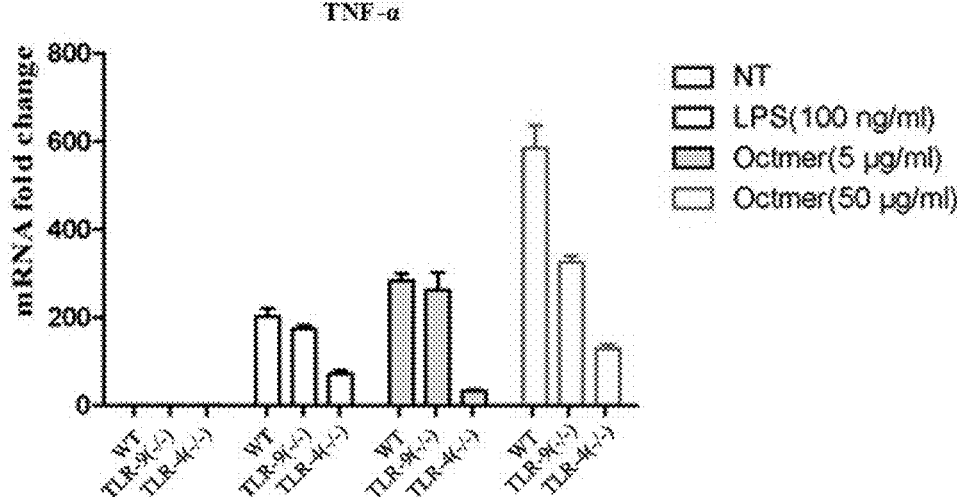

FIGS. 26A-B show the levels of IL-1β and TNF among WT, TLR9−/− and TLR4−/− mouse as induced by IFP35.

Figure 27A:
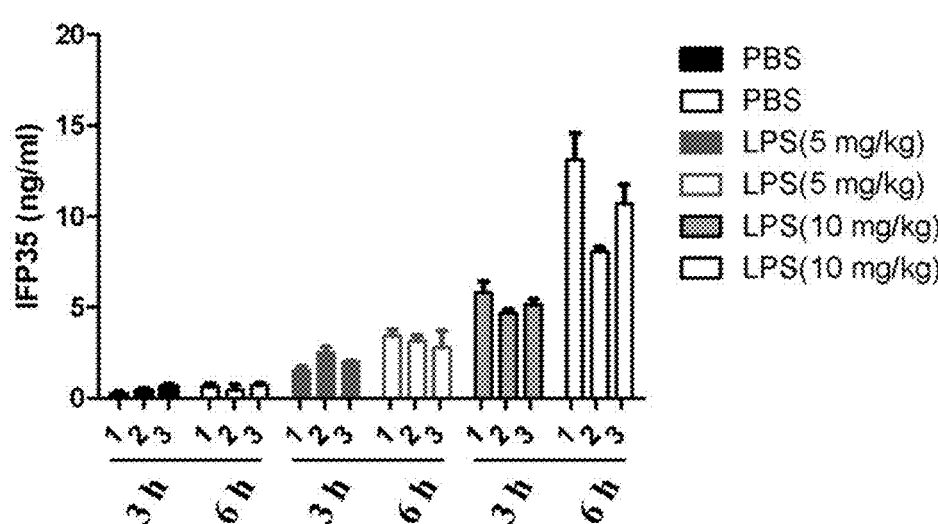
Figure 27B:
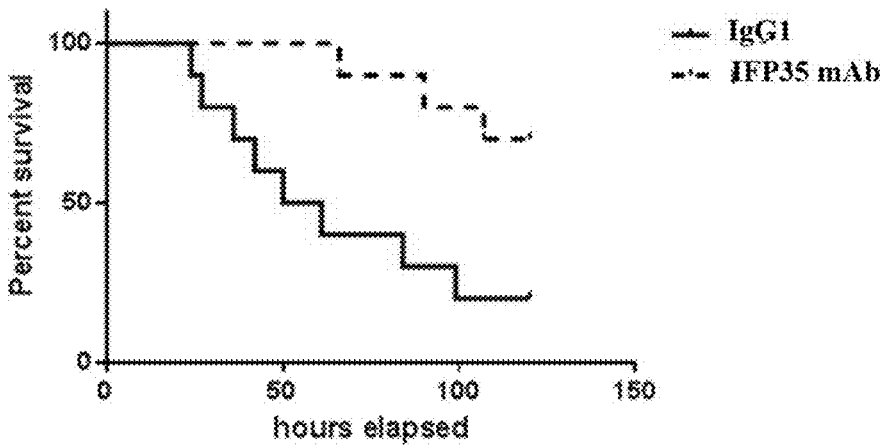

FIG. 27A shows the amount of IFP35 in the serum of septic mice. FIG. 27B shows the survival rate of the septic mice was increased when administrated with IFP35 monoclonal antibodies.

FIG. 28 shows that the block of IFP35 attenuated the release of induced IL-6 by LPS in mice.

FIG. 29 shows the abundance of NMI in cell lysate and supernatant of Thp1 cells stimulated by *salmonella.*

FIGS. 30A-B demonstrate that mouse source NMI protein can up-regulate the transcription of TNFα and IL-1β in Thp1 cells.

FIG. 31 shows the detection of the aggregation state of NMI.

Figure 32:
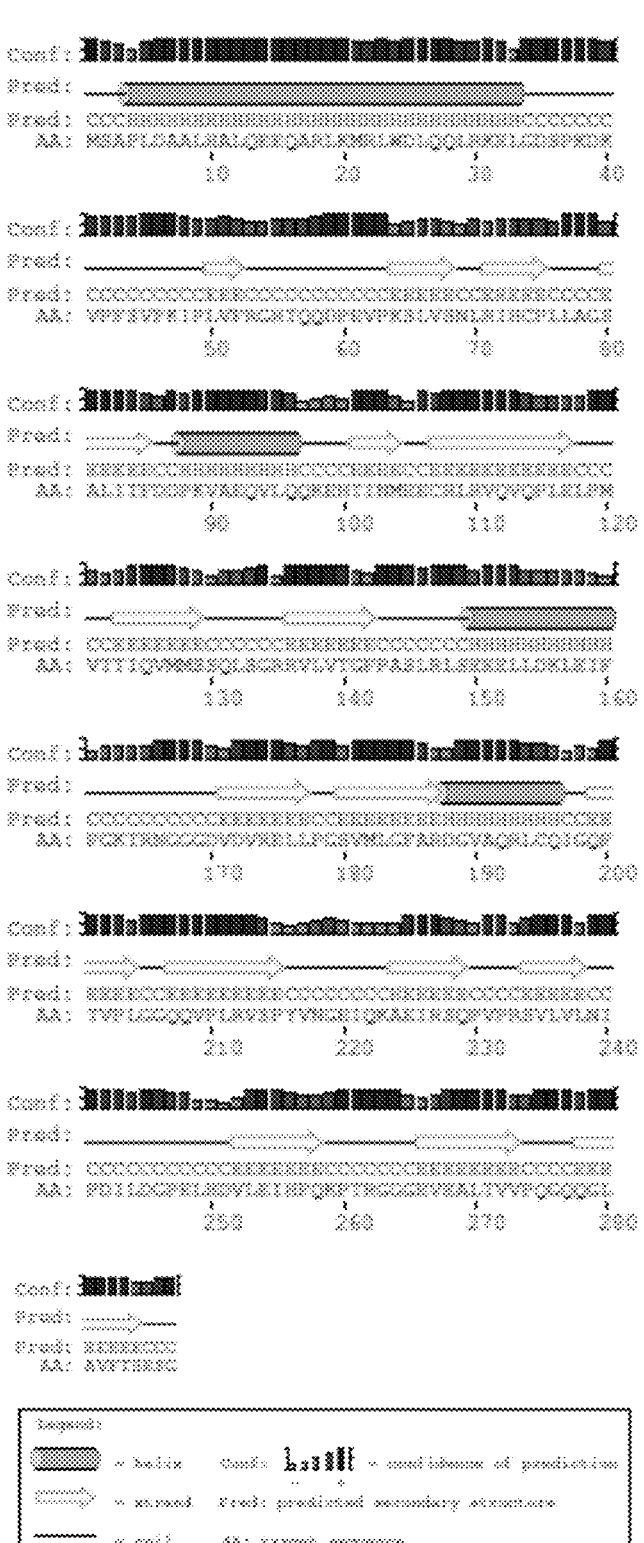

FIG. 32 shows a secondary structure prediction of human IFP35.

Figure 33B:
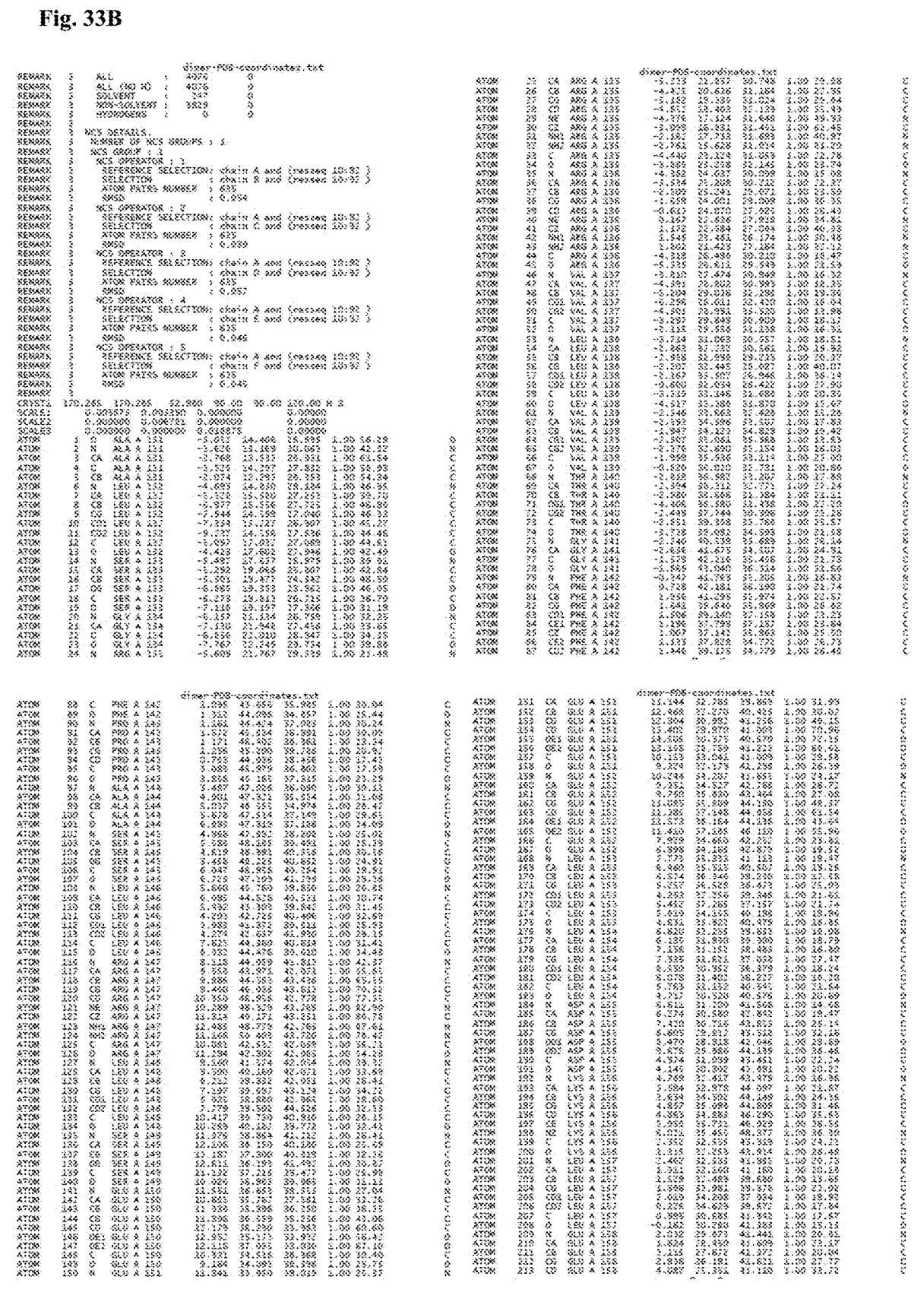
Figure 33C:
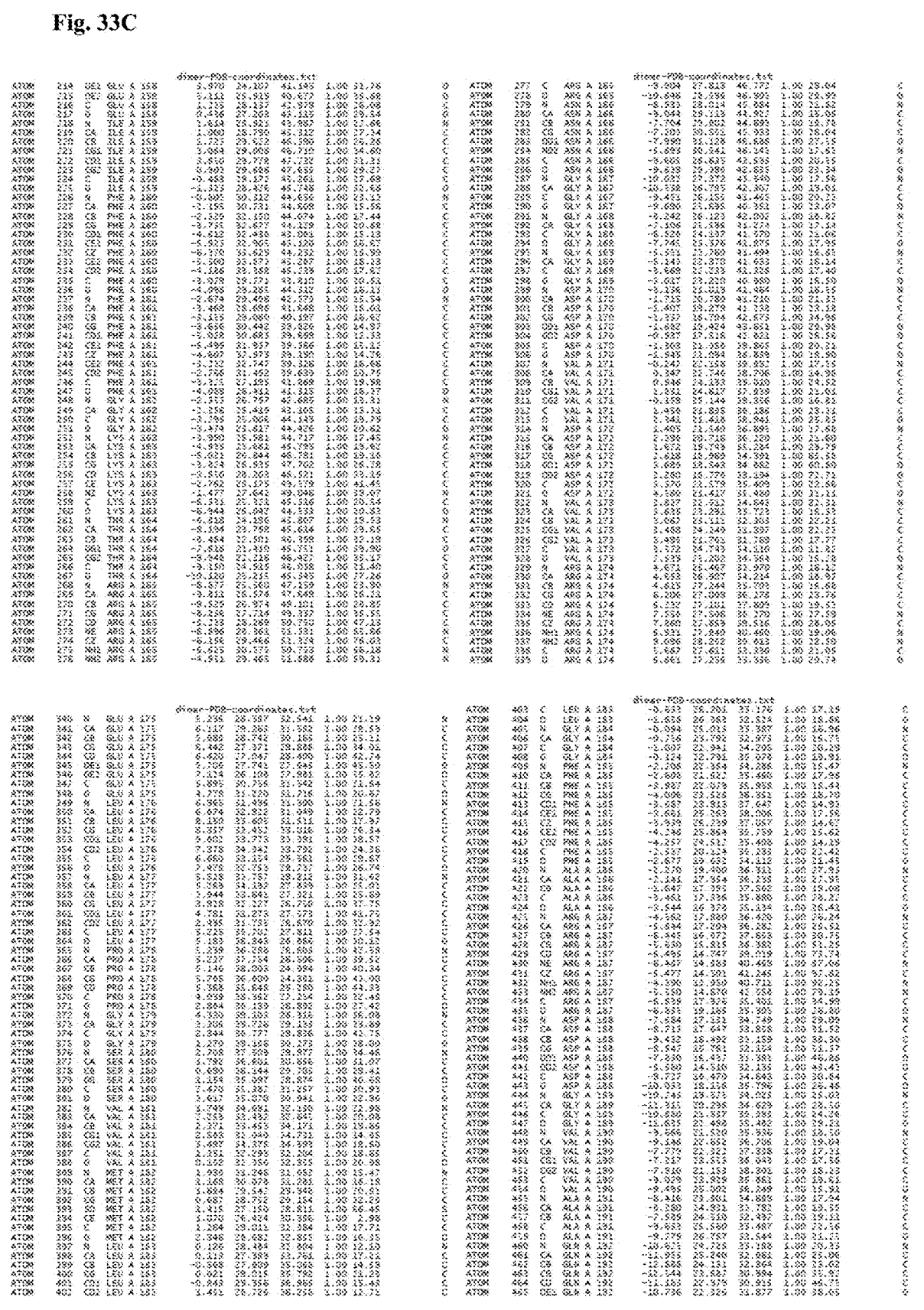
Figure 33D:
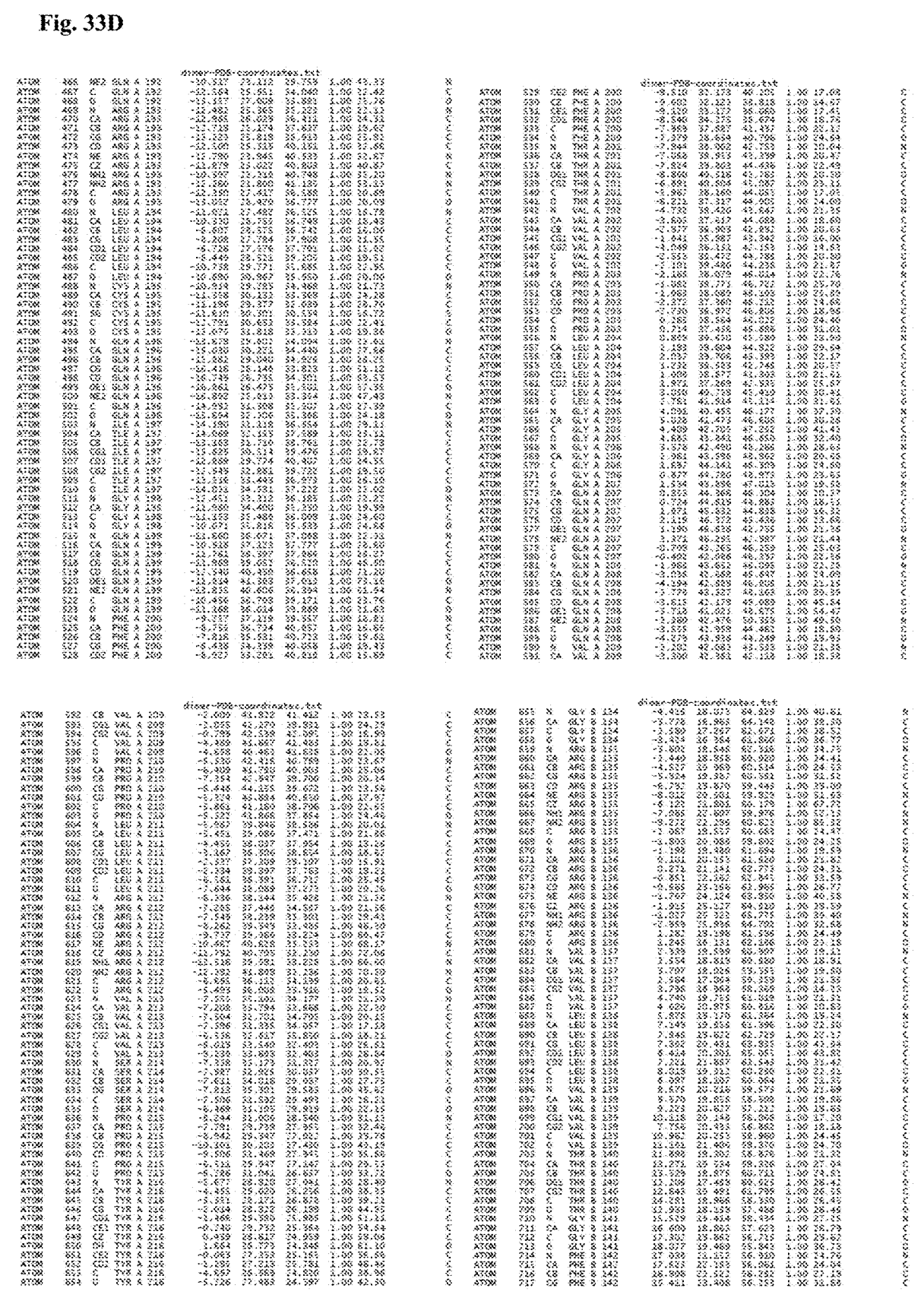
Figure 33E:
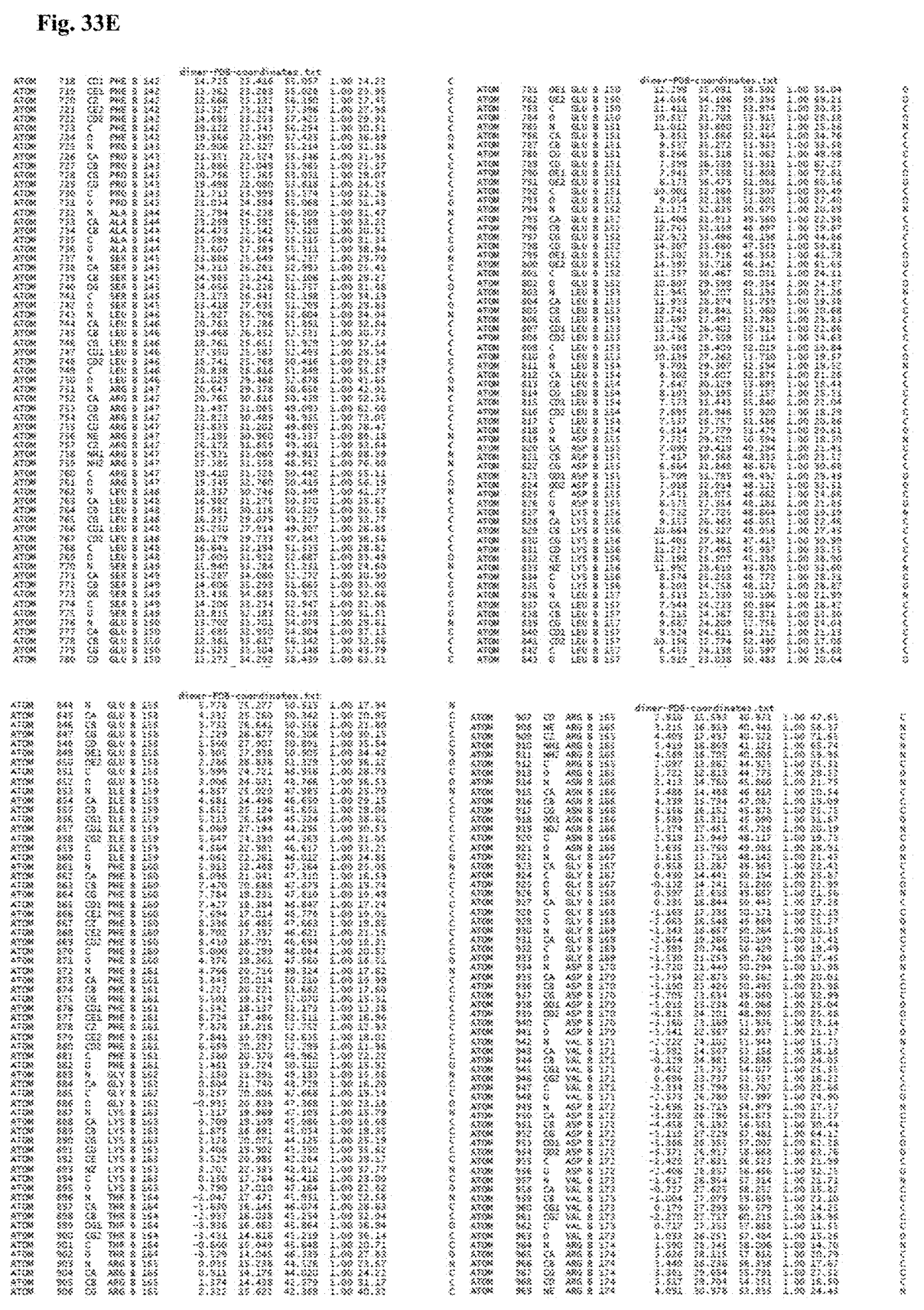
Figure 33F:
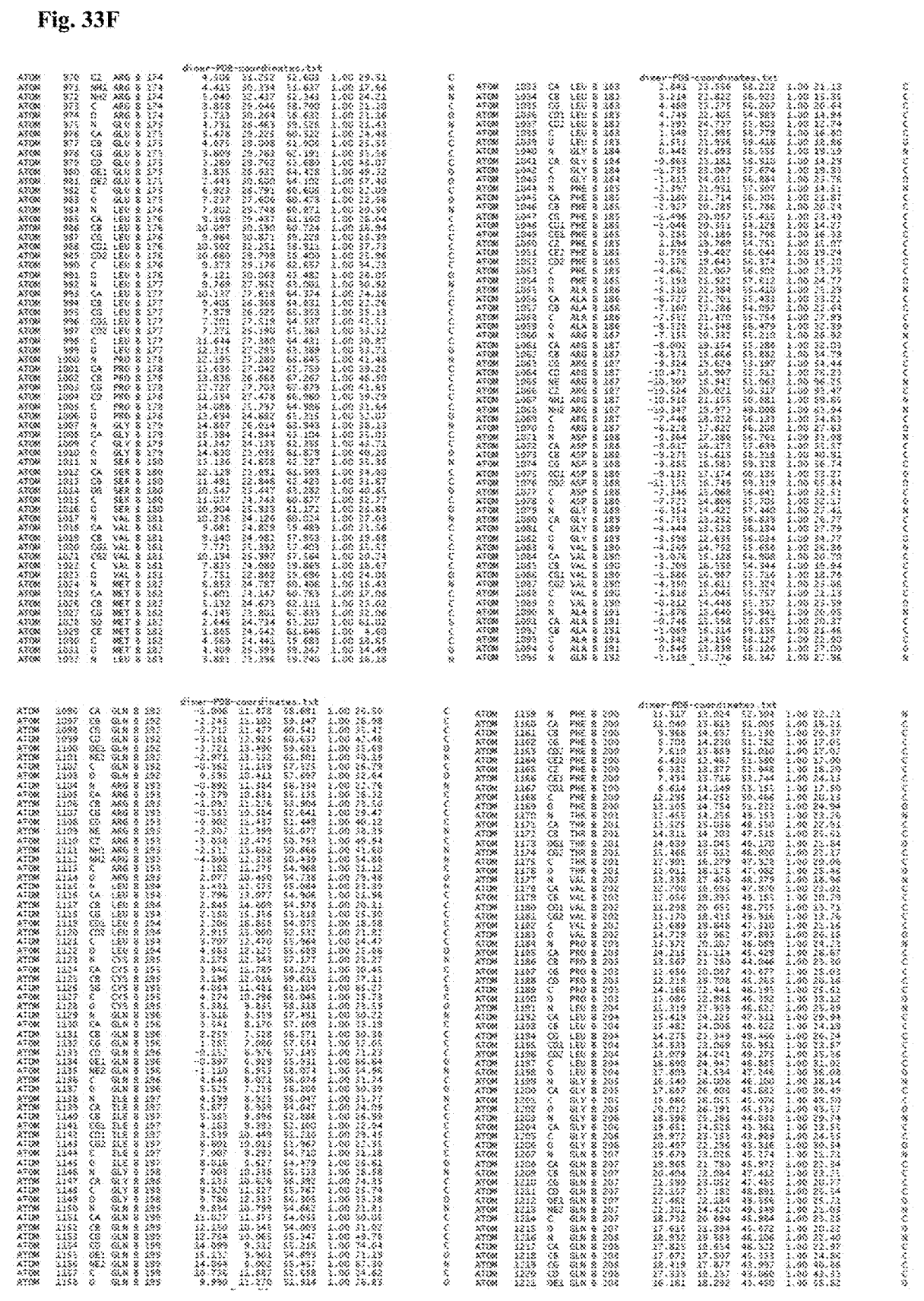
Figure 33G:
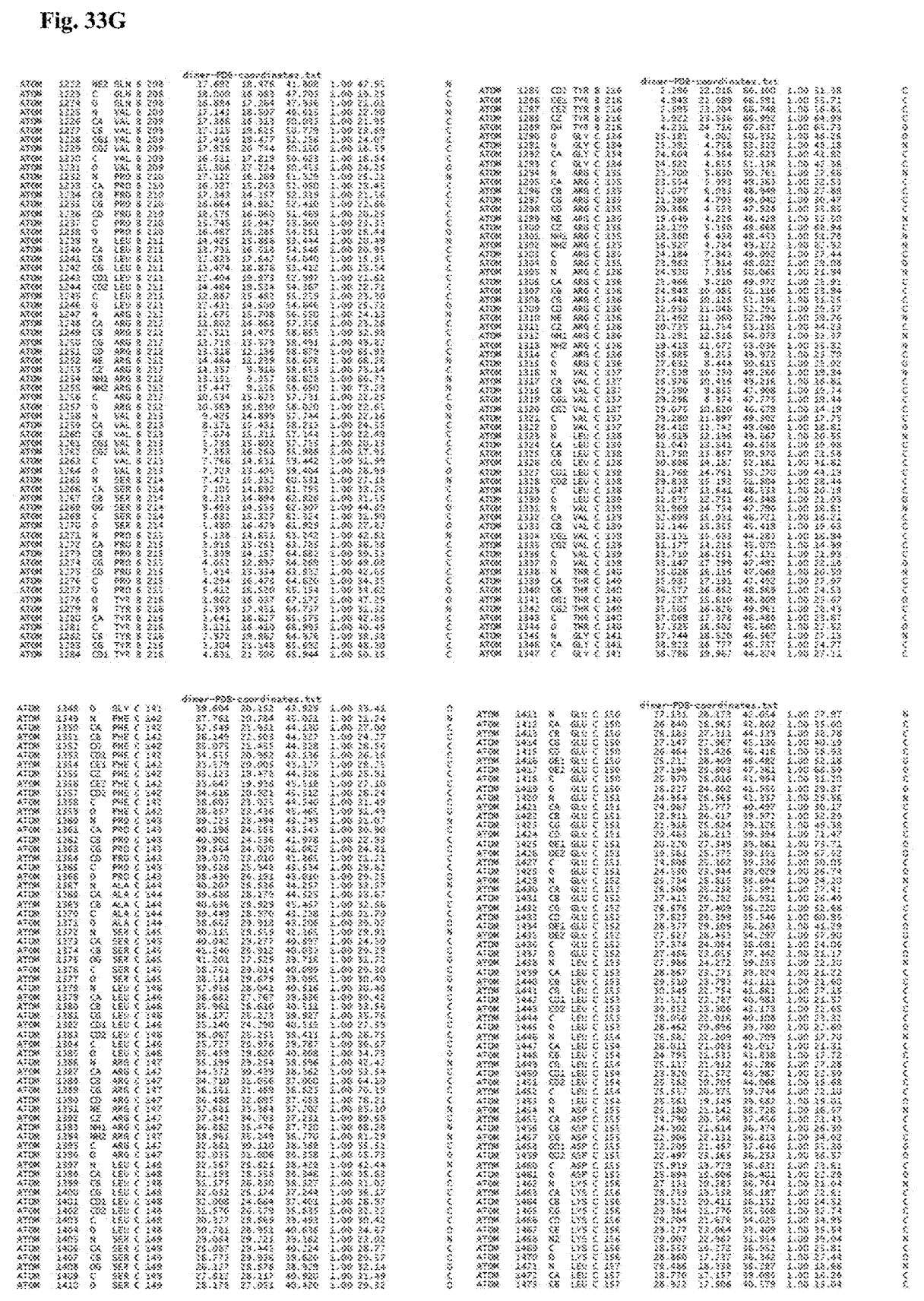
Figure 33H:
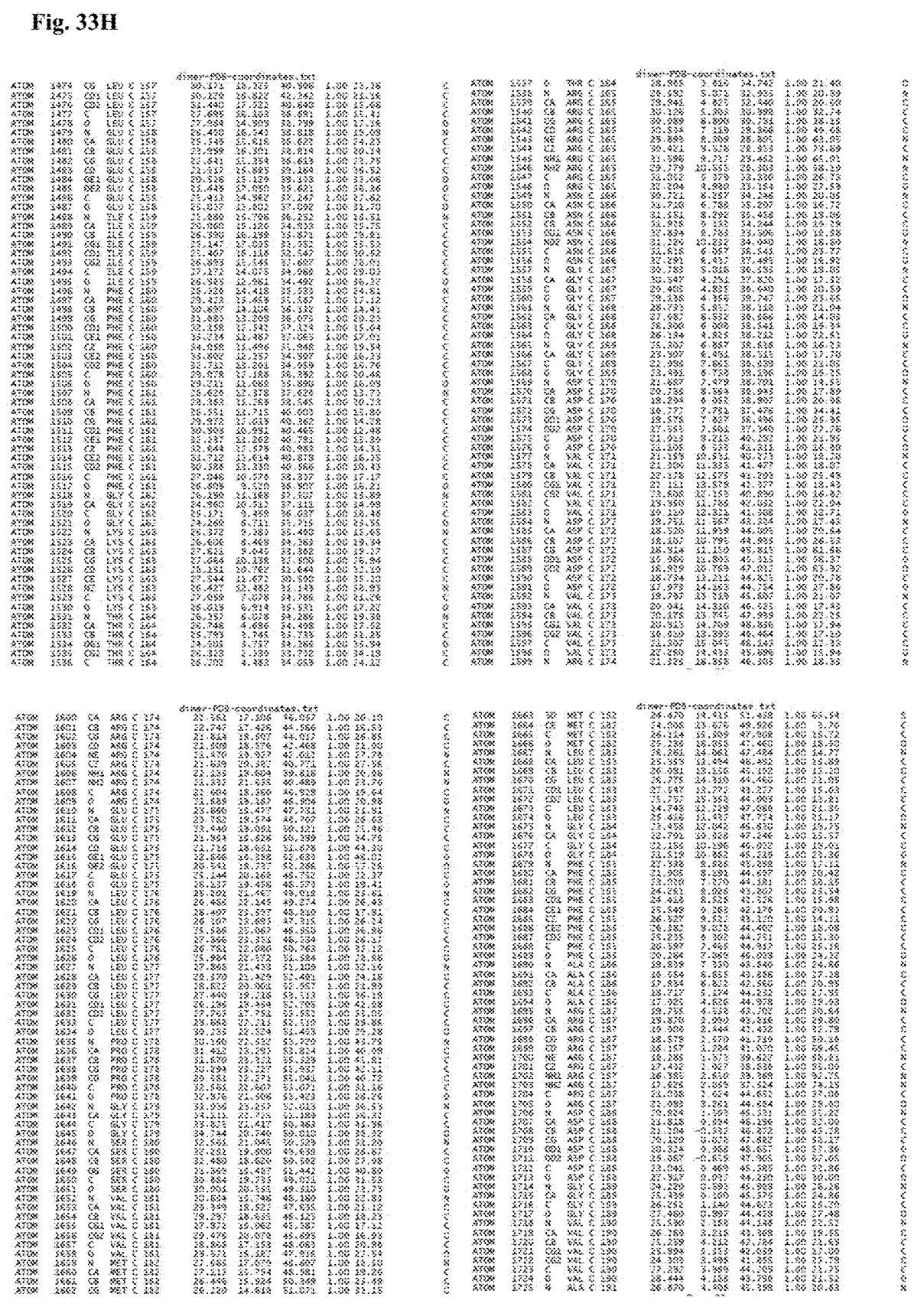
Figure 33I:
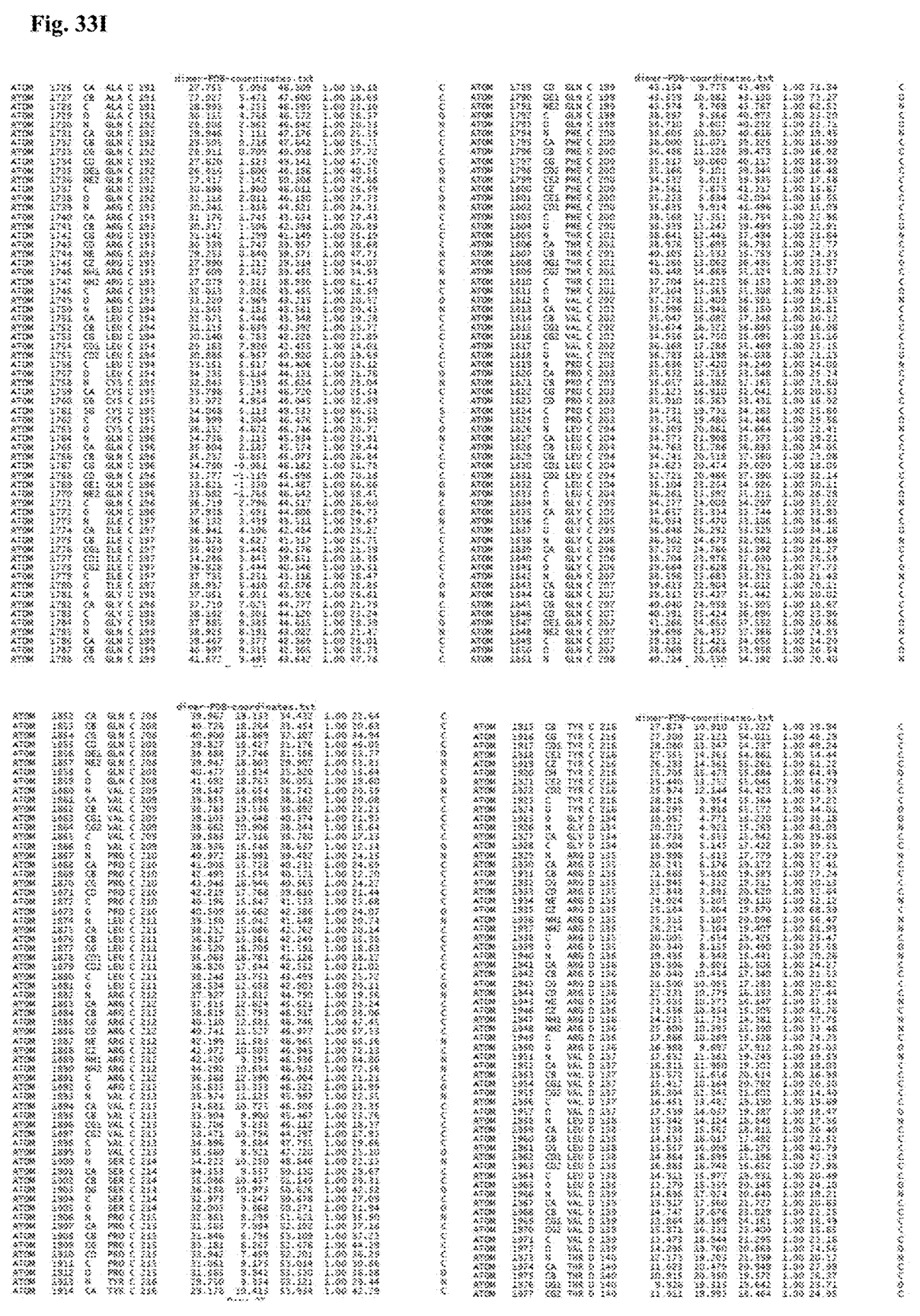
Figure 33J:
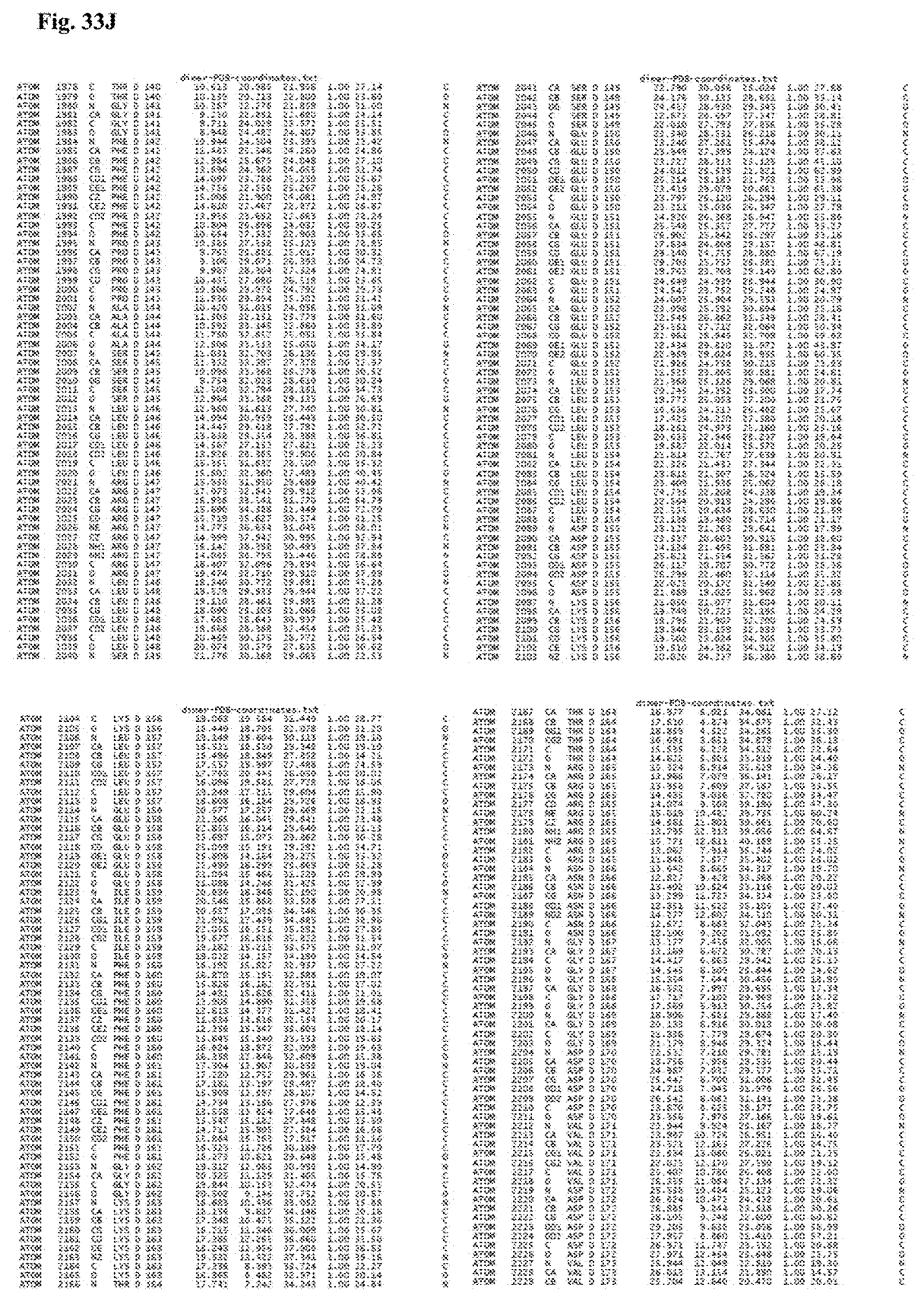
Figure 33K:
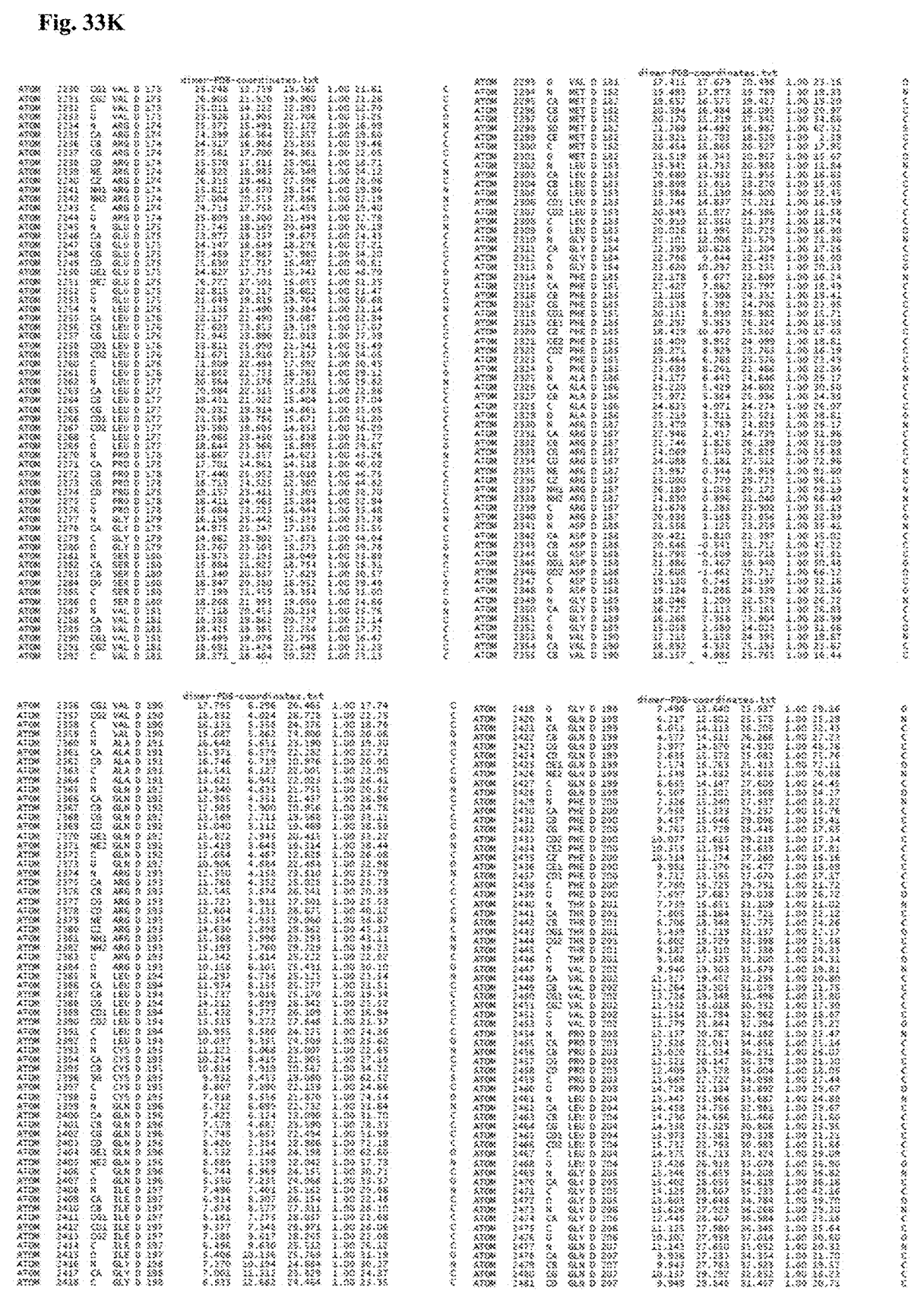
Figure 33L:
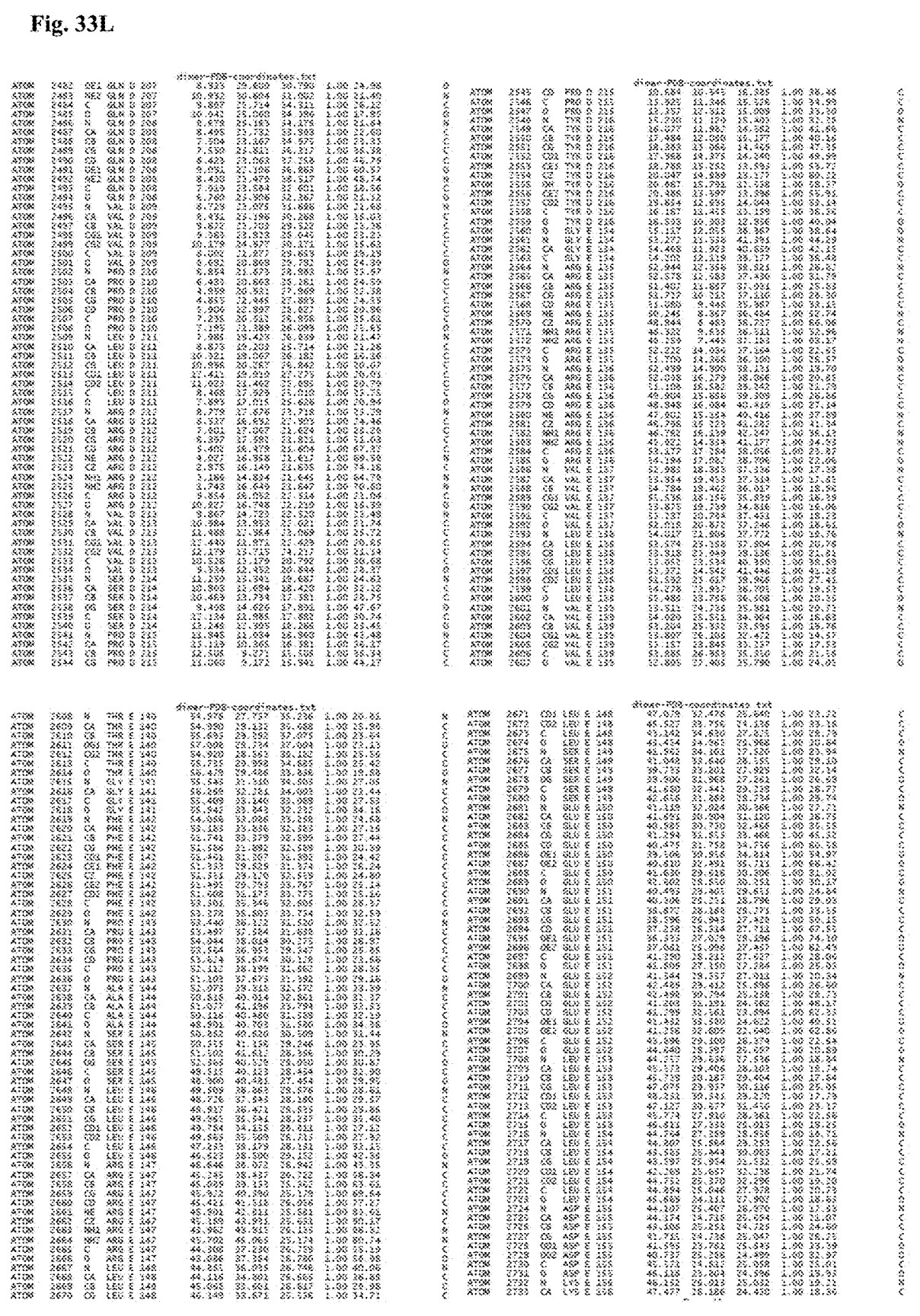
Figure 33M:
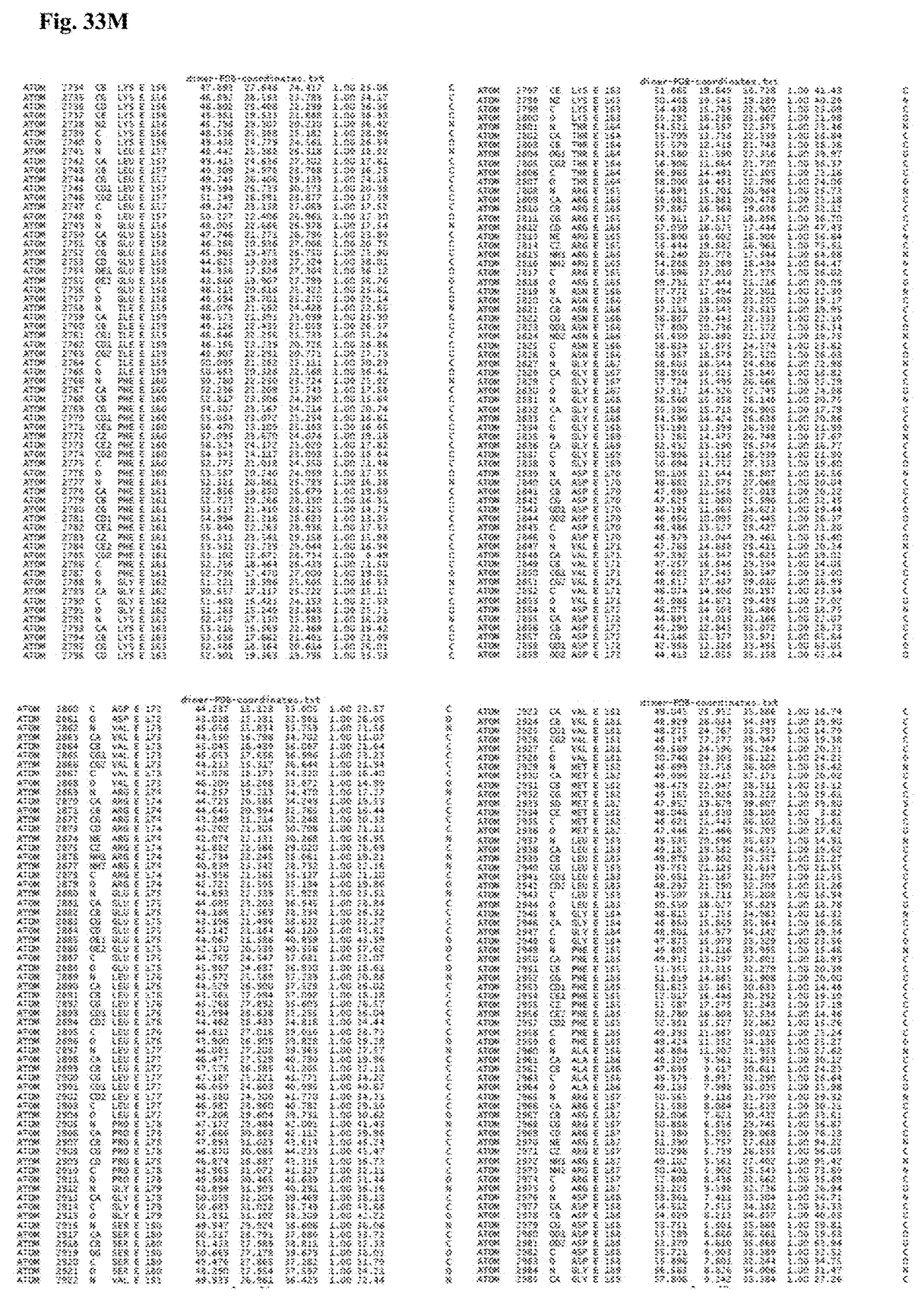
Figure 33N:
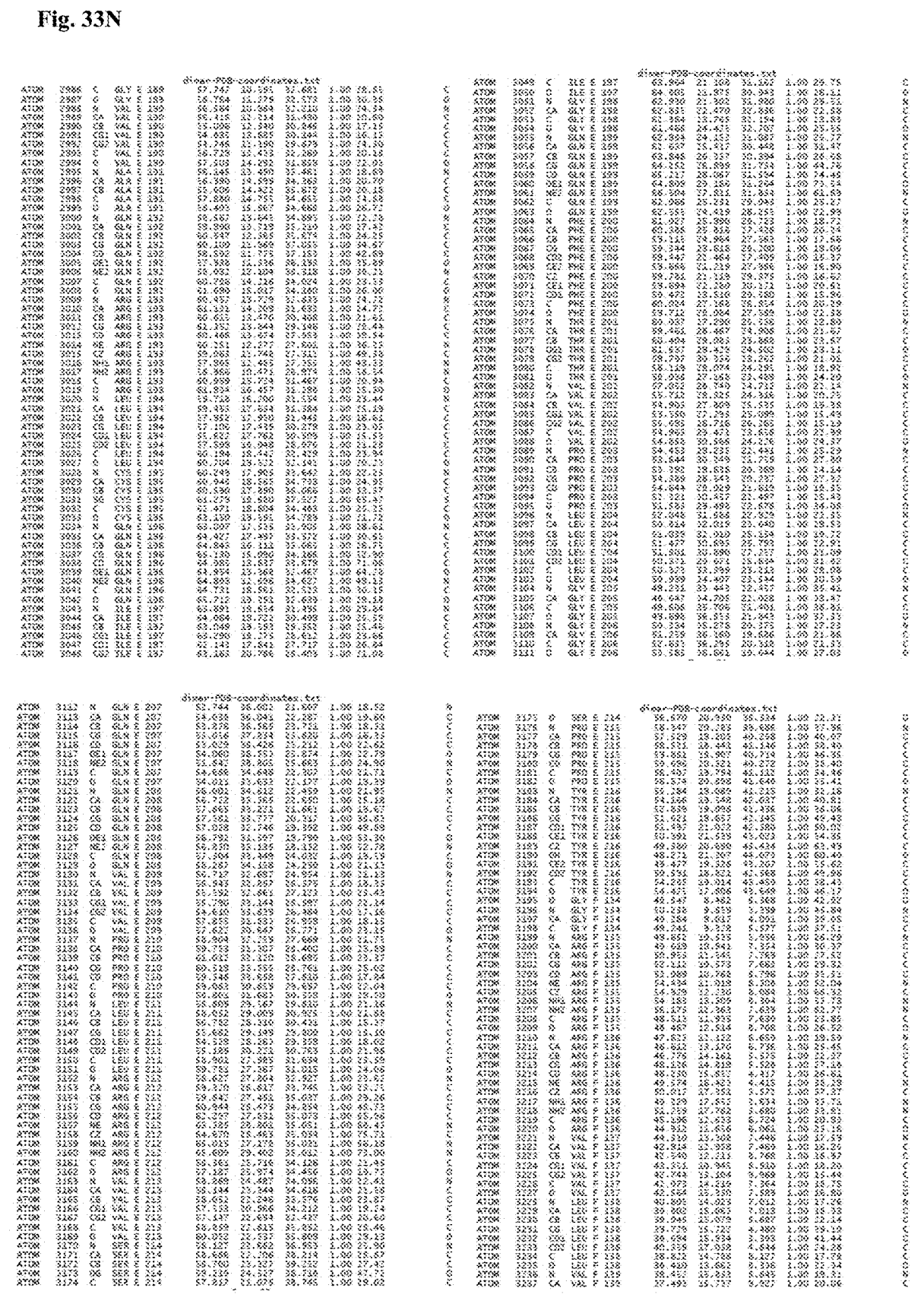
Figure 33O:
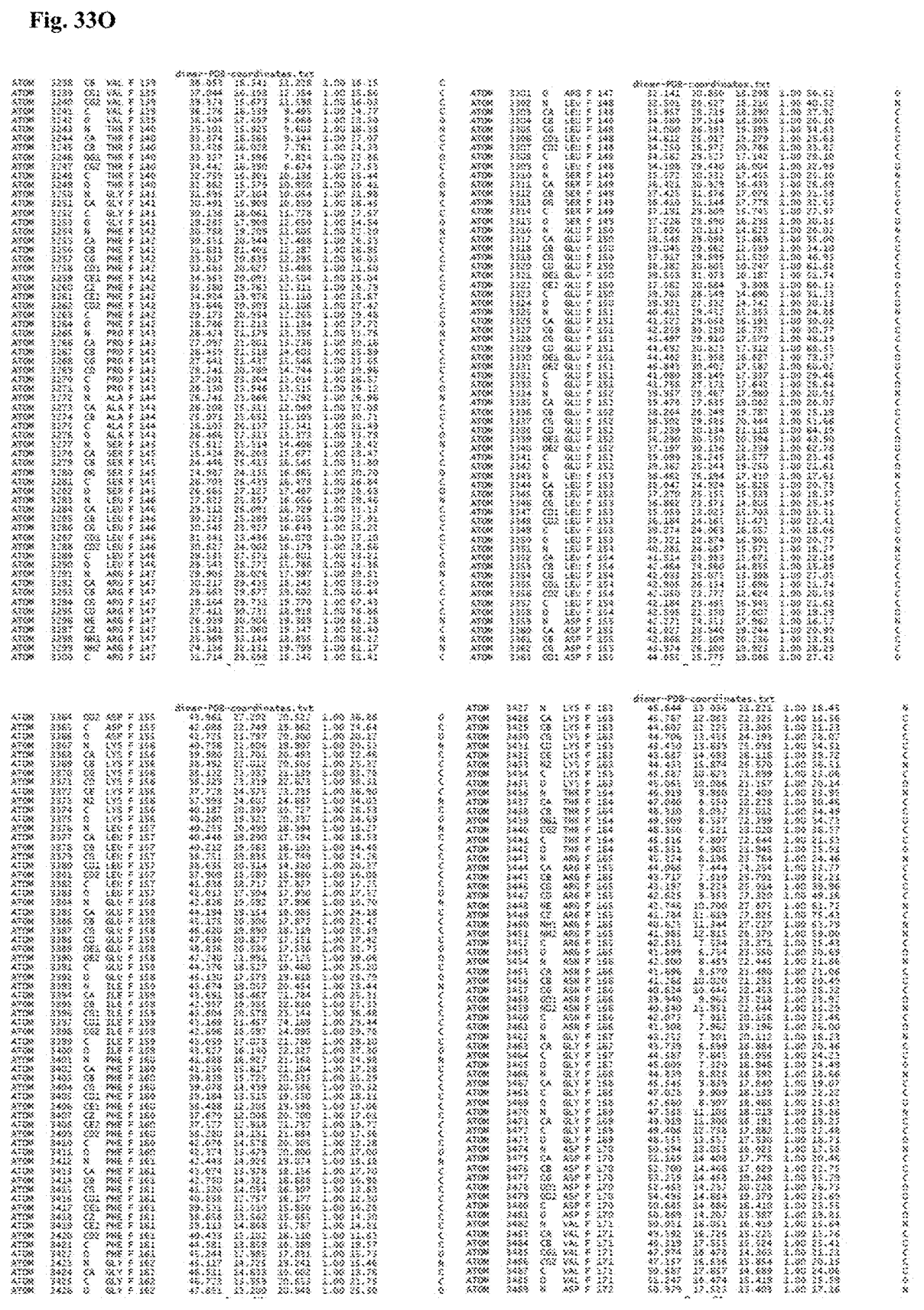
Figure 33P:
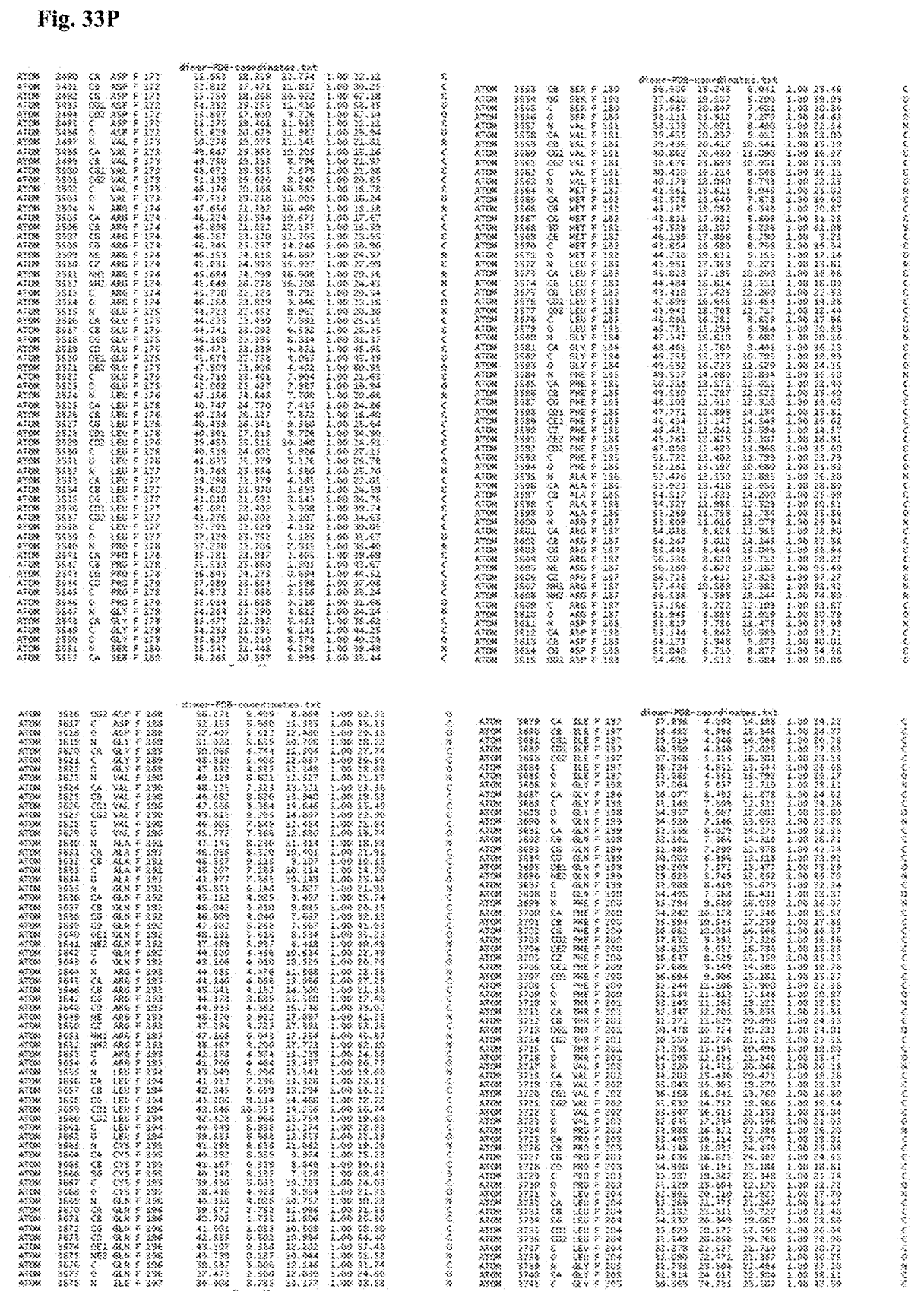
Figure 33Q:
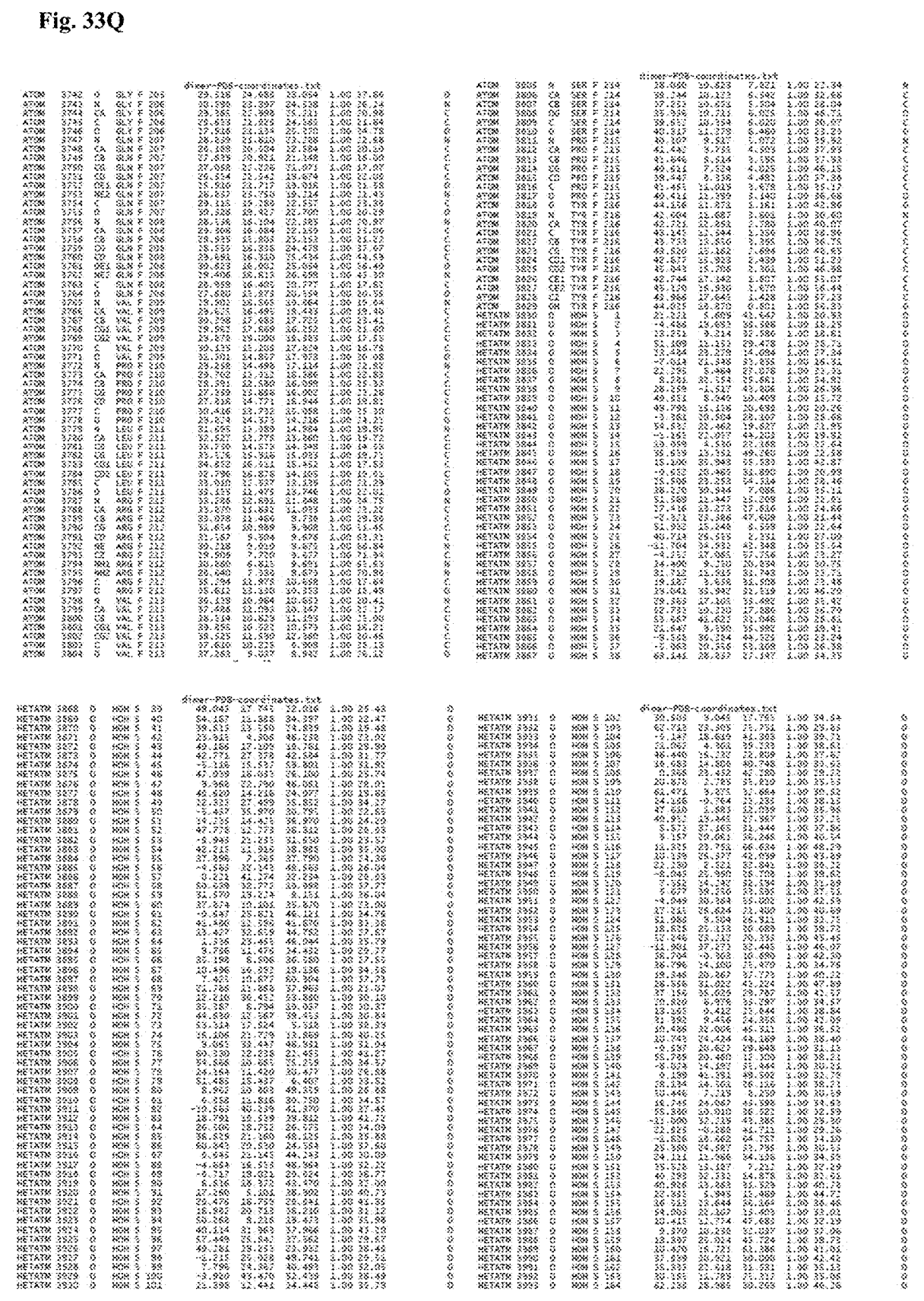
Figure 33R:
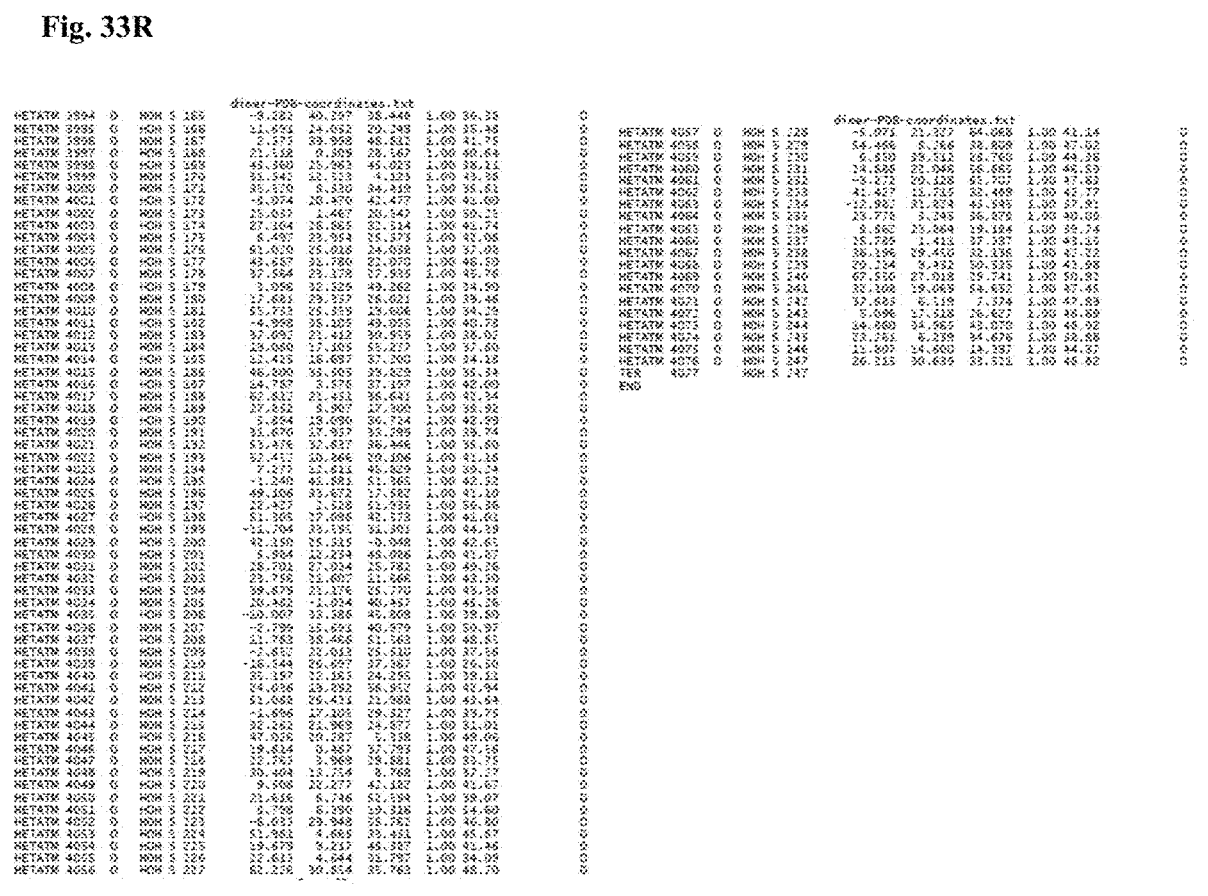

FIGS. 33A-R show the crystal structure coordinates of the NID-H dimer.

Figure 34A:
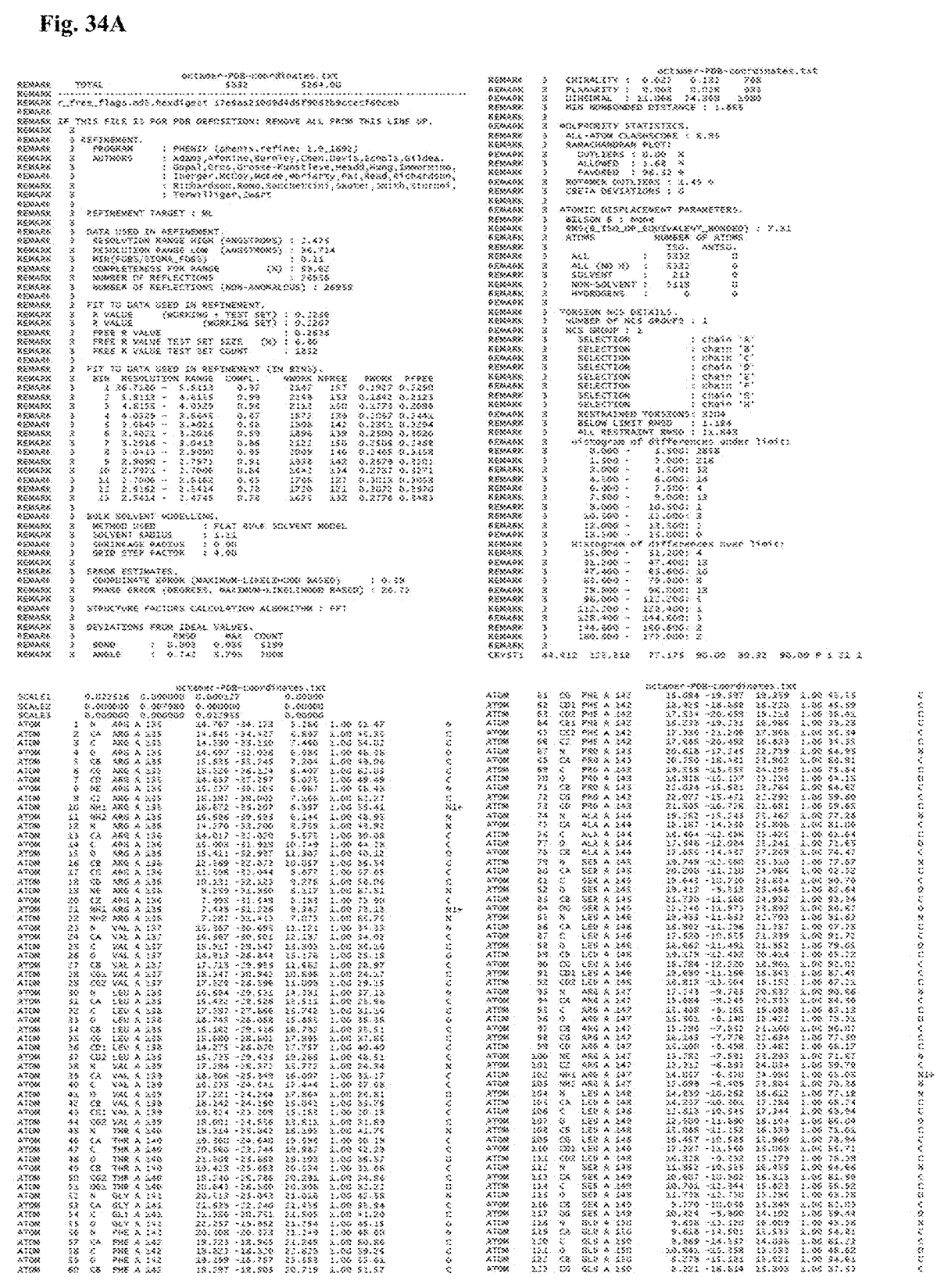
Figure 34B:
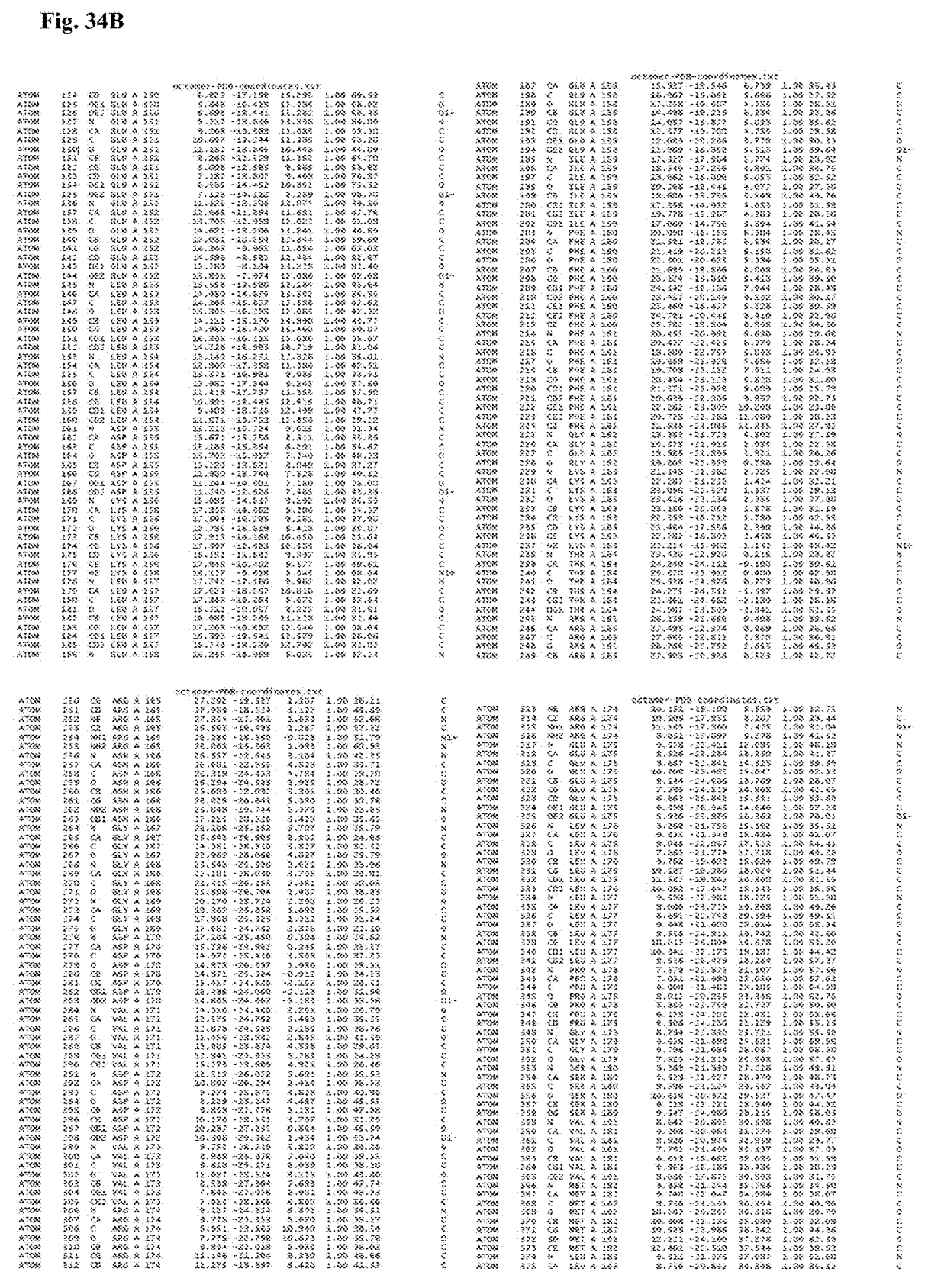
Figure 34D:
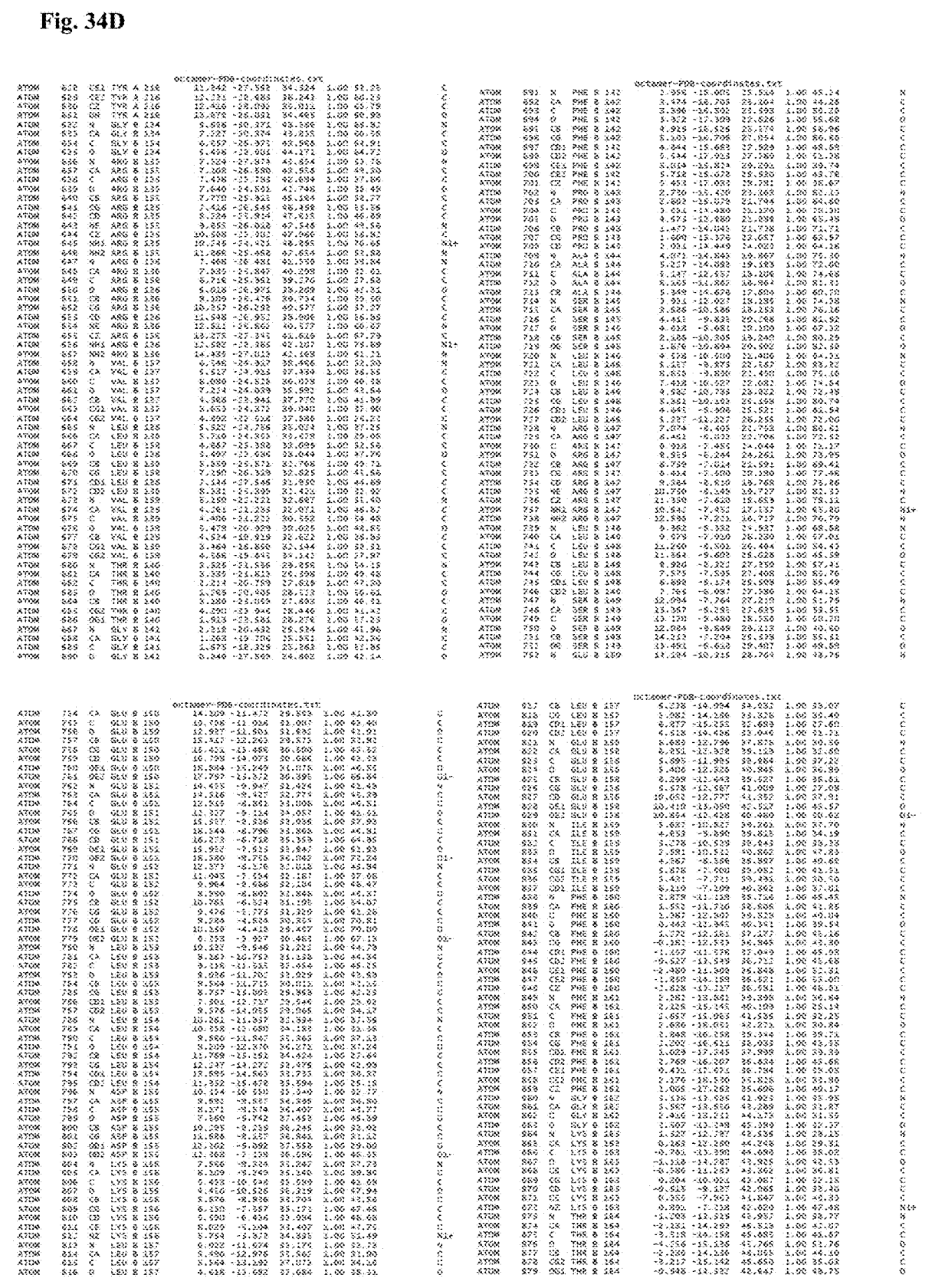
Figure 34F:
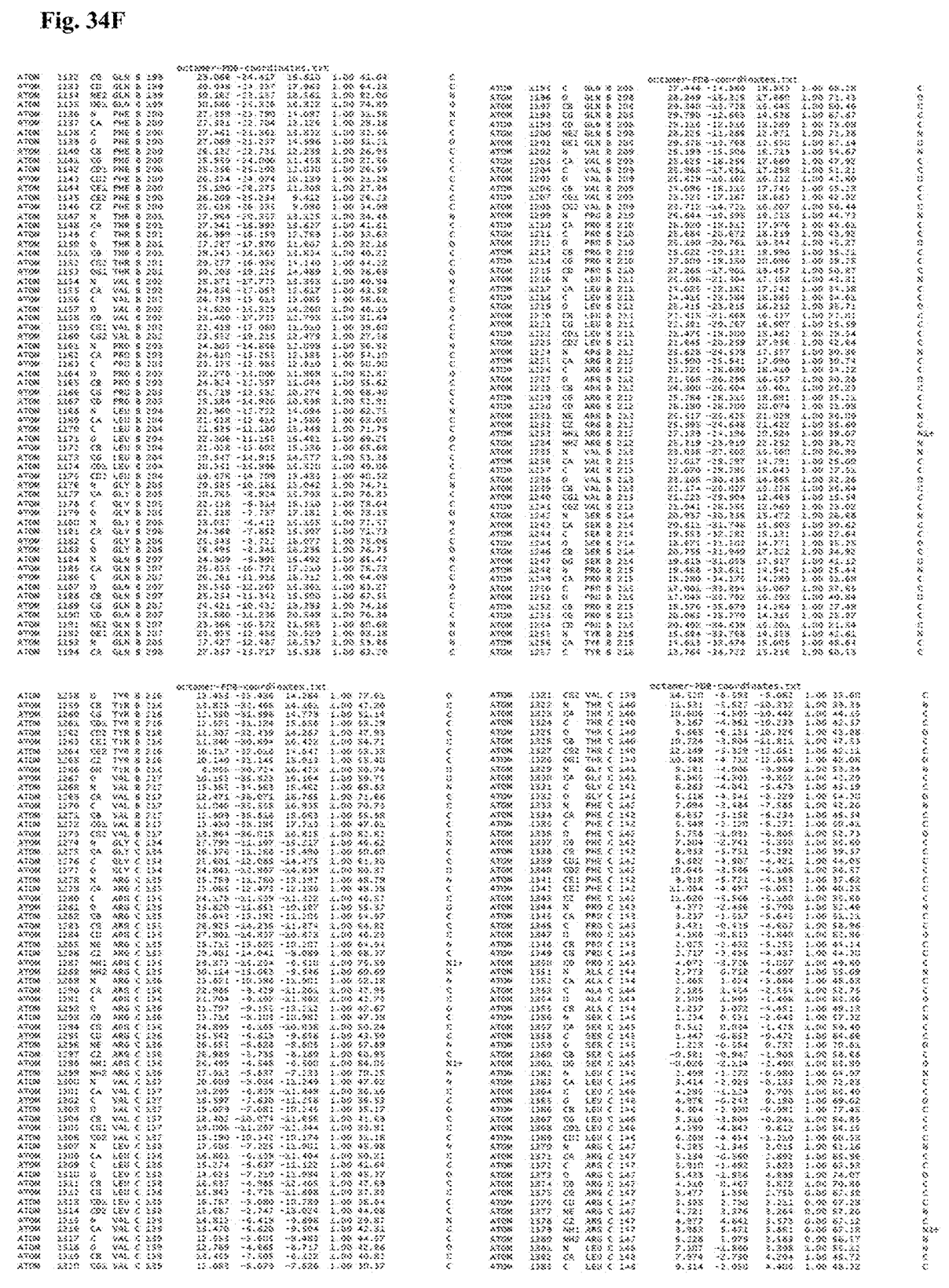
Figure 34G:
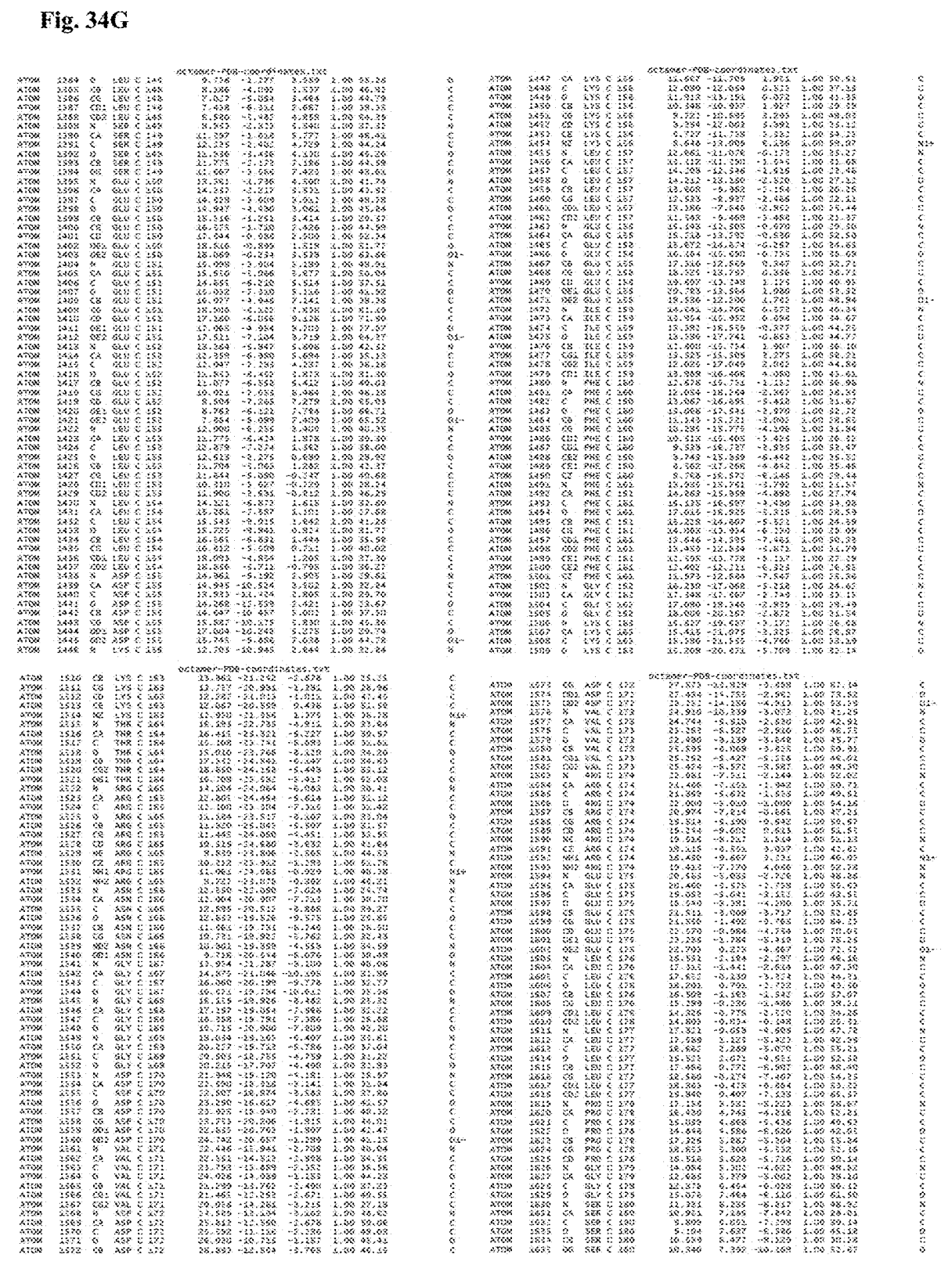
Figure 34H:
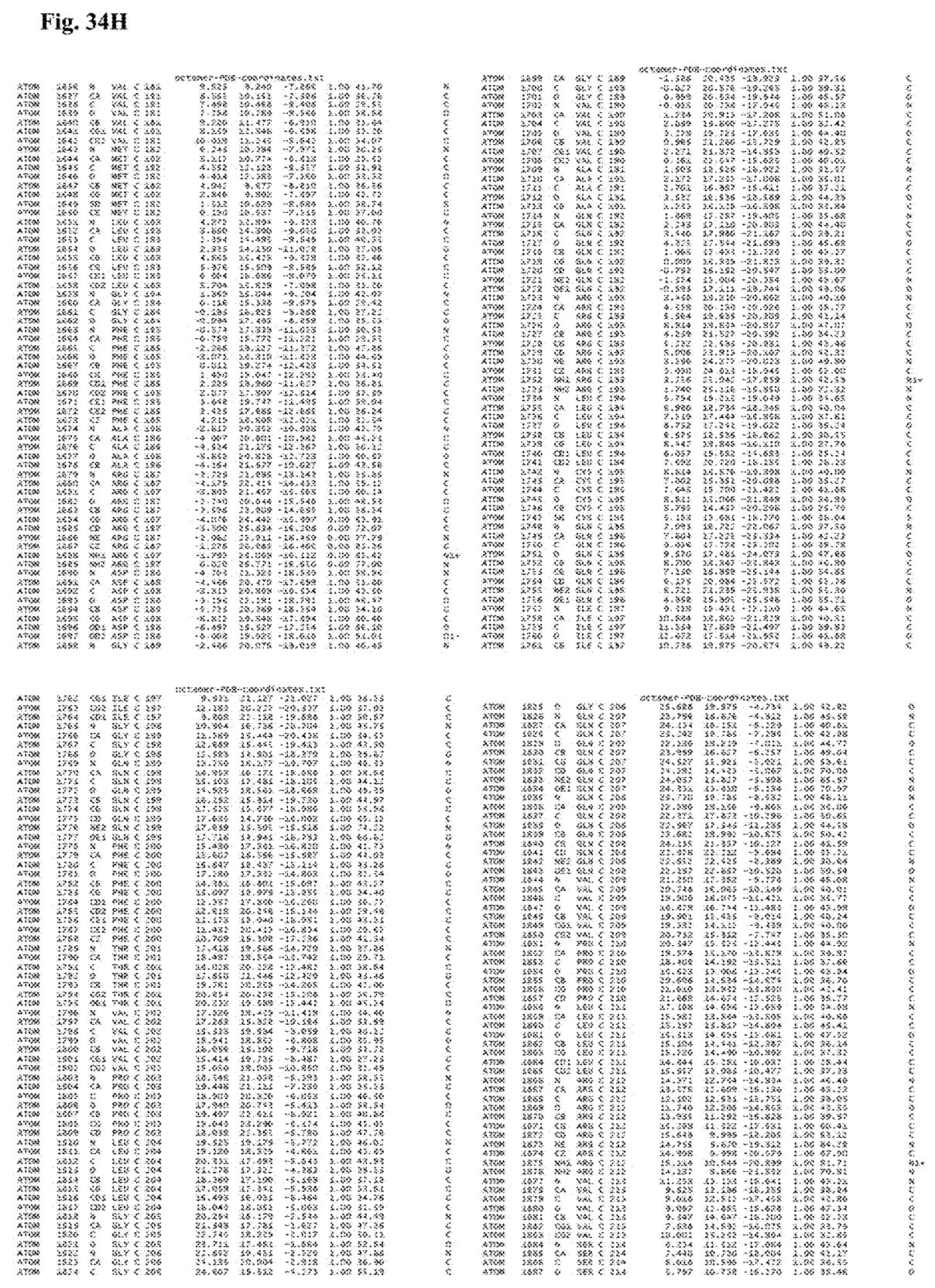
Figure 34I:
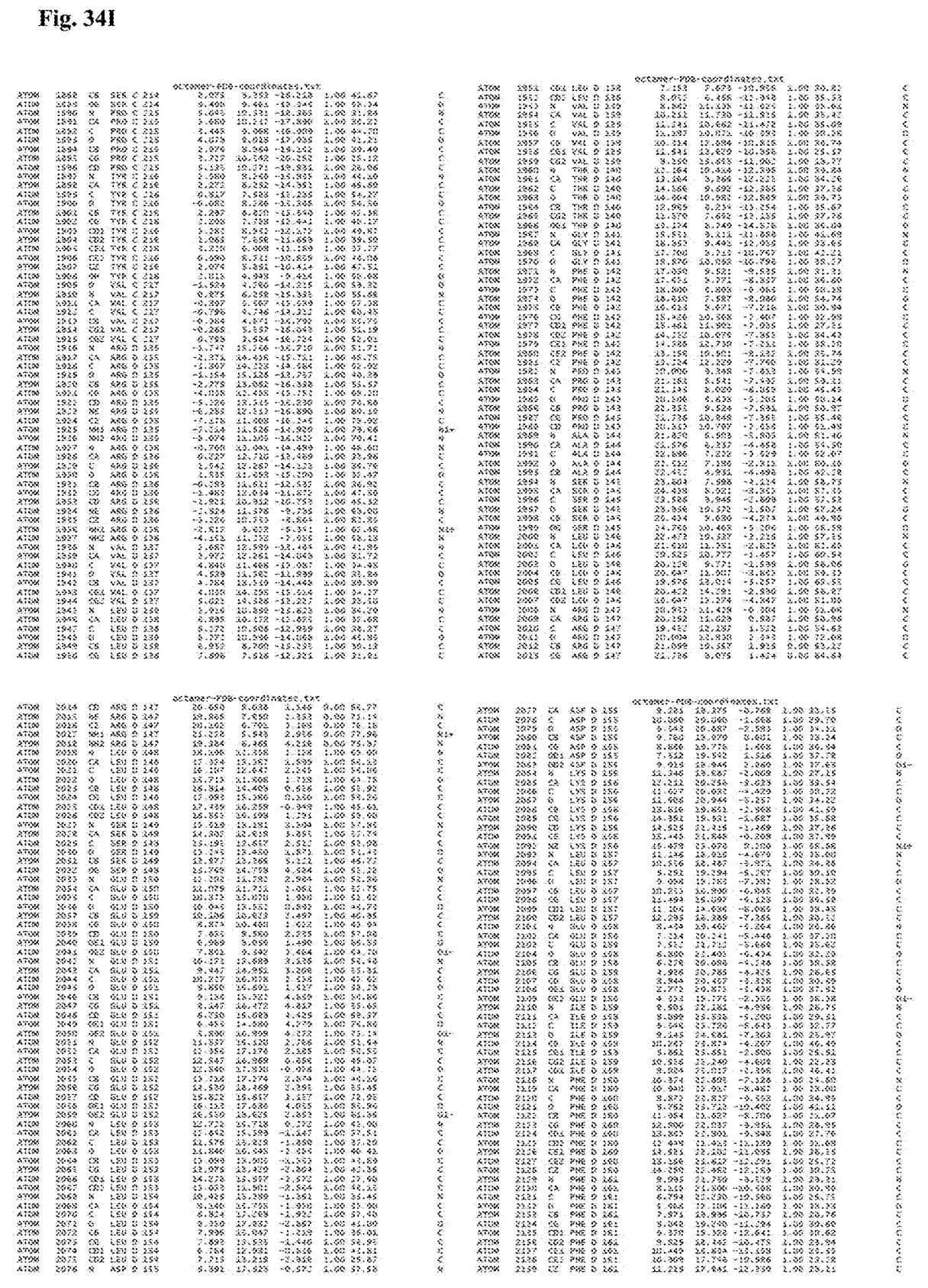
Figure 34J:
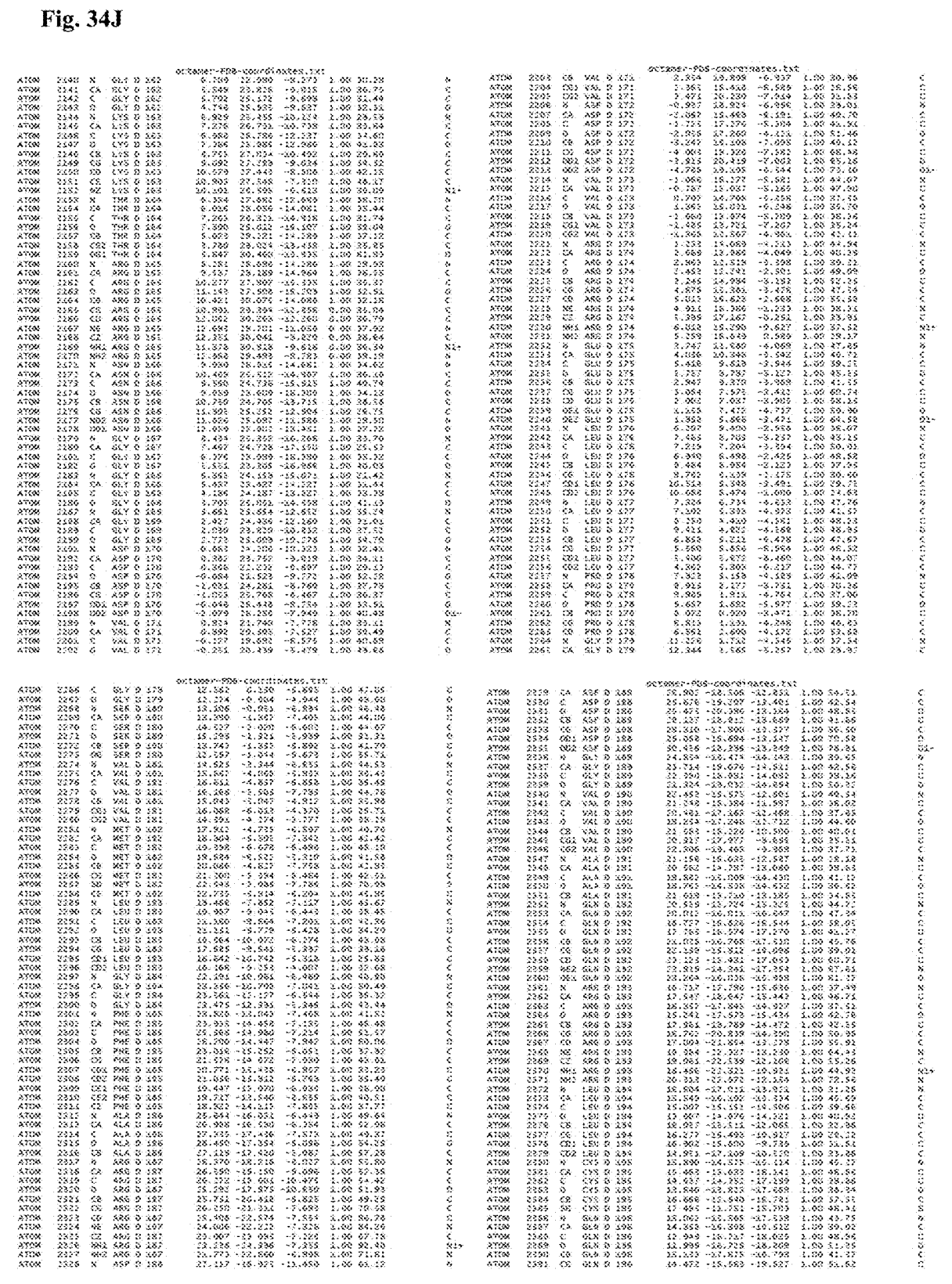
Figure 34K:
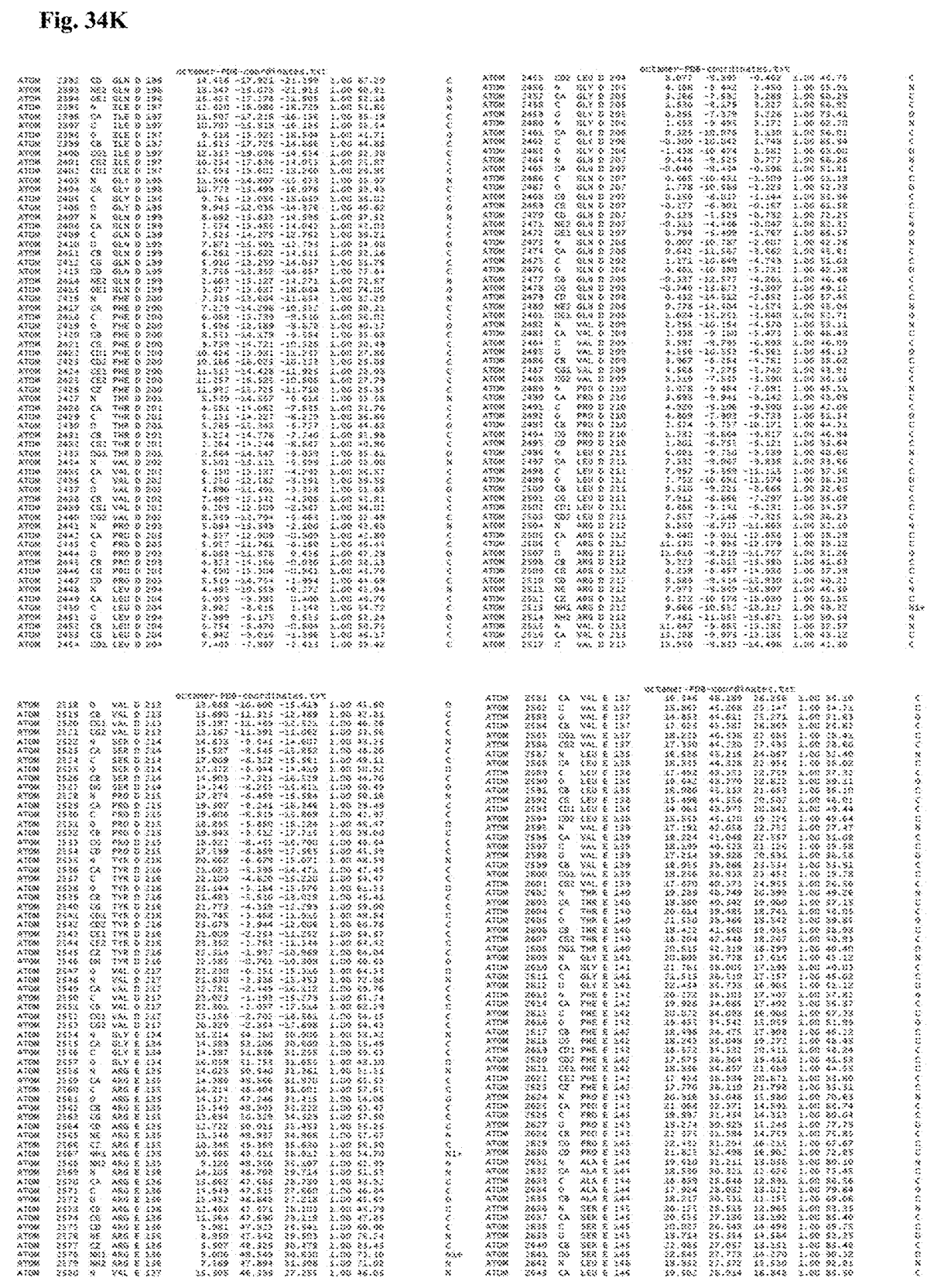
Figure 34L:
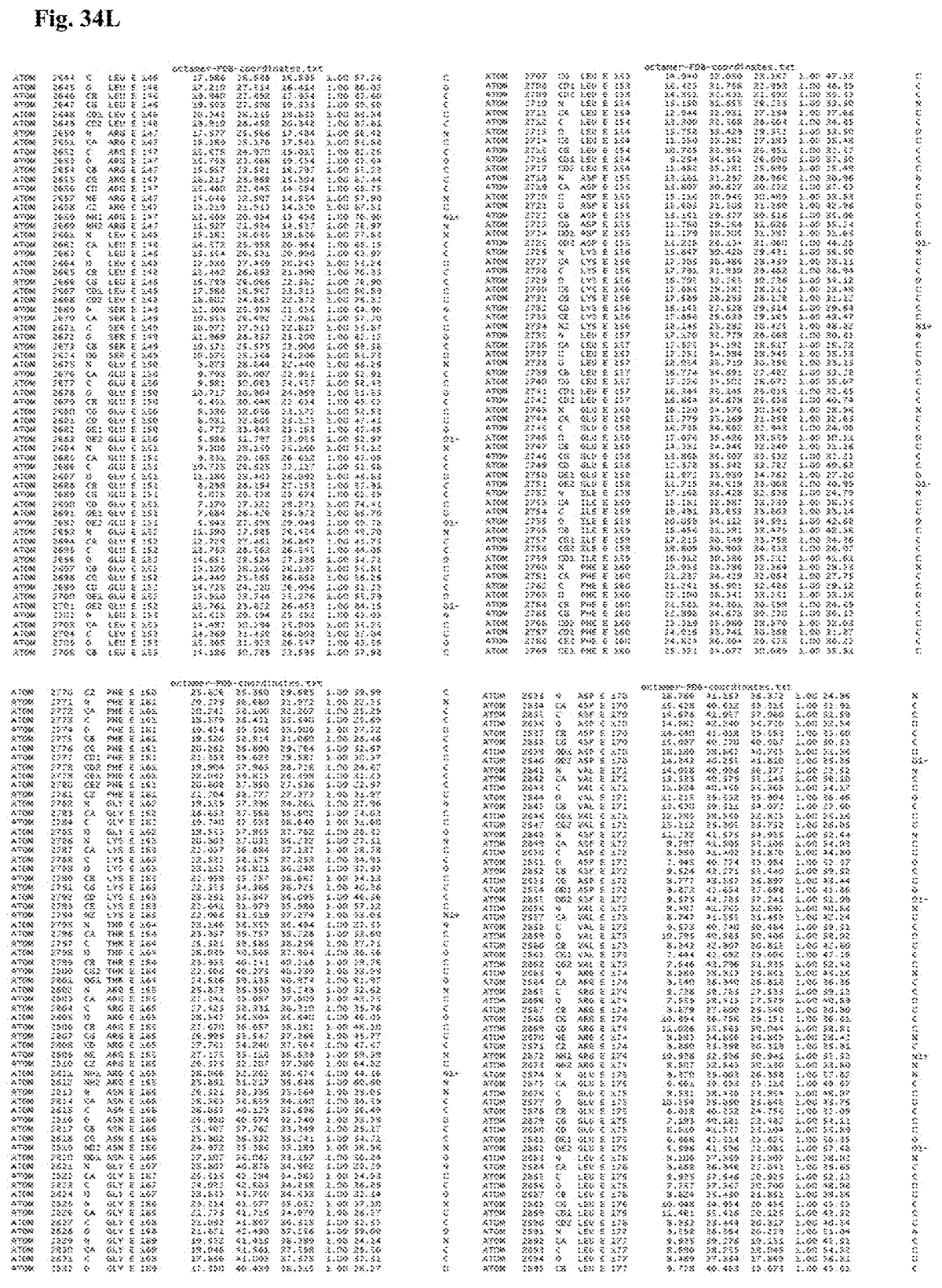
Figure 34M:
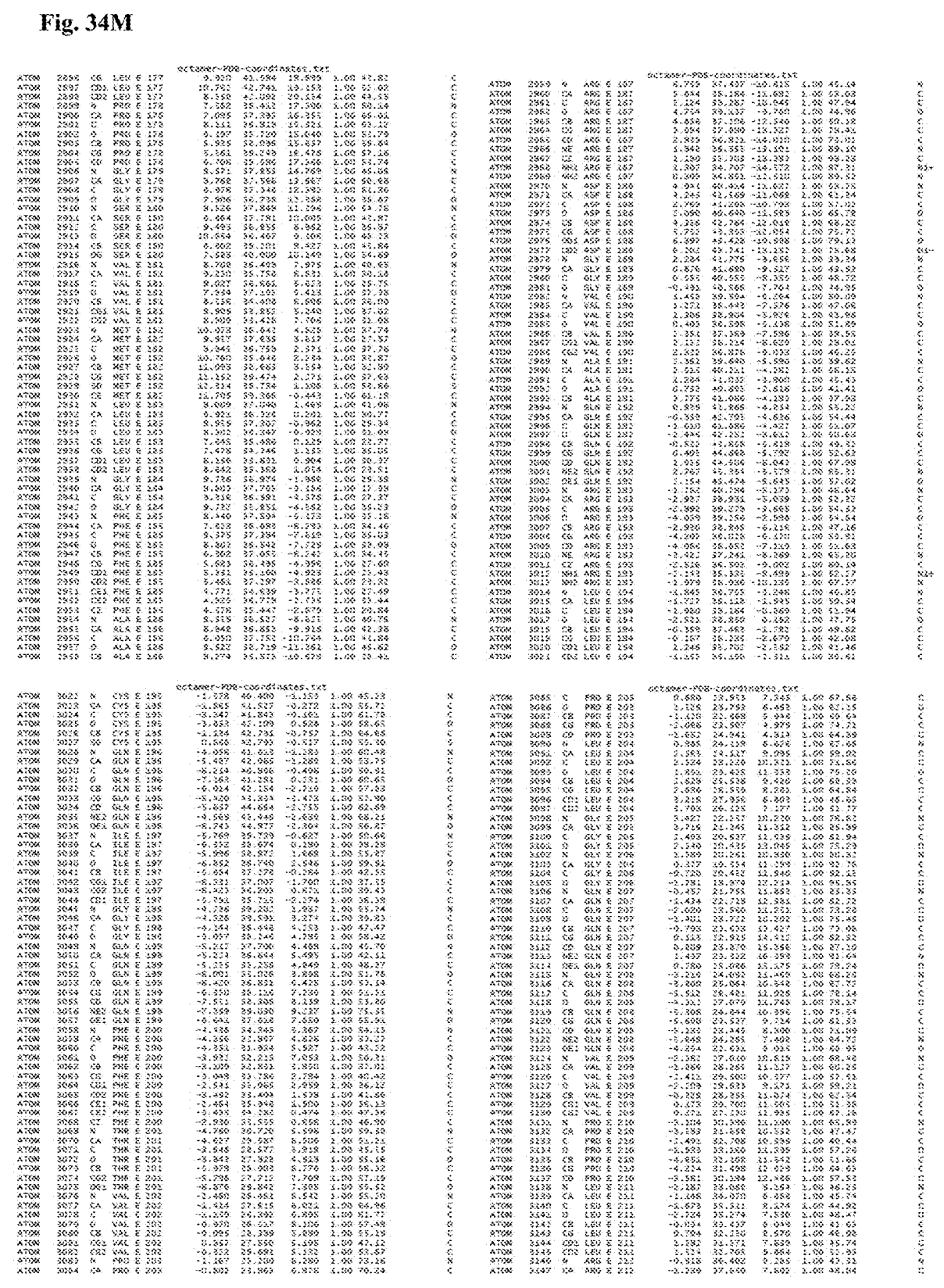
Figure 34N:
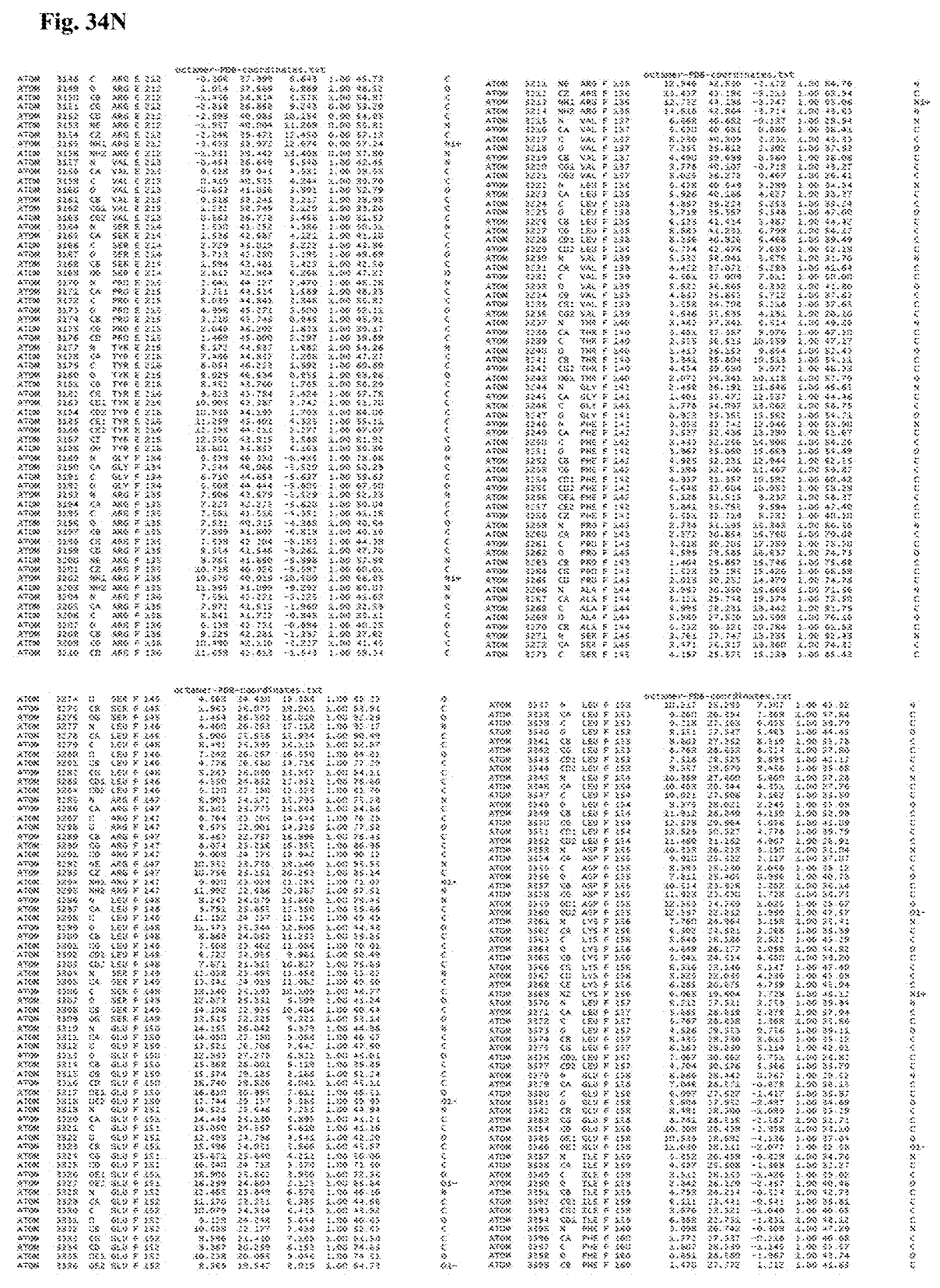
Figure 34O:
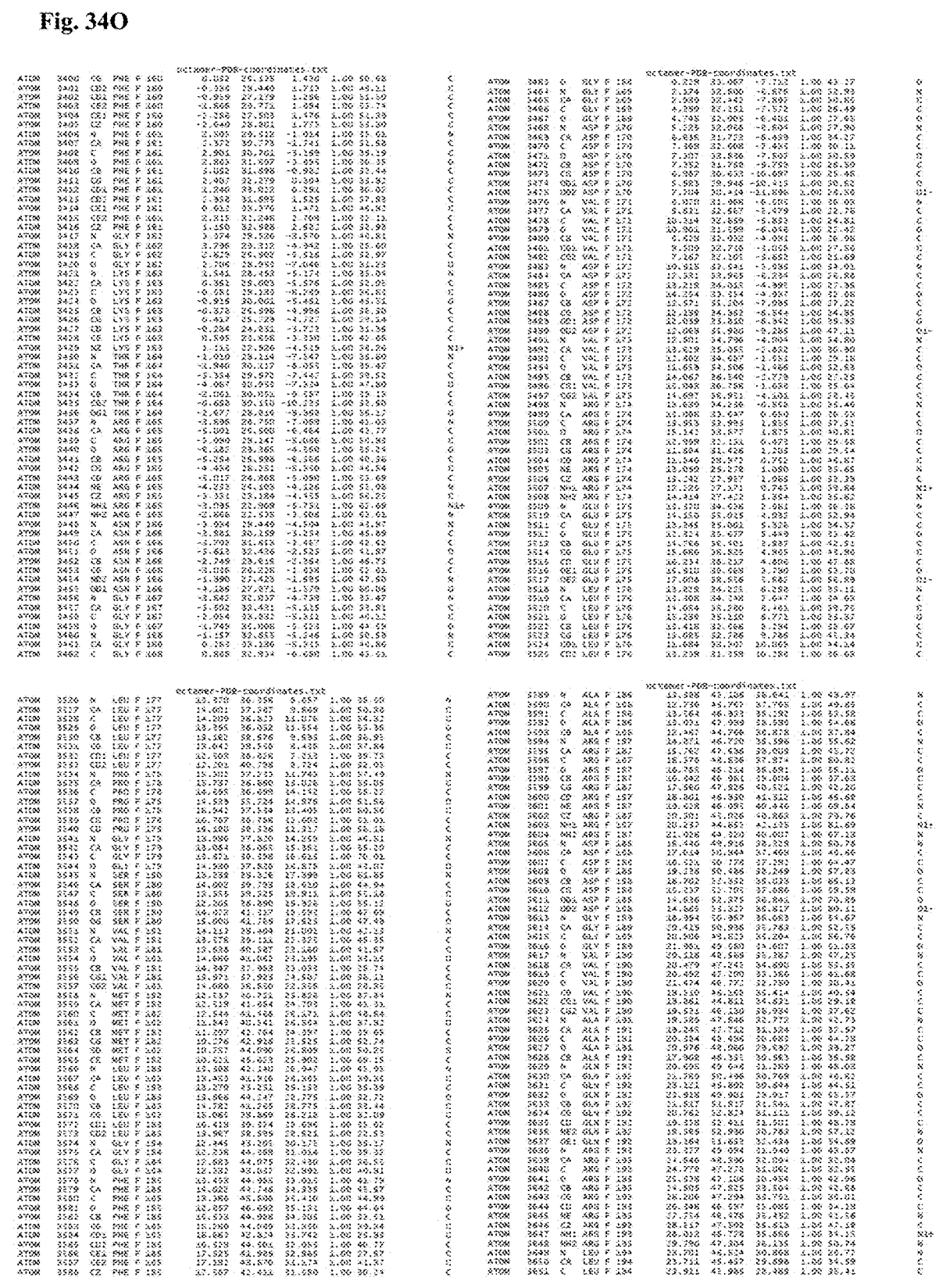
Figure 34P:
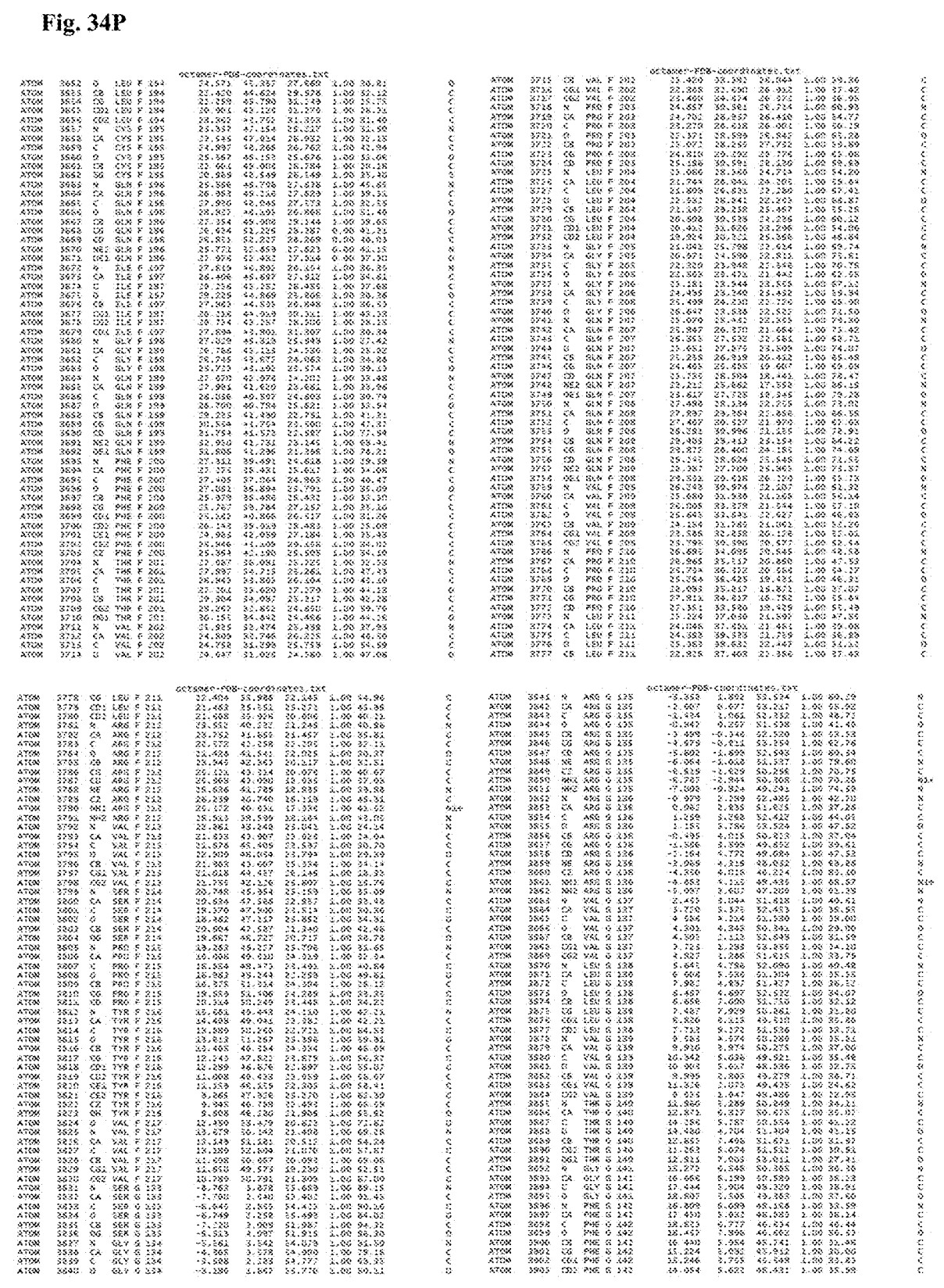
Figure 34Q:
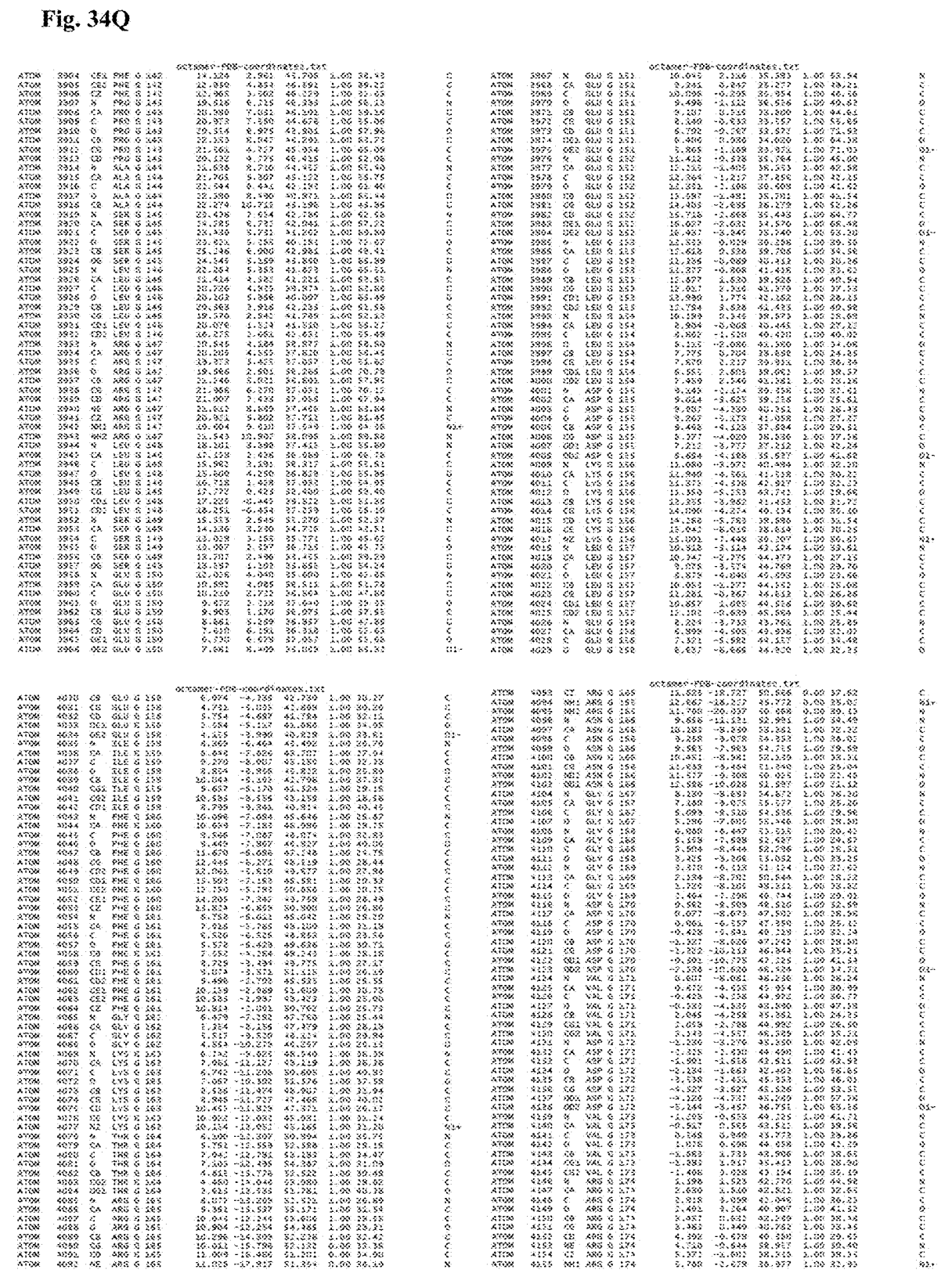
Figure 34R:
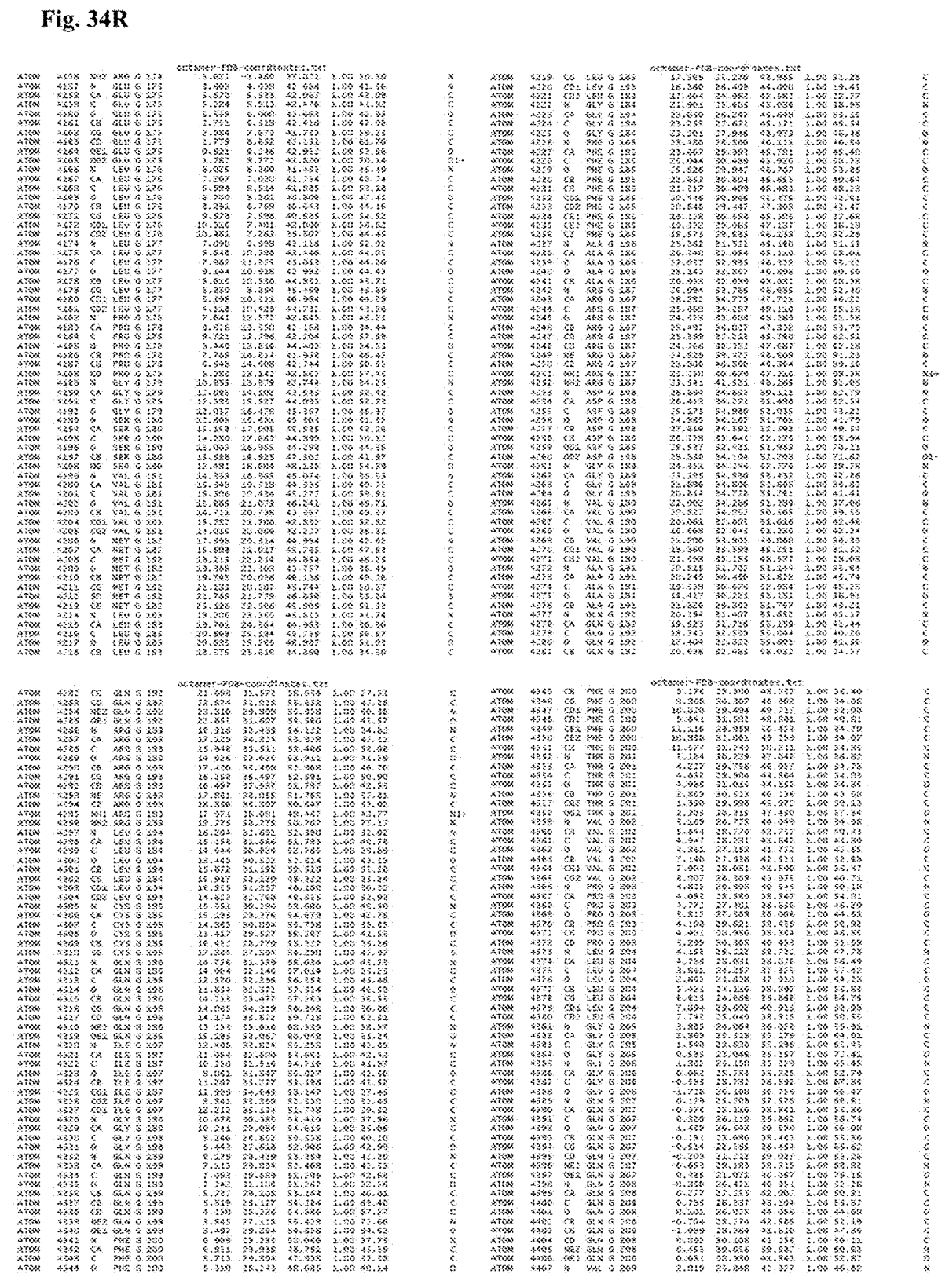
Figure 34S:
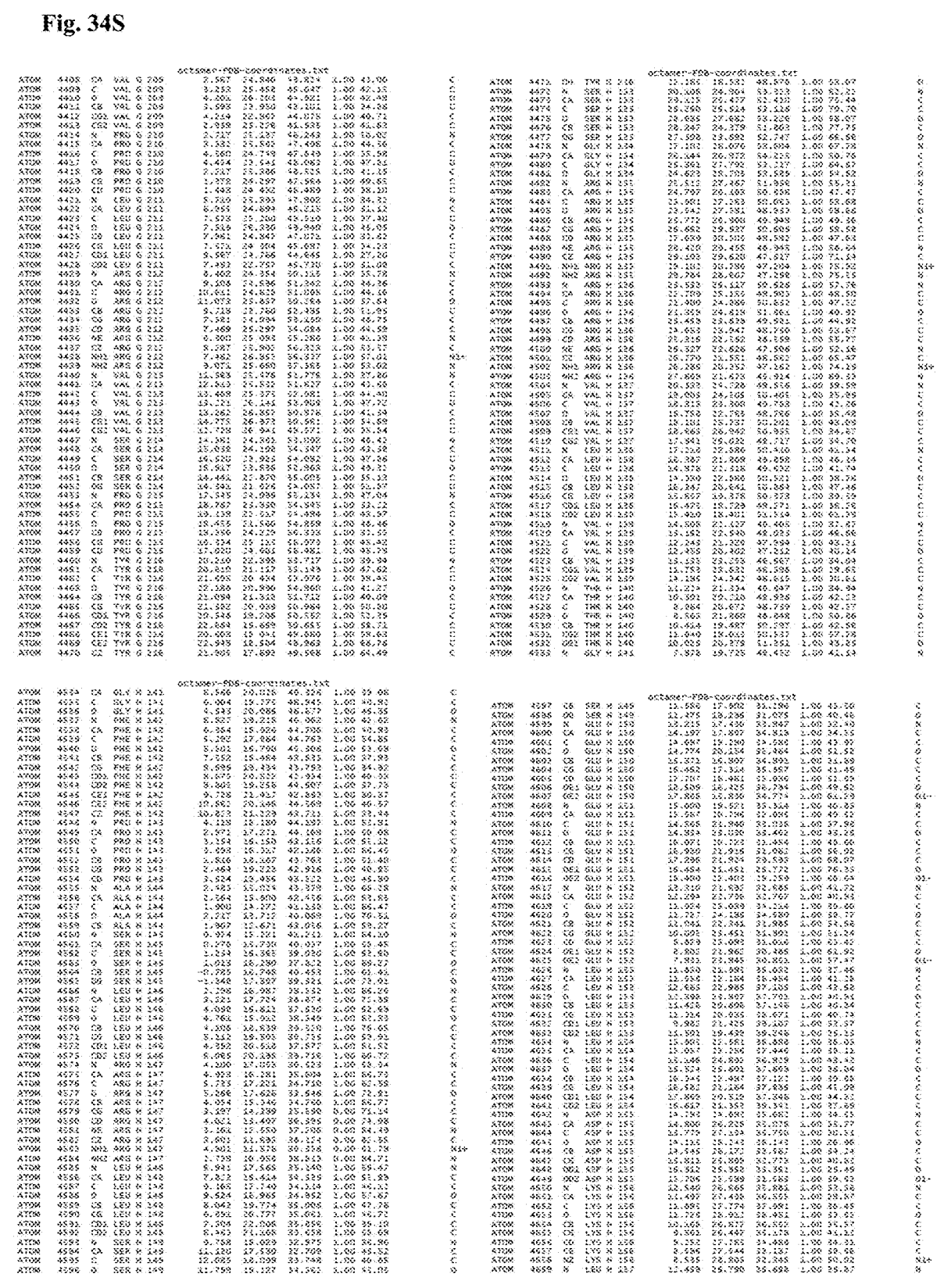
Figure 34T:
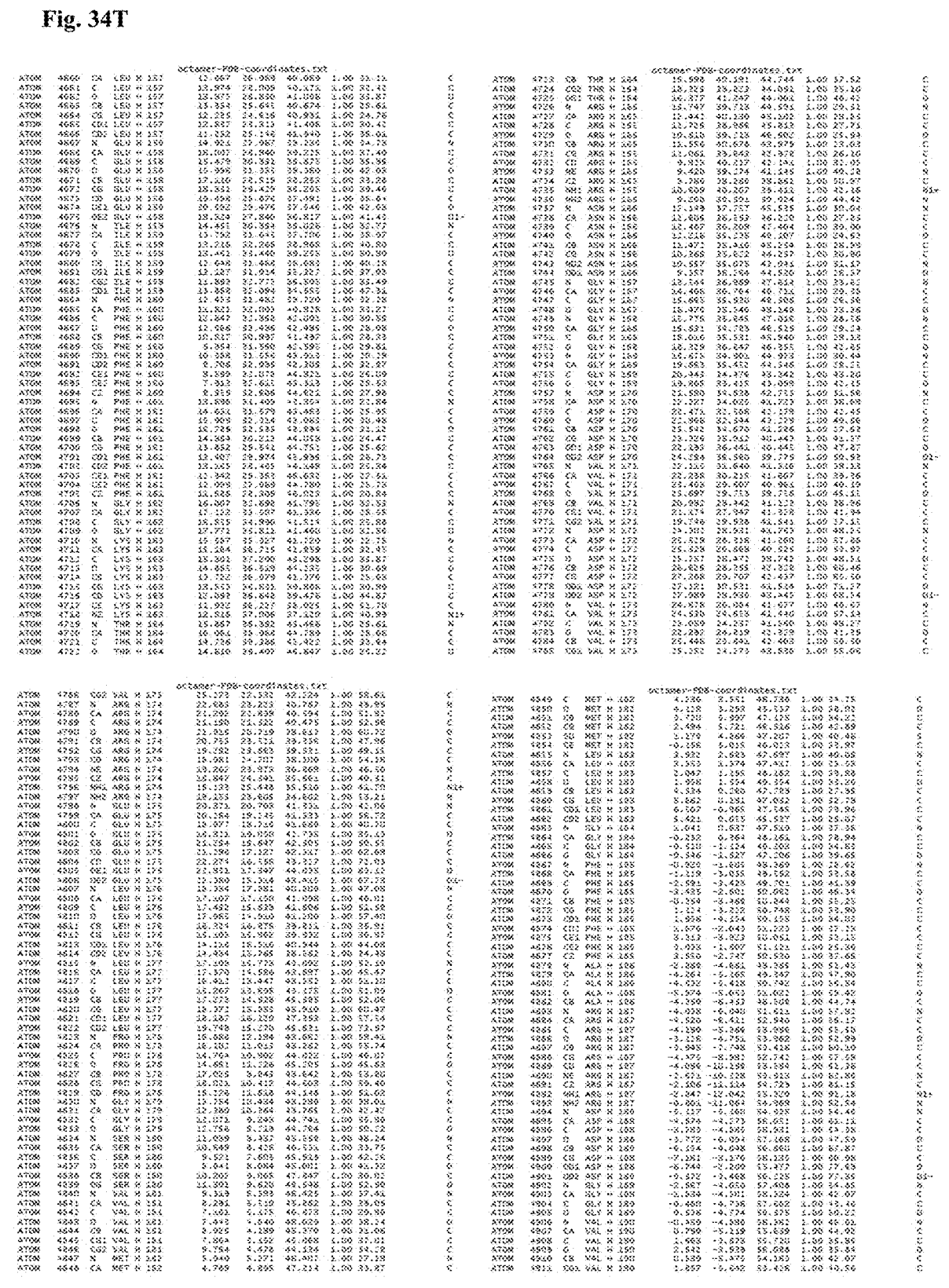
Figure 34U:
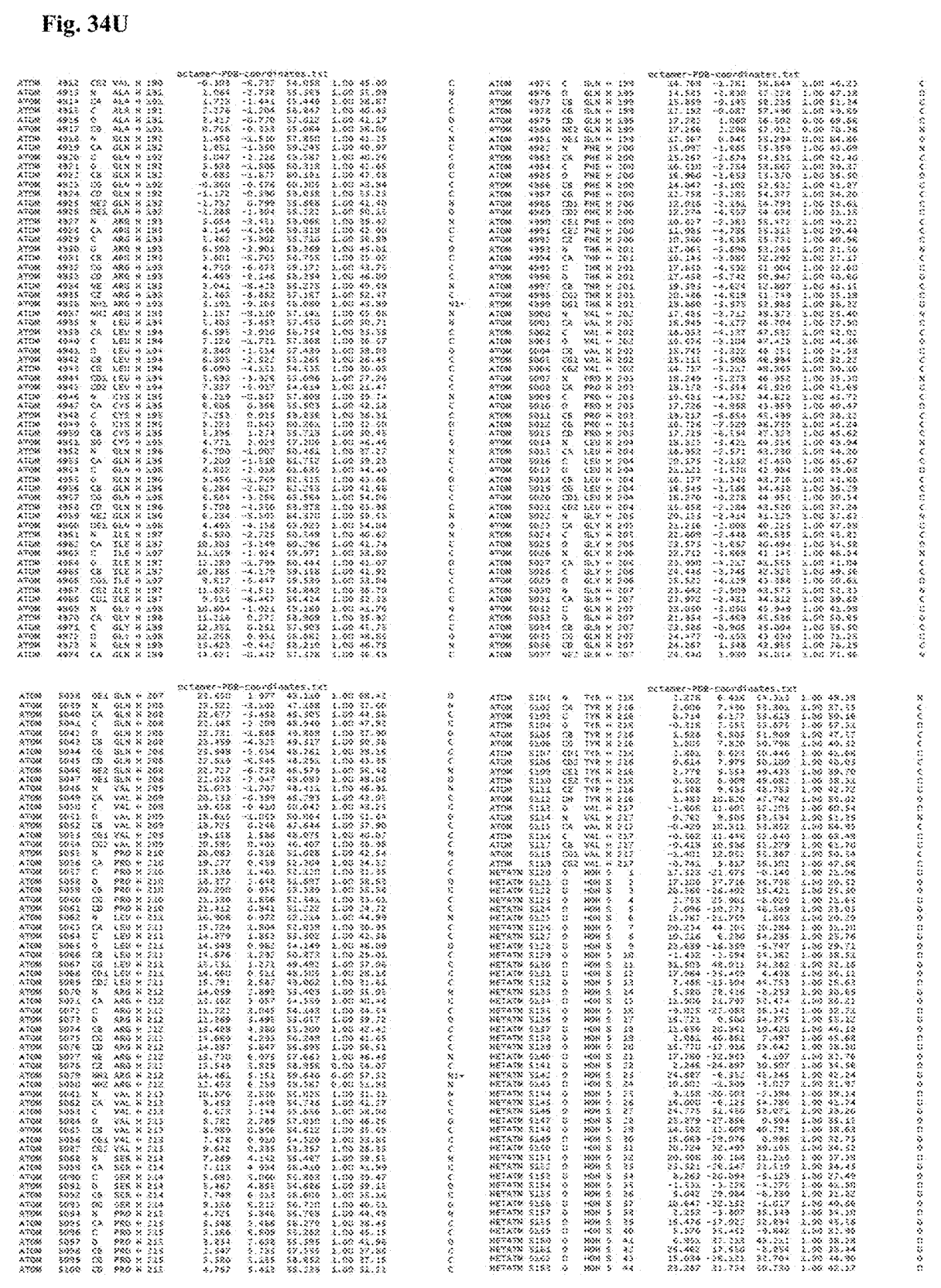
Figure 34V:
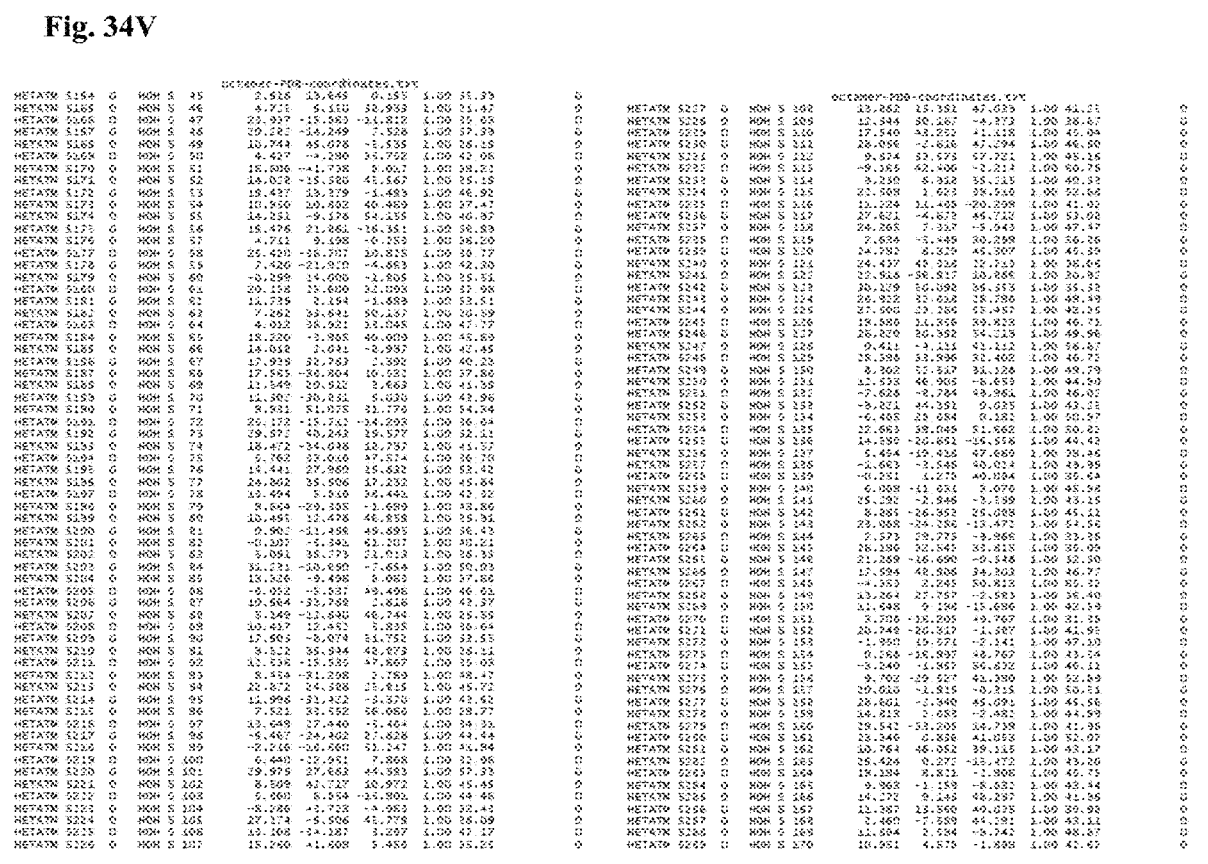

FIGS. 34A-V show the crystal structure coordinates of the NID-H octamer.

DETAILED DESCRIPTION OF THE INVENTION

A. General Techniques

The practice of the present invention will employ, unless otherwise indicated, conventional techniques of molecular biology (including recombinant techniques), microbiology, cell biology, biochemistry, immunology, and pharmacology, which are within the skill of the art. Such techniques are explained fully in the literature, such as, Molecular Cloning: A Laboratory Manual, $2^{nd}$ ed. (Sambrook et al., 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et al., eds., 1987, and periodic updates); PCR: The Polymerase Chain Reaction (Mullis et al., eds., 1994); and Remington, The Science and Practice of Pharmacy. $20^{1t}$ ed., (Lippincott, Williams & Wilkins 2003).

Definitions

Unless defined otherwise, all technical and scientific terms used herein have the same meaning as is commonly understood by one of ordinary skill in the art to which this invention belongs. All patents, patent applications (published or unpublished), and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

The terms "polypeptide," "oligopeptide," "peptide," and "protein" are used interchangeably herein to refer to polymers of amino acids of any length, e.g., at least 5, 6, 7, 8, 9, 10, 20, 30, 40, 50, 100, 200, 300, 400, 500, 1,000 or more amino acids. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, the terms "variant" is used in reference to polypeptides that have some degree of amino acid sequence identity to a parent polypeptide sequence. A variant is similar to a parent sequence, but has at least one substitution, deletion or insertion in their amino acid sequence that makes them different in sequence from a parent polypeptide. Additionally, a variant may retain the functional characteristics of the parent polypeptide, e.g., maintaining a biological activity that is at least 50%, 60%, 70%, 80%, 90%, 95%, 98%, or 99% of that of the parent polypeptide.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule, and can be an immunoglobulin of any class, e.g., IgG, IgM, IgA, IgD and IgE. IgY, which is the major antibody type in avian species such as chicken, is also included within the definition. As used herein, the term encompasses not only intact polyclonal or monoclonal antibodies, but also fragments thereof (such as Fab, Fab', F(ab')2, Fv), single chain (ScFv), mutants thereof, naturally occurring variants, fusion proteins comprising an antibody portion with an antigen recognition site of the required specificity, humanized antibodies, chimeric antibodies, and any other modified configuration of the immunoglobulin molecule that comprises an antigen recognition site of the required specificity.

As used herein, the term "antigen" refers to a target molecule that is specifically bound by an antibody through its antigen recognition site. The antigen may be monovalent or polyvalent, i.e., it may have one or more epitopes recognized by one or more antibodies. Examples of kinds of antigens that can be recognized by antibodies include polypeptides, oligosaccharides, glycoproteins, polynucleotides, lipids, etc.

As used herein, the term "epitope" refers to a portion of an antigen, e.g., a peptide sequence of at least about 3 to 5, preferably about 5 to 10 or 15, and not more than about 1,000 amino acids (or any integer there between), which define a sequence that by itself or as part of a larger sequence, binds to an antibody generated in response to such sequence. There is no critical upper limit to the length of the fragment, which may, for example, comprise nearly the full-length of the antigen sequence, or even a fusion protein comprising two or more epitopes from the target antigen. An epitope for use in the subject invention is not limited to a peptide having the exact sequence of the portion of the parent protein from which it is derived, but also encompasses sequences identical to the native sequence, as well as modifications to the native sequence, such as deletions, additions and substitutions (conservative in nature).

As used herein, the term "specifically binds" refers to the binding specificity of a specific binding pair. Recognition by an antibody of a particular target in the presence of other potential targets is one characteristic of such binding. Specific binding involves two different molecules wherein one of the molecules specifically binds with the second molecule through chemical or physical means. The two molecules are related in the sense that their binding with each other is such that they are capable of distinguishing their binding partner from other assay constituents having similar characteristics. The members of the binding component pair are referred to as ligand and receptor (anti-ligand), specific binding pair (SBP) member and SBP partner, and the like. A molecule may also be an SBP member for an aggregation of molecules; for example an antibody raised against an immune complex of a second antibody and its corresponding antigen may be considered to be an SBP member for the immune complex.

As used herein, a "tag" or an "epitope tag" refers to a sequence of amino acids, typically added to the N- and/or C-terminus of a polypeptide. The inclusion of tags fused to a polypeptide can facilitate polypeptide purification and/or detection. Typically a tag or tag polypeptide refers to polypeptide that has enough residues to provide an epitope recognized by an antibody or can serve for detection or purification, yet is short enough such that it does not interfere with activity of chimeric polypeptide to which it is linked. The tag polypeptide typically is sufficiently unique so an antibody that specifically binds thereto does not substantially cross-react with epitopes in the polypeptide to which it is linked. Suitable tag polypeptides generally have at least 5 or 6 amino acid residues and usually between about 8-50 amino acid residues, typically between 9-30 residues. The tags can be linked to one or more chimeric polypeptides in a multimer and permit detection of the multimer or its recovery from a sample or mixture. Such tags are well known and can be readily synthesized and designed. Exemplary tag polypeptides include those used for affinity purification and include His tags, the influenza hemagglutinin (HA) tag polypeptide and its antibody 12CA5; the c-myc tag and the 8F9, 3C7, 6E10, G4, B7 and 9E10 antibodies thereto; and the Herpes Simplex virus glycoprotein D (gD) tag and its antibody. See, e.g., Field et al. (1988) *Mol. Cell. Biol.* 8:2159-2165; Evan et al. (1985) *Mol. Cell. Biol.* 5:3610-3616; Paborsky et al. (1990) *Protein Engineering* 3:547-553.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-2'-O-allyl, 2'-fluoro- or 2'-azido-ribose, carbocyclic sugar analogs, a-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR 2 ("amidate"), P(O)R, P(O)OR', CO or CH 2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

As used herein, the term "homologue" is used to refer to a nucleic acid which differs from a naturally occurring nucleic acid (e.g., the "prototype" or "wild-type" nucleic acid) by minor modifications to the naturally occurring nucleic acid, but which maintains the basic nucleotide structure of the naturally occurring form. Such changes include, but are not limited to: changes in one or a few nucleotides, including deletions (e.g., a truncated version of the nucleic acid) insertions and/or substitutions. A homologue can have enhanced, decreased, or substantially similar properties as compared to the naturally occurring nucleic acid. A homologue can be complementary or matched to the naturally occurring nucleic acid. Homologues can be produced using techniques known in the art for the production of nucleic acids including, but not limited to, recombinant DNA techniques, chemical synthesis, etc.

As used herein, "substantially complementary or substantially matched" means that two nucleic acid sequences have at least 90% sequence identity. Preferably, the two nucleic acid sequences have at least 95%, 96%, 97%, 98%, 99% or 100% of sequence identity. Alternatively, "substantially complementary or substantially matched" means that two nucleic acid sequences can hybridize under high stringency condition(s).

In general, the stability of a hybrid is a function of the ion concentration and temperature. Typically, a hybridization reaction is performed under conditions of lower stringency, followed by washes of varying, but higher, stringency. Moderately stringent hybridization refers to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions are conditions equivalent to hybridization in 50% formamide, 5×Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.lx SSPE, and 0.1% SDS at 65° C. Low stringency hybridization refers to conditions equivalent to hybridization in 10% formamide, 5×Denhardt's solution, 6×SSPE, 0.2% SDS at 22° C., followed by washing in 1x SSPE, 0.2% SDS, at 37°

C. Denhardt's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M (EDTA). Other suitable moderate stringency and high stringency hybridization buffers and conditions are well known to those of skill in the art.

As used herein, the term "RNA interference" or "RNAi" refers generally to a process in which a double-stranded RNA molecule or a short hairpin RNA molecule reducing or inhibiting the expression of a nucleic acid sequence with which the double-stranded or short hairpin RNA molecule shares substantial or total homology. The term "short interfering RNA" or "siRNA" or "RNAi agent" refers to an RNA (or RNA analog) sequence comprising between about 10-50 nucleotides (or nucleotide analogs) that elicits RNA interference. See Kreutzer et al., WO 00/44895; Zernicka-Goetz et al., WO 01/36646; Fire, WO 99/32619; Mello & Fire, WO 01/29058. As used herein, siRNA molecules include RNA molecules encompassing chemically modified nucleotides and non-nucleotides. The term "ddRNAi agent" refers to a DNA-directed RNAi agent that is transcribed from an exogenous vector. The terms "short hairpin RNA" or "shRNA" refer to an RNA structure having a duplex region and a loop region. In certain embodiments, ddRNAi agents are expressed initially as shRNAs.

As used herein, "vector (or plasmid)" refers to discrete elements that are used to introduce heterologous DNA into cells for either expression or replication thereof. Selection and use of such vehicles are well known within the skill of the artisan. An expression vector includes vectors capable of expressing DNA's that are operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, "a promoter region or promoter element" refers to a segment of DNA or RNA that controls transcription of the DNA or RNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in prokaryotes include the bacteriophage T7 and T3 promoters, and the like.

As used herein, "operatively linked or operationally associated" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' untranslated portions of the clones to eliminate extra, potential inappropriate alternative translation initiation (i.e., start) codons or other sequences that may interfere with or reduce expression, either at the level of transcription or translation. Alternatively, consensus sites can be inserted immediately 5' of the start codon and may enhance expression. See, e.g., Kozak (1991) *J Biol. Chem.* 266:19867-19870. The desirability of (or need for) such modification may be empirically determined.

"Treating" or "treatment" or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent or treatment, the subject shows observable and/or measurable reduction in or absence of one or more signs and symptoms of the particular disease. Reduction of the signs or symptoms of a disease may also be felt by the patient. A patient is also considered treated if the patient experiences stable disease. In some embodiments, treatment with a therapeutic agent is effective to result in the patients being disease-free 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art. In some embodiments, "treatment" means any manner in which the symptoms of a condition, disorder or disease are ameliorated or otherwise beneficially altered. Treatment also encompasses any pharmaceutical use of the compositions herein. In some embodiments, "amelioration" of the symptoms of a particular disorder by administration of a particular pharmaceutical composition refers to any lessening, whether permanent or temporary, lasting or transient that can be attributed to or associated with administration of the composition.

The term "prediction" or "prognosis" is used herein to refer to the likelihood that a patient will respond either favorably or unfavorably to a drug or set of drugs, or the likely outcome of a disease. In one embodiment, the prediction relates to the extent of those responses or outcomes. In one embodiment, the prediction relates to whether and/or the probability that a patient will survive or improve following treatment, for example treatment with a particular therapeutic agent, and for a certain period of time without disease recurrence. The predictive methods of the invention can be used clinically to make treatment decisions by choosing the most appropriate treatment modalities for any particular patient. The predictive methods of the present invention are valuable tools in predicting if a patient is likely to respond favorably to a treatment regimen, such as a given therapeutic regimen, including for example, administration of a given therapeutic agent or combination, surgical intervention, steroid treatment, etc.

As used herein the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy, 20th ed., (Lippincott, Williams & Wilkins 2003). Except insofar as any conventional media or agent is incompatible with the active compound, such use in the compositions is contemplated.

A "pharmaceutically acceptable salt" is intended to mean a salt of a free acid or base of a compound represented herein that is non-toxic, biologically tolerable, or otherwise biologically suitable for administration to the subject. See, generally, Berge, et al., *J. Pharm. Sci.*, 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, y-hydroxybutyrates, glycolates, tartrates, and mandelates.

As used herein, the term "therapeutically effective amount" or "effective amount" refers to an amount of a therapeutic agent that when administered alone or in combination with an additional therapeutic agent to a cell, tissue, or subject is effective to prevent or ameliorate a disease or disorder associated with abnormally high level of IFP35 and/or NMI in a subject. A therapeutically effective dose further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. In some embodiment, "an effective amount of a compound for treating a particular disease" is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Repeated administration may be required to achieve the desired amelioration of symptoms.

The term "combination" refers to either a fixed combination in one dosage unit form, or a kit of parts for the combined administration where a compound and a combination partner (e.g., another drug as explained below, also referred to as "therapeutic agent" or "co-agent") may be administered independently at the same time or separately within time intervals, especially where these time intervals allow that the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a compound and a combination partner, are both administered to a patient simultaneously in the form of a single entity or dosage. The term "non-fixed combination" means that the active ingredients, e.g., a compound and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

As used herein, "biological sample" refers to any sample obtained from a living or viral source or other source of macromolecules and biomolecules, and includes any cell type or tissue of a subject from which nucleic acid or protein or other macromolecule can be obtained. The biological sample can be a sample obtained directly from a biological source or a sample that is processed. For example, isolated nucleic acids that are amplified constitute a biological sample. Biological samples include, but are not limited to, body fluids, such as blood, plasma, serum, cerebrospinal fluid, synovial fluid, urine and sweat, tissue and organ samples from animals and plants and processed samples derived therefrom.

The terms "level" or "levels" are used to refer to the presence and/or amount of a target, e.g., a protein or polynucleotide, and can be determined qualitatively or quantitatively. A "qualitative" change in the target, protein or polynucleotide level refers to the appearance or disappearance of a target, protein or polynucleotide that is not detectable or is present in samples obtained from normal controls. A "quantitative" change in the levels of one or more targets, proteins or polynucleotides refers to a measurable increase or decrease in the target, protein or polynucleotide levels when compared to a healthy control.

A "healthy control" or "normal control" is a biological sample taken from an individual who does not suffer from a disease or disorder associated with abnormally high level of IFP35 and/or NMI. A "negative control" is a sample that lacks any of the specific analyte the assay is designed to detect and thus provides a reference baseline for the assay.

As used herein, "mammal" refers to any of the mammalian class of species. Frequently, the term "mammal," as used herein, refers to humans, human subjects or human patients. "Mammal" also refers to any of the non-human mammalian class of species, e.g., experimental, companion or economic non-human mammals. Exemplary non-human mammals include mice, rats, rabbits, cats, dogs, pigs, cattle, sheep, goats, horses, monkeys, Gorillas and chimpanzees.

As used herein, "production by recombinant means" refers to production methods that use recombinant nucleic acid methods that rely on well-known methods of molecular biology for expressing proteins encoded by cloned nucleic acids.

As used herein, the term "subject" is not limited to a specific species or sample type. For example, the term "subject" may refer to a patient, and frequently a human patient. However, this term is not limited to humans and thus encompasses a variety of non-human animal or mammalian species.

As used herein, a "prodrug" is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

As used herein, "test substance (or candidate compound)" refers to a chemically defined compound (e.g., organic molecules, inorganic molecules, organic/inorganic molecules, proteins, peptides, nucleic acids, oligonucleotides, lipids, polysaccharides, saccharides, or hybrids among these molecules such as glycoproteins, etc.) or mixtures of compounds (e.g., a library of test compounds, natural extracts or culture supernatants, etc.) whose effect on IFP35 and/or NMI is determined by the disclosed and/or claimed methods herein.

As used herein, high-throughput screening (HTS) refers to processes that test a large number of samples, such as samples of diverse chemical structures against disease targets to identify "hits" (see, e.g., Broach, et al., High throughput screening for drug discovery, Nature, 384:14-16 (1996); Janzen, et al., High throughput screening as a discovery tool in the pharmaceutical industry, Lab Robotics Automation: 8261-265 (1996); Fernandes, P.B., Letter from the society president, J Biomol. Screening, 2:1 (1997); Burbaum, et al., New technologies for high-throughput screening, Curr. Opin. Chem. Biol., 1:72-78 (1997)). HTS operations are highly automated and computerized to handle sample preparation, assay procedures and the subsequent processing of large volumes of data.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Other objects, advantages and features of the present invention will become apparent from the following specification taken in conjunction with the accompanying drawings.

C. Methods for Treating and/or Preventing a
Disease or Disorder Associated with Abnormally
High Level and/or Activity of the IFP35 Family of
Proteins The IFP35 family proteins, including IFP35 and NMI, can be rapidly up-regulated by type I or type II interferon in numerous immune cells. Yang et al., PLoS One 7, e50932 (2012); Das et al., Journal of Virology 88, 3103-3113 (2014); Zhu et al., Cell 96, 121-130 (1999); and Lebrun et al., Journal of Interferon & Cytokine Research 18, 767-771 (1998). The functions of IFP35 family members are not clear. IFP35 family members are predicted to consist of a Leucine-zipper (L-zip) domain in their N-termini, followed by two tandem structural and functional unknown NMI/IFP35 domains (NIDs). In the early report, people found IFP35 and NMI located in the cytoplasm using immuno-fluorescence microscopy. Lebrun et al., Journal of Interferon & Cytokine Research 18, 767-771 (1998). They could assemble into high molecular mass complex (HMMC) mediated by their NID domains and further into functional unknown speckle-like aggregations. Zhou et al., JBC 275, 21364-21371 (2000); and Chen et al., JBC 275, 36278-84 (2000). It was known that IFP35 could recognize specific viral nucleic acids from bovine foamy virus, and inhibit the virus transcription. Tan et al., Journal of Virology 82, 4275-4283 (2008). However, recent results suggested that it could support vesicular stomatitis virus replication, by specifically interacted with RIG-1 (retinoic acid-inducible gene I) and negatively regulated the host innate immune response. Das et al., Journal of Virology 88, 3103-3113 (2014). Investigations of NMI mainly focused on its inhibitory effects on the proliferation and metastasis of cancer cells, by regulating multiple signaling pathways. Li et al., Mol Biol Cell 23, 4635-4646 (2012); Fillmore et al., International Journal of Cancer 125, 556-64 (2009); and Li et al., JBC 277, 20965-73 (2002). To further explore the potential functions and mechanisms of IFP35 family members, the inventors determined the X-ray crystallography structure of the NID domain in IFP35. It was found that IFP35 and NMI could serve as DAMPs for immune modulation. Some DAMP proteins were reported to be recognized by specific cell-surface receptor, TLR4, with the help of MD2 and other associated proteins. See Yang et al., PNAS 107, 11942-11947 (2010); Nagai et al., Nature Immunology 3, 667-672 (2002); and Zanoni et al., Cell 147, 868-880 (2011). A complex signal cascade can be trigged to activate the transcription factor NF-κB, resulting in cytokines release and enhanced host inflammatory response. See Meylan et al., Nature Immunology 5, 503-507 (2004); Moynagh, Trends in Immunology 26, 469-476 (2005); and Lu et al., Cytokine 42, 145-151 (2008).

In some aspects, disclosed herein is a use of a truncated IFP35 protein (e.g., octamer of the truncated protein) or a truncated NMI protein in preparation of an agent for regulating the inflammatory response. In some aspects, disclosed herein is a use of a truncated IFP35 protein (e.g., octamer of the truncated protein) or a truncated NMI protein in preparation of antineoplastic products. In some aspects, by using a IFP35 antibody or NMI antibody to neutralize IFP35 or NMI in cells or the humoral fluids, it can effectively regulate IFP35 or NMI protein overexpression-induced excessive inflammatory response, inhibit inflammatory effect, avoid the generation of body and tissue damage by inflammation and dramatically improve the survival rate of a subject, such as a subject with a bacterial or viral infection or autoimmune disease. In some embodiments, the subject is with a viral infection (such as influenza virus, SARS, MERS, HBV, HCV), bacterial infection (such as *Mycobacterium tuberculosis*), fungal infection, and/or infection caused by other pathogens. In some aspects, the infections provoke expression of a IFP35 family protein, such as IFP35 and/or NMI expression. Overexpression of IFP35 and/or NMI in the infected patients may lead to severe damage of their organs and bodies. Abnormally high level of IFP35 may lead to tissue or organ damage because of provoking of cytokine storm.

Thus, the present compositions and/or methods can be used to treat, ameliorate, and/or prevent a number of infectious diseases, infection states, inflammation, autoimmune disease, graft-versus-host disease, or conditions associated with over-activation of the immune system in a subject. Pathogenic viruses include, but are not limited to, Retroviridae (e.g., human immunodeficiency viruses, such as HIV-1 (also referred to as HTLV-III, LAV or HTLV-III/LAV, or HIV-III); and other isolates, such as HIV-LP; Picornaviridae (e.g., polio viruses, hepatitis A virus; enteroviruses, human coxsackie viruses, rhinoviruses, echoviruses); Caliciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviruses and rotaviruses); Bimaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses); Poxyiridae (variola viruses, vaccinia viruses, pox viruses); and Iridoviridae (e.g., African swine fever virus); Hepatitis C virus; and unclassified viruses (e.g., the agent of delta hepatitis (thought to be a defective satellite of hepatitis B virus); Norwalk and related viruses, and astroviruses).

Pathogenic bacteria include, but are not limited to, *Helicobacterpyloris, Borelia burgdorferi, Legionella pneumophila, Mycobacteria* sps (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyrogenes* (Group A Streptococcus), *Streptococcus agalactiae* (Group B Streptococcus), *Streptococcus* (viridans group), *Streptococcus faecalis, Streptococcus bovis, Streptococcus* (anaerobic sps.), *Streptococcus pneumoniae,* pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasteurella multocida, Bacteroides* sp., *Fusobacterium nucleatum,* pathogenic strains of *Escherichia coli, Streptobacillus moniliformis, Treponema pallidum, Treponema pertenue, Leptospira,* and *Actinomyces israelli.*

Infectious fungi include, but are not limited to, Cryptococcus neoformans, Histoplasma capsulatum, Coccidioides immitis, Blastomyces dermatitidis, Chlamydia trachomatis, Candida albicans.

Infectious protozoa include, but are not limited to, Plasmodium spp., e.g., Plasmodium falciparum; Trypanosomes, e.g., Trypanosoma cruzi; and Toxoplasma gondii.

Allergens include, but are not limited to, pollens, insect venoms, animal dander dust, fungal spores and drugs (e.g. penicillin). Examples of natural, animal and plant allergens include proteins specific to the following genera: Canine (*Canis familiaris*); Dermatophagoides (e.g. *Dermatophagoides farinae*); Felis (*Felis domesticus*); Ambrosia (*Ambrosia artemiisfolia; Lolium* (e.g. *Lolium perenne* or *Lolium multiflorum*); Cryptomeria (*Cryptomeria japonica*); Alternaria (*Alternaria alternata*); Alder; Alnus (*Alnus gultinosa*); Betula (*Betula verrucosa*); Quercus (*Quercus alba*); Olea (*Olea europa*); Artemisia (*Artemisia vulgaris*); Plantago (e.g. *Plantago lanceolata*); Parietaria (e.g. *Parietaria officinalis* or *Parietaria judaica*); Blattella (e.g. *Blattella germanica*); Apis (e.g. Apis *multiflorum*); Cupressus (e.g. *Cupressus sempervirens, Cupressus arizonica* and *Cupressus macrocarpa*); Juniperus (e.g. *Juniperus sabinoides, Juniperus virginiana, Juniperus communis* and *Juniperus ashei*); Thuya (e.g. *Thuya orientalis*); Chamaecyparis (e.g. *Charnaecyparis obtusa*); Periplaneta (e.g. *Periplaneta americana*); Agropyron(e.g. *Agropyron repens*); Secale (e.g. *Secale cereale*); Triticum (e.g. *Triticum aestivum*); Dactylis (e.g. *Dactylis glomerata*); Festuca(e.g. *Festuca elatior*); Poa (e.g. *Poa pratensis* or *Poa compressa*); Avena (e.g. *Avena sativa*); Holcus (e.g. *Holcus lanatus*); Anthoxanthum (e.g. *Anthoxanthum odoratum*); Arrhenatherum (e.g. *Arrhenatherum elatius*); Agrostis(e.g. *Agrostis alba*); Phleum (e.g. *Phleum pratense*); Phalaris (e.g. *Phalaris arundinacea*); Paspalum (e.g. *Paspalum notatum*); Sorghum (e.g. *Sorghum halepensis*); and Bromus (e.g. *Bromus inermis*). Use of epitopes from the above allergens in the present methods for antibody detection and analysis is also envisaged.

In some aspects, the present compositions and/or methods can also be used for relieving disease-induced or associated suppression of a subject's immune system, such as cancer-induced or associated suppression of the subject's immune system. For example, by administering a IFP35 family protein or analog or derivative therefore, the subject's immune response can be activated and/or augmented in order to overcome the disease-causing vector's ability to evade an immune reaction. This therapeutic approach is applicable to disease states whereby immune system suppression has been demonstrated, such as bacterial infections, parasitic infections including malaria and typanosomiasis, viral infections, peptic ulcers and gastric cancer due to *H. Pylori* infection together with prevention of pregnancy.

In some aspects, provided herein are the amino acid residues that are involved in binding with a IFP35 receptor or an antagonist antibody against IFP35. In one aspect, the domain-swapping dimer form an arc intersecting surface area, and the dimer provides some residues such as Ser145, Asp172, Val173, Leu177, Arg212, Gln199, Gln207, Gln208, Pro210, Ser214, Thr201, and Tyr216 to form a large exposed surface as shown in FIGS. 16A-C. Among the residues, residues Glu150, Glu175, Leu177, Gln207, and Gln208 are in a more prominent position (FIG. 16A). Consequently, they are more likely to bind the receptor or antibody.

In some aspects, other residues on the inner surface of the ring structure formed by the IFP5-NID octamer participate in the interaction with other proteins. These residues can include Ser145, Arg147, Glu150, Glu151, Val173, Gly206, Gln207, and Gln208. In some aspects, Arg147, Gln207, Gln208, Glu150, and Glu151 provide extended side chains that protrude from the inner surface of octamer ring structure (FIG. 16B).

Based on the structure of the dimer or the octamer, there are some relatively large amino acid residues near the top of the amino terminus and the carboxyl terminus of the p sheet barrel-like structure of the single monomer or domain-swapping monomer; these relatively large amino acid residues extend outwards. These residues can include Arg187, Glu188, G1n192, Gln196, Arg212, and Tyr216, and they are close in distance. Furthermore, some amino acid residues may participate in binding to other proteins, antibodies, or small molecules (FIG. 16C).

These residues above are located on the surface of the structure. In some embodiments, these residues participate in binding with the receptor or the antibody and are the key position for drug inhibition.

In some aspects, the present inventors have expressed, purified, and crystalized IFP35 and NMI, and have also determined the structure of one fragment of IFP35. The fragment of IFP35 can induce inflammatory response and further IFP35 and NMI can be secreted out from the cell to stimulate intense inflammatory response. It can be effective to control the excessive inflammatory response caused by the excessive secretory expression of IFP35 or NMI through neutralization of IFP 35 or NMI in cell solution or body fluids using a IFP35 antibody or a NMI antibody. In some aspects, the present disclosure avoids the damage of the body and the tissue and raises the survival rates of the subjects. The results indicate that a disease or condition associated with the excessive expression of IFP35 and NMI, such as bacterial infections, virus invasions, autoimmune diseases, tumor, and other infections, may be controlled by the reduction of the concentration of IFP35 and/or NMI. Meanwhile, diseases caused by the defect or deficiency of the expression and/or procession (such as secretion) of IFP35 and/or NMI may be improved through the addition of the proteins.

Below is a sequence alignment of human IFP35 (hIFP) (SEQ ID NO: 2), mouse IFP35 (mIFP) (SEQ ID NO: 4), human NMI (hNMI) (SEQ ID NO: 8) and mouse NMI (mNMI) (SEQ ID NO: 6), using CLUSTAL 2.1 multiple sequence alignment.

```
hNMI        MEADKDDTQQILKEHSPD-EFIKDEQNKGLIDEITKKNIQLKKEIQKLETELQEATKEFQ   59
mNMI        MDADKDNIKQACDERSAEMDDMRGEQSMGLVHEIMSENKELDEEIKKLEAELQSDAREFQ   60
hIFP        ----------------------MSAPLDAALHALQEEQARLKMRLWDLQQLRKELGDSPK   38
mIFP        ----------------------MSVTLQTVLYSLQEEQARLKMRLQELQQLKRERTGSPG   38
            .     :    : .:: .*. .: .*:       :. .

hNMI        IKEDIPETKMKFLSVETPENDSQLSNISCSFQVSSKVPYEIQKGQALITFEKEEVAQNVV   119
mNMI        IKENVPEKKLKLTSVESPKDGCHFSNSSCSFQVSSQILYELQEGQALITFEKEEVAQNVI   120
hIFP        DKVPFSVPKIPLVFRGHTQQDPEVPKSLVS---NLRIHCPLLAGSALITFDDPKVAEQVL   95
mIFP        AKIPFSVPEVPLVFQGQTKQGRQVPKFVVS---NLKVCCPLPEGSALVTFEDPKVVDRLL   95
            .  .. ::  :    .:::. ...:   *    . ::    :  *.**:**:. :*.:.::
```

```
                                    -continued
hNMI       SMSKHHVQIKDVNLEVTAKPVPLNSGVRFQVY--VEVSKMKINVTEIPD--TLREDQMRD  175
mNMI       SMGNHVVQMEGTPVKVSAHPVPLNTGVRFQVH--VDISKMKINVTGIPD--ELSEEQTRD  176
hIFP       QQKEHTINMEECRLRVQVQPLELPMVTTIQVMMSSQLSGRRVLVTGFPASLRLSEEELLD  155
mIFP       QQKEHRVNLEDCRLRVQVQPLELPVVTNIQV--SSQPDNHRVLVSGFPAGLRLSEEELLD  153
           . :*  ::::   :.*  .:*: *    . :**    :.  :: *: :*    * *:: * hNMI       KLELSFSKSRNGGGEVDRVDYDRQSGSAVITFVEIGVADKILKKKEYPLYINQTCHRVTV  235
mNMI       KLELSFCKSRNGGGEVESVDYDRKSRSAVITFVETGVVDKILKKKTYPLYMNQKCHSVAV  236
hIFP       KLEIFFGKTRNGGGDVDVR--ELLPGSVMLGFARDGVAQRLCQIGQFTVPLGGQQVPLRV  213
mIFP       KLEIFFGKAKNGGGDVETR--EMLQGTVMLGFADEEVAQHLCQIGQFRVPLDRQQVLLRV  211
           ::::  *  *::****:*:    :     :.:: *.   *.::: :    :  : :.     : * hNMI       SPYTEIHLKKYQIFSGTSKRTVLLTGMEGIQMDEEIVEDLINIHFQRAKNGGGEVDVVKC  295
mNMI       SPCIERCLEKYQVFSAVSKKTVLLTGLEGIPVDEETGEDLLNIHFQRKNNGGGEVEVVKC  296
hIFP       SPYVNGEIQKAEIRSQPVPRSVLVLNIPDI-LDGPELHDVLEIHFQKPTRGGGEVEALTV  272
mIFP       SPYVSGEIQKAEIKFQQAPHSVLVTNIPDV-MDAQELHDILEIHFQKPTRGGGEVEALTV  270
           **  .  ::* ::    ::**:  .:  .:  :*   .*::::****:  ..*****:.:.

hNMI       S-LGQPHIAYFEE------  (SEQ ID NO: 8)                          307
mNMI       S-LDQSFAAYFKEEARETI  (SEQ ID NO: 6)                          314
hIFP       VPQGQQGLAVFTSESG---  (SEQ ID NO: 2)                          288
mIFP       VPSGQQGLAIFTSESS---  (SEQ ID NO: 4)                          286
```

In some embodiments, provided herein is a method of using a IFP35 family protein in provoking an immune response. In another embodiment, provided herein is a method of inhibiting and/or reducing a IFP35 family protein, such as IFP35 and NMI, in order to inhibit cytokine storm, such as by infection of bacteria, viruses or organ damaging induced by abnormal high level of IFP35/NMI by food or drug. The organ may include lung, kidney, liver or others organs.

In some embodiments, provided herein is an antagonist compound for a IFP35 family protein, such as an antibody or a small molecule compound, for treating or preventing a disease or condition associated with or caused by abnormal levels of the IFP35 family protein.

In other embodiments, provided herein is a method for applying the crystal structure method for further designing and/or selecting an antibody or compound. In one aspect, the structure is used to see how drugs or antibody binds to the target protein, and then the antibody or compound can be further modified. From the target protein/antibody co-crystal structure, epitope of the target protein can also be identified.

Embodiment 1: Application of truncated IFP35 protein in preparing reagents/products to provoke immune response and inflammation or in preparing anti-tumor products, wherein said truncated IFP35 is human IFP35 or mouse IFP35, wherein said truncated human IFP35 is as 1) or 2) below:

1) protein with residues as in SEQ ID NO: 2, from residues 136-216;

2) said protein sequence as in 1), wherein 1-10 additional residues are added to the sequence's amino or/and carboxyl terminus, and the sequence homology is at least about 90% to the sequence of 1);

wherein said truncated mouse IFP35 is as 3) or 4) below:

3) protein with residues as in SEQ ID NO: 4, from residues 134-216;

4) said protein sequence as in 3), wherein 1-10 additional residues are added to the sequence's amino or/and carboxyl terminus, and the sequence homology is at least about 90% to the sequence of 3).

Embodiment 2: A method of Embodiment 1, wherein the truncated human IFP35 protein as shown in SEQ ID NO: 2, from residues 124-220.

Embodiment 3: A method in preparing products to provoke immune response/inflammation by IFP35 protein or in preparing products to against tumor/cancer, wherein said sequence of IFP35 protein is shown as in SEQ ID NO: 2 or SEQ ID NO: 4.

Embodiment 4: A method in preparing products to provoke immune response/inflammation by IFP35 mutant proteins or in preparing products to against tumor/cancer, wherein said IFP35 mutant protein has at least one mutation and/or modification of a residue involved in binding a IFP35 receptor or an inhibitory antibody, which mutation and/or modification leads to reduced or no binding of IFP35 to the IFP35 receptor or inhibitory antibody, wherein said residue involved in receptor binding/antibody binding is Ser145, Asp172, Val 173, Leu 177, Arg212, Gln199, Gln207, Gln 208, Pro210, Ser214, Thr201, Tyr216, Glu150, Glu175, Gln208, Arg147, Glu151, or Gly206, or any combination thereof. According to the structure comparison results, corresponding position residues that are in sequences from other sources of IFP35 and NMI are within the present disclosure. According to the structure comparison results, IFP35 and NMI both have two NID domains, these two NID domains are homologs to each other, therefore, corresponding NID region residues of IFP35 and NMI outside the structure determined IFP35 NID domain are within the present disclosure.

Embodiment 5: The method according to any of Embodiments 1-4, wherein the method induces immune response/inflammation to increase expression of inflammation factors, recruitments of neutrophils or stimulate NF-κB pathway, wherein said inflammation factors include: IL-1β, TNF-α, iNOS, or CD86, and wherein said stimulating NF-κB pathway is to increase IκBα to reduce the total IκBα amount.

Embodiment 6: A method to inhibit diseases by abnormal high amount of IFP35 induced over immune response or application of product that inhibit IFP35 protein to inhibit inflammation factor expression/reaction.

Embodiment 7: The method of Embodiment 6, wherein said inhibitory product or reagent is a IFP35 antibody that inhibits IFP35 protein activity, and/or wherein the antibody is monoclonal or polyclonal, and/or wherein said disease is sepsis, and/or wherein said inflammation factors include: IL-1β, TNF-α, iNOS, or CD86.

Embodiment 8: Use of a truncated NMI protein in preparing reagents/products to provoke immune response and inflammation or in preparing anti-tumor products, wherein said truncated NMI is truncated human NMI or mouse NMI, wherein said truncated human NMI protein has a sequence set forth in SEQ ID NO: 8, from residues 155-240, and said truncated mouse NMI protein has a sequence set forth in SEQ ID NO: 6, from residues 151-250.

Embodiment 9: A method in preparing products to provoke immune response/inflammation by NMI protein or in preparing products to against tumor/cancer, wherein said NMI protein is human or mouse NMI protein, said sequence of human NMI is set forth in SEQ ID NO: 8, or said sequence of mouse IFP35 is set forth in SEQ ID NO: 6.

Embodiment 10: A method in preparing products to provoke immune response/inflammation by NMI mutant proteins or in preparing products to against tumor/cancer, wherein said NMI mutant protein is that involved residues are mutated, leading to no binding of NMI to NMI receptor or inhibitory antibody.

Embodiment 11: The method according to any of Embodiments 8-11, wherein said provoking the immune response/inflammation stimulates inflammation factors expression and/or stimulates NF-κB pathway signaling, wherein said inflammation factors include: IL-1β, TNF-α, iNOS, or CD86, and wherein said stimulating NF-κB pathway is to increase IκBα to reduce the total IκBα amount.

Embodiment 12: A method of preparing a product that inhibits NMI protein activity to treat diseases induced by abnormal high expression of NMI or a product that inhibits NMI to inhibit inflammation factors expression.

Embodiment 13: The method according to Embodiment 12, wherein said product is a NMI antibody, optionally wherein said antibody is a monoclonal or polyclonal antibody, optionally wherein said disease is sepsis, optionally wherein said inflammation factors include: IL-1β, TNF-α, iNOS, or CD86.

Embodiment 14: A method to over-express and crystallize truncated IFP35 protein, comprising:
  1) Using bacteria cells to express the truncated protein as said in Embodiment 1;
  2) Purifying said truncated IFP35 protein;
  3) Crystalizing the purified truncated protein.

Embodiment 15: The method according to Embodiment 14, further comprising: cloning the truncated IFP35 NID fragment genes to a vector (e.g., pGEX-6p-1 vector) in order to express a N terminal GST-tagged fusion protein (GST-IFP35-NID), then transforming this plasmid vector to an *E. coli* cell, after IPTG induction, then collecting bacteria for purification, wherein said purification step comprises: an affinity chromatography (glutathione column) step, removing of GST fusion tag by enzyme, and/or an ion exchange column step, and/or a gel filtration column step.

Embodiment 16: A method to crystalize NMI protein or its truncations, comprising:
  1) Expressing the NMI truncation proteins described as in Embodiment 8 in eukaryotic cells;
  2) Purifying these truncated proteins;
  3) Crystallizing these proteins.

Embodiment 17: The method according to Embodiment 14, further comprising: cloning the truncated NMI NID fragment genes to a vector (e.g., pGEX-6p-1 vector) in order to express a N terminal GST-tagged fusion protein (GST-NMI-NID), then transforming this plasmid vector to an *E. Coli* cell, after IPTG induction, then collecting bacteria for purification, wherein said purification step comprises: an affinity chromatography (glutathione column) step, removing of GST fusion tag by enzyme, and/or an ion exchange column step, and/or a gel filtration column step.

Embodiment 18: A method of designing or modifying a IFP35 family protein, such as IFP35 and NMI, in order to treat tumor, immune deficient diseases, etc., by targeting the IFP35 family protein to treat the disease.

Embodiment 19: A structure having a root mean square deviation (RMSD) in its core region less than about 1.5 anstrom to the IFP35-NID structure disclosed herein, according to the atom coordinates of the IFP35-NID crystal structure disclosed herein.

Embodiment 20. An atomic level structure having a root mean square deviation (RMSD) less than 1.5 astrom to the core region of IFP35-NID domain (includes residues 136-216).

Embodiment 21. A IFP35 antibody, 1D7, produced against human IFP35 in mouse, and deposited in China General Microbiological Culture Collection Center (CGMCC) under CGMCC 9573.

Embodiment 22. A IFP35 truncation protein having a human or mouse origin, wherein said human IFP35 truncation is:
  1) A protein with sequence as shown in SEQ ID NO: 4, from residues 134-216; or
  2) A protein with sequences same to 1) but with additional 1-10 residues at its amino or carboxyl terminus, wherein the homology of the protein to the protein in 1) is at least about 90%.

Embodiment 23. A IFP35 family protein having a mutation at a residue involved in binding of the IFP35 family protein to a receptor or a neutralizing antibody, wherein the mutation disrupts or reduces binding to the receptor or neutralizing antibody, wherein the residue is: Ser145, Asp172, Val 173, Leu 177, Arg212, Gln199, Gln207, Gln 208, Pro210, Ser214, Thr201, Tyr216, Glu150, Glu175, Gln208, Arg147, Glu151, or/and Gly206 of human IFP set forth in SEQ ID NO: 2, or a residue in the IFP35 family protein that corresponds to the listed residue of SEQ ID NO: 2.

Embodiment 25. A NMI truncation protein from residues 155-240 (for human NMI set forth in SEQ ID NO: 8) and from residues 151-250 (for mouse NMI forth in SEQ ID NO: 6).

D. Pharmaceutical Compositions for Treating and/or Preventing a Disease or Disorder Associated with Abnormally High Level and/or Activity of IFP35 and/or NMI In another aspect, the present disclosure provides for a pharmaceutical composition for treating and/or preventing a disease or disorder associated with abnormally high level of IFP35 and/or NMI in a subject, which pharmaceutical composition comprises an effective amount of an agent that prevents or reduces production and/or an activity of IFP35 and/or NMI in a subject and a pharmaceutically acceptable carrier or excipient.

The present pharmaceutical compositions can be used to treat and/or prevent any suitable disease or disorder associated with abnormally high level of IFP35 and/or NMI in a subject.

In some embodiments, the present pharmaceutical compositions can be used to treat a disease or disorder associated with abnormally high level of IFP35 and/or NMI. In other embodiments, the present pharmaceutical compositions can be used to prevent a disease or disorder associated with abnormally high level of IFP35 and/or NMI.

Any suitable agents can be used in the present pharmaceutical compositions to treat and/or prevent any suitable disease or disorder associated with abnormally high level of IFP35 and/or NMI in a subject. For example, a suitable agent can be used to reduce copy number of IFP35 and/or NMI gene, to block or reduce replication of IFP35 and/or NMI gene, to block or reduce transcription of IFP35 and/or NMI gene, to block or reduce translation of IFP35 and/or NMI mRNA, and/or to inhibit one, some or all activities of IFP35 and/or NMI. In some embodiments, the agent comprises a polynucleotide (such as an siRNA, shRNA, or miRNA) targeting the gene encoding IFP35 and/or NMI. The siRNA can target any suitable portion of the IFP35 and/or NMI gene. For example, the siRNA can target a portion of the IFP35 and/or NMI gene that encodes one or more NIDs. In other embodiments, the agent comprises an antisense RNA targeting the gene encoding IFP35 and/or NMI. The anti-sense RNA can target any suitable portion of the IFP35 and/or NMI gene.

In still other embodiments, the agent inhibits or modifies a nuclear factor that controls IFP35 and/or NMI transcription. Any suitable agent that inhibits or modifies a nuclear factor that controls IFP35 and/or NMI transcription can be used in the present methods.

In yet other embodiments, the agent comprises an anti-body that specifically binds to IFP35 and/or NMI. The antibody can specifically bind to any suitable portion of the IFP35 and/or NMI. For example, the antibody can specifi-cally bind to one or more NIDs of IFP35 and/or NMI. In another example, the antibody can specifically bind to a portion of IFP35 and/or NMI that interacts with the cellular IFP35 and/or NMI receptors.

In some aspects, disclosed herein is an antibody or antigen binding fragment thereof that specifically binds to IFP35 and/or NMI, and the antibody or antigen binding fragment thereof comprises a heavy chain variable region comprising a complementarity determining region (CDR) consisting of the amino acid sequences of a CDR in the heavy chain variable region sequence set forth in SEQ ID NO: 9 and/or a light chain variable region comprising a CDR consisting of the amino acid sequence of a CDR in the light chain variable region sequence set forth in SEQ ID NO:10. In one embodi-ment, the antibody or antigen binding fragment thereof comprises a heavy chain variable region set forth in SEQ ID NO: 9 and a light chain variable region set forth in SEQ ID NO:10. Conservative substitution(s) may be introduced into the CDRs and/or framework regions (FRs) of an antibody disclosed herein.

```
                                      (SEQ ID NO: 9)
V Q L V E S G P E L K K P G E T V K I S C K A S G

Y T F T N Y G M N W V K Q A P G K G L K W M G W I

N T Y T G E P T F A D D F K G R F A F S L E T S A

S T A Y L Q I N N L K N E D T A T Y F C A R Y G Y

S W A M D Y W G Q G T S V T V S S A S T.

(SEQ ID NO: 10)
D I V M T Q S P A I M S A S P G E K V T M T C S A

S S S V S Y M H W Y Q Q K S G T S P K R W I Y D T

S K L A S G V P A R F S G S G S G T S Y S L T I S

S M E A E D A A T Y Y C Q Q W S S N P P I T F G A

G T K L E I K.
```

In one aspect, disclosed herein is an isolated polynucle-otide encoding an antibody or antigen binding fragment thereof that specifically binds to IFP35 and/or NMI. In some embodiments, the antibody or antigen binding fragment thereof comprises a heavy chain variable region comprising a complementarity determining region (CDR) consisting of the amino acid sequence of a CDR in the heavy chain variable region sequence set forth in SEQ ID NO: 9 and/or a light chain variable region comprising a CDR consisting of the amino acid sequences of a CDR in the light chain variable region sequence set forth in SEQ ID NO: 10. In some aspects, the antibody or antigen binding fragment thereof comprises a heavy chain variable region set forth in SEQ ID NO: 9 and a light chain variable region set forth in SEQ ID NO:10. In other embodiments, the isolated poly-nucleotide comprises the nucleic acid sequence sent forth in SEQ ID NO: 11 and/or SEQ ID NO: 12.

```
                                     (SEQ ID NO: 11)
TGGTCGACGCTGAGGAGACGGTGACTGAGGTTCCTTGACCCCAGTAGTC

CATAGCCCAAGAGTACCCGTATCTTGCACAGAAATATGTAGCCGTGTCC

TCATTCTTGAGGTTGTTGATCTGCAAATAGGCAGTGCTGGCAGAGGTTT

CCAAAGAGAAGGCAAACCGTCCCTTGAAGTCATCAGCAAATGTTGGCTC

TCCAGTGTAGGTGTTTATCCAGCCCATCCACTTTAAACCCTTTCCTGGA

GCCTGCTTCACCCAGTTCATTCCATAGTTTGTGAAGGTATACCCAGAAG

CCTTGCAGGAGATCTTGACTGTCTCTCCTGACTCCTTAAGCTGCACCT.

(SEQ ID NO: 12)
GACATTGTGATGACCCAGTCTCCAGCAATCATGTCTGCATCTCCAGGGG

AGAAGGTCACCATGACCTGCAGTGCCAGCTCAAGTGTAAGTTACATGCA

CTGGTACCAGCAGAAGTCAGGCACCTCCCCCAAAAGATGGATTTATGAC

ACATCCAAACTGGCTTCTGGAGTCCCTGCTCGCTTCAGTGGCAGTGGGT

CTGGGACCTCTTACTCTCTCACAATCAGCAGCATGGAGGCTGAAGATGC

TGCCACTTATTACTGCCAGCAGTGGAGTAGTAACCCACCCATCACGTTC

GGTGCTGGCACCAAGCTGGAAATCAAA.
```

The terms "complementarity determining region," and "CDR," are known in the art to refer to non-contiguous sequences of amino acids within antibody variable regions, which confer antigen specificity and binding affinity. In general, there are three (3) CDRs in each heavy chain variable region (CDR-H1, CDR-H2, CDR-H3) and three (3) CDRs in each light chain variable region (CDR-L1, CDR-L2, CDR-L3).

The precise amino acid sequence boundaries of a given CDR can be readily determined using any of a number of well-known schemes, including those described by Kabat et al. (1991), "Sequences of Proteins of Immunological Inter-est," 5th Ed. Public Health Service, National Institutes of Health, Bethesda, MD ("Kabat" numbering scheme), Al-Lazikani et al., (1997) JMB 273,927-948 ("Chothia" num-bering scheme), MacCallum et al., J. Mol. Biol. 262:732-745 (1996), "Antibody-antigen interactions: Contact analysis and binding site topography," *J. Mol. Biol.* 262, 732-745." (Contact" numbering scheme), Lefranc MP et al., "IMGT unique numbering for immunoglobulin and T cell receptor variable domains and Ig superfamily V-like domains," *Dev Comp Immunol,* 2003 January;27(1):55-77 ("IMGT" numbering scheme), and Honegger A and Pluck-thun A, "Yet another numbering scheme for immunoglobu-lin variable domains: an automatic modeling and analysis tool," *J Mol Biol,* 2001 June 8; 309(3):657-70, (AHo num-bering scheme).

The boundaries of a given CDR may vary depending on the scheme used for identification. For example, the Kabat scheme is based structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

Thus, unless otherwise specified, the terms "CDR" and "complementary determining region" of a given antibody or region thereof, such as a variable region, as well as individual CDRs (e.g., "CDR-H1, CDR-H2) of the antibody or region thereof, should be understood to encompass the complementary determining region as defined by any of the known schemes described herein above.

As used herein, the term "conservative substitution" refers to substitutions of amino acids and/or amino acid sequences that are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al., MOLECULAR BIOLOGY OF THE GENE, The Benjamin/Cummings Pub. Co., p. 224 (4th Edition 1987)). For example, such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, pages 13-15 "Biochemistry" 2nd ED. Lubert Stryer ed (Stanford University); Henikoff et al., PNAS 1992 Vol 89 10915-10919; Lei et al., J Biol Chem 1995 May 19; 270 (20):11882-6). Other substitutions are also permissible and may be determined empirically or in accord with known conservative substitutions.

In yet other embodiments, the agent can comprise a variant form of IFP35 and/or NMI. Any suitable variant form of IFP35 and/or NMI can be used in the present methods. For example, the variant form of IFP35 and/or NMI can be a mutant IFP35 and/or NMI and/or a fragment of IFP35 and/or NMI.

The pharmaceutical compositions can be administered via any suitable route. For example, the pharmaceutical compositions can be administered via an oral, nasal, inhalational, parental, intravenous, intraperitoneal, subcutaneous, intramuscular, intradermal, topical, or rectal route.

In some embodiments, the present pharmaceutical compositions can further comprise another suitable therapeutic or preventive substance or treatment. For example, the pharmaceutical compositions can further comprise an effective amount of a drug for the treatment and/or prevention of a proliferation disorder, a neoplasm, a tumor or a cancer in the subject.

The present pharmaceutical compositions can be used at any suitable amount or dosage. For example, the present pharmaceutical compositions can be administered at an amount that reduces production and/or an activity of IFP35 and/or NMI in the subject to a level that is substantially identical to a production and/or an activity level of IFP35 and/or NMI in a comparable subject that does not have a disease or disorder associated with abnormally high level of IFP35 and/or NMI.

The present pharmaceutical compositions can be used to treat and/or prevent a disease or disorder in any suitable subject. For example, the subject can be a mammal. In some embodiments, the mammal is a human. In other embodiments, the subject is a non-human animal or non-human mammal, e.g., experimental, companion or economic non-human animal or non-human mammal.

E. Use of an Effective Amount of an Agent that Prevents or Reduces Production and/or an Activity of IFP35 and/or NMI in a Subject for the Manufacture of a Medicament In still another aspect, the present disclosure provides for a use of an effective amount of an agent that prevents or reduces production and/or an activity of IFP35 and/or NMI in a subject for the manufacture of a medicament for treating and/or preventing a disease or disorder associated with abnormally high level of IFP35 and/or NMI in said subject.

An agent that prevents or reduces production and/or an activity of IFP35 and/or NMI in a subject can be used for the manufacture of a medicament for treating and/or preventing any suitable disease or disorder associated with abnormally high level of IFP35 and/or NMI in said subject.

In some embodiments, agent that prevents or reduces production and/or an activity of IFP35 and/or NMI in a subject can be used for the manufacture of a medicament for treating any suitable disease or disorder associated with abnormally high level of IFP35 and/or NMI in said subject. In other embodiments, agent that prevents or reduces production and/or an activity of IFP35 and/or NMI in a subject can be used for the manufacture of a medicament for preventing any suitable disease or disorder associated with abnormally high level of IFP35 and/or NMI in said subject.

Any suitable agents can be used for the manufacture of a medicament for treating any suitable disease or disorder associated with abnormally high level of IFP35 and/or NMI in a subject. For example, a suitable agent can be used to reduce copy number of IFP35 and/or NMI gene, to block or reduce replication of IFP35 and/or NMI gene, to block or reduce transcription of IFP35 and/or NMI gene, to block or reduce translation of IFP35 and/or NMI mRNA, and/or to inhibit one, some or all activities of IFP35 and/or NMI. In some embodiments, the agent comprises an siRNA targeting the gene encoding IFP35 and/or NMI. The siRNA can target any suitable portion of the IFP35 and/or NMI gene. For example, the siRNA can target a portion of the IFP35 and/or NMI gene that encodes one or more NID domains.

In other embodiments, the agent comprises an antisense RNA targeting the gene encoding IFP35 and/or NMI. The antisense RNA can target any suitable portion of the IFP35 and/or NMI gene. For example, the antisense RNA can target a portion of the IFP35 and/or NMI gene that encodes one or more NID domains.

In still other embodiments, the agent inhibits or modifies a nuclear factor that controls IFP35 and/or NMI transcription. Any suitable agent that inhibits or modifies a nuclear factor that controls IFP35 and/or NMI transcription can be used for the manufacture of a medicament for treating and/or preventing a disease or disorder associated with abnormally high level of IFP35 and/or NMI in a subject.

In yet other embodiments, the agent comprises an antibody that specifically binds to IFP35 and/or NMI. The antibody can specifically bind to any suitable portion of the IFP35 and/or NMI. For example, the antibody can specifically bind to one or more NID domains of IFP35 and/or NMI. In another example, the antibody can specifically bind to a portion of a NID domain of IFP35 and/or NMI.

In yet other embodiments, the agent can comprise a variant form of IFP35 and/or NMI. Any suitable variant form of IFP35 and/or NMI can be used in the present methods. For example, the variant form of IFP35 and/or NMI can be a mutant IFP35 and/or NMI and/or a fragment of IFP35 and/or NMI, e.g., a fragment comprising one or more NID domains of IFP35 and/or NMI, or a fragment comprising a portion of a NID domain of IFP35 and/or NMI. The agent can also comprise fusion proteins between a variant form of IFP35 and/or NMI and a heterologous protein (such as an Fc portion).

The medicament can be manufactured for administration via any suitable route. For example, the medicament can be administered via an oral, nasal, inhalational, parental, intravenous, intraperitoneal, subcutaneous, intramuscular, intradermal, topical, or rectal route.

In some embodiments, the present medicaments can further comprise another suitable therapeutic or preventive substance or treatment. For example, the medicaments can further comprise an effective amount of a drug for the treatment and/or prevention of a proliferation disorder, a neoplasm, a tumor or a cancer in the subject.

The present medicaments can be used at any suitable amount or dosage. For example, the present medicaments can be administered at an amount that reduces production and/or an activity of IFP35 and/or NMI in the subject to a level that is substantially identical to a production and/or an activity level of IFP35 and/or NMI in a comparable subject that does not have a disease or disorder associated with abnormally high level of IFP35 and/or NMI.

The present medicaments can be used to treat and/or prevent a disease or disorder in any suitable subject. For example, the subject can be a mammal. In some embodiments, the mammal is a human. In other embodiments, the subject is anon-human animal or non-human mammal, e.g., experimental, companion or economic non-human animal or non-human mammal.

Any suitable formulation of the compounds described herein can be prepared. See, generally, Remington's Pharmaceutical Sciences, (2000) Hoover, J. E. editor, 20th edition, Lippincott Williams and Wilkins Publishing Company, Easton, Pa., pages 780-857. A formulation is selected to be suitable for an appropriate route of administration. Some routes of administration are oral, parenteral, by inhalation, topical, rectal, nasal, buccal, vaginal, via an implanted reservoir, or other drug administration methods. In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. Pharmaceutically acceptable salts are obtained using standard procedures well known in the art, for example, by a sufficiently basic compound such as an amine with a suitable acid, affording a physiologically acceptable anion. Alkali metal (e.g., sodium, potassium or lithium) or alkaline earth metal (e.g., calcium) salts of carboxylic acids also are made.

Where contemplated compounds are administered in a pharmacological composition, it is contemplated that the compounds can be formulated in admixture with a pharmaceutically acceptable excipient and/or carrier. For example, contemplated compounds can be administered orally as neutral compounds or as pharmaceutically acceptable salts, or intravenously in a physiological saline solution. Conventional buffers such as phosphates, bicarbonates or citrates can be used for this purpose. Of course, one of ordinary skill in the art may modify the formulations within the teachings of the specification to provide numerous formulations for a particular route of administration. In particular, contemplated compounds may be modified to render them more soluble in water or other vehicle, which for example, may be easily accomplished with minor modifications (salt formulation, esterification, etc.) that are well within the ordinary skill in the art. It is also well within the ordinary skill of the art to modify the route of administration and dosage regimen of a particular compound in order to manage the pharmacokinetics of the present compounds for maximum beneficial effect in a patient.

The agents as described herein can be or can be made generally soluble in organic solvents such as chloroform, dichloromethane, ethyl acetate, ethanol, methanol, isopropanol, acetonitrile, glycerol, N,N-dimethylformamide, N,N-dimetheylaceatmide, dimethylsulfoxide, etc. In one embodiment, the present invention provides formulations prepared by mixing an agent with a pharmaceutically acceptable carrier. In one aspect, the formulation may be prepared using a method comprising: a) dissolving a described agent in a water-soluble organic solvent, a non-ionic solvent, a water-soluble lipid, a cyclodextrin, a vitamin such as tocopherol, a fatty acid, a fatty acid ester, a phospholipid, or a combination thereof, to provide a solution; and b) adding saline or a buffer containing 1-10% carbohydrate solution. In one example, the carbohydrate comprises dextrose. The pharmaceutical compositions obtained using the present methods are stable and useful for animal and clinical applications.

Illustrative examples of water soluble organic solvents for use in the present methods and compositions include and are not limited to polyethylene glycol (PEG), alcohols, acetonitrile, N-methyl-2-pyrrolidone, N,N-dimethylformamide, N,N-dimethylacetamide, dimethyl sulfoxide, or a combination thereof. Examples of alcohols include but are not limited to methanol, ethanol, isopropanol, glycerol, or propylene glycol.

Illustrative examples of water soluble non-ionic surfactants for use in the present methods and compositions include and are not limited to CREMOPHOR® EL, polyethylene glycol modified CREMOPHOR® (polyoxyethyleneglyceroltriricinoleat 35), hydrogenated CREMOPHOR® RH40, hydrogenated CREMOPHOR® RH60, PEG-succinate, polysorbate 20, polysorbate 80, SOLUTOL® HS (polyethylene glycol 660 12-hydroxystearate), sorbitan monooleate, poloxamer, LABRAFIL® (ethoxylated persic oil), LABRASOL® (capryl-caproyl macrogol-8-glyceride), GELUCIRE® (glycerol ester), SOFTIGEN® (PEG 6 caprylic glyceride), glycerin, glycol-polysorbate, or a combination thereof.

Illustrative examples of water soluble lipids for use in the present methods and compositions include but are not limited to vegetable oils, triglycerides, plant oils, or a combination thereof. Examples of lipid oils include but are not limited to castor oil, polyoxyl castor oil, corn oil, olive oil, cottonseed oil, peanut oil, peppermint oil, safflower oil, sesame oil, soybean oil, hydrogenated vegetable oil, hydrogenated soybean oil, a triglyceride of coconut oil, palm seed oil, and hydrogenated forms thereof, or a combination thereof.

Illustrative examples of fatty acids and fatty acid esters for use in the present methods and compositions include but are not limited to oleic acid, monoglycerides, diglycerides, a mono- or di-fatty acid ester of PEG, or a combination thereof.

Illustrative examples of cyclodextrins for use in the present methods and compositions include but are not limited to alpha-cyclodextrin, beta-cyclodextrin, hydroxypropyl-beta-cyclodextrin, or sulfobutyl ether-beta-cyclodextrin.

Illustrative examples of phospholipids for use in the present methods cyclodextrin include but are not limited to soy phosphatidylcholine, or distearoyl phosphatidylglycerol, and hydrogenated forms thereof, or a combination thereof.

One of ordinary skill in the art may modify the formulations within the teachings of the specification to provide numerous formulations for a particular route of administration. In particular, the compounds may be modified to render them more soluble in water or other vehicle. It is also well within the ordinary skill of the art to modify the route of administration and dosage regimen of a particular compound in order to manage the pharmacokinetics of the present compounds for maximum beneficial effect in a patient.

F. Method of Diagnosis, Prognosis or Treatment Monitoring

In yet another aspect, the present disclosure provides for a method of diagnosis, prognosis or treatment monitoring of a disease or disorder associated with abnormally high level of IFP35 and/or NMI in a subject, which method comprises assessing the level and/or an activity of IFP35 and/or NMI in a subject suspected of or being treated for a disease or disorder associated with abnormally high level of IFP35 and/or NMI.

The present methods can be used for diagnosis, prognosis or treatment monitoring of any suitable disease or disorder associated with abnormally high level of IFP35 and/or NMI in a subject.

In some embodiments, the present methods are used for diagnosis of a disease or disorder associated with abnormally high level of IFP35 and/or NMI in a subject, and wherein a level and/or an activity of IFP35 and/or NMI in a subject that is at least 10%, 20%, 30%, 40%, 50%, 60%, 70%, 80%, 90%, 100%, 150%, 200%, 300%, 400%, or 500% higher than a level and/or an activity of IFP35 and/or NMI in a comparable subject that does not have a disease or disorder associated with abnormally high level of IFP35 and/or NMI, e.g., a proliferation disorder, a neoplasm, a tumor or a cancer, indicates that the subject has the disease or disorder associated with abnormally high level of IFP35 and/or NMI.

In some embodiments, the present methods are used for treatment monitoring of a disease or disorder associated with abnormally high level of IFP35 and/or NMI in a subject to adjust further treatment of the subject, e.g., to increase or decrease the dosage, or to extend, shorten or stop the treatment.

In some embodiments, the present methods comprise assessing the level of IFP35 and/or NMI in a subject suspected of or being treated for a disease or disorder associated with abnormally high level of IFP35 and/or NMI. In other embodiments, the present methods comprise assessing an activity of IFP35 and/or NMI in a subject suspected of or being treated for a disease or disorder associated with abnormally high level of IFP35 and/or NMI. Any suitable IFP35 and/or NMI activity can be assessed, e.g., binding to a cellular receptor or an antibody. In still other embodiments, the present methods comprise assessing the level and an activity of IFP35 and/or NMI in a subject suspected of or being treated for a disease or disorder associated with abnormally high level of IFP35 and/or NMI.

The level and/or an activity of IFP35 and/or NMI can be assessed at any suitable level. For example, the level and/or an activity of IFP35 and/or NMI can be assessed at the DNA, RNA and/or protein level. The level of IFP35 and/or NMI DNA and/or RNA can be assessed using any suitable means or methods. For example, the level of IFP35 and/or NMI DNA and/or RNA can be assessed using a polynucleotide that is complementary to at least 10, 15, 20, 30, 40, 50, 60, 70, 80, 90, 100, 200, 300, 400, 500, 600, 700, 800, 900, 1,000 or more consecutive nucleotides in the IFP35 and/or NMI DNA or RNA. The level of IFP35 and/or NMI protein can be assessed using any suitable means or methods. For example, the level of IFP35 and/or NMI protein can be assessed using an antibody that specifically binds to IFP35 and/or NMI. Any suitable antibody can be used. For example, the antibody can specifically bind to a portion of a NID domain, or one or more NID domains of IFP35 and/or NMI. In still another example, the antibody is a polyclonal antibody.

In yet another aspect, the present disclosure provides for a kit of diagnosis, prognosis or treatment monitoring of a disease or disorder associated with abnormally high level of IFP35 and/or NMI in a subject, which kit comprises means for assessing the level and/or an activity of IFP35 and/or NMI in a subject suspected of or being treated for a disease or disorder associated with abnormally high level of IFP35 and/or NMI.

Any suitable means can be used in the present kits. For example, the means can be used in assessing an activity of IFP35 and/or NMI. In another example, the means can be a polynucleotide that is complementary to at least 10, 15, 20, 30, 40, 50, 60, 70, 80, 90, 100, 200, 300, 400, 500, 600, 700, 800, 900, 1,000 or more consecutive nucleotides in the IFP35 and/or NMI DNA or RNA for assessing the level of IFP35 and/or NMI DNA and/or RNA. In still another example, the means can be an antibody that specifically binds to IFP35 and/or NMI for assessing the level of IFP35 and/or NMI protein. The suitable means can be contained in any suitable single or multiple containers, e.g., test tubes, microtiter plates, etc. The suitable means can also be immobilized on any suitable single or multiple surfaces, e.g., beads, chips or microfluidic devices, etc.

In yet another aspect, the present disclosure provides for a method of companion diagnostics of a disease or disorder associated with abnormally high level of IFP35 and/or NMI in a subject, which method comprises determining the genetic status of IFP35 and/or NMI gene in a subject being treated for the disease or disorder associated with abnormally high level of IFP35 and/or NMI.

The genetic status of IFP35 and/or NMI gene in a subject can be assessed using any suitable methods or means. For example, the genetic status of IFP35 and/or NMI gene in a subject can be determined using a polynucleotide that is complementary to at least 10, 15, 20, 30, 40, 50, 60, 70, 80, 90, 100, 200, 300, 400, 500, 600, 700, 800, 900, 1,000 consecutive nucleotides in the IFP35 and/or NMI DNA or RNA.

In yet another aspect, the present disclosure provides for a kit of companion diagnostics of a disease or disorder associated with abnormally high level of IFP35 and/or NMI in a subject, which kit comprises means for determining the genetic status of IFP35 and/or NMI gene in a subject being treated for the disease or disorder associated with abnormally high level of IFP35 and/or NMI.

Any suitable means can be used in the present kits. For example, the present kits can comprise a polynucleotide that is complementary to at least 10, 15, 20, 30, 40, 50, 60, 70, 80, 90, 100, 200, 300, 400, 500, 600, 700, 800, 900, 1,000 consecutive nucleotides in the IFP35 and/or NMI DNA or RNA for determining the genetic status of IFP35 and/or NMI gene in a subject. The suitable means can be contained in any suitable single or multiple containers, e.g., test tubes, microtiter plates, etc. The suitable means can also be immobilized on any suitable single or multiple surfaces, e.g., beads, chips or microfluidic devices, etc.

The present methods can be conducted in any suitable manner. For example, the present methods can be conducted manually. In another example, the present methods can be conducted in a semi-automatic or an automatic fashion. The present methods can be conducted at any suitable location. For example, the present methods can be conducted at a hospital, a clinic, a doctor's office, a clinical lab, a pharmacy, an office or a home. The present methods can be conducted at by any suitable personnel. For example, the present methods can be conducted by a physician, a nurse, a lab technician, a caregiver or a patient.

The present kits can comprises additional suitable components, e.g., means for obtaining a sample from a subject, assay standard, identifier of the test subject and/or test instructions, etc. The present kits can be standalone kits or can be part of an assay system, e.g., automated assay systems.

G. Methods for Identifying a Modulator of IFP35 and/or NMI

In yet another aspect, the present disclosure provides for a method for identifying a modulator of IFP35 and/or NMI, which method comprises: a) contacting IFP35 and/or NMI with a test substance and assessing an activity of IFP35 and/or NMI that has been contacted by said test substance; b) assessing an activity of said IFP35 and/or NMI that has not been contacted by said test substance; and c) comparing said activities of IFP35 and/or NMI assessed in steps a) and b), and identifying said test substance as a modulator of IFP35 and/or NMI when said activities of IFP35 and/or NMI assessed in steps a) and b) are different.

Any suitable test substances can be used in the present methods. For example, the test substances can be small molecules, a polypeptide library comprising mutants and/or fragments of IFP35 and/or NMI, antibodies that specifically bind IFP35 and/or NMI, siRNAs or antisense RNAs.

In some embodiments, the present methods can be used to identify an inhibitor of an activity of IFP35 and/or NMI.

In some embodiments, the present methods can be used to identify a drug for treating and/or preventing a disease or disorder associated with abnormally high level of IFP35 and/or NMI in a subject. The present methods can be used to identify a drug for treating and/or preventing any suitable disease or disorder associated with abnormally high level of IFP35 and/or NMI in a subject. For example, the disease or disorder associated with abnormally high level of IFP35 and/or NMI in a subject can be a proliferation disorder, a neoplasm, a tumor or a cancer.

The present methods can be conducted using any suitable assay format. Preferably, the present methods can be conducted using a high-throughput assay format.

In some embodiments, the present disclosure provides for a modulator of IFP35 and/or NMI or a drug candidate that is identified by present methods.

H. EXAMPLES

Example 1: IFP35 Family Members as Early Endogenous DAMPs Abstract

In this example, the structures of a hybrid NID domain (NID-H) of IFP35 were determined. NID-H could fold into an open or a closed conformation. NID-H in the open conformation showed high virulence to mice by inducing cytokine cascade in macrophages, characterized by the up-regulation of the expression of some early inflammation factors. Furthermore, IFP35 and NMI were released into the cell culture media of monocytes or macrophages, 1 hour after stimulated by LPS or IFN-γ. The accumulation of IFP35 and NMI were also detected in the serum of LPS shocked mice and septic patients. A neutralizing antibody toIFP35 NID-H attenuated the LPS induced inflammatory response, and effectively improved the survival rate of septic mice. Besides, IFP35 or NMI knock-out mice were resistant to LPS challenge. Compared to HMGB-1, a known late DAMP, the IFP35 family members could serve as endogenous ligands of TLR4, leading to the activation of the transcription factor NF-κB. Therefore, in some aspects, IFP35 family members with one or more NID domains, including IFP35 and NMI, could serve as early endogenous DAMPs. In some aspects, use of IFP35 and/or NMI or binding partners in the diagnosis and/or treatment of infection and injury is provided.

Results

1. The Structures of NID Revealed its Open and Closed Conformations.

According to sequence analysis, IFP35 has an L-zip domain at its N-terminus containing the first 80 amino acids, following by two tandem NID domains covering the 81-170 and 177-268 amino acids, respectively (FIG. 1A). Truncated protein constructs were constructed according to secondary structure prediction. A truncated IFP35 protein containing the $124^{th}$ to the $220^{th}$ amino acids expressed well in *E. coli*. Since this truncated IFP35 protein spreads across the two predicted NID domains, it was termed NID-H (heterozygous NID) (FIG. 1A). During the purification process, NID-H was found to exist in at least two stable aggregation states, dimer and octamer (FIG. 2A).

Well-diffracted NID-H crystals with both dimeric and octameric states were obtained. The crystal of dimeric NID-H with seleno-L-methionine derivation diffracted at 2.2 A. The structure was determined by single-wavelength anomalous diffraction (SAD) method (Table 1). The SAD method is disclosed in Chayen & Saridakis, Nature methods 5, 147-153 (2008). The NID-H folds into barrel-like structure, formed by five β-strands and two α-helixes which connect with each other in the order of β1-α1-β2-β3-α2-β4-β5 (FIG. 1B). Several pairs of residues on helix al and the following loop (L1) connecting al and 012 play important roles for dimer formation. Based on the structure, at least five pairs of interactions could be observed (FIG. 1C), including: the hydrophobic interaction between the side chains of Ile159 from each monomer; the electronic interactions between Lys163 and Glu158, as well as Asp155 and Lys156; the interaction between the side chain of Asp170 and the amino group on the backbone of Thr164; the interaction between the side chain of Arg165 and carbonyl group on the backbone of Val171.

TABLE 1

Data collection and refinement statistics

| | Dimer (Se-Met) | Octamer (Native) |
|---|---|---|
| Data Collection | | |
| Beamline | BL17U1 | BL17U1 |
| Wavelength (Å) | 0.9798 | 0.9792 |
| Resolution range (Å) | 40.0-2.3 (2.34-2.30)[a] | 50.0-2.5 (2.54-2.50) |
| Space group | H3 | P2$_1$ |
| Cell dimensions | | |
| a, b, c (Å) | 170.3, 170.3, 53.0 | 44.4, 125.3, 77.2 |
| α, β, γ (°) | 90.0, 90.0, 120.0 | 90.0, 90.3, 90.0 |
| Total reflections | 25,256 (1,263) | 29,326 (1,447) |
| Unique reflections | 1,148 | 6,110 |
| Completeness (%) | 99.9 (100.0) | 97.8 (99.9) |
| Mean I/σ | 74.2 (21.3) | 21.1 (5.4) |
| Multiplicity | 22.0 (22.5) | 4.8 (5.4) |
| R$_{sys}$ (%) | 12.5 (69.9) | 10.8 (57.9) |
| Refinement | | |
| Resolution range (Å) | 32.38-2.30 | 36.71-2.50 |
| R$_{work}$/R$_{free}$ (%) | 18.1/22.9 | 20.6/25.3 |
| Rmsd bond length (Å) | 0.002 | 0.003 |
| Rmsd bond angles (°) | 0.619 | 0.639 |
| Ramachandran plot | | |
| Most favored (%) | 98.2 | 97.6 |
| Additional allowed (%) | 1.8 | 2.4 |
| Disallowed (%) | 0.0 | 0.0 |
| Average B factor (Å$^2$) | 29.0 | 55.0 |

[a]Values in parentheses are for the highest resolution shell.

Subsequently, the octameric structure of NID-H was determined at 2.8 Å resolution by molecular replacement (MR) method (FIG. 1D, Table 1). A domain-swapping conformation between two monomers can be observed in the octameric structure. The specific manner is that β1-α1-β2 from one monomer interact with β3-α2-β4-β5 from another monomer and fold into a barrel-like structure (FIG. 1D). In this way, two monomers piled up head-to-end and interact tightly in the dimer. For clarity, this domain-swapping dimer was named the open conformational dimer (o-dimer). The dimer without domain-swapping is called the closed conformational dimer (c-dimer). Four o-dimers further interact with each other through α1-α1 interactions, as described in c-dimer, and form a ring like structure (FIG. 2B). The monomer in o-dimer is quite similar to that in the c-dimer (FIG. 1E). The root mean square deviation (RMSD) between them is only about 0.7 Å. The major difference is that the β-turn (T1) in c-dimer connecting β2 and β33 is straightened in the o-dimer, in which it forms a loop (L2) and connects the two barrel-like structures. The crystal structure coordinates of the dimer structure and the octamer structure are provided in FIGS. 33A-R and FIGS. 34A-V, respectively.

Using Dali server, a powerful structure comparison tool, known structures in PDB were compared to the barrel-like structure of NID-H. The NID-H structure was found to be very similar to that of RNA recognition motif (RRM) (FIG. 2C). The RRMs are widely used to identify RNAs of different sequences and structures. However, there is no obvious RNA binding site in the structure of NID-H indicated by its surface charge distribution. EMSA experiment using NID-H and RNAs with different sequences were also performed, and no interaction between NID-H and the tested RNA sequences was found (data not shown).

2. The Open Conformation of IFP35 NID-H Stimulated Immune Response.

NID-H domain was used as antigen to stimulate polyclonal antibodies production in mice for IFP35 detection. The NID-H octamer caused a 100% mortality rate for all four mice used. Besides, all the mice died with swelled belly and obviously increased ascites. This phenomenon indicated that the NID-H octamer might have cellular toxicity. Because IFP35 typically is specifically expressed in immune cells, such as monocytes, macrophages, dendritic cells and lymphocytes, the NID-H octamer could stimulate inflammatory response.

The transcription level of pro-inflammatory factors, such as TNF-α and IL-1β, were up-regulated in the presence of NID-H octamer in murine macrophage-like RAW264.7 cells (FIG. 3A). This result was similar to lipopolysaccharide (LPS) induced inflammatory cytokines production. By comparison, the NID-H dimer (c-dimer) did not have this effect. Based on these results, NID-H in its octameric structure tends to induce cytokine storm related to TNF-α and IL-1β.

Since the c-dimer itself could not induce inflammation, the o-dimer in the NID-H octamer could serve as the active conformation. To verify whether the octameric skeleton is necessary for its cellular toxicity, a mutant with three point mutations, K156E/K163E/R165E, on the al helix as shown in FIG. 1C, was constructed. These mutations were supposed to partially destroy the c-dimer formation, which leads to the de-polymerization of the octamer. Therefore, some independent o-dimer should be produced. The results showed that the mutated and/or modified dimer could partially up-regulate the transcription of TNF-α and IL-1β (FIG. 3B), which could be ascribed to the formation of independent o-dimers. The results showed that o-dimer is the actitive state of NID-H to induce cytokine storm.

Figure 4:
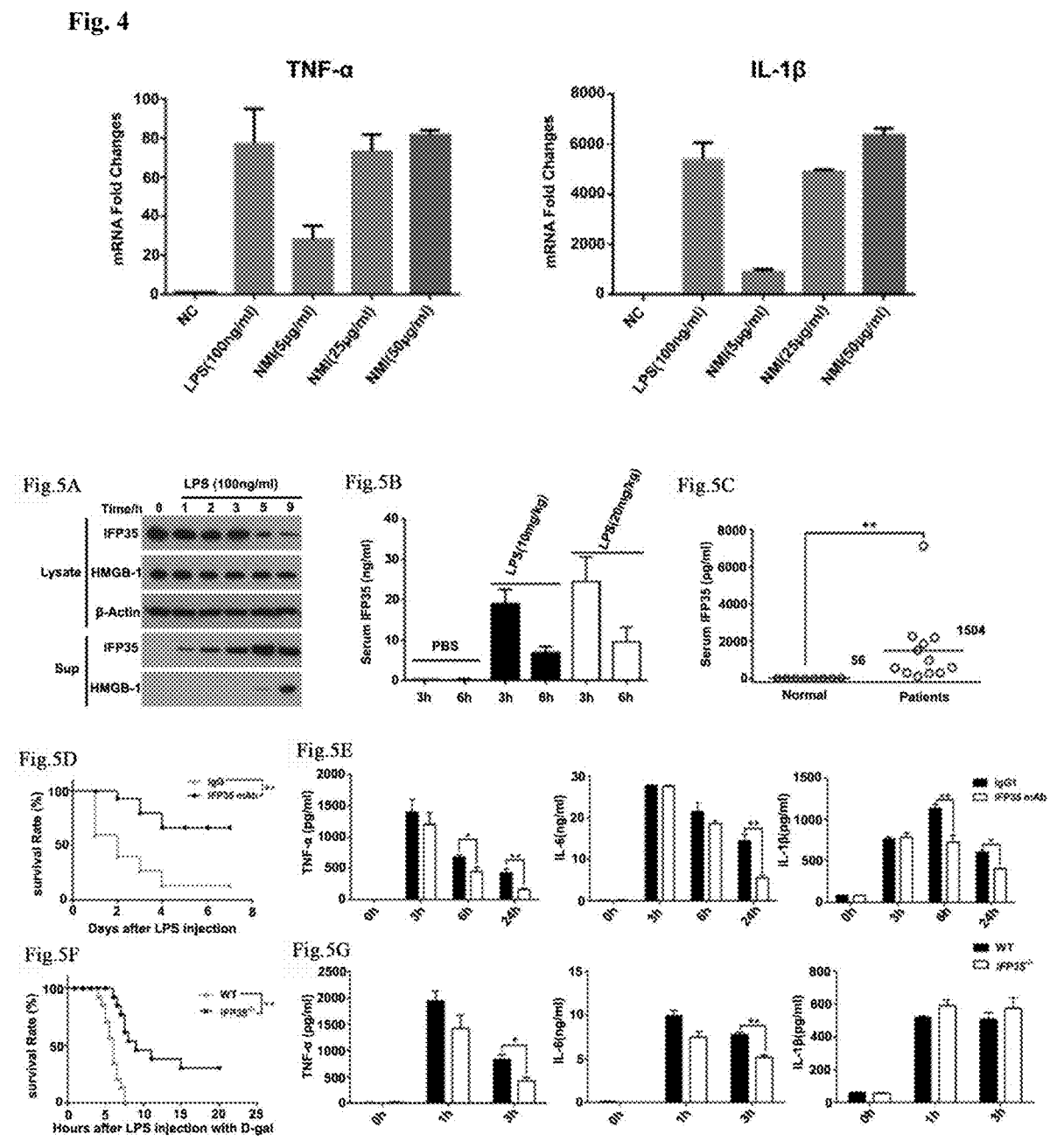

Since NID-H can activate the innate immune response, IFP35 full length protein was expressed. However, IFP35 had low yield in eukaryotic cells and formed inclusion body in E. coli., probably due to the hydrophobic L-zip domain at its N terminus. A truncated IFP35 with 34 amino acids deletion at its N terminal (ΔN) was constructed and expressed using prokaryotic expression system. Soluble ΔN protein was obtained, and the ΔN protein stimulated the transcription of TNF-α and IL-1β more effectively than NID-H octamer (FIG. 3C). Compared to the effective dose of NID-H (about 10-50 μg/ml), the effective dose of ΔN was about 1 μg/ml, which was comparable to that of HMGB-1 or Mrps. Besides, ΔN has a strong effects to stimulate the release of inflammation cytokines such as TNF-α at low dose. Detected by ELISA, 100-200 μg/ml TNF-α could be released into culture by RAW 264.7 cells, stimulated by ΔN or LPS at 1 μg/ml. (FIG. 3D). Moreover, when RAW264.7 cells were stimulated using recombinant mNMI protein, similar inflammation response was also detected (FIG. 4). Based on these results, IFP35 family members can serve as endogenous DAMP proteins.

A secondary structure prediction of human IFP35 is shown in FIG. 32. According to the prediction, in some aspects, removal of the first 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74. 75, 76, 77, or 78 residues in human IFP35 would produce similar results as ΔN used in this example.

3. IFP35 Family Members Possess the Typical Characteristics of Endogenous DAMP.

DAMPs, including HSPs, HMGB-1, Mrp8 and Mrp14, are secreted by cells and are then recognized by the pattern recognition receptors (PRRs) on the cell surface. Kawai et al., Immunity 34, 637-650 (2011); Wu & Chen, Annual Review of Immunology 32, 461-488 (2014); and Zhong et al., Frontiers in Immunology 4, 333 (2013). IFP35 and NMI were reported to localize in cytoplasm after being up-regulated by IFN-γ. However, in this example, with in 3 hour after stimulated by IFN-γ, or within 1 hour after stimulated by LPS or Salmonella, IFP35 and NMI were secreted and detected in the culture supernatant of RAW 264.7 cells (FIG. 5A, FIGS. 6A-B, FIGS. 18A-C, FIG. 19, FIGS. 20A-B and FIGS. 21A-B). In the following several hours, IFP35 and NMI accumulated in the culture in a time-dependent manner as revealed by immunoblot result. In contrast, early and late mediators of endotoxemia, TNF-α and HMGB-1, were released at several minutes and at 6-8 hours, respectively. Wang et al., Science 285, 248-251 (1999); and Tracey et al., Science 234, 470-474 (1986). IFP35 was reported to bind NMI in cells, forming HMMC and further into speckle-like aggregations. Chen et al., JBC 275, 36278-84 (2000). Secreted IFP35 and NMI in the culture of RAW264.7 cells stimulated by Salmonella SR-11 were analyzed using gel filtration and western blot. The results showed that secreted IFP35 existed as monomer and NMI existed as dimer in solution (FIG. 6C and FIG. 6D). Similar to HMGB-1 and Mrps, there is no obvious transmembrane signal peptide in the sequences of the IFP35 family members. Therefore, the IFP35 family of proteins can serve as early DAMPs.

DAMPs were reported to be closely related to the infection and injury. Hirsiger et al., Mediators of Inflammation, 315941 (2012); and Bianchi, Journal of Leukocyte Biology 81, 1-5 (2007). The concentrations of known DAMPs, such as HMGB-1 and Mrps, are significantly increased in the serum of septic patients. Wang et al., Science 285, 248-251 (1999); Austermann et al., Cell Reports 9, 2112-2123 (2014); and Sunden-Cullberg et al., Critical Care Medicine 33, 564-573 (2005). In order to determine if IFP35 and NMI were released in serum during infection, mice were challenged using LPS and detected them in the serum of septic mice. IFP35 and NMI were secreted within 3 hours after LPS exposure. Compared with the control group, the serum IFP35 and NMI in LPS administrated mice increased sharply with a dose dependent manner, up to about 120 ng/ml within 6 hours (FIG. 5B and FIG. 6E). In addition, serum of the patients with sepsis was analyzed and the concentrations of IFP35 in almost all of the 12 samples were elevated. Although great deviations existed among these cases, probably caused by different pathogens and physical conditions, the serum IFP35 could be quantified at 1-1ng/ml, while the protein was barely detectable in the serum of normal individuals (FIG. 5C and FIG. 6F). These results demonstrated that IFP35 is released into serum during infection.

Different from HMGB-1, IFP35 family members could be released within the first hour after LPS stimulation. Administration of antibodies to NID-H (anti-NID-H) before lethal dose (LD$_{100}$) of LPS exposure could provide effective protection to mice. Compared with the 0% survival rate in control, more than 60% of the anti-NID-H treated mice survived in 7 days after LPS exposure (FIG. 5D). Because the toxic effects of LPS are partly mediated by inflammatory cytokines such as TNF-α, IL-1β and IL-6, the concentrations of these cytokines in serum after the administration of LPS and anti-IFP35 monoclonal antibody were examined. Consistent with this phenomenon, administration of anti-NID-H could decrease the release of some toxic inflammatory factors in the serum of septic mice such as TNF-α, IL-1 and IL-6, by about 20%-50% (FIG. 5E). IFP35 and NMI knock-out mice were produced using CRISPPR-Cas9 technology. Ran et al., Nature Protocols 8, 2281-2308 (2013). The reaction to bacterial LPS in conjunction with galactosamine (D-gal) is a well-characterized model of endotoxic shock in mice that is mediated by inflammatory cytokines. Vogl et al., Nature Medicine 13, 1042-1049 (2007); and Galanos et al., PNAS 76, 5939-5943 (1979). After intraperitoneal injection of LPS and D-gal, wild-type animals showed symptoms of acute illness and died within 5-8 h. In contrast, IFP35$^{-/-}$ mice were less severely affected and survived significantly longer (FIG. 5F). Resistant of IFP35$^{-/-}$ and NMI$^{-/-}$ mice to LPS-induced lethal toxicity was also observed when mice were injected with a large amount of LPS without D-gal. Compared with the normal mice whose lethality is almost 100% under administration of lethal dose of LPS, the lethality of NMI knock-out mice are improved (FIG. 6G). During LPS exposure, the concentrations of known pro-inflammatory factors were greatly decreased in the serum of these knock-out mice (FIG. 5G and FIG. 6H). Therefore, all these results demonstrated that IFP35 could serve as DAMP and cause strong inflammatory response.

4. IFP35 Stimulates the Cytokines Storm Potentially Based on the TLR4 Pathway.

Based on previous reports, HMGB-1 and Mrps induce immune response through triggering the activation of NF-κB by TLR4 signal pathway. Vogl et al., Nature Medicine 13, 1042-1049 (2007); Yang et al., PNAS 107, 11942-11947 (2010); and Yu et al., Shock 26, 174-179 (2006). Accordingly, several key players in this pathway were detected and their effects in immune response induced by IFP35 family members were analyzed. First of all, the activation of NF-κB promoter by NID-H was detected using luciferase assay. HEK293 cells were transiently transfected with plasmids such as TLR4, CD14, MD2 and luciferase following NF-κB promoter. 24 hours after transfection, cells were incubated with 10 μg/ml purified octameric NID-H protein. The luciferase activity is dependent on the transcription level of luciferase gene by transcriptional factor, phosphorated NF-κB, hence it was used to represent the activation of NF-κB. The luciferase activity trigged by NID-H was not strong but obvious (FIG. 7A). The activity of LPS can be blocked by polymyxin B, an effective antibiotic for Gram-negative infections. However, the activity of NID-H was not affected. Since IFP35(ΔN), a N-terminal truncation of IFP35, has high efficiency to trigger the inflammation response, its abilities to active transcription factors were also detected. The results showed that purified ΔN induced strong NF-κB and AP-1 promoter activities. In contrast, it has no effects to IRF3 promoter (FIG. 7B). These results suggest that IFP35 active NF-κB and AP-1 but not IRF-3, probably through Myd88 dependent pathway and the mechanism of IFP35 family members should be parallel to the known DAMPs. After stimulation by interferon, IFP35 family members can be released as danger signal, then lead to cytokine storm through TLR4-MyD88-NF-κB/AP-1 signaling pathway.

DISCUSSION

In this example, the structure of the NID domain, the characteristic domain of IFP35 family members, was determined. It is found that the open conformation of NID-H could activate the innate immune response. The results indicate that the IFP35 family members can act as early DAMPs and activate transcriptional factor NF-κB through the TLR4 pathway and lead to cytokine storm. However, the structures and functions of IFP35 family members still need be discussed and illustrated.

1. The Structures of the Tandem NID Domains

There are two tandem NID domains in both IFP35 and NMI. The structure of NID-H crosses two predicted NID domains in IFP35. It could be divided into two fragments, β1-α1-β2 (termed as "A part") and β3-α2-β4-β5 (termed as "B part"), covering 131-179 and 180-228 amino acids in the sequence, respectively. Based on the secondary structure prediction results, the fragment covering 80-130 contains β-α-β-β secondary structure elements, and it was termed "B' part", compared to B part. Similarly, an "A' part" covering 229-276 contains β-α-β secondary structure elements. By sequence alignment, parts A' and B' are comparable with parts A and B (FIG. 8A). Residues involved in the hydrophobic core of NID-H structure were found out as shown in FIG. 8B. These residues are almost completely conserved in these two groups, A with A' and B with B' (FIG. 8A). Therefore, members in the same group can replace with each other. According to previous domain predication, A and B' belong to the first NID domain, while A' and B belong to the second. According to the structure of NID-H, the structure of the two tandem NID domains in IFP35 could fold into a double-barrel structure (FIG. 8C).

In this model, the NID-H region, consisting of part A and part B, exist as the open conformation. The skeletons of the tandem NIDs model and NID-H o-dimer structure are similar. Nevertheless, there are many differences between them. For example, the surface residues in A' and B' are not exactly same with those in A and B. Besides, it is reasonable that the relative position of these two NIDs should be flexible, which might be adjusted during receptor recognization. In contrast, the o-dimer conformation of the NID-H is stable because it is fixed in ring structure of the octamer. Based on these, it is understandable that the NID-H ocatmer only has about 5-10% activity compared with AN. A long loop (LL) is supposed to be existed in the putative NID domain. It connects the two parts of the NID domain, which fold into a P-a-P-P-LL-P-a-p structure. In IFP35, these two long loops cover 115-130 and 220-228 amino acids, respectively. The features of these amino acids indicate that these two loops are flexible. Therefore, these two loops might take part in the HMMC formation in cells or receptor recognition on the out membrane. The structure and functional mechanism of NMI, the homologous protein of IFP35 could also be inferred from the structure of IFP35 (FIG. 9).

2. The recognition between IFP35 andTLR4

To verify the recognition between IFP35 and TLR4, an in vitro binding assay was used to pull down IFP35 by TLR4, TLR4/MD2 and TLR4/MD2/CD14 complex. The bait was fused with 6*His and immobilized on Ni-NTA beads. The treated beads were used to pull down full-length or truncated IFP35 proteins, including purified NID-H octamer,ΔN, and released IFP35 in RAW cell culture. The results showed that only the release IFP35 could be captured by TLR4/MD2 complex in the presence of CD14 (Data not shown). Therefore, TLR4, MD2 and CD14 can work coordinately during IFP35 recognition.

3. The Differences Between IFP35 Family Members and Known DAMPs

Although the IFP35 family members can stimulate NF-κB through TLR4 pathway, similar to the known late DAMPs, in fact, they are expected to have more differences. As early DAMPs, IFP35 and NMI are released in the first hour after cells are stimulated by pathogens, compared to the 6-8 hours for HMGB-1. Playing crucial role in the early state of immune response, IFP35 family members may crosstalk with known other early inflammatory factors such as TNF-α, IL-1β. From the results herein, the antibody of NID-H are effective to down regulate the expression of these inflammatory cytokines, so it could provide more efficient protection for LPS challenged mice. Besides, their concentrations in patients' serum are far from that of HMGB-1, but comparable to other cytokines, they are more likely to work as signal molecules rather than effectors.

On one hand, IFP35 tends to aggregate because it contains a hydrophobic L-zip domain, on the other hand, it is easy to degrade due to the flexibility of two NID domains. Therefore, IFP35 protein could not fold well in many expression systems. The released IFP35 by immune cells are limited and glycosylated. A NID-H fragment which folds into an active octameric conformation has a high yield in E. coli. Since the active conformation is stabilized and the binding surface is exposed in the octamer structure, the NID-H octamer will be very powerful for monoclonal antibody screening. A monoclonal antibody of NID-H neutralized IFP35 and provided protection for septic mice. Besides, soluble ΔN could also be used to prepare monoclonal antibody. Even though further evidences are still needed, their applications in fighting against infections and injuries could be expected.

These data demonstrated a type of early DAMP, IFP35 family members. They are released when the immune cells are stimulated by pathogen or interferon, and further enhance the immune response through TLR4 Signal pathway. The structure of NID-H shed light on the mechanism of these new DAMPs. The results herein provide a way in diagnosis and treatment for infection and injury related diseases.

Methods

Plasmid Construction. The cDNA of Homo sapiens IFP35 and Mus musculus NMI were amplified from reverse-transcribed cDNA from THP1 and RAW264.7 cells (accession No.: NP_005524.2 and NP_001135421.1). Standard methods for primer design, PCR amplification, digestion and recovery were used. The DNA sequences corresponding to amino acids 124-240 and 35-289 of human IPF35 protein (NID-H and ΔN) were inserted into pGEX-6p-1 vector (Invitrogen) using the BamH I and Xho I sites with an N-terminal GST tag. And the DNA sequences of mouse NMI protein was inserted into RSFDuet vector (Novagen) using the BamH I and Xho I sites. All the plasmids were verified by DNA sequencing.

IFP35 (NID-H and ΔN) purification. The plasmids were transformed into Escherichia coli BL21 (DE3) expression strain (for native protein expression) and Escherichia coli B834 (DE3) expression strain (for Selenomethionine derivative (Se-Met) expression). Cells for native or Se-Met protein expression were cultured in the presence of 0.1 g/L Ampicillin in Lenox Broth medium or in SelenoMet Medium Base (Molecular Dimensions Limited) at 37° C. until the $OD_{600}$ reached 0.8-1.0 and were then induced with 0.5 mM isopropyl-β-D-thiogalactopyranoside (IPTG) at 37° C. for 5 hours.

Cells containing over-expressed native or Se-Met IFP35 (residues 124-220) were harvested and resuspended in cold 1x PBS buffer (137 mM NaCl, 2.7 mM KCl, 10 mM $Na_2HPO_4$, 1.8 mM $KH_2PO_4$, pH 7.4), and lysed by passing the cell suspension two times through an EmulsiFlex-C5 homogenizer (Avestin) at 5,000 psi and 15,000 psi, respectively. Cell lysate was centrifuged at 30,700 g/4° C./40 min and the supernatant was incubated with Glutathione Sepharose 4B resin (GE Healthcare) at a ratio of 100 ml supernatant per ml resin at 4° C. for 30-60 min. After incubation, the GST resin was washed with 1x PBS buffer and equilibrated with a buffer of 150 mM NaCl, 20 mM Tris-HCl, pH 8.0. The recombinant protein was eluted with 20 mM GSH and the GST tag was cleaved overnight at 4° C. by PreScission Protease (PPase). After cleavage, the recombinant protein was further purified through a HiTrap Q HP (GE Healthcare) column and eluted with a linear gradient of 150 to 1,000 mM NaCl. A HiLoad 16/60 Superdex 200 (GE Healthcare) column (prep grade) equilibrated with 150 mM NaCl, 20 mM Tris-HCl, pH 8.0 was used as the last purification step. Protein content of each fraction from elution peaks was analyzed by SDS-PAGE. Two peaks with target protein were pooled separately, concentrated, flash-frozen in liquid nitrogen, and stored at −80° C. until further use.

NMI, GFP-NID-H and GFP-NMI purification. The plasmids were transformed into E. coli strain BL21 (DE3). Cells were cultured in LB medium at 37° C. with 100 mg/L ampicillin. When the OD600 reached 0.8-1.0, the culture was induced by addition of isopropyl-thio-D-glactosidase (IPTG) (Sigma) to a final concentration of 0.5 mM for 20 h at 16° C. Cells were harvested by centrifugation at 5000 rpm for 10 min. Pellets were resuspended in Tris buffer (20 mM Tris at pH 8.0, 150 mM NaCl) and lysed by sonication. The lysate was separated by centrifugation at 16,000 rpm for 30 min, and the recovered supernatant was applied to a Ni-NTA affinity column (Qiagen), followed by intensive washing with washing buffer (20 mM Tris at pH 8.0, 150 mM NaCl, 50 mM imidazole).Recombinant protein was eluted from the Ni-NTA affinity column using elution buffer (20 mM Tris at pH 8.0, 150 mM NaCl, 500 mM imidazole) and further purified by gel filtration with a Superdex200 column (GE Healthcare) using Tris buffer as described above on an FPLC protein purification system.

The purity and integrity of all recombinant proteins were verified by Coomassie blue staining after SDS-PAGE, with a purity predominantly >90%.The LPS content in all proteins preparations is undetectable or <10 pg/mg protein as measured by Limulus assay.

Crystallization and Data Collection Both the native and Se-Met IFP35 fragments exhibited two oligomeric states on the Superdex 200 column: octamer and dimer. Both forms of protein were used for crystallization screening. Ultimately, the native IFP35 (residues 124-220) was crystallized in its octameric form by the hanging drop method with a drop consisting of 1 μL 6 mg/mL protein and 1 μL well solution (0.2 M (NH₄)₂SO₄, 0.1 M Bis-Tris-HCl, 20% [w/v] PEG3350, pH 5.4) at 16° C. for 14 days. Crystals of Se-Met IFP35 (residues 124-220) were grown in its dimeric form by the hanging drop method from a solution consisting of 1 μL 10 mg/mL protein and 1 μL well solution (0.2 M (NH₄) 2SO₄, 0.1 M Bis-Tris-HCl, 22% [w/v] PEG3350, 0. 1 M K Na Tartrate, pH 5.5) at 16° C. for 50 days.

Crystals were flash-frozen in liquid nitrogen until data collection. For Se-Met crystals, an additional 20% [v/v] Glycerol was used as a cryo-protectant. The X-ray diffraction data of native and Se-Met proteins were collected on beamline BL17U at Shanghai Synchrotron Radiation Facility (SSRF) at wavelengths of 0.9798 A and 0.9792 Å, respectively. The collected data were integrated and scaled using HKL-2000 (Otwinowski, Methods in Enzymology 276, 307-326 (1997)), Selenium-labeled positions in Se-Met protein were determined using SHELXD from the CCP4 suite (Schneider et al., Acta Crystallographica, Section D, Biological Crystallography 58, 1772-1779 (2002); and Winn et al., Acta Crystallographica, Section D, Biological Crystallography 67, 235-242 (2011)) and six selenium sites were found.

Structure Determination and Refinement. The structure of IFP35 (residues 124-220) in dimeric form was determined using SAD in the Phenix suite. Adams et al., Acta Crystallographica, Section D, Biological Crystallography 66, 213-221 (2010). AutoSol was used to obtain the initial phase. The missing region in the model was rebuilt with AutoBuild or Coot. Emsley et al., Acta Crystallographica, Section D, Biological Crystallography 66, 486-501 (2010). The model was further refined with phenix.refine in iterative cycles until R values converged. Six molecules were found in one asymmetric unit with a Matthews coefficient value calculated to 2.39 Å³ Da⁻¹ and the solvent content was 48.6%. Matthews, J Mol Biol 33, 491-497 (1968).

Structure of the octameric form was solved by molecular replacement using Phaser-MR (Adams et al., Acta Crystallographica, Section D, Biological Crystallography 66, 213-221 (2010)) and the dimeric structure as a search model. The model was rebuilt with Coot (Emsley et al., Acta Crystallographica, Section D, Biological Crystallography 66, 486-501 (2010)) and refined with phenix.refine. Adams et al., Acta Crystallographica, Section D, Biological Crystallography 66, 213-221 (2010). At the final step, TLS refinement was introduced and the TLS groups were suggested by the TLSMD server. Painter et al., Acta Crystallographica, Section D, Biological Crystallography 62, 439-450 (2006). Eight molecules were found in the asymmetric unit. The calculated Matthews coefficient and solvent content were 2.61 Å³ Da⁻¹ and 52.8%, respectively. Matthews, J Mol Biol 33, 491-497 (1968). Inter-molecular interactions were analyzed by PISA. Krissinel et al., J Mol Biol 372, 774-797 (2007). All crystal structure-related figures were prepared with PyMOL (www.pymol.org).

Antibodies and reagents. Anti-IFP35 antibody was obtained from Abnova (DO1P). Anti-HMGB1 antibody was obtained from Abcam (ab79823). Anti-β-Actin antibody was obtained from Sigma-Aldrich (A5441). Anti-CD11b (M1/70) and Gr-1 (RB6-8C5) antibody was obtained from BD Biosciences. Anti-IkBa antibody and pIkBa antibody were obtained from Abcam. IFNγ, trichloroacetic acid (TCA), Lipopolysaccharide (LPS) from E. coli 055:5 and D-galactosamine (D-gal) were purchased from Sigma-Aldrich. MCSF was purchased from Peprotech.

Cells and cell culture conditions. RAW 264.7 macrophages (from ATCC) were cultured in high-glucose Dulbecco's modified Eagle's medium supplemented with 10% fetal bovine serum at 37° C. B6/C57 mice-derived wt, Tlr3⁻/⁻, Tlr4⁻/⁻, Tlr7⁻/⁻, Tlr9⁻/⁻, Myd88⁻/⁻ BMDM cells were cultured in high-glucose Dulbecco's modified Eagle's medium supplemented with 10% fetal bovine serum and 20 ng/ml MCSF at 37° C. THP1 cells were cultured in RPMI 1640 medium supplemented with 10% fetal bovine serum at 37° C. RAW 264.7 macrophages, BMDM and THP1 cells were seeded in 6-well plates at a density of 2×10⁶ cells/well and grown overnight. Then the cells were stimulated with LPS (100 ng/mL), varying concentrations of Salmonella SR-11, IFN-γ,purified recombinant proteins IFP35-NID or NMI for different times as indicated in the figure legends.

RNA isolation and q-PCR. The total RNA was extracted from RAW 264.7, THP1 and BMDM cells using Trizol reagent (Invitrogen) according to the manufacturer's instructions. The first strand of cDNA was synthesized from 1ug of total RNA using random primers and MMLV reverse transcriptase (Invitrogen). Real-time RT-PCR was performed using the SYBR Green PCR kit (Bio-Rad) and Real-time quantitative polymerase chain reaction analyses were performed using the CFX96 Real-Time PCR System (Bio-Rad). Each measurement was set up in duplicates, and three independent experiments were performed. The primer sequences were as follows:

```
mouse (m) GAPDH:
sense,
                        (SEQ ID NO: 13)
CAGAACATCATCCCTGCATC;

antisense,
                        (SEQ ID NO: 14)
TACTTGGCAGGTTTCTCCAG;

mTNFα:
sense,
                        (SEQ ID NO: 15)
CCAGTGTGGGAAGCTGTCTT;

antisense,
                        (SEQ ID NO: 16)
AAGCAAAAGAGGAGGCAACA;

mIL-1β:
sense,
                        (SEQ ID NO: 17)
AAGGAGAACCAAGCAACGACAAAA;

antisense,
                        (SEQ ID NO: 18)
TGGGGAACTCTGCAGACTCAAACT.
```

Western blot. RAW 264.7 macrophages and THP1 cells were pretreated with 100 ng/mL LPS or *Salmonella* SR-11 for 1 h, 2 h, 3 h, 5 h and 9 h. Then the cells were washed twice with cold PBS, scraped, and collected in lysis buffer (20mMTris, pH 7.4, 150 mM NaCl, 5 mM EDTA, 0.5% NP-40, 10% glycerol, protease inhibitor cocktail(Roche)). The whole cell lysates were incubated at 4° C. for 45 min, followed by centrifugation (12 000 g×15 min, 4° C.). Secretory protein in the cell culture supernatant was collected by trichloroacetic acid (TCA)/acetone precipitation. The cell culture supernatant was added 0.11 volumes of ice-cold 100% TCA and placed on ice for 2 h, followed by centrifuge at 20,000 g for 30 min. Then carefully remove the supernatant, add 500 μL of acetone, centrifuge at 20,000 g for 10 min, carefully remove the supernatant and dry the protein pellet in a vacuum evaporator. Protein samples were separated by SDS-PAGE, transferred to a PVDF membrane, and probed with specific antibodies against IFP35, HMGB1, and NMI.

BMDM cells were treated with purified recombinant proteins IFP35-NID or NMI for 5 min, 15 min, 30 min, 60 min. Then the cells were washed twice with cold PBS, scraped, and collected in lysis buffer. The whole cell lysates were incubated at 4° C. for 45 min, followed by centrifugation. Protein samples were prepared for western blot. IkBa, pIkBa, β-Actin were detected by WB.

LPS-induced shock model. LPS from *E. coli* 055:B5 and D-gal were diluted in pyrogen-free saline. A combination of LPS (50 g per kg body weight) and D-gal (1.0 g per kg body weight) was injected intraperitoneally in IFP35$^{-/-}$, NMI$^{-/-}$ and wild-type mice. Resistant of IFP35$^{-/-}$ and NMI$^{-/-}$ mice to LPS induced lethl toxicity were also observed when mice were injected with a large amount of LPS (50 mg per kg body weight) without D-gal. Observe and record the mortality of mice for 1 week.

IFP35 monoclonal antibody protects LPS shocked mice. In the survival experiment, IFP35 mAb and IgG1 (10 μg per mouse) were injected intraperitoneally in B6/C57 mice 4 h before the injection of LPS (50 mg per kg body weight). Additional doses (10 μg per mouse) were administered at 2 h after LPS injection. Delayed doses (10 μg per mouse) was administrated every 24 hours for 4 times. Observe and record the mortality of mice for week.

Determination of cytokine concentrations. IFP35 and NMI in human and mouse serum were measured with ELISA kits (CUSABIO).Release of cytokines (IL-1β, IL-6, and TNFα) in the culture supernatants or in mouse serum were measured by ELISA Kit (Biolegend, Thermo Fisher).

Generation of IFP35$^{-/-}$ mice. Genomic engineering of IFP35 was achieved with the CRISPR/Cas9 system as described.

Flow cytometry. Recombinant protein IFP35 NID-H, NMI or PBS were injected intraperitoneally in B6/C57 mice for 24 h, respectively. The mouse ascites was incubated with antibody to CD11b and Gr-1, followed by FITC-conjugated secondary antibody. Cells were analyzed on a FACSCalibur machine (BD Biosciences) to detect the peritoneal neutrophils and data were analyzed using CellQuestPro software.

B6/C57 mice-derived wt or Tlr4$^{-/-}$ cells were incubated with GFP-NID-H and GFP-NMI in PBS buffer (containing 2% FBS) for 1 h. Cells were analyzed on a FACSCalibur machine (BD Biosciences) and data were analyzed using CellQuestPro software.

Citation of the publications or documents herein is not intended as an admission that any of the foregoing is pertinent prior art, nor does it constitute any admission as to the contents or date of these publications or documents.

Example 2: Use of IFP35 Family Proteins

IFP35 and NMI can be rapidly up-regulated by interferon (IFN). The protein level of IFP35 in cells is low without the induction of IFN. IFP35 and NMI can be induced by type I or type II interferon (IFNα/β/γ) in numerous immune cells. The amount of IFP35 protein and mRNA level increased dramatically after stimulation of IFN γ for 6 h and reached the maximum level at 24 h, revealed a 25-fold increase compared with non-treatment. Most cells can express NMI, and similarity with IFP35, the expression of NMI increased 2-20 fold after IFN treatment.

*Homo sapiens* IFP35 is located in the 17q21, with a NCBI Accession No. NP_005524.2. The cDNA sequence encodes a 288-amino acid protein with a deduced molecular mass of 31.8 KDa. A natural mutant with methionine at position 128 mutated and/or modified to valine (M128V) exists. *Homo sapiens* NMI is located on chromosome 2, with a NCBI Accession No. AAC 12949.1, including 307 amino acids.

IFP35 and NMI are homologous protein. According to the structure prediction, they both include two tandem N-Myc binding protein/IFP35 domain (Nmi/IFP35 domains, NIDs). According to sequence analysis, IFP35 has an L-zip domain at its N-terminus containing the first 80 amino acids, following by two tandem NID domains covering the 81-170 and 177-268 amino acids, respectively.

IFP35 and NMI are co-located in the cytoplasm in different cell types by immunofluorescence microscopy techniques. NMI and IFP35 proteins can form a high molecular mass complex (HMMC) of 300-400 kDa through NID domain as determined by native gel electrophoresis and gel filtration which suppress the IFP35 degradation by proteasome. IFP35 and NMI can form speckle-like aggregations after stimulation of IFNγ called NMI/IFP35 speckles (NIS).

In IFNγ-treated apoptotic cells, the NIS dissociates, but the high molecular mass complex does not dissociate.

It is reported that IFP35 can regard as antiviral protein and inhibit the Bovine Foamy Virus replication. The second NID domain of IFP35 can bind the long terminal repeat sequences of early regulatory protein BTas (Bovine trans-activator protein) of Bovine Foamy Virus, thus inhibiting the transcription activity to suppress the virus infecting cells. In addition, high throughput screening showed that IFP35 protein could interact with CLEC4G (C-type lectin domain family member 4 G) in the Ras-MAPK/P13K pathway.

NMI can participate in the JAK-STAT pathway induced by IFN. NMI interacts with all STATs except Stat2, and enhances the association of mutual activation factor CBP/p300, thus enhances STATs-mediated transcription level of downstream genes.

The mRNA level of NMI in malignant breast cancer cell lines decreased 25-45 fold compared to the normal breast cells and the protein level of NMI was also significantly lower than the normal breast cells. Continuous telomerase activity is considered as one of the prerequisite for cancer, and NMI can bind breast cancer susceptibility protein BRCA1 (breast cancer type 1 susceptibility protein) and c-Myc to form a ternary complexes and dowvn-regulate the promoter activity of anthropogenic telomerase reverse tran-scriptase gene (human telomerase reverse transcriptase gene, hTERT). hTERT promoter activity was decreased by about 75% when co-transfected the Flag-Nmi and HA-BRCA1 into cells. In addition, when detected the protein Dkk1 (Dickkopf-1) in the Wnt/β-catenin pathway, the data suggest that overexpression NMI inhibits the Wnt/β-catenin signaling via up-regulation of Dkk1 and retards tumor growth.

NMI can up-regulate the negative feedback regulating factors SMAD7 in the TGF/SMAD β signaling pathway to inhibit TGF/SMAD β signaling pathways and reduce the aggressiveness and mobility of the breast cancer cells. IFP35 and NMI are associated with inflammatory signals.

FIGS. 10A-B illustrate the process of IFP35 protein purification. FIG. 10A: SDS-PAGE analysis of IFP35-NID. The left lane: molecule marker. Lane 1: GST-tagged IFP35-NID after purification of affinity chromatography. Lane 2: the mixture of proteins after digestion by PPase. Lane 3: the IFP35-NID eluted from the GST resin column. Lane 4: IFP35-NID purified after size-exclusion chromatography. FIG. 10B: Size-exclusion chromatography analysis (super-dex-200(16/60)). The elution volume of the peak suggesting the aggression state of the protein is close to dimer FIGS. 11A-C show the different oligomer states of IFP35. FIG. 11A: Anion exchange column analysis. FIG. 11B: Size-exclusion chromatography analysis. The elution vol-umes of two peaks suggesting different oligomer formation. FIG. 11C: SDS-PAGE analysis for the whole process of purification. Lane 1: GST-tagged IFP35. Lane 2: IFP35 eluted from the GST column. Lane 3: IFP35 after digestion by PPase. Lane 4: sample binding to anion exchange col-umn. Lane 5: sample that did not bind to anion exchange column. Lane 6: protein eluted from size-exclusion chro-matography superdex-200 (the elution volume of the peak was 72-74 ml). Lane 7: protein eluted from size-exclusion chromatography superdex-200 (the elution volume of the peak was 90-92 ml).

Figure 12A:
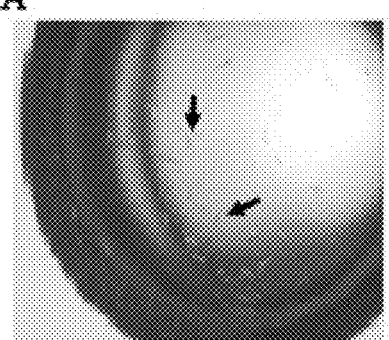
Figure 12B:
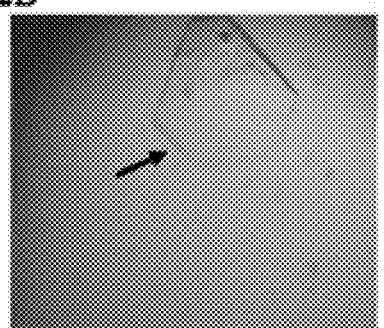
Figure 12C:
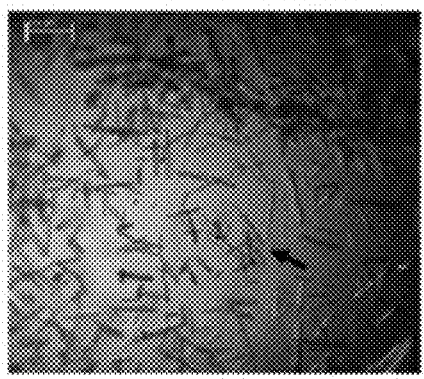
Figure 12D:
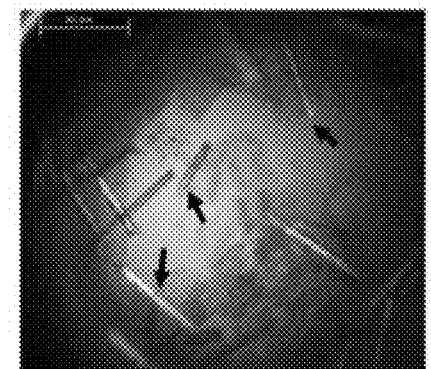

FIGS. 12A-D show the IFP35-NID crystal. FIG. 12A: Native octamer crystal. The protein was crystalized in reservoir solution with 0.2 M ammonium sulfate, 0.1M Bis-tris, 25% [w/v] PEG3350, pH5.5, in which the drop was set up at 1 μl protein and 1 μl reservoir solution. The crystal was grown for 14 days at the temperature of 289k. FIG. 12B: Native octamer crystal. The native IFP35-NID (residues 124-220) was crystallized in its octameric form by the hanging drop method with a drop containing 1 μL protein and 1 μL well solution (0.2 M $(NH4)_2SO_4$, 0.1 M Bis-Tris-HCl, 20% [w/v] PEG3350, pH 5.4), with 30% [w/v] d-glu-cose as an additive, at 16° C. for 1-14 days. FIG. 12C: Crystals of Se-Met IFP35-NID (residues 124-220) were grown in its dimeric form, with the hanging drop method from a solution consisting of 1 μL protein and 1 μL well solution (0.2 M $(NH4)_2SO_4$, 0.1 M Bis-Tris-HCl, 22% [w/v] PEG3350, pH 5.4) at 16° C. for 7 days. Scale bar=100 μm FIG. 12D: Crystals of Se-Met IFP35 (residues 124-220) were grown in its dimeric form, with the hanging drop method from a solution consisting of 1 μL protein and 1 μL well solution (0.2 M $(N14)_2SO_4$, 0.1 M Bis-Tris-HCl, 22% [w/v] PEG3350, pH 5.5) at 16° C. for 30 days. Scale bar=200 gm. The crystals are identified with arrows.

Figure 13A:
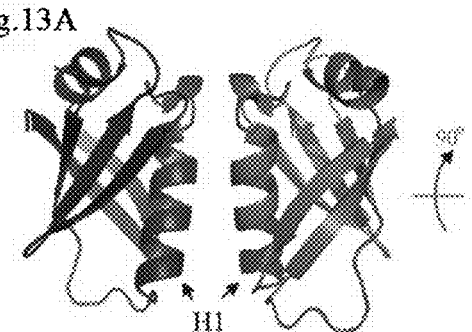
Figure 13B:
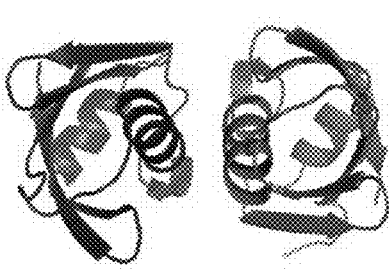
Figure 13C:
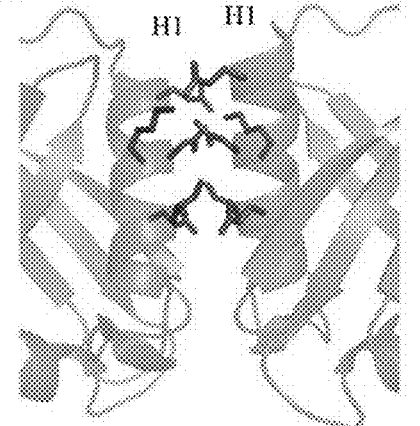
Figure 13D:
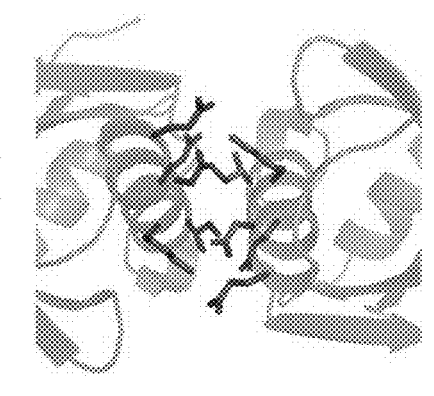

FIGS. 13A-D show the structure of the dimeric IFP35-NID. FIGS. 13A-B are the whole structure from different views. FIGS. 13C-D indicate residues (shown in sticks) involved in the intra-molecule interaction from different views. H1 indicates a-helix mainly involved in dimer for-mation. A single molecule is shown in red or blue.

FIGS. 14A-D show the structure of the octameric IFP35-NID. Monomers are shown in different colors. The octamer were formed with four domain-swapping dimers in the manner similar to the interaction that form the dimer. The amino terminal and carboxyl terminal of molecule A are indicated with A-N and A-C.

FIGS. 15A-B show the structure of dimer with domain-swapping conformation. The domain-swapping model of octamer. A-dimer and B-dimer are extracted from the octamer. Red and blue indicate one molecule respectively. Two molecules can bind to each other. The dimers finally form a ring structure of octamer through interaction between the side H1 α-helix of one dimer and the Hla-helix of its neighbor dimer.

FIGS. 16A-C show the residues of some areas. FIG. 16A: Residues on the arc intersecting surface area (atoms on side chain are labelled and shown in sticks, atoms on the main chain are not labelled). FIG. 16B: Residues on the inner surface of the octamer ring structure (atoms on side chain are labelled and shown in sticks, atoms on the main chain are not labelled). FIG. 16C: Residues on the head of a monomer within a dimer (from two molecules, atoms on side chain are labelled and shown in sticks, atoms on the main chain are not labelled). The whole structure are shown in ribbons, differ-ent colors indicate different molecules.

FIGS. 17A-D show the purification of the recombinant NMI. FIG. 17A: The SDS-PAGE of the mouse NMI-NID fragment. FIG. 1713: The size exclusion chromatography results of NMI-NID. FIG. 17C: The SDS-PAGE of the full length mouse NMI with 6*His tag. FIG. 17D: The size exclusion chromatography result of full length mouse NMI with 6* His tag at its N terminal.

FIGS. 18A-C reveal the expression level of IFP35 and HMGB1 (as a control) when stimulated by *salmonella.*

FIG. 19 shows that the abundance of IFP35 changed with time as measured by immunofluorescence when stimulated by *salmonella.*

FIGS. 20A-B show the abundance of IFP35 secreted to the medium at different periods when cells are infected by the virus. FIG. 20A: The abundance of secreted IFP35 at different times measured by westem blot while the cells are infected by A59 and MHV68 with different MOI. FIG. 2013:

The abundance of secreted HMGB1 at different times measured by western blot while the cells are infected by A59 and MHV68 with different MOI.

FIGS. 21A-B show a model of mouse peritonitis. FIG. 21A: In the model of peritonitis induced by mouse Standard strains of *Salmonella typhimurium* SR-11, IFP35 was released to the medium when injected live SR-11 to the model. FIG. 21B: IFP35 are released to the medium in case of that inflammasome is stimulated by LPS and ATP.

FIGS. 22A-D show the contribution of the IFP35 with different oligomer states during the process of stimulating inflammation. Expression level of some inflammation factors are measured as indicated in the figure.

FIG. 23 shows the result of Flow cytometry analysis, which illustrates octameric IFP35-nid can recruit large amount of neutrophil granulocytes.

FIG. 24 shows exogenous octameric IFP35-NID can stimulate NF-κB pathway in macrophages.

FIGS. 25A-B illustrate that IFP35 can stimulate inflammation through myd88 signal pathway.

FIGS. 26A-B show the levels of IL-1β and TNF among WT, Tlr9$^{-/-}$ and Tlr4$^{-/-}$ mouse as induced by IFP35.

FIG. 27A shows the amount of IFP35 in the serum of septic mice. FIG. 27B shows the survival rate of the septic mice was increased when administrated with IFP35 monoclonal antibodies.

FIG. 28 shows that the block of IFP35 attenuated the release of induced IL-6 by LPS in mice.

FIG. 29 shows the abundance of NMI in cell lysate and supernatant of Thp1 cells stimulated by *salmonella.*

FIGS. 30A-B demonstrate that mouse source NMI protein can up-regulate the transcription of TNFα and IL-1' in Thp1 cells.

FIG. 31 shows the SDS-PAGE detection of the aggregation state of NMI by running size exclusion chromatography. The digits labeled on each protein lanes indicate elution volume. Since there is a sustained NMI elution profile, the result suggested that NMI may exist as different oligomers in mouse serum.

FIG. 32 shows a secondary structure prediction of human IFP35 (performed by PSIPred (http://bioinf.cs.ucl.ac.uk/psipred/)).

The experimental methods used in the following protocols are all conventional methods unless otherwise specified. All the materials and reagents used in the following protocols can be commercially obtained unless otherwise specified. The results of IFP35-NID1 and IFP35-NID2 in the following protocols have no significant differences.

The expression, purification, and crystallization of IFP35 and NMI.

1. Plasmid Construction

The cDNA of *Homo sapiens* IFP35 and *Mus musculus* NMI were amplified from reverse-transcribed cDNA from THP1 and RAW264.7 cells (Accession No.: NP_005524.2 and NP_001135421.1). The sequence of IFP35 was verified to be the wild variant of M128V by DNA sequencing.

SEQ ID NO: 1 is the cDNA sequence of *Homo sapiens* IFP35. SEQ ID NO: 2 is the amino acid sequence of *Homo sapiens* IFP35. In one aspect, a NID of IFP35 is encoded by nucleic acid 372 to 660 of SEQ ID NO: 1 (from the 5' end), which encodes amino acid residues 124 to 220 of SEQ ID NO: 2 (from the N-terminus). In one aspect, a NID of IFP35 is encoded by nucleic acid 408 to 648 of SEQ ID NO: 1 (from the 5' end), which encodes amino acid residues 136 to 216 of SEQ ID NO: 2 (from the N-terminus).

SEQ ID NO: 3 is the cDNA sequence of *Mus musculus* IFP35. SEQ ID NO: 4 is the amino acid sequence of *Mus musculus* IFP35.

SEQ ID NO: 5 is the cDNA sequence of *Mus musculus* NMI. SEQ ID NO: 6 is the amino acid sequence of *Mus musculus* NMI. NMI-NID is encoded by nucleic acid 453 to 750 of SEQ ID NO: 5 (from the 5' end), which encodes amino acid residues 151 to 250 of SEQ ID NO: 6 (from the N-terminus).

SEQ ID NO: 7 is the cDNA sequence of *Homo sapiens* NMI. SEQ ID NO: 8 is the amino acid sequence of *Homo sapiens* NMI. NMI-NID is encoded by nucleic acid 465 to 720 of SEQ ID NO: 7 (from the 5' end), which encodes amino acid residues 155 to 240 of SEQ ID NO: 8 (from the N-terminus).

The PCR primers used in this protocol are synthesized by Beijing Synthesis, Sangon Biological Engineering (Shanghai) Co., LTD. The superstar high-fidelity DNA polymerases used were purchased from GenStar Biosolutions Co., Ltd. The restriction endonucleases were bought from Takara biotechnology (Dalian) Co., LTD. The agarose was purchased from Biowest (US). The quick gel extraction kit was purchased from Beijing Transgen Biotechnology Co., LTD. The *E. coli* expression vector pGEX-6p-1 is from GE Healthcare Incorporation. The DH5a, BL21 (DE3) chemically competent cells and B834 defect competent cells are purchased from Invitrogen Company. DNA sequencing was performed by Beijing Liuhe Genomics Technology Co., LTD.

2. Protein Expression and Purification

Tryptone and yeast extracts used to cultivate *E. coli* are purchased from Thermo Fisher Oxoid (UK). High pressure homogenization cell cracker EmulsiFlex-C5 used for cell crash is purchased from Avestin (Canada). Prescission protease (Ppase) is purified from a *E. coli* strain. GST affinity column (Glutathione Sepharose 4B), anion exchange column (HiTrap_Q_HP_5 ml), size-exclusion chromatography column (HiLoad_16/60_Superdex200_prep grad and Superdex 200 10/300 GL, 24 ml), protein purification system (AKTApurifier) are purchased from GE healthcare life sciences. The NanoDrop 2000 spectrophotometer used for concentration detection is purchased from Thermo (US).

Other biochemical Reagents used are purchased from Sigma Aldrich Company or Beijing Chemical Reagent Company.

3. Crystallization and Data Collection

Crystallization screening kits and Se-Met are purchased from Hampton Research Incorporation. Buffers including Tris-base, Bis-Tris, and polymer PEG3350 are purchased from Sigma-Aldrich (US). Home Source X-ray diffractometer is purchased from Rigaku Incorporation (Japan).

IFP35 Expression, Purification, and Crystallization

For purification, many tags such as 6×HIS, GST, or MBP can be chosen. Take GST-tagged protein as an example, the DNA sequences corresponding to amino acids 1-288,128-216 and 136-216 of *Homo sapiens* IPF35 protein were inserted into pGEX-6p-1 vector (Invitrogen) using the BamH I and Xho I sites with an N-terminal GST tag. All the plasmids were verified by DNA sequencing. The recombinant protein obtained in this way can be cleaved by Pre-Scission Protease (PPase). The recombinant plasmids of full-length IFP35 and other fragments are constructed in the similar way.

pGEX-6p-1 vector has GST tag and PPase cleavage site in front of the multiple cloning site.

(1). Plasmid Construction

Take the cDNA sequence of IFP35 as the template, pairs of primers for PCR amplification were used to get full length IFP35 protein-coding gene, IFP35 NID1 encoding gene, IFP35 NID2 encoding gene respectively, which were digested by BamH1 and EcoRI restriction endonucleases and then ligated to the vector pGEX-6p-1 cleaved by the same restriction enzymes. Following the ligation reaction, the ligated plasmid DNA was transformed into competent cells such as *E coli* DH5a (Invitrogen) using heat-shock method. The bacteria were spread thin on the plate with consistent antibiotic resistance (100 µg/ml ampicillin) and plates were incubated at 37° C. overnight. The next day, several colonies were picked into 2 ml LB medium and cultivated at 37° C. for 10 h for plasmid extraction to confirm the presence of the recombinant plasmid by DNA sequencing. Once it has been established that the insert is in the proper orientation and the correct junctions are present, the plasmids are used for protein expression.

By DNA sequencing, Plasmid 1 is the GST-IFP35 recombinant plasmid containing SEQ ID NO: 1 inserted into pGEX-6p-1 using the BamH I and Xho I sites. Plasmid 2 is the GST-IFP35-NID1 recombinant plasmid containing DNA sequence 372-660 from the 5' end of SEQ ID NO: 1, which is inserted into pGEX-6p-1 using the BamH I and Xho I sites and was added with a termination codon. Plasmid 3 is the GST-IFP35-NID2 recombinant plasmid containing DNA sequence 408-648 from the 5' end of SEQ ID NO: 1, which is inserted into pGEX-6p-1 using the BamH I and Xho I sites and was added with a termination codon.

The primers for amplification of full-length IFP35:

```
Upstream primers:
                                   (SEQ ID NO: 19)
5' GGTAGATCTATGTCAGCCCCACTGGATG3';

Downstream primers:
                                   (SEQ ID NO: 20)
5' GGT GAATTCCTAGCCTGACTCAGAGGTGAAGACT3'.
```

The primers for amplification of IFP35-NID1 (amino acids 124-220 of SEQ ID NO: 2):

```
Upstream primers:
                                   (SEQ ID NO: 21)
5' GGTGGATCCCCAGGTGATGATGTCCAGCCA3';

Downstream primers:
                                   (SEQ ID NO: 22)
5'GGTGAATTCTTACTCCCCGTTCACATACGGAGAGAC3'.
```

The primers for amplification of IFP35-NID2 (amino acids 36-216 of SEQ ID NO:-2):

```
Upstream primers:
                                   (SEQ ID NO: 23)
5' GGTGAATTCAGGGTGTTGGTCACTGGATTTCCT3';

Downstream primers:
                                   (SEQ ID NO: 24)
5' GGTGAATTCTTACTCCCCGTTCACATACGGAGAGAC3'.
```

(2). Protein Expression

*E. coli* BL21 (DE3) cells were transformed with the recombinant plasmids and grown on LB agar plates containing 100 µg/ml ampicillin. Following overnight incubation at 37° C., single colonies were transferred into 100 ml LB broth containing 100 µg/ml ampicillin and grown overnight at 37° C. with shaking (200 rev min-1). The cells were diluted 1/400 in flasks containing 1L LB broth supplemented with 100pg ml-1 ampicillin and cultivated at 37° C. with continuous shaking (200 rev min-1) until an OD600 nm of 0.6 was reached. The cells were subsequently treated with 1 mM IPTG to induce the expression of recombinant proteins. After 5 h of incubation with continuous shaking (200 rev min-1) at 37° C., the cells were harvested by centrifugation at 4000 rev min-1 for 30 min at 4° C.

Cells containing over-expressed proteins were harvested and resuspended 10/1 in cold 1x PBS buffer (137 mM NaCl, 2.7 mM KCl, 10 mM Na$_2$HPO$_4$, 1.8 mM KH2PO4, pH 7.4), and lysed by passing the cell suspension two times through an EmulsiFlex-C5 homogenizer (Avestin) at 5,000 psi and 15,000 psi, respectively. Cell lysate was centrifuged at 30,700 g/4° C./40 min and collect the supernatant.

(3). Protein Purification

1) Affinity Chromatography

After centrifugation, the supernatant was incubated with Glutathione Sepharose 4B resin (GE Healthcare) at a ratio of 100 ml supernatant per ml resin at 4° C. for 30-60 min. After incubation, the GST resin was added to the gravity column for the separation of the resin from the solution mixture, then the column was washed about 10 resin volumes with 1 ×PBS buffer to bind the GST-tagged proteins on the resin.

Next, the GST resin was equilibrated with a buffer of 150 mM NaCl, 20 mM Tris-HCl, pH 8.0. The recombinant protein was cleaved overnight at 4° C. by PreScission Protease (PPase) and then eluted with 2 column volumes buffer containing 15 mM GSH, 150 mM NaCl, 20 mM Tris-HCl, pH 8.0. at the speed of 1 mL/min for 30 min. After cleavage and elution, IFP35, IFP35 NID1, and IFP35 NID2 (all the elution volumes are about 50 ml) were obtained.

2) Anion-Exchange Chromatography

Proteins digested by protease PPase enzyme were injected into anion exchange column (HiTrap_Q_HP_5 ml, GE Healthcare company), which is fixed to the FPLC purifier (GE Healthcare) and was balanced with 20mMTris-HCl (PH8.0), 50 mM NaCl before injection. With the elution buffer (20mMTris HCl (PH8.0), 1 M NaCl) to carry on the gradient elution at the flow rate of 1 ml/min and the elution volume 100 ml, samples of the corresponding protein were collected according to the 280 nm and 260 nm ultraviolet absorption.

3) Size-Exclusion Chromatography

A HiLoad 16/60 Superdex 200 (GE Healthcare) column (prep grade) equilibrated with 150 mM NaCl, 20 mM Tris-HCl, 5% gly, pH 8.0 was used as the next purification step after anion-exchange chromatography. The column was fixed to the FPLC purifier (GE Healthcare) as the same and the flow rate was 1ml/min eluted for 120 min. The full-length human IFP35 protein and IFP35-NID were collected at elution volume of about 45 ml and 90-92 ml respectively. Finally, the purified IFP35 (elution volume of 45 ml), IFP35 NID1 (elution volume is 90-92 ml), and IFP35 NID2 (elution volume is 90-92 ml) were obtained.

Size-exclusion chromatography of IFP35-NID1 and IFP35-NID2 are shown in FIGS. 10A-B. The elution volumes of IFP35-NID1 and IFP35-NID2 samples are 90-92 m corresponding to the molecular weight 17-43KD. Results of centrifugal analysis and crystal structure indicated that the IFP35-NID1 and IFP35-NID2 were dimers.

During the purification of IFP35-NID1 and IFP35-NID2, two different oligomer states of the proteins corresponding to the elution volumes of 72 ml and 90-92 ml can be obtained (FIGS. 11A-C). When the proteins were eluted down from the resin column before the digestion of PPase, two peaks, one at volume 72 ml and the other at volume 90-92 ml, were observed. The peak at volume 72 ml corresponded to molecular weight of 70kd-100kd, and the peak at volume 90-92 ml corresponded to the dimer. The peaks of elution volumes of IFP35-NID1 and IFP35-NID2 suggested dimer and octamer.

The SDS-PAGE analysis ofIFP35-NID1 and IFP35-NID2 had no significant differences.

4) Se-Met IFP35-NID Purification

The purification of Se-Met IFP35-NID was similar to native IFP35-NID. The difference is the application of *Escherichia coli* B834 (DE3) expression strain (for Sele-nomethionine derivative (Se-Met) expression) and the M9 medium with additive Se-Met. Methionine of proteins expressed by b834 with M9 medium was replaced with Se-Met. Crystal obtained in this method can be used to determine crystal phase and further for structure determina-tion.

(4). Protein Crystalization

1) Crystallization

Both the native and Se-Met IFP35-nid1 and IFP35-nid2 fragments exhibited two oligomeric states on the Superdex 200 column: octamer and dimer. Both forms of protein were used for crystallization screening performed using multiple conditions from the commercially available kits (Hampton Research). The purified proteins are centriguged at 14000 rpm/10min/4° C. to remove precipitation and bubble. Crys-tallization trials were carried out by the sitting-drop vapor-diffusion method, mixing 1 μl of the protein sample with an equal volume of screening solution on the Siliconized slides and equilibrated over 200pl of the latter in the reservoir. The crystals are grown at 16° C. Crystals of IFP35-NID1 are shown in FIGS. 12A-D.

2) Structure Determination and Refinement

In the crystal structure of dimeric IFP35-NID1 or IFP35-NID2 (FIGS. 13A-D), there are six molecules within each asymmetric unit, and the structure of the six IFP35-NID1 or IFP35-NID2 molecules are the same. Electron density chart can clearly show that residues of amino acids 136 to 216 in IFP35, but the crystal structure can not clearly completely display the residues (124-135) at the amino terminus and the residues (216-220) at the carboxyl terminus. This phenom-enon illustrated that the core of the IFP35-NID domain structure is mainly composed of amino acids 136-216, the increase or decrease of individual residues at the carboxyl terminal and amino terminal is not important to the overall structure. Hence, these residues are dispensable in crystal structure analysis and crystallization experiments. In IFP35-NID structure, five antiparallel beta piece (named B1-B5 according to the sequence order respectively) made up the barrel structure, which surrounded an alpha helix (H1) to form a complete barrel structure (FIG. 13A and FIG. 13B).

IFP35-NID2 formed dimer on the interface where alpha helix (H1) located through hydrogen bonds and hydrophobic interaction, van der Waals force and so on (FIG. 13C and FIG. 13D). The size of the interaction surface calculated by PISA (Protein Interface, Surface and Assemblies) is about 586.5 A square. Residues mainly participated in dimer formation included Glu150, Glu151, Asp155, Lys158, IIe159, Arg165 and Asp172 on the alpha helix (H1).

Eight NID-1 or 2 molecules interacted with each other and formed a ring like structure. The monomer in octamer is quite similar to the monomer in the dimer that the monomer folds into barrel-like structure formed by five β-strands and two α-helixes. Several pairs of residues on helix al in octameric structure play important roles for interaction between molecules and to mediate dimer formation, which are the same as the dimeric structure. As for the difference, the antiparallel β2 and β3 (177Lue-216Tyr) in dimer is straightened in octamer and inserted into the structure of the adjacent molecule being part of the neighbor NID domain. In this way, two monomers piled up a dimer and formed a domain-swapping conformation between two monomers, which makes it different from the dimer.

For clarity, this domain-swapping dimer was named open conformational dimer (o-dimer). By comparison, the above mentioned dimer without domain-swapping is called closed conformational dimer (c-dimer). The o-dimer folded in the same way as c-dimer, so the structure of the swapping NID domain is similar to that of the monomer in c-dimer (FIGS. 15A-B). When the adjacent o-dimer interact using the same Hila helix used in c-dimer, the four o-dimer formed the four-angle star structure (FIGS. 14A-D). The eight monomer was marked A to G started from N-terminal in the clockwise orientation and the whole structure could be divided into four pairs of o-dimer A/B, C/D, E/F and G/H respectively, among which the structural details of A/B and E/F or C/D and G/H are similar and structural differences of the loop distinguished A/B and E/F from C/D and G/H. For the four domain-swapping dimers (o-dimer) formed the four-angle star, the diameter of the inner hole is 35 Å and The outer diameter is 80 Å. The octamer formed a new arc intersecting surface through cross-over of two swapping molecules, which is absent from c-dimer. The octameric ring structure was absent from c-dimer. The structural differences may be the basis for the functional differences between different oligomer states.

Based on the octameric structure, some residues are observed to be involved in structure formation, and others are observed to be mainly exposed on the surface of the whole structure and are supposed to be interacted with other proteins. These external residues mainly distributed in three areas as follows:

The domain-swapping dimer form an arc intersecting surface area on which the dimer provide some residues such as Ser145, Asp172, Val173, Leu177, Arg212, Gln199, Gln207, Gln208, Pro210, Ser214, Thr201, and Tyr216 to form a large exposed surface(FIG. 16A). Among them, residues Glu150, Glul75, Leu177, Gln207, and Gln208 are in a more prominent position (FIG. 16A).

Other residues on the inner surface of the ring structure formed by the octameric IFP5-NID can participate in the interaction with other proteins. These residues include Ser145, Arg147, Glu150, Glu151, Val173, Gly206, Gln207, and Gln208. In some aspects, Arg147, Gln207, Gln208, Glu150, and Glu151 provide extended side chains that protrude from the inner surface of octamer ring structure (FIG. 16B).

Based on the structure of the dimer or the octamer, there are some relatively large amino acid residues near the top of the amino terminus and the carboxyl terminus of the 0 sheet barrel-like structure of the single monomer or domain-swapping monomer; these relatively large amino acid resi-dues extend outwards. These residues can include Arg187, Glu188, Gln192, Gln196, Arg212, and Tyr216, and they are close in distance. Furthermore, some amino acid residues may participate in binding to other proteins, antibodies, or small molecules (FIG. 16C).

3) Data Collection and Structure Determination

The prepared crystal was tested on Rigaku-007 X-ray diffractometer and the diffraction data were collected on beamline BL17U at Shanghai Synchrotron Radiation Facil-ity (SSRF). X-ray diffraction data were calculated with existing common structure determination or analysis soft-ware or package including data analysis software such as HKL2000 and Mosflm, Image processing software coot and pymol, Heavy atoms solve software shelx, and Structure refinement software Phenix and CCP4. Mainly used methods here are Single wavelength anomalous scattering and molecular displacement.

The X-ray diffraction data of Se-Met proteins were collected on beamline BL17U at Shanghai Synchrotron Radiation Facility (SSRF) at wavelengths of 0.979 Å. 720 images were collected with Rotation range 10 per image and were integrated and scaled using HKL-2000. After calculation, the resolution ratio was 2.3 Å and the space group was H3. Selenium-labeled positions elenium-labeled positions in Se-Met protein were determined using SAD OF SHELXD and six selenium sites were found. AutoSol was used to obtain the initial phase. The model was rebuilt with AutoBuild and was further refined with coot and phenix.refine.

The 2.5 Å X-ray diffraction data of native octameric crystal was obtained at Shanghai Synchrotron Radiation Facility as the same. Structure of the octameric form was solved by molecular replacement using Phaser-MR in Phenix and the dimeric structure as a search model, and was further refined with coot and phenix.refine.

All the results above indicated that the full-length IFP35 or the NID fragments predicted could not express or were expressed as high polymer, making it difficult to get proteins with uniform states. However, the second half of the first NID domain and the first half of the second NID domain (residues 124-220 or 134-216, which are named IFP35-NID1 and IFP35-NID2, respectively, which are collectively referred to as IFP35-NID because of the similar purification results) were expressed and purified well. Using methods above, a large amount of high purity soluble IFP35-NID can be obtained, especially when they were fused to GST. GST fused protein is referred to as GST-IFP35-NID.

During purification, there were two stable aggregation states of IFP35-NID and well-diffracted crystals with both states can be obtained.

Expression and purification of NMI

Take the cDNA sequence of NMI as the template, pairs of primers for PCR amplification were used to get full length human NMI protein-coding genes (1-924 from 5' end of SEQ ID NO: 7), human NMI-NID (residues corresponding to amino acid residues 155-240) encoding gene (465-720 from 5' end of SEQ ID NO: 7), *Mus musculus* NMI encoding gene (1-945 from 5' end of SEQ ID NO: 5), *Mus musculus* NMI-NID (residues corresponding to amino acid residues 151-250) encoding gene (453-750 from 5' end of SEQ ID NO: 5), respectively, which were digested by BamH1 and XhoI restriction endonucleases and then ligated to the vector pGEX-6p-1 cleaved by the same restriction enzymes. In this way, the recombinant plasmids that express GST-human-NMI, GST-human-NMI-NID, GST-mouse-NMI, and GST-mouse-NMI-NID, with added termination codon at the 3' terminus, were obtained.

Primers for amplification of full-length human NMI:

```
Upstream primer:
                            (SEQ ID NO: 25)
5' GGT GGATCC ATGGAAGCTGATAAAGATGAC 3';

Downstream primer:
                            (SEQ ID NO: 26)
5' GGT CTCGAG CTATTCTTCAAAGTATGCTATGTG 3'.
```

Primers for amplification of human NMI (155-240):

```
Upstream primer:
                            (SEQ ID NO: 27)
5' GGT GGATCC TCTAAAATGAAAATCAATGTTAC 3';

Downstream primer:
                            (SEQ ID NO: 28)
5' GGT CTCGAG TTATTCTGTGTATGGAGAAACAG 3.
```

Primers for amplification of full-length mouse NMI:

```
Upstream primer:
                            (SEQ ID NO: 29)
5' CGCGGATCCATGGATGCTGATAAAGACAAC 3';

Downstream primer:
                            (SEQ ID NO: 30)
5' CCGCTCGAGTCATATGGTTTCTCTGGCCTC 3'.
```

Primers for amplification of mouse NMI (151-250):

```
Upstream primer:
                            (SEQ ID NO: 31)
5' CGCGGATCCGTTCATGTGGACATTTCTAAAATG 3';

Downstream primer:
                            (SEQ ID NO: 32)
5' CCGCTCGAGTCAAAACACCTGGTACTTTTCTAAG 3'.
```

The mouse and human full length or fragments of NMI were expressed using *E. coli* prokaryotic expression system. Reagents and expression methods used are basically the same as IFP35 protein expression.

The protocol for NMI expression was essentially the same with IFP35. The protocol of NMI purification was essentially the same with IFP35. The purification was divided into 4 steps: GST gravity column affinity chromatography, cleavage of GST with PPase, anion exchange chromatography, and gel filtration chromatography.

1) GST Affinity Chromatography

After centrifugation, the supernatant was incubated with Glutathione Sepharose 4B resin (GE Healthcare) at a ratio of 100 ml supernatant per ml resin at 4° C. for 1-2 h. After incubation, the GST resin was added to the gravity column for the separation of the resin from the solution mixture. Then the column was washed with 1×PBS buffer until there were no miscellaneous proteins on the resin.

The GST tagged NMI was eluted the elution buffer containing 10 mM GSH and then cleaved by PPase for 8 h at 4° C. After cleavage and elution, mouse NMI and mouse NMI-NID were obtained (the elution volumes were about 30 ml respectively). Proteins were eluted with buffer contained 10 mM GSH, 150 mM NaCl, 20 mM Tris-HCl, pH 8.0. at the speed of 1 mL/min for 30 min.

2) Size-Exclusion Chromatography

Proteins digested by PPase were further purified by Size-exclusion chromatography (HiLoad_16/60_Superdex 200prep grad and Superdex 200 10/300 GL, 24 ml). The column was balanced with 150 mM NaCl, 20 mM Tris-HCl, 5% gly, pH 8.0, and the flow rate was 1ml/min eluted for 120 min. The full-length *Mus musculus* NMI protein and NMI-NID were collected at elution volume of about 30 ml and 120 ml respectively. Finally, the purified NMI (elution volume of 30 ml), NMI NID (elution volume of 120 ml) were obtained.

The full-length and fragments of *Mus musculus* NMI can be expressed in *E. coli* and purified, but no different oligomer states similar to IFP35-NID were observed in NMI-NID. The full-length NMI and fragments of NMI exhibited polymerized states.

Human NMI and NMI-NID were purified in the same way as *Mus musculus* NMI related proteins.

This example shows that there are two oligomer states of IFP35-NID: dimer and octamer. The two NID domains in IFP35 are probably not two independent domains but two swapping-interacting domains. The two aggregation states of the IFP35-NID indicated that IFP35 may have two different oligomer states in cells which most likely are in accordance with the functions. NMI had similar function with IFP35, and their structures may be similar. However, NMI did not have different oligomer states when compared to IFP35. NMI secreted out from cells was homogenous polymer states. Based on estimation by the weight, the secreted NMI was possibly a dimer or a tetramer.

In the subsequent function experiments, it was found that only octameric IFP35-NID can induce the same inflammation induced by NMI, suggesting that the octameric IFP35-NID possessed same structural features with the full-length IFP35. Therefore, finding amino acids on the octameric surface which are involved in the binding of IFP35 to receptors and blocking the binding may block IFP35 from functioning normally. Similarly, inhibitory antibodies for IFP35 and/or NMI can be developed to target the amino acid residues that participate in the interaction of IFP35 with its cellular receptors.

Example 3 Analysis of IFP35 Immune Function

IFP35 causes excessive immune response

*Homo sapiens* IFP35-NID1, IFP35-NID2, or IFP35-NID-H domain (dimer or octamer) can be used as antigen to stimulate mice immune response. Four mice were used for each protein, each mouse immune for four times, 0.2 mg protein per body was injected intraperitoneally in mice. Then mice strengthen immune once every 14 days after the first time of immune, a total of four times.

In the immune process, using *Homo sapiens* IFP35-NID dimer to immune mice can get corresponding antibody as expected and NID-H octamer caused swelled belly when immune to the third time and almost all the mice died with swelled belly when immune to the fourth time. The NID-H octamer could stimulate inflammatory response. RAW 264.7 macrophages (from ATCC) were cultured in high-glucose Dulbecco's modified Eagle's medium supplemented with 10% fetal bovine serum at 37° C.

IFP35-NID1 and IFP35-NID2 had no significant difference.

IFP35 immunological function in vivo

BMDM cell culture: Kill the mice through breaking the mice neck, take the two hind legs of mice, soak the legs in 70% alcohol for 1 min, and try to eliminate the muscles of the back bone, flush the marrow cavity with PBS. Then centrifuge at 400 g for 100 min and carefully remove the supernatant. Erythrocyte cells were collected in cell lysis buffer and then add 10 ml PBS to neutralize the cell lysis buffer. The BMDM cells cultured in high-glucose Dulbecco's modified Eagle's medium supplemented with 10% fetal bovine serum, 1% penicillin-streptomycin, 1% L-glutamine and 20 ng/ml MCSF at 37° C.

RAW 264.7 macrophages (from ATCC) were cultured in high-glucose Dulbecco's modified Eagle's medium supplemented with 10% fetal bovine serum at 37° C.

1. Infection by *Salmonella* in Macrophages264.7 and BMDM Causes IFP Release

Cells were washed three times with preheat PBS. Raw 264.7 and BMDM cells were digested by pancreatic enzyme and counted by the hemocytometer to confirm the number of the cells in every hole. 1 ml of preheating DMEM was added to the cell culture dishes. *Salmonella* SR-11 were centrifuged at 12000 RPM for 10 min and washed twice with PBS. Salmonella were suspended and counted by the hemocytometer. The Raw264.7 cells were added the Salmonella according to the multiplex of infection (1:100 or 1:10), while BMDM cells according to the multiplex of infection (1:10 or 1:2). Cell culture dishes were centrifuged at 1500 RPM for 10 min at room temperature which is benefit for bacteria to adsorb on the cells. When Raw264.7 cells were infected with Salmonella for 1 hour and BMDM were infected with Salmonella for 0.5 hours, the salmonella in the cell culture were removed and 100 g/ml Amikacin DMEM was added in the medium. When Raw 264.7 cells were infected with Salmonella for 3 hour and BMDM cells were infected with Salmonella for 1 hour, 10 g/ml Amikacin DMEM was added in the medium. Secretory protein in the cell culture supernatant was collected after Raw 264, 7 and BMDM cells were infected with Salmonella for 1, 3, 5, 9 h or 0.5, 1, 2, 4 h, respectively.

Concentrate the cell culture supernatant and extract the whole cell lysates after cells were infected with Salmonella: Concentrate the cell culture supernatant: (1) The cell culture supernatant was added 0.1 volumes of ice-cold 100% TCA and placed on ice for 2 h. (2) Centrifuge at 12,000 g for 30 min at 4° C. (3) Carefully remove the supernatant, wash the sediment twice with cold acetone. (4)Centrifuge at 12,000 g for 10 min at 4° C. (5) The sediment was heated at 95° C. for 5 minutes in the 30ul 1 ×SDS-PAGE loading buffer.

Extract the whole cell lysates after cells were infected with Salmonella: (1) Collect the cells: Remove the cell culture supernatant, wash the cells twice with PBS, add 1ml PBS to the cell culture dishes, scrape the cells with cell scratcher, transfer the cell suspension to 1.5 ml tube with pipet, centrifuge at 1500 RPM for 5 min and remove the supernatant. Cell sedimentation is used to extract total protein. (2)Cell lysis: Take appropriate amount of RIPA lysis buffer, add PMSF to the lysis buffer with a final concentration of 1 mm, proteinase inhibitors cocktail (Roche).Add 150ul RIPA lysis buffer to each hole in the cell culture dishes and split the cells for 15 min on ice. (3)Collect the cell lysis buffer: centrifuge at 12000 RPM for 5 min at 4° C. after cells were splitted completely and transfer the supernatant to a new tube. (4) Boil the sampe: The cell lysis buffer was heated at 95° C. for 5 minutes in the 150ul 2 x SDS-PAGE loading buffer.

As shown in FIGS. 18A-C, there is no or little IFP35 in the in the cell culture supernatant. However, within 1 hour after stimulated by Salmonella, released IFP35 could be detected in the culture supernatant of RAW 264.7 cells. In the following several hours, they cumulated in the culture in time-dependent manner. In contrast, the release time of IFP35 is earlier than the known danger signals HMGB-1.And the protein level of IFP35 in cells decrease (FIG. 18A). Same results were obtained when BMDM and PBDM cells were used (FIG. 18B and FIG. 18C).

To better observe the change of intracellular IFP35 protein content after infected with salmonella, immunofluorescence method was used to detect the IFP35 protein. As shown in FIG. 19, IFP35 was stained by red and DAPI was stained by blue. The two different schemes of infection, which is the ratio of the cells number to MOI is 1:2 or 1:10 respectively, were used to observe the change of IFP35 protein content from 0 to 3 hours. It was found that the intracellular IFP35 protein content gradually reduced as the extension of time, and the IFP35 reduced faster in the higher MOI infected cells. It further proved that the infection induced IFP35 accumulation was not occurring inside the cells, but largely secreted to the outside of the cells. This result is in agreement with the previous research that the change of the intracellular IFP protein content.

2. The Release of IFP35 in the Virus Infection

Experimental method: The Raw264.7 cells were added the virus according to the multiplex of infection. Collect the cell culture supernatant in time-dependent manner. Centrifuge at 200 g for 30 min at 4° C. Collect the supernatant by trichloroacetic acid (TCA), western blot.

Whether DNA virus (MHV68), or RNA viruses (A59) infect the Raw264.7 in vitro, IFP35 release as early as 8 hours after infection when the multiplex of infection(MOI) is 0.2. Under the same conditions, HMGB1 is not release Increase the multiplex of infection to 5, HMGB1 release obviously after infection for 24 h. Similar with bacterial infected cells in vitro, IFP35 release earlier than HMGB1, illustrated that IFP35 is a very important danger signal molecules.

3. The Model of Mice Peritonitis

FIG. 21A shows that in the standard strains of salmonella SR-11 caused mice peritonitis model, IFP35 could be released. Injecting with Live salmonella (Live SR-11) caused mice peritonitis, IFP35 could be released to the mice ascites. While injecting with symbiotic *E. coli* (*E. coli* Stable3) and heat death of salmonella (HK SR-11, heat killed SR-11) does not cause inflammation and IFP35 could not be detected. The result illustrated that IFP35 has correlation with the inflammatory response.

The establishment of the standard strains of salmonella SR-11 caused mice peritonitis model. Wash the mice ascites with 8 ml PBS after inject bacteria for 2 h, 4 h, 8 h, extract 4 ml ascites wash buffer. Trichloroacetic acid (TCA) precipitation and detect the IFP35 by western blot. (1) C57/B6 mice, male, 8 to 10 weeks, weight about 20 g, ban water and food for 4 hours. (2) Each mice inject $2*10^{-5}$ bacteria. (3) Wash the mice ascites with 8 ml PBS after inject bacteria for 2 h, 4 h, 8 h, extract 4 ml ascites wash buffer. (4)Centrifuge at 200 g for 10 min at 4° C., collect the cell culture, Trichloroacetic acid (TCA) precipitation. (5) Detect the IFP35 by western blot.

As shown in FIG. 21B, when LPS, ATP activate inflammasome, IFP35 could be released. Experimental Method: (1) Raw264.7 cells were stimulated by LPS (1 pg/ml) for 4 h; (2) Cells were continue stimulated by ATP (5 mM) for 10, 30, 60 min; (3) Centrifuge at 200 g for 10 min at 4° C., collect the cell culture, Trichloroacetic acid (TCA) precipitation; (4) Detect the IFP35 by western blot.

IFP35 in Inflammatory Response

1. IFP35 Induces the Production of Inflammatory Cytokines

Experiment procedure: Wipe out the endotoxin of IFP35 dimer and octamer in the example 1, add them to the BMDM cell culture medium (final concentration of 5, 25, 50 μg/ml), stimulate for 4 hours and detect the known pro-inflammatory factors, TNF-α and IL-1β using Q-PCR, GAPDH as internal.

Q-PCR Amplification Primers:

```
IL-1β:
Sense:
                            (SEQ ID NO: 33)
5'AAGGAGAACCAAGCAACGACAAAA 3';

Antisense:
                            (SEQ ID NO: 34)
5'TGGGGAACTCTGCAGACTCAAACT 3'.
```

```
                       -continued
TNF-α:
Sense:
                            (SEQ ID NO: 35)
5'CCAGTGTGGGAAGCTGTCTT 3';

Antisense:
                            (SEQ ID NO: 36)
5'AAGCAAAAGAGGAGGCAACA 3'.

GAPDH:
Sense:
                            (SEQ ID NO: 37)
5'AGGTCGGTGTGAACGGATTTG 3';

Antisense:
                            (SEQ ID NO: 38)
5'TGTAGACCATGTAGTTGAGGTCA3'.
```

As shown in FIGS. 22A-D, the known pro-inflammatory factors, TNF-α, IL-1P, iNOS andCD86 can be up-regulated in the presence of NID-H octamer in BMDM cells, but the NID-H dimer did not have this effect. The result demonstrated that different aggregation states of IFP35-NID have different effect.

IFP35 NID1 and IFP35 NID2 use the same method and the results have no significant difference.

2. IFP35 Leads to Excessive Inflammatory Response

IFP35-NID dimer and octamer were injected into mouse peritoneal. 8 hours later, IFP35-NID octamer caused an acute inflammatory response, manifested by neutrophil accumulation. This effect should be the reason why the mice abdominal distension and death in the early inflammatory response. The result demonstrated that IFP35-NID octamer not only induce the macrophage to produce inflammation factor in vitro, but also have the ability to regulate inflammatory responses in mice.

3. IFP35 Activates the NF-κB Pathway in Macrophages

The activation of NF-κB by IFP35-NID octamer was observed. NF-κB pathway is an important pathway of macrophage activation. Detection method: Add endotoxin free protein of IFP35-NID dimer and octamer to the Raw264.7 cells, stimulate for 15, 30, and 60 min. The cells were collected in the RIPA (Proteinase inhibitor cocktail, Roche) buffer for 30 min on ice. Centrifuge at 12,000 rpm for 10 min at 4° C. Collect the supernatant and heat at 95° C. for 10 minutes in the SDS-PAGE loading buffer. Save the sample at −70 degrees. Western blot was used to detect the phosphorylation of suppressor IκBα in the NF-κB signaling pathway. Phospho-1κBα and IκBα antibody were from CST. Results as shown in FIG. 24, after adding the prokaryotic expressed different polymeric state of endotoxin free protein, expression of the octamer of IFP35-NID recombined protein increased the phosphorylation of IκBα, but reduced the total IκBα protein level. It suggested the octamer of IFP35-NID recombined protein could activate NF-κB signaling pathway. Taken together, these results indicated that the octamer may induce macrophage activation to produce a large number of inflammatory cytokines by activating NF-κB signaling pathway, but not the dimer.

The cell surface receptor of IFP35

Since IFP35 induced inflammatory response by secreted to extracellular or in body fluids, the example aims to identify the cell surface receptor that mediated IFP35 activity, and then to detect the biological function of TLR-Myd88 pathway in this process.

BMDM cell culture: Kill the mice through breaking the mice neck, take the two hind legs of mice, soak the legs in 70% alcohol for 1 min, and try to eliminate the muscles of the back bone, flush the marrow cavity with PBS. Then centrifuge at 400 g for 100 min and carefully remove the supernatant. Erythrocyte cells were collected in cell lysis buffer and then add 10 ml PBS to neutralize the cell lysis buffer. The BMDM cells cultured in high-glucose Dulbecco's modified Eagle's medium supplemented with 10% fetal bovine serum, 1% penicillin-streptomycin, 1% L-glutamine and 20 ng/ml MCSF at 37° C.

IFP35 or NMI stimulation: Add IFP35-NID dimer, octamer or NMI (5, 25, or 50 pg/mL) to stimulate the BMDM cells for 4 h, IL-1l3, and TNF-α were detected by Q-PCR.

Extract the cell total RNA: The total RNA was extracted from BMDM cells using the RNA extract Kit from KangWei Company(Cat No. CW 0597). The total RNA was extracted from RAW 264.7 cells using Trizol reagent (Invitrogen).

Reverse transcription: The first strand of cDNA was synthesized from 1 ug of total RNA using PrimeScript™ II 1st Strand cDNA Synthesis Kit (Cat.No.6210A).Real-time RT-PCR was performed using the SYBR@Premix Ex Taq™ (Tli RNaseH Plus) and ROX plus Q-PCR kit (Cat.NO.RR42LR). As shown in FIGS. 25A-B, treating Myd88 knock-out BMDM cells using IFP35-NID protein, the activity of NID-H were sharply reduced in these cells, IL-1β (FIG. 25A) and TNF-α(FIG. 25B) could not be induced by IFP35-NID. IFP35 likely binds to the TLR receptor in the cell surface to active NF-κB through Myd88 dependent pathway and produce inflammation factors.

TLR-4 and TLR-9 are the two main cell surface receptor proteins which can induce the inflammation response. As shown in FIGS. 26A-B, TLR4 mediate the increase of IL-1 R (FIG. 26A) and TNF-α (FIG. 26B) through the IFP35-NID. Compared the NID-H octamer could up-regulated the TNF-α and IL-1β in WT, TLR9 −/− and TLR4 −/− mice BMDM cells, IFP35 family proteins can also be identified by TLR4, directly or indirectly.

IFP35 Monoclonal Antibody in Treating the Diseases Caused by Excessive Inflammatory Response Such as Sepsis Because IFP35-NID can activate macrophages and induce inflammation response, IFP35 may play a role in sepsis in which IFP35 can exacerbate cytokine storm in sepsis and lead to the death of mice.

1. The Expression of IFP35 in Sepsis Mice

The establishment of LPS-induced shock model: (1) the B6/C57 mice were banned water and food for 1 night; (2) LPS (5 mg and 10 mg per kg body weight) was injected intraperitoneally in mice the next day morning; (3) Take the blood using the capillary 3 hours after injection; (4) Remove the mice eye and take blood 6 hours after injection.

Detect the concentration of IFP35 in the LPS-induced shock model using ELISA. (1) Antibodies are coated: purified monoclonal antibody of IFP35 1D7 diluted with PBS to 2 mg/ml, 100 ml per hole in enzyme label plate, 4° C., over night; (2) Wash: wash three times with PBST (0.05% Tween-20); (3)Block: PBST (0.05% Tween-20) containing 2% BSA place on shaking table to fade, room temperature, 1 h; (4)Add diluted standard and samples,100 ul per hole, 4° C., over night; (5) Wash: wash three times with PBST (0.05% Tween-20), wash twice with ddH₂0. (6) Color:Add 100 ul TMB to each well, avoid light, place on shaking table for 10-20 min. (7) Stop the reaction: Add 50 ul 2M H₂SO₄ to each well; (8)Enzyme label plate,450 nm scan OD.

Quantitative detecting the IFP35 concentration in blood of sepsis mice model shows high concentration of IFP35 in the blood of LPS-induced sepsis mice, which reaches nanogram level (about 8 ng). But the level of HMGB1 is pg600-800 according to the previous paper. And it depends on the time or dose of LPS injection (for 3 hours and 6 hours, LPS dose of 5 mg and 10 milligrams per kilogram of body weight).

2. Increased Survival Rate of Septic Mice by Injecting IFP35 Monoclonal Antibodies IFP35 monoclonal antibody ID7 was injected into mice. As shown in FIGS. 27A-B, IFP35 monoclonal antibody could increase the survival rate of septic mice. The results demonstrated that IFP35 monoclonal antibody ID7 could protect the mice from death effectively in bacteremic model. The medial death time of mice that accepted the treatment of 1D7 (n=10) was 107 hours, while it was 50 hours of the control.

3. For Detecting the Expression of Inflammation Factor IL-6 in Mice after

IFP35 monoclonal antibody injection, the specific method was as follows: IL-6 ELISA kit was from BD Biosciences, the detailed operating information see the specification of the product.

Results as shown in FIG. 28, for the mice with severe sepsis, the IL-6 protein was highly expressed in body fluids of mice by injecting IFP35 antibody (1D7) but not in non-injected.

IFP35 and Anti-Tumor Treatment

The protein level of NMI is reduced in some tumors. Since IFP35 and NMI highlighted a variety of functions in biological progressions, such as promoting inflammatory response of biological organisms, activating immune system, and promoting the release of inflammatory cytokines, the injection of purified IFP35 or NMI into blood may activate and/or enhance anti-tumor treatments. Therefore, IFP35 or NMI protein might be a promising anti-cancer drug.

Example 4 NMI Immune Function Analysis

NMI Cause Excessive Immune Response

Full length NMI and NMI-NID used as antigen to stimulate mice immune response. Four mice were used for each protein, each mouse immune for four times, 0.2 mg protein per body was injected intraperitoneally in mice. Then mice strengthen immune once every 14 days after the first time of immune, a total of four times.

In the immune process, using Mouse NMI-NID to immune mice can cause swelled belly when immune to the third time and almost all the mice died with swelled belly when immune to the fourth time. So it is difficult to get antibodies in mice. Thus, the NID-H octamer may stimulate inflammatory response.

NMI Immunological Function Research In Vivo

1. NMI is Secreted to the Extracellular Space when Cells are Infected by Bacteria The NMI and IFP35 are homologous protein. IFP35 and NMI can assemble into high molecular mass complex (HMMC). In this example, NMI was detected.

BMDM cell culture: Kill the mice through breaking the mice neck, take the two hind legs of mice, soak the legs in 70% alcohol for 1 min, and try to eliminate the muscles of the back bone, flush the marrow cavity with PBS. Then centrifuge at 400 g for 100 min and carefully remove the supernatant. Erythrocyte cells were collected in cell lysis buffer and then add 10 ml PBS to neutralize the cell lysis buffer. The BMDM cells cultured in high-glucose Dulbecco's modified Eagle's medium supplemented with 10% fetal bovine serum, 1% penicillin-streptomycin, 1% L-glutamine and 20 ng/ml MCSF at 37° C.

RAW 264.7 macrophages (from ATCC) were cultured in high-glucose Dulbecco's modified Eagle's medium supplemented with 10% fetal bovine serum at 37° C.

2. Infection by salmonella in THP1 cells and detection of the protein level of NMI in the cell lysate and supernatant.

Experimental method: Collect the THP1 cells in the 15 ml tube, centrifuge at 500 g for 5 min, remove the supernatant, wash the cells with preheat PBS, centrifuge at 500 g for 5 min, remove the supernatant. Suspend the cells with DMEM and count the cells by the hemocytometer. Add $3\times10^5$ cells in every hole. Add 1 ml of preheating DMEM to the cell culture dishes. Salmonella SR —11 were centrifuged at 12000 RPM for 10 min and washed twice with PBS. Salmonella were suspended and counted by the hemocytometer. The THP1 cells were added the Salmonella according to the multiplex of infection (1:100 or 1:10). Cell culture dishes were centrifuged at 1500 RPM for 10 min at room temperature which is benefit for bacteria to adsorb on the cells. When THP1 cells were infected with Salmonella for 1 hour, remove the salmonella in the cell culture and add 100 μg/ml Amikacin DMEM in the medium. When THP1 cells were infected with Salmonella for 3 hour, add 10 gg/ml Amikacin DMEM in the medium. Secretory protein in the cell culture supernatant was collected after THP1 cells were infected with Salmonella for 1, 3, 5, and 9 h.

Concentrate the cell culture supernatant and extract the whole cell lysates after cells were infected with Salmonella: Concentrate the cell culture supernatant: The cell culture supernatant was added 0.1 volumes of ice-cold 100% TCA and placed on ice for 2 h. Centrifuge at 12,000 g for 30 min at 4° C. Carefully remove the supernatant, wash the sediment twice with cold acetone. (4)Centrifuge at 12,000 g for 10 min at 4° C. (5) The sediment was heated at 95° C. for 5 minutes in the 30 ul 1 x SDS-PAGE loading buffer.

Extract the whole cell lysates after cells were infected with Salmonella: (1) Collect the cells: Collect the THP1 cells in the 15 ml tube, centrifuge at 500 g for 5 min, remove the supernatant, wash the cells with preheat PBS, centrifuge at 500 g for 5 min,r emove the supernatant. Cell sedimentation is used to extract total protein. (2) Cell lysis: Take appropriate amount of RIPA lysis buffer, add PMSF to the lysis buffer with a final concentration of 1 mm, proteinase inhibitors cocktail (Roche). Add 150 ul RIPA lysis buffer to each hole in the cell culture dishes and split the cells for 15 min on ice. (3)Collect the cell lysis buffer: centrifuge at 12000 RPM for 5 min at 4° C. after cells were split completely and transfer the supernatant to a new tube. (4) Boil the sample: The cell lysis buffer was heated at 95° C. for 5 minutes in the 150 ul 2 x SDS-PAGE loading buffer.

THP1 cell culture: THP1 cells were cultured in high-glucose Dulbecco's modified Eagle's medium supplemented with 10% fetal bovine serum at 37° C.

As shown in FIG. 29, there is no or little NMI in the in the cell culture supernatant. However, within 1 hour after stimulated by Salmonella, released NMI could be detected in the culture supernatant of THP1 cells. Meanwhile, the NMI in the cells does not change much. The result demonstrated that NMI could be secreted into the extracellular when infected by the bacteria.

NMI in Inflammatory Response

Add the mouse full length NMI to the TIHP1 cell culture medium (final concentration of 5, 25, 50 μg/ml), stimulate for 4 hours and detect the known pro-inflammatory factors, TNF-α and IL-1β.

Raw264.7 cell culture: Cells were cultured in high-glucose Dulbecco's modified Eagle's medium supplemented with 10% fetal bovine serum at 37° C.

Extract the cell total RNA: The total RNA was extracted from BMDM cells using the RNA extract Kit from KangWei Company (Cat No. CW 0597). The total RNA was extracted from RAW 264.7 cells using Trizol reagent (Invitrogen).

Reverse transcription: The first strand of cDNA was synthesized from 1 ug of total RNA using PrimeScript™ II 1st Strand cDNA Synthesis Kit (Cat.No.6210A).Real-time RT-PCR was performed using the SYBR@Premix Ex Taq™ (Tli RNaseH Plus) and ROX plus Q-PCR kit (Cat.NO.RR42LR).

As shown in FIGS. 30A-B, add control, LPS, NMI protein (5 μg/mL, 25 μg/mL or 50 μg/mL), the known pro-inflammatory factors, TNF-α and IL-1β can be up-regulated in the presence of NMI in THP1 cells. The result demonstrated that NMI also could induce other inflammatory factors similar with IFP35.

NMI-NID1 and full length NMI were tested using the same method and the results are not significantly different.

NMI Protein Aggregation State

The aggregation state of NMI that secreted by cells after stimulated by bacteria were tested. NMI can be secreted into cell culture medium when salmonella infected the THP1 cells. As shown in FIG. 31, 10 ml cell culture medium which contains the secreted NMI concentrate to 2 ml using Millipore concentration tube. The samples separated by chromatographic separation using Superdex S-200 molecular sieve column. And then, the eluted samples were tested by western and the elution peak position of NMI was tested by NMI antibody. The numbers in the figure is the volume of the elution buffer. It shows that the top of NMI elution peak primary at 78 ml, the corresponding molecular weight is from 70 KDa to 140 KDa.

The cell surface receptor of NMI

Since NMI can be secreted out of the cell and into body fluid to induce inflammation response, this example aims to identify the cell surface receptor of NMI and then to detect the biological function of TLR-Myd88 pathway in this process.

BMDM cell culture: Kill the mice through breaking the mice neck, take the two hind legs of mice, soak the legs in 70% alcohol for 1 min, and try to eliminate the muscles of the back bone, flush the marrow cavity with PBS. Then centrifuge at 400 g for 100 min and carefully remove the supernatant. Erythrocyte cells were collected in cell lysis buffer and then add 10 ml PBS to neutralize the cell lysis buffer. The BMDM cells cultured in high-glucose Dulbecco's modified Eagle's medium supplemented with 10% fetal bovine serum, 1% penicillin-streptomycin, 1% L-glutamine and 20 ng/ml MCSF at 37° C.

Extract the cell total RNA: The total RNA was extracted from BMDM cells using the RNA extract Kit from KangWei Company (Cat No. CW 0597). The total RNA was extracted from RAW 264.7 cells using Trizol reagent (Invitrogen).

Reverse transcription: The first strand of cDNA was synthesized from 1 ug of total RNA using PrimeScript™ II 1st Strand cDNA Synthesis Kit (Cat.No.6210A).Real-time RT-PCR was performed using the SYBR(@Premix Ex Taq™ (Tli RNaseH Plus) and ROX plus Q-PCR kit (Cat.NO.RR42LR).

NMI Monoclonal Antibody in Treating the Diseases Caused by Excessive Inflammatory Response Such as Sepsis Because of the high similarity of NMI structure and function with IFP35, and the cooperation of these two proteins, inhibition of NMI may have the same effect with IFP35 to inhibit the NMI-induced overactive immune response. Therefore, the NMI inhibitor is expected to treat septicemia, virus infection-induced NMI over-expression, and autoimmune diseases and so on, like IFP35 inhibitors.

The Expression of NMI in Sepsis Mice

The establishment of LPS-induced shock model: (1) the B6/C57 mice were banned water and food for 1 night; (2) LPS (5 mg and 10 mg per kg body weight) was injected intraperitoneally in mice the next day morning; (3) Take the blood using the capillary 3 hours after injection; (4) Remove the mice eye and take blood 6 hours after injection.

Detect the concentration of NMI in the LPS-induced shock model using ELISA. Quantitative detecting the NMI concentration in blood of sepsis mice model, it shows high concentration of NMI in the blood of LPS-induced sepsis mice, that reaches nanogram level. But the level of HMGB1 is pg600-800 according to the previous paper. And it depends on the time or dose of LPS injection (for 3 hours and 6 hours, LPS dose of 5 mg and 10 milligrams per kilogram of body weight). NMI monoclonal antibody can increase the survival rate of septic mice.

Overreaction for Immune Response

The Different Length of Purified Proteins that Expressed by Exogenous prokaryotic system, were injected into mice abdominal cavity, 100 mg protein per mouse, after eliminating the endotoxin. The recruitment of some immune cells by IFP35 and NMI in mice abdominal cavity, such as neutrophils, was detected by flow cytometry.

NMI in Cancer Treatment

Based on the present disclosure of IFP and NMI, drugs can be developed to treat sepsis, inflammation storm, autoimmune diseases and other diseases, which are associated with abnormally high levels of IFP35 and/or NMI expression, secretion, and/or activity. In some aspects, provided herein are (1) small compounds or peptides to inhibit IFP35 and NMI release; (2) antibodies to IFP35 and/or NMI to suppress the generation and function of IFP35 and NMI; (3) a small molecule to interference the formation of IFP35 or NMI polymer in vivo; (4) agents that inhibit the secretion of interferon to reduce the generation of IFP35; (5) agents that inhibit the interaction between IFP35 and NMI with their cell surface receptors to suppress IFP35 and/or NMI function; (6) agents that inhibit the interaction of IFP35 and NMI with their receptors to suppress their function. Likewise, under the condition of low immunity or immune suppression, such as in tumor tissues, the function of immune response could enhance by supply IFP35 or NMI to the organism or a part of it.

The techniques to achieve this purpose may: (1) directly inject IFP35 or NMI protein or their targeted derivative into the organism; (2) directly offer a derived peptide or small molecule by IFP35 or NMI or their targeted derivative. In addition, in terms of diagnosis of sepsis and inflammatory response, ELISA kits can be developed. Because it is only a fragment of IFP35 that expressed and crystallized in vitro, the full length of IFP35 may not have to form polymers to perform the function to induct cytokine storm. In mice, using the neutralizing monoclonal antibody of IFP35 could inhibit cytokine storm. This result suggests that IFP35 is a factor which causes cytokine storm no matter what polymeric state it exists. Therefore, IFP35 might be a primary reason that causes cytokine storm, which makes it become a target for inhibition of cytokine storm. Thus, the proper use of IFP35 monoclonal antibody or other inhibitory molecules of IFP35 could be helpful to inhibit cytokine storm. Because of the high similarity of NMI structure and function with IFP35, and the cooperation of these two proteins that both secrete to the outside of the cells, and the functions like induce the generation of cell inflammation factors, it indicate that NMI may have the same or similarity function with IFP35. Therefore, the inhibition of NMI could also inhibit the inflammation, and also be able to protect animals from overreacted inflammation response. Therefore, in some aspects, death or injury induced by overproduction of NMI or NMI mediated excessive inflammatory response can be avoided. Due to the less expression of NMI in some tumors, supplement of NMI provides an anti-tumor function. The similarity of NMI with IFP35 shows the two aspects of function, one is to enhance the immunity of organism to inhibit cancer or avoid infection, second is that they could become the target of tumor treatment to curb excessive immune function by inhibiting their activity, and then to prevent and treat the organism damage by inflammatory outbreak. Taken together, these results indicate the crucial function to induce inflammation response by IFP35 and NMI expression, and further demonstrate their significant value in medical science.

Example 5 Generation of IFP35 Antibody

To clone the sequences of the variable regions in the antibody, 7 pairs PCR primer were designed for the light chains variable region (VL), according to the 6 families of light chain. Primers P1-P7 are 7 upstream primers starting from FWR1 region, and P8 is the downstream primer ended at the end of FWR4 region. According to the 4 families of heavy chains variable regions, 5 pairs of heavy chain VH primers were designed for PCR amplification. Primers P9-P12 are the upstream primers, starting from FWR1 region; Primer 13 is the downstream primer ended at the end of FWR4.

The sequences of these primers are listed below:

```
P1
                            (SEQ ID NO: 39)
GACATTGTGATGWCACAGTCTCC;

P2
                            (SEQ ID NO: 40)
GATRTTKTGATGACYCARRCTCC;

P3
                            (SEQ ID NO: 41)
GACATTGTGCTGACCCAATCTCC;

P4
                            (SEQ ID NO: 42)
GACATTGTGCTGACACAGTCTCC;

P5
                            (SEQ ID NO: 43)
SAAAWTGTKCTCACCCAGTCTCC;

P6
                            (SEQ ID NO: 44)
GAYATYMAGATGACMCAGWC;

P7
                            (SEQ ID NO: 45)
GAYATTGTGATGACMCAGWCT;

P8 (VL-R)
                            (SEQ ID NO: 46)
TTTBAKYTCCAGCTTGGTSCC;

P9
                            (SEQ ID NO: 47)
AGGTGCAGCTKMAGGAGTCAGG;
```

-continued

P10

(SEQ ID NO: 48)

AGGTYCAGCTKCARSARTCT;

P11

(SEQ ID NO: 49)

AGGTCCARCTGCAGCAGYCT;

P12

(SEQ ID NO: 50)

AGGTGMAGCTKGWGGARTCTGG;

P13 (VH-R)

(SEQ ID NO: 51)

TGGTCGACGCTGAGGAGACGGT.

IFP35 antibody hybridoma cell were cultured and collected, using Trizol reagents (Life Technologies Inc.) to extract total RNA. Then using the extracted RNA as template to synthesize cDNA by using cDNA synthesis reagent kit from Life Technologies Inc. The PCR fragment products of light chain variable regions and heavy chain regions were recovered from the agarose gel and then cloned to T-vector (GE Healthcare). These constructs were transformed to *E. coli* DH5a competent cells and single clones were selected and sequenced.

Sequencing comparison results of our heavy and light chains comparing with sequences in NCBI BLAST shows that our sequences harbor similar feature of mouse IgG.

(SEQ ID NO: 12)

GACATTGTGATGACCCAGTCTCCAGCAATCATGTCTGCATCTCCAGGGGA

GAAGGTCACCATGACCTGCAGTGCCAGCTCAAGTGTAAGTTACATGCACT

GGTACCAGCAGAAGTCAGGCACCTCCCCCAAAAGATGGATTTATGACACA

TCCAAACTGGCTTCTGGAGTCCCTGCTCGCTTCAGTGGCAGTGGGTCTGG

GACCTCTTACTCTCTCACAATCAGCAGCATGGAGGCTGAAGATGCTGCCA

CTTATTACTGCCAGCAGTGGAGTAGTAACCCACCCATCACGTTCGGTGCT

GGCACCAAGCTGGAAATCAAA

Mus musculus isolate AIDKO-glmmB-1 immunoglobulin kappa light chain variable region gene, partial sequence Sequence ID: gb |EF543888.1|Length: 444 Number of Matches: 1

Mus musculus isolate AIDKO-glmmB-1 immunoglobulin kappa light chain variable region gene, partial sequence cds Sequence ID:gb |HQ446555.1| Length. 331 Number of Matches: 1

---

Range 1: 31 to 329 Genbank Graphics

▼ Next Match ▲ Previous Match

| Score | Expect | Identities | Gaps | Strand |
|---|---|---|---|---|
| 547 bits(296) | 3e-152 | 298/299(99%) | 0/299(0%) | Plus/Plus |

Query    16   CAGACTCCAGCAATCATGTCTGCATCTCCAGGGGAGAAGGTCACCATGACCTGCAGTGCC   75
              |||  ||||||||||||||||||||||||||||||||||||||||||||||||||||||||
Sbjct    31   CAGTCTCCAGCAATCATGTCTGCATCTCCAGGGGAGAAGGTCACCATGACCTGCAGTGCC   90

Query    76   AGCTCAAGTGTAAGTTACATGCACTGGTACCAGCAGAAGTCAGGCACCTCCCCCAAAAGA   135
              ||||||||||||||||||||||||||||||||||||||||||||||||||||||||||||
Sbjct    91   AGCTCAAGTGTAAGTTACATGCACTGGTACCAGCAGAAGTCAGGCACCTCCCCCAAAAGA   150

Query    136  TGGATTTATGACACATCCAAACTGGCTTCTGGAGTCCCTGCTCGCTTCAGTGGCAGTGGG   195
              ||||||||||||||||||||||||||||||||||||||||||||||||||||||||||||
Sbjct    151  TGGATTTATGACACATCCAAACTGGCTTCTGGAGTCCCTGCTCGCTTCAGTGGCAGTGGG   210

Query    196  TCTGGGACCTCTTACTCTCTCACAATCAGCAGCATGGAGGCTGAAGATGCTGCCACTTAT   255
              ||||||||||||||||||||||||||||||||||||||||||||||||||||||||||||
Sbjct    211  TCTGGGACCTCTTACTCTCTCACAATCAGCAGCATGGAGGCTGAAGATGCTGCCACTTAT   270

Query    256  TACTGCCAGCAGTGGAGTAGTAACCCACCCATCACGTTCGGTGCTGGGACCAAGCTGGA   314
              |||||||||||||||||||||||||||||||||||||||||||||||||||||||||||
Sbjct    271  TACTGCCAGCAGTGGAGTAGTAACCCACCCATCACGTTCGGTGCTGGGACCAAGCTGGA   329

---

Query   136  TGGATTTATGACACATCCAAACTGGCTTCTGGAGTCCCTGCTCGCTTCAGTGGCAGTGGG   195
             ||||||||||||||||||||||||||||||||||||||||||||||||||||||||||||
Sbjct   151  TGGATTTATGACACATCCAAACTGGCTTCTGGAGTCCCTGCTCGCTTCAGTGGCAGTGGG   210

Query   196  TCTGGGACCTCTTACTCTCTCACAATCAGCAGCATGGAGGCTGAAGATGCTGCCACTTAT   255
             |||||||||||||||||||||||||||||||||||||||||||||||||||||||||||
Sbjct   211  TCTGSGACCTCTTACTCTCTCACAATCAGCAGCATGGAGGCTGAAGATGCTGCCACTTAT   270

Query   256  TACTGCCAGCAGTGGAGTAGTAACCCACCCATCACGTTCGGTGCTGGGACCAAGCTGGA   314
             ||||||||||||||||||||||||||||||||||||||||||||||||||||||||||
Sbjct   273  TACTGCCAGCAGTGGAGTAGTAACCCACCCATCACGTTCGGTGCTGGGACCHAGCTGGA   329

(SEQ ID NO: 11)
TGGTCGACGCTGAGGAGACGGTGACTGAGGTTCCTTGACCCCAGTAGTC

CATAGCCCAAGAGTACCCGTATCTTGCACAGAAATATGTAGCCGTGTCC

TCATTCTTGAGGTTGTTGATCTGCAAATAGGCAGTGCTGGCAGAGGTTT

CCAAAGAGAAGGCAAACCGTCCCTTGAAGTCATCAGCAAATGTTGGCTC

TCCAGTGTAGGTGTTTATCCAGCCCATCCACTTTAAACCCTTTCCTGGA

GCCTGCTTCACCCAGTTCATTCCATAGTTTGTGAAGGTATACCCAGAAG

CCTTGCAGGAGATCTTGACTGTCTCTCCTGACTCCTTAAGCTGCACCT

Mus musculus clone nat28H immunoflobulin heavy chain
variable region mRNA, partial cds Sequence ID:gb
|HQ446555.1| Legnth, 331 Number of Matches: 1

---

Range 1: 8 to 331 Genbank Graphics

---

▼ Next Match ▲ Previous Match

| Score | Expect | Identities | Gaps | Strand |
|---|---|---|---|---|
| 518 bits(280) | 3e-143 | 313/328(95%) | 5/328(1%) | Plus/Plus |

```
Query    10   CTGAGGAGACGGTGACTGAGGTTCCTTGACCCCAGTAGTCCATAGCCC-AAGAGTACCCG    68
              ||||||||||||||||||||||||||||||||||||||||||||||||| | | | |
Sbjct   331   CTGAGGAGACGGTGACTGAGGTTCCTTGACCCCAGTAGTCCATAGCCCTCACGG-A---G   276

Query    89   TATCTTGCACAGAAATATGTAGCCGTGTCCTCATTCTTGAGGTTGTTGATCTGCAAATAG   128
              | |||||||||||||||||||||||||||||||| ||||||||||||||||||||||||||
Sbjct   275   TTTCTTGCACAGAAATATGTAGCCGTGTCCTCATTTTTGAGGTTGTTGATCTGCAAATAG   216

Query   129   GCAGTGCTGGCAGAGGTTTCCAAAGAGAAGGCAAACCGTCCCTTGAAGTCATCAGCAAAT   188
              ||||||||||||||||||||||||||||||||||||||||||||||||||||||||| ||
Sbjct   215   GCAGTGCTGGCAGAGGTTTCCAAAGAGAAGGCAAACCGTCCCTTGAAGTCATCAGCATAT   156

Query   189   GTTGGCTCTCCAGTGTAGGTGTTTATCCAGCCCATCCACTTTAAACCCTTTCCTGGAGCC   246
              ||||||||||||||||||||||||||||||||||||||||||||||||||||||||||||
Sbjct   155   GTTGGCTCTCCAGTGTAGGTGTTTATCCAGCCCATCCACTTTAAACCCTTTCCTGGAGCC    96

Query   249   TGCTTCACCCAGTTCATTCCATAGTTTGTGAAGGTATACCCAGAAGCCTTGCAGGAGATC   306
              ||||||||||||||||||||||||||||||||||||||||||||||||||||||||||||
Sbjct    95   TGCTTCACCCAGTTCATTCCATAGTTTGTGAAGGTATACCCAGAAGCCTTGCAGGAGATC    36

Query   309   TTGACTGTCTCTCCTGACTCCTTAAGCT   336
              ||||||||||||| | || ||| ||||
Sbjct    35   TTGACTGTCTCTCCAGGCTTCTTCAGCT     8
```

---

Translated light chain protein sequence and heavy chain
protein sequence based on the DNA sequences:

Light Chain:
(SEQ ID NO: 10)
D I V M T Q S P A I M S A S P G E K V T M T C S A

S S S V S Y M H W Y Q Q K S G T S P K R W I Y D T

S K L A S G V P A R F S G S G S G T S Y S L T I S

S M E A E D A A T Y Y C Q Q W S S N P P I T F G A

-continued

G T K L E I K;

Heavy Chain:
(SEQ ID NO: 9)
V Q L V E S G P E L K K P G E T V K I S C K A S G

Y T F T N Y G M N W V K Q A P G K G L K W M G W I

N T Y T G E P T F A D D F K G R F A F S L E T S A

S T A Y L Q I N N L K N E D T A T Y F C A R Y G Y

S W A M D Y W G Q G T S V T V S S A S T.

---

The invention claimed is:

1. A method of detecting autoimmune disease associated with abnormally high level and/or activity of Interferon-induced Protein 35 kD (IFP35) in a subject, wherein the method comprising:

a) obtaining a biological sample from the subject, wherein the biological sample is selected from blood, plasma, serum, cerebrospinal fluid, synovial fluid, urine, sweat, tissue and organ samples from animals and plants and processed samples derived therefrom; and b) detecting the level and/or an activity of IFP35 with an antibody that specifically binds to a portion of a N1D domain, or one or more NID domains of IFP35 by immunodetection techniques, wherein the level is at least 10% higher than a level and/or an activity of IFP35 in a healthy control or exceeds 46±16 pg/mL; and c) administering to the subject having autoimmune disease associated with abnormally high level and/or activity of IFP35 an antibody or antigen-binding fragment that specifically binds to IFP35;

wherein:

1) said immunodetection techniques comprise Enzyme-Linked Immunosorbent Assay (ELISA), Western blotting and Immunofluorescence Assay;

2) said autoimmune disease is Rheumatoid Arthritis, Systemic Lupus Erythematosus, Psoriasis, Inflammatory Bowel Disease, anti-NMDA receptor encephalitis, Multiple Sclerosis or Neuromyelitis Optica Spectrum Disorder (NMOSD);

3) said abnormally high level and/or activity is at least 10% higher than a level and/or activity in a healthy control or exceeds 46±16 pg/mL; said activity is the activity to binding to a cellular receptor or an antibody.

2. The method of claim 1, wherein the autoimmune disease associated with abnormally high level and/or activity of IFP35 is associated with cytokine storm, wherein the cytokine is IL-6 and TNFα.

* * * * *